United States Patent
Nakano et al.

(10) Patent No.: US 10,714,693 B2
(45) Date of Patent: Jul. 14, 2020

(54) POLYCYCLIC COMPOUND AND ORGANIC ELECTROLUMINESCENCE DEVICE INCLUDING THE SAME

(71) Applicants: SAMSUNG DISPLAY CO., LTD., Yongin-si, Gyeonggi-do (KR); KYUSHU UNIVERSITY, NATIONAL UNIVERSITY CORPORATION, Fukuoka (JP)

(72) Inventors: Hiromi Nakano, Yokohama (JP); Shuri Sato, Yokohama (JP); Yoshimasa Fujita, Yokohama (JP); Nobutaka Akashi, Yokohama (JP); Takuma Yasuda, Fukuoka (JP); JiYoung Lee, Fukuoka (JP)

(73) Assignees: Samsung Display Co., Ltd., Yongin-si (KR); Kyushu University, National University Corporation, Fukuoka-shi (JP)

( * ) Notice: Subject to any disclaimer, the term of this patent is extended or adjusted under 35 U.S.C. 154(b) by 486 days.

(21) Appl. No.: 15/474,030

(22) Filed: Mar. 30, 2017

(65) Prior Publication Data
US 2017/0352817 A1    Dec. 7, 2017

(30) Foreign Application Priority Data
Jun. 2, 2016    (KR) .................. 10-2016-0068876

(51) Int. Cl.
| H01L 51/54 | (2006.01) |
| C09K 11/06 | (2006.01) |
| H01L 51/00 | (2006.01) |
| C07D 405/04 | (2006.01) |
| C07D 491/107 | (2006.01) |
| H01L 51/50 | (2006.01) |

(52) U.S. Cl.
CPC ........ *H01L 51/0072* (2013.01); *C07D 405/04* (2013.01); *C07D 491/107* (2013.01); *C09K 11/06* (2013.01); *H01L 51/0052* (2013.01); *H01L 51/0061* (2013.01); *H01L 51/0071* (2013.01); *H01L 51/0073* (2013.01); *C09K 2211/1007* (2013.01); *C09K 2211/1029* (2013.01); *C09K 2211/1033* (2013.01); *C09K 2211/1088* (2013.01); *H01L 51/5012* (2013.01)

(58) Field of Classification Search
None
See application file for complete search history.

(56) References Cited

U.S. PATENT DOCUMENTS

| 2015/0280138 A1 | 10/2015 | Xu et al. |
| 2016/0141516 A1* | 5/2016 | Numata ............... C07D 405/14 544/73 |

FOREIGN PATENT DOCUMENTS

| JP | 2012-138585 A | 7/2012 |
| JP | 2016-210913 A | 12/2016 |

(Continued)

OTHER PUBLICATIONS

Liu et al. Adv. Mater. 2016, 26, 2002-2008. (Year: 2016).*

*Primary Examiner* — Andrew K Bohaty
(74) *Attorney, Agent, or Firm* — Lewis Roca Rothgerber Christie LLP

(57) ABSTRACT

A polycyclic compound and an organic electroluminescence device including the same. The polycyclic compound according to an example embodiment is represented by the following Formula 1.

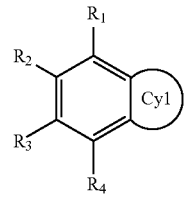

[Formula 1]

wherein in Formula 1, Cy1 is carbonyl-containing five- or six-membered and substituted or unsubstituted cyclic hydrocarbon or substituted or unsubstituted heterocycle, and $R_1$ to $R_4$ are each independently a hydrogen atom or a group represented by the following Formula 2 or 3.

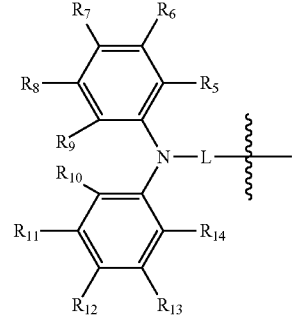

[Formula 2]

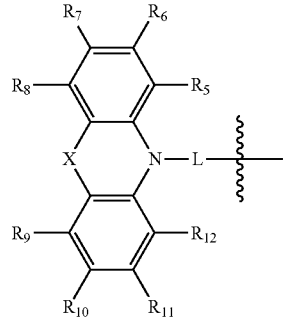

[Formula 3]

20 Claims, 1 Drawing Sheet

(56) References Cited

FOREIGN PATENT DOCUMENTS

| | | |
|---|---|---|
| KR | 10-2013-0010015 A | 1/2013 |
| KR | 10-2015-0030132 A | 3/2015 |
| WO | WO 2010/134350 A1 | 11/2010 |
| WO | WO 2013/081088 A1 | 6/2013 |
| WO | WO 2015/002213 A1 | 1/2015 |
| WO | WO-2016046034 A1 * | 3/2016 ............. C09B 19/00 |

* cited by examiner

POLYCYCLIC COMPOUND AND ORGANIC ELECTROLUMINESCENCE DEVICE INCLUDING THE SAME

CROSS-REFERENCE TO RELATED APPLICATION

Korean Patent Application No. 10-2016-0068876, filed on Jun. 2, 2016, in the Korean Intellectual Property Office, and entitled: "Polycyclic Compound And Organic Electroluminescence Device Including the Same," is incorporated by reference herein in its entirety.

BACKGROUND

1. Field

Embodiments relate to a polycyclic compound and an organic electroluminescence device including the same.

2. Description of the Related Art

The development of an organic electroluminescence display as an image display is being actively conducted. The organic electroluminescence display is different from a liquid crystal display and is a so called self-luminescent display. The organic electroluminescence display may emit light via the recombination of holes and electrons injected from a first electrode and a second electrode in an emission layer, and light emission from a luminescent material including an organic compound in the emission layer.

SUMMARY

Embodiments are directed to a polycyclic compound represented by the following Formula 1:

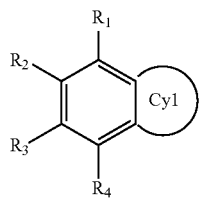

[Formula 1]

In Formula 1, Cy1 may be carbonyl-containing, five- or six-membered, substituted or unsubstituted cyclic hydrocarbon or substituted or unsubstituted heterocycle, and $R_1$ to $R_4$ may each independently be a hydrogen atom or a group represented by one of the following Formula 2 or 3,

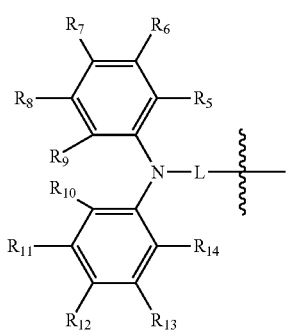

[Formula 2]

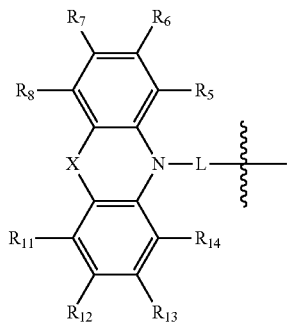

[Formula 3]

In Formulae 2 and 3, L may be a direct linkage or substituted or unsubstituted arylene group having 6 to 30 carbon atoms forming a ring, $R_5$ to $R_{14}$ may each independently be a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring, X may be a direct linkage, $CR_{15}R_{16}$, $SiR_{17}R_{18}$, $GeR_{19}R_{20}$, $NR_{21}$, O, or S, and $R_{15}$ to $R_{21}$ may each independently be a substituted or unsubstituted aryl group having 6 to 12 carbon atoms forming a ring, where the aryl group may combine with an adjacent group to form a ring.

The polycyclic compound represented by Formula 1 may be represented by the following Formula 1-1 or 1-2:

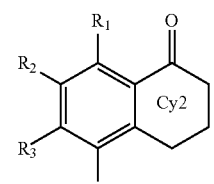

[Formula 1-1]

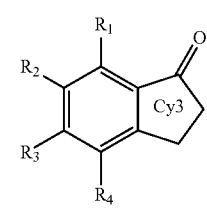

[Formula 1-2]

In Formulae 1-1 and 1-2, Cy2 and Cy3 may each independently be a substituted or unsubstituted cyclic hydrocarbon or substituted or unsubstituted heterocycle, and $R_1$ to $R_4$ are the same as described herein.

The polycyclic compound represented by Formula 1 may be represented by the following Formula 1-3 or 1-4:

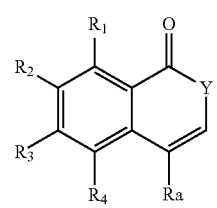

[Formula 1-3]

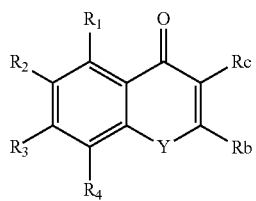
[Formula 1-4]

In Formulae 1-3 and 1-4, Y may be O or $NR_{22}$, $R_{22}$ may be a hydrogen atom, substituted or unsubstituted alkyl group having 1 to 15 carbon atoms, or substituted or unsubstituted aryl group having 6 to 30 carbon atoms forming a ring, Ra to Rc may each independently be a hydrogen atom or substituted or unsubstituted alkyl group having 1 to 15 carbon atoms, and $R_1$ to $R_4$ are the same as described herein.

The polycyclic compound represented by Formula 1 may be represented by the following Formula 1-5 or 1-6:

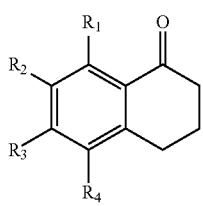
[Formula 1-5]

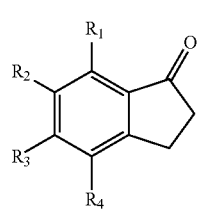
[Formula 1-6]

In Formulae 1-5 and 1-6, $R_1$ to $R_4$ are the same as described herein.

The polycyclic compound represented by Formula 1 may be represented by the following Formula 1-7:

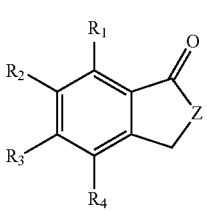
[Formula 1-7]

In Formula 1-7, Z may be O or $NR_{23}$, $R_{23}$ may be hydrogen atom, substituted or unsubstituted alkyl group having 1 to 15 carbon atoms, or substituted or unsubstituted aryl group having 6 to 30 carbon atoms forming a ring, and $R_1$ to $R_4$ are the same as described herein.

The polycyclic compound represented by Formula 1 may be represented by the following Formula 1-8:

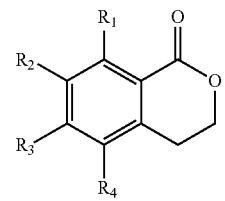
[Formula 1-8]

In Formula 1-8, $R_1$ to $R_4$ are the same as described herein.

The polycyclic compound represented by Formula 1 may be represented by one of the following Formulae 1-9 to 1-24:

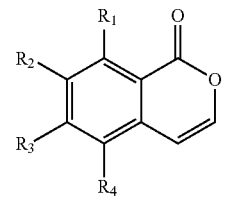
[Formula 1-9]

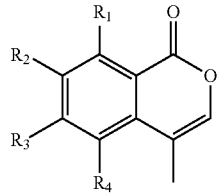
[Formula 1-10]

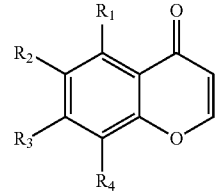
[Formula 1-11]

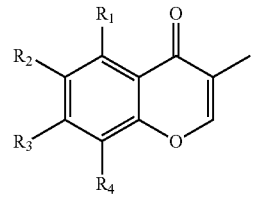
[Formula 1-12]

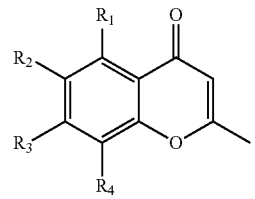
[Formula 1-13]

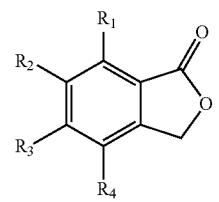
[Formula 1-14]

[Formula 1-15]
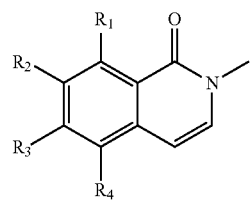

[Formula 1-16]
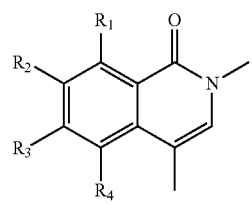

[Formula 1-17]
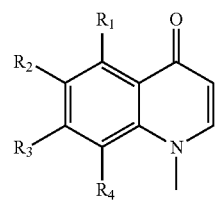

[Formula 1-18]
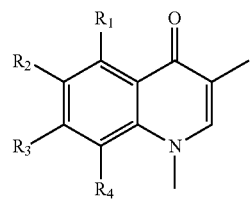

[Formula 1-19]
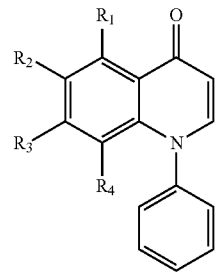

[Formula 1-20]
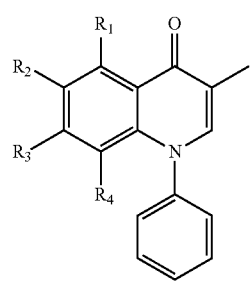

[Formula 1-21]
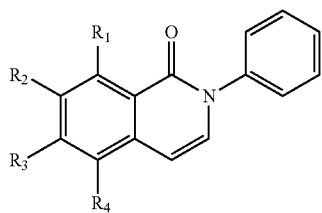

[Formula 1-22]
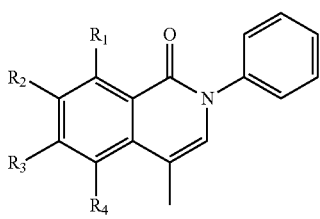

[Formula 1-23]
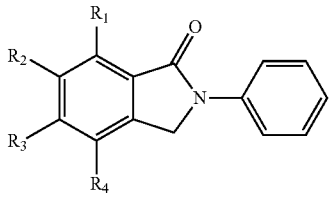

[Formula 1-24]
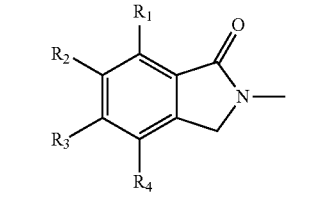

In Formulae 1-9 to 1-24, $R_1$ to $R_4$ are the same as described herein.

One of $R_2$ and $R_3$ may be represented by Formula 2 or 3, and the other one of $R_2$ and $R_3$, $R_1$, and $R_4$ may be a hydrogen atom.

L may be a direct linkage.

$R_1$ to $R_4$ may each independently be a hydrogen atom or a group represented by one of Formula 2 and the following Formulae 3-1 to 3-4:

[Formula 3-1]
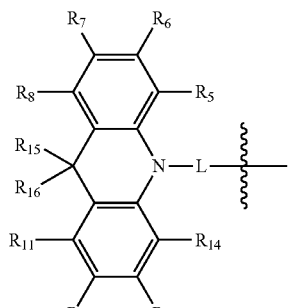

[Formula 3-2]
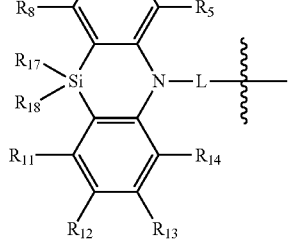

-continued

[Formula 3-3]

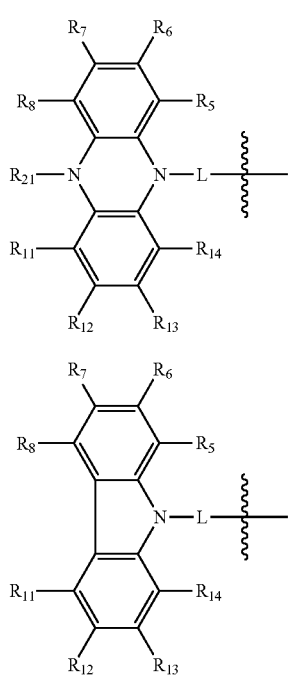

[Formula 3-4]

In Formulae 3-1 to 3-4, L, R₅ to R₁₈, and R₂₁ are the same as described herein.

R₁ to R₄ may each independently be a hydrogen atom or one of Formula 2 and the following Formulae 3-5 to 3-11:

[Formula 3-5]

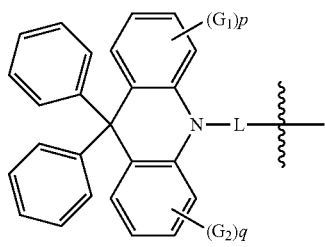

[Formula 3-6]

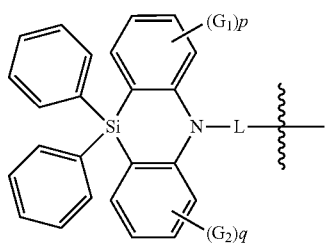

[Formula 3-7]

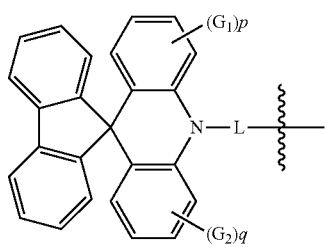

-continued

[Formula 3-8]

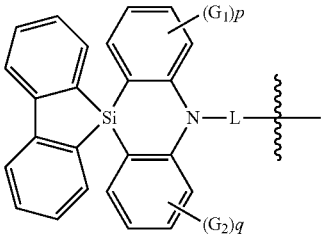

[Formula 3-9]

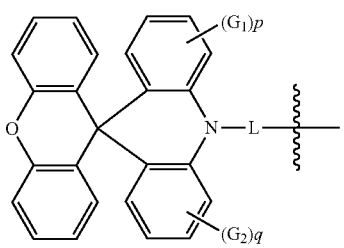

[Formula 3-10]

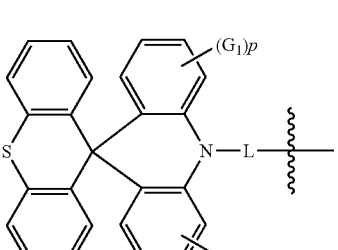

[Formula 3-11]

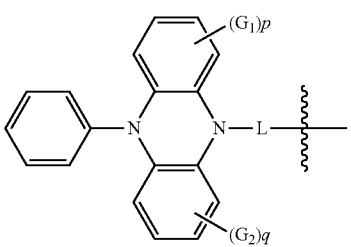

In Formulae 3-5 to 3-11, $G_1$ and $G_2$ may each independently be a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring, p and q may each independently be an integer of 0 to 4, and L is the same as described herein.

$R_5$ to $R_{14}$ may each independently be a hydrogen atom, halogen atom, trialkylsilyl group, diphenylamine group, methyl group, phenyl group, or carbazole group.

The polycyclic compound represented by Formula 1 may be one of the compounds represented in Compound Group 1.

Embodiments are also directed to an organic electroluminescence device, including a first electrode, an emission layer; and a second electrode, the emission layer being between the first electrode and the second electrode, the emission layer including a polycyclic compound represented by the following Formula 1:

[Formula 1]

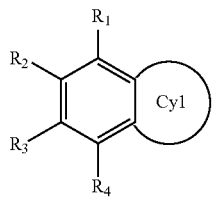

In Formula 1, Cy1 may be carbonyl-containing five- or six-membered, substituted or unsubstituted cyclic hydrocarbon or substituted or unsubstituted heterocycle, and $R_1$ to $R_4$ may each independently be a hydrogen atom or a group represented by the following Formula 2 or 3,

[Formula 2]

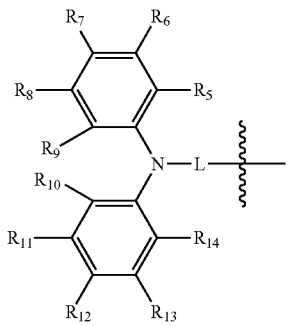

[Formula 3]

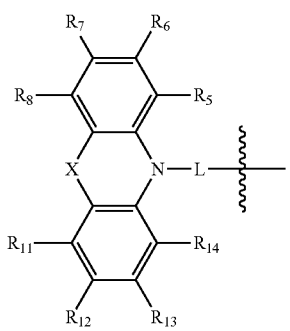

In Formulae 2 and 3, L may be a direct linkage or substituted or unsubstituted arylene group having 6 to 30 carbon atoms forming a ring, $R_5$ to $R_{14}$ may each independently be a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring, X may be a direct linkage, $CR_{15}R_{16}$, $SiR_{17}R_{18}$, $GeR_{19}R_{20}$, $NR_{21}$, O, or S, $R_{15}$ to $R_{21}$ may each independently be a substituted or unsubstituted aryl group having 6 to 12 carbon atoms forming a ring, where the aryl group may combine with an adjacent group to form a ring.

The polycyclic compound represented by Formula 1 may have a value of absolute difference of about 0.2 eV or less between a singlet energy level and a triplet energy level.

The polycyclic compound represented by Formula 1 may exhibit thermally activated delayed fluorescence.

The polycyclic compound represented by Formula 1 may be represented by one of the following Formulae 1-3 to 1-8:

[Formula 1-3]

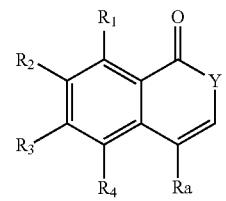

[Formula 1-4]

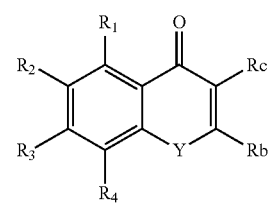

[Formula 1-5]

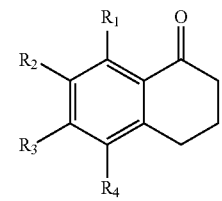

[Formula 1-6]

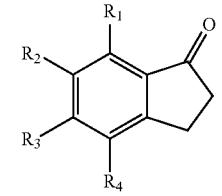

[Formula 1-7]

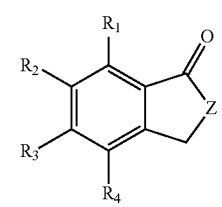

[Formula 1-8]

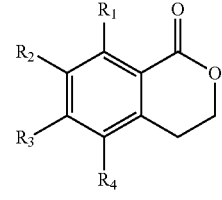

In Formulae 1-3 and 1-4, Y may be O or $NR_{22}$, $R_{22}$ may be hydrogen atom, substituted or unsubstituted alkyl group having 1 to 15 carbon atoms, or substituted or unsubstituted aryl group having 6 to 30 carbon atoms forming a ring, Ra to Rc may each independently be a hydrogen atom or substituted or unsubstituted alkyl group having 1 to 15 carbon atoms, In Formula 1-7, Z may be O or $NR_{23}$, $R_{23}$ may be hydrogen atom, substituted or unsubstituted alkyl group having 1 to 15 carbon atoms, or substituted or unsubstituted aryl group having 6 to 30 carbon atoms forming a ring, and In Formulae 1-3 to 1-8, $R_1$ to $R_4$ are the same as described herein.

One of $R_2$ and $R_3$ may be represented by Formula 2 or 3, and the remaining one of $R_2$ and $R_3$, $R_1$, and $R_4$ may be a hydrogen atom.

L may be a direct linkage.

The polycyclic compound represented by Formula 1 may one of the compounds represented in Compound Group 1.

BRIEF DESCRIPTION OF THE DRAWINGS

Features will become apparent to those of skill in the art by describing in detail example embodiments with reference to the attached drawings in which.

DETAILED DESCRIPTION

Figure 1:
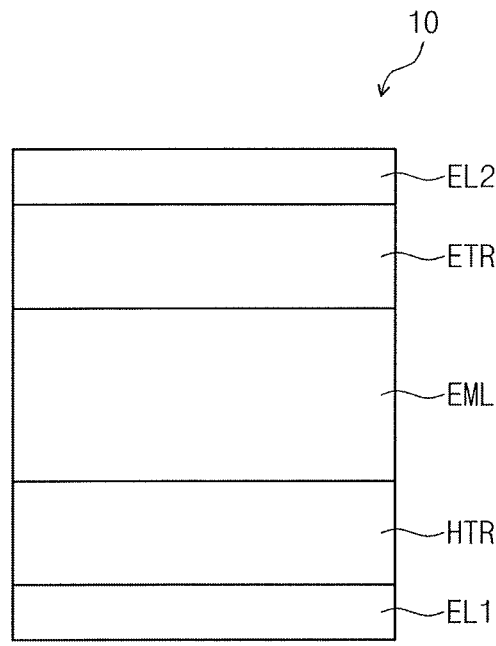
FIG. 1 illustrates a schematic cross-sectional view of an organic electroluminescence device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art.

In the drawing figures, the dimensions of layers and regions may be exaggerated for clarity of illustration. Like reference numerals refer to like elements throughout.

It will be understood that, although the terms first, second, etc., may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being 'on' another part, it can be directly on the other part, or intervening layers may also be present. When a layer, a film, a region, a plate, etc., is referred to as being 'under' another part, it can be directly under the other part, or intervening layers may also be present.

In the present disclosure, the symbol

means a position to be connected.

In the present disclosure, "substituted or unsubstituted" may mean substituted with at least one substituent selected from the group of a deuterium atom, halogen atom, cyano group, nitro group, amino group, silyl group, boron group, arylamine group, phosphine oxide group, phosphine sulfide group, alkyl group, alkenyl group, aryl group, and heteroaryl group or unsubstituted. In addition, each of the substituent illustrated above may be a substituted or unsubstituted. For example, biphenyl may be interpreted as aryl group, or phenyl substituted with phenyl group.

In the present disclosure, the term "forming a ring by combining with an adjacent group" may mean forming a substituted or unsubstituted cyclic hydrocarbon, or substituted or unsubstituted heterocycle by combining with an adjacent group. The cyclic hydrocarbon may include an aliphatic cyclic hydrocarbon and aromatic cyclic hydrocarbon. The heterocycle may include an aliphatic heterocycle and aromatic heterocycle. The cyclic hydrocarbon and heterocycle may be a monocycle or polycycle. In addition, the ring formed by combining with an adjacent group may be connected with another ring to form a spiro structure.

In the present disclosure, the term "adjacent groups" may mean a substituent substituted with an atom directly connected with another atom substituted with a corresponding substituent, a different substituent substituted with an atom substituted with a corresponding substituent, or a substituent disposed stereoscopically at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, halogen may include a fluorine atom, a chlorine atom, a bromine atom, or an iodine atom.

In the present disclosure, the alkyl may have a linear or branched chain or a cycle shape. The carbon number of the alkyl group may be 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the present disclosure, the aryl means a functional group or substituent derived from aromatic cyclic hydrocarbon. The aryl may be monocyclic aryl or polycyclic aryl. The carbon number of the aryl for forming a ring may be 6 to 30, 6 to 20, or 6 to 15. Examples of the aryl may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc.

In the present disclosure, the fluorenyl may be substituted, or two substituents may be combined to form a spiro structure.

In the present disclosure, the heteroaryl may be heteroaryl including at least one of O, N, P, or S as a heteroatom. The carbon number of the heteroaryl for forming a ring may be 2 to 30, or 2 to 20. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzofuranyl, etc.

In the present disclosure, the explanation on the aryl group may be applied to the arylene group, the arylene being divalent.

In the present disclosure, the silyl group may include alkylsilyl and arylsilyl. Examples of the silyl may include trimethylsilyl, triethylsilyl, t-butyl dimethylsilyl, vinyl dimethylsilyl, propyl dimethylsilyl, triphenylsilyl, diphenylsilyl, phenylsilyl, etc.

In the present disclosure, the boron group group may include alkyl boron and aryl boron. Examples of the boron group may include trimethyl boron, triethyl boron, t-butyl dimethyl boron, triphenyl boron, diphenyl boron, phenyl boron, etc.

In the present disclosure, the alkenyl group may be linear or branched. The carbon number is not specifically limited, however it may be 2 to 30, 2 to 30, or 2 to 10. Examples of the alkenyl may include vinyl, 1-butenyl, 1-pentenyl, 1,3-butadienyl aryl, styrenyl, styrylvinyl, etc.

In the present disclosure, the carbon number may be, for example, 1 to 30. The amine may include an alkylamine and arylamine. Examples of the amine may include methylamine, dimethylamine, phenylamine, diphenylamine, naphthylamine, 9-methyl-anthracenylamine, triphenylamine, etc.

Hereinafter, a polycyclic compound according to an example embodiment will be described.

The polycyclic compound according to an example embodiment is represented by the following Formula 1.

[Formula 1]

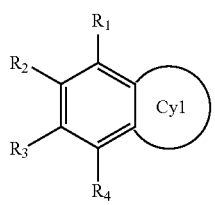

In Formula 1, Cy1 is carbonyl-containing five- or six-membered ring. Cy1 is substituted or unsubstituted ring or substituted or unsubstituted heterocycle. Cy1 may be a ring including a double bond.

In Formula 1, $R_1$ to $R_4$ may each independently be a hydrogen atom or a group represented by the following Formula 2 or 3.

[Formula 2]

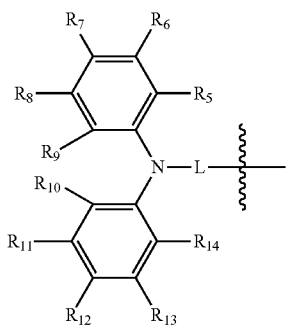

[Formula 3]

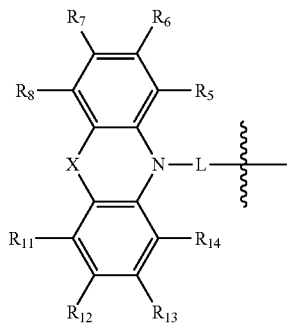

In Formulae 2 and 3, L is a direct linkage or substituted or unsubstituted arylene group having 6 to 30 carbon atoms forming a ring, $R_5$ to $R_{14}$ are each independently a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group of 6 to 30 carbon atoms forming a ring, or substituted or unsubstituted heteroaryl group having 2 to 30 carbon atoms forming a ring, X is a direct linkage, $CR_{15}R_{16}$, $SiR_{17}R_{18}$, $GeR_{19}R_{20}$, $NR_{21}$, O, or S, $R_{15}$ to $R_{21}$ are each independently a substituted or unsubstituted aryl group having 6 to 12 carbon atoms forming a ring, where the aryl group may combine with an adjacent group to form a ring.

The direct linkage may be, for example, a single bond.

The polycyclic compound according to an example embodiment may include an electron acceptor and an electron donor. For example, the polycyclic compound according to an example embodiment is a carbonyl-containing dicyclic ring represented by Formula 1, and amine represented by Formula 2 or 3 is the electron donor.

In Formula 1, Cy1 is substituted or unsubstituted monocycle. Thus, the compound represented by Formula 1 is a dicyclic compound including a benzene ring and a monocycle represented by Cy1.

The carbonyl of Cy1 may be positioned in ortho relation with the benzene ring of Formula 1. For example, the polycyclic compound represented by Formula 1 may be represented by the following Formula 1-1 or 1-2.

[Formula 1-1]

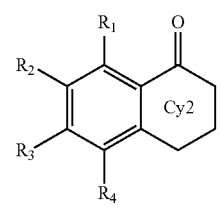

[Formula 1-2]

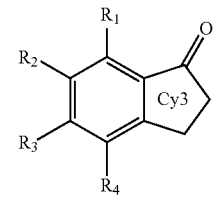

In Formulae 1-1 and 1-2, Cy2 and Cy3 are each independently a substituted or unsubstituted cyclic hydrocarbon, or substituted or unsubstituted heterocycle, and $R_1$ to $R_4$ are the same as described above. Cy2 is a six-membered ring. Cy3 is a five-membered ring.

Cy2 and Cy3 may each independently be a ring including a double bond.

The polycyclic compound represented by Formula 1 may be represented by the following Formula 1-3 or 1-4.

[Formula 1-3]

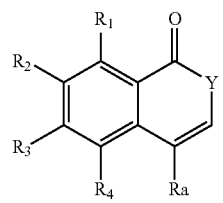

[Formula 1-4]

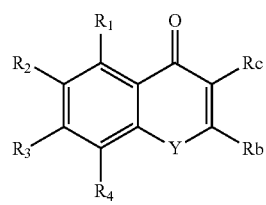

In Formulae 1-3 and 1-4, Y is O or $NR_{22}$, $R_{22}$ is a hydrogen atom, substituted or unsubstituted alkyl group having 1 to 15 carbon atoms, or substituted or unsubstituted aryl group having 6 to 30 carbon atoms forming a ring, Ra to Rc are each independently a hydrogen atom or substituted or unsubstituted alkyl group having 1 to 15 carbon atoms, and $R_1$ to $R_4$ are the same as described above.

In Formula 1-3, Y may be O. In Formula 1-3, Y may be $NR_{22}$. $NR_{22}$ may be a substituted or unsubstituted alkyl group having 1 to 10 carbon atoms. $R_{22}$ may be methyl. $R_{22}$ may be a substituted or unsubstituted aryl group having 6 to 20 carbon atoms forming a ring. $R_{22}$ may be phenyl.

In Formula 1-3, Ra may be hydrogen or substituted or unsubstituted alkyl group having 1 to 5 carbon atoms. In Formula 1-3, Ra may be a hydrogen atom or methyl.

In Formula 1-4, Y may be O. In Formula 1-4, Y may be $NR_{22}$. $NR_{22}$ may be a substituted or unsubstituted alkyl having 1 to 10 carbon atoms. $R_{22}$ may be methyl. $R_{22}$ may be a substituted or unsubstituted aryl group having 6 to 20 carbon atoms forming a ring. $R_{22}$ may be phenyl.

In Formula 1-4, at least one of Rb and Rc may be a hydrogen atom. In Formula 1-4, Rb may be a hydrogen atom, and Rc may be a substituted or unsubstituted alkyl group having 1 to 10 carbon atoms. In Formula 1-4, Rb may be a hydrogen atom, and Rc may be methyl. In Formula 1-4, Rb may be a substituted or unsubstituted alkyl group having 1 to 10 carbon atoms, and Rc may be a hydrogen atom. In Formula 1-4, Rb may be methyl, and Rc may be a hydrogen atom.

Cy1 may be a cyclic hydrocarbon not including a double bond. For example, the polycyclic compound represented by Formula 1 may be represented by the following Formula 1-5 or 1-6.

[Formula 1-5]

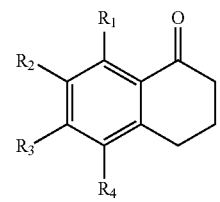

[Formula 1-6]

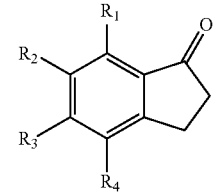

In Formulae 1-5 and 1-6, $R_1$ to $R_4$ are the same as described above.

Cy1 may be a heterocycle not including a double bond. For example, the polycyclic compound represented by Formula 1 may be represented by the following Formula 1-7.

[Formula 1-7]

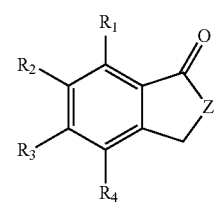

In Formula 1-7, Z is O or $NR_{23}$, $R_{23}$ is a hydrogen atom, substituted or unsubstituted alkyl group having 1 to 15 carbon atoms, or substituted or unsubstituted aryl group having 6 to 30 carbon atoms forming a ring, and $R_1$ to $R_4$ are the same as described above.

In Formula 1-7, Z may be O. In Formula 1-7, Z may be $NR_{23}$. $NR_{23}$ may be a substituted or unsubstituted alkyl group having 1 to 10 carbon atoms or substituted or unsubstituted aryl group having 6 to 20 carbon atoms forming a ring. $R_{23}$ may be methyl or phenyl. $R_{23}$ may be methyl. $R_{23}$ may be phenyl.

As described above, Cy1 may be a heterocycle not including a double bond. For example, the polycyclic compound represented by Formula 1 may be represented by the following Formula 1-8.

[Formula 1-8]

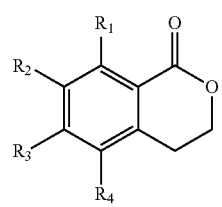

In Formula 1-8, $R_1$ to $R_4$ are the same as described above.

The polycyclic compound represented by Formula 1 may be represented by one of the following Formulae 1-9 to 1-24, etc.

[Formula 1-9] 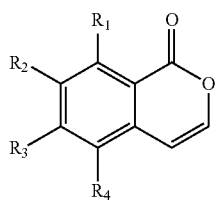
[Formula 1-10] 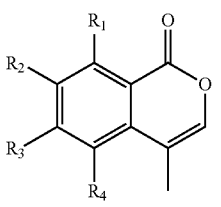
[Formula 1-11] 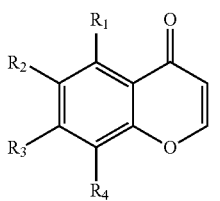
[Formula 1-12] 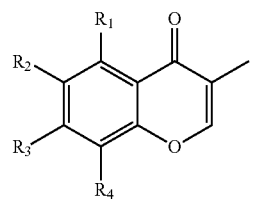
[Formula 1-13] 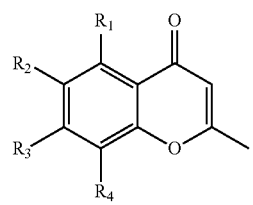
[Formula 1-14] 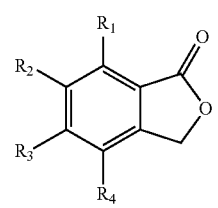
[Formula 1-15] 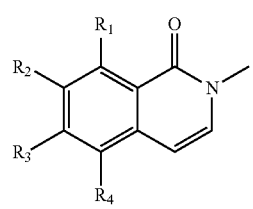
[Formula 1-16] 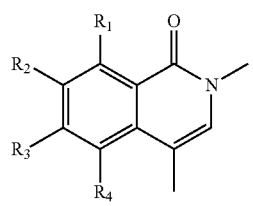
[Formula 1-17] 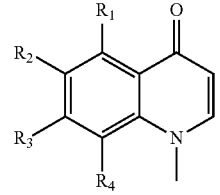
[Formula 1-18] 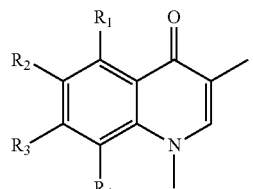
[Formula 1-19] 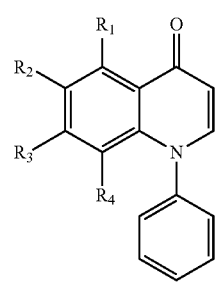
[Formula 1-20] 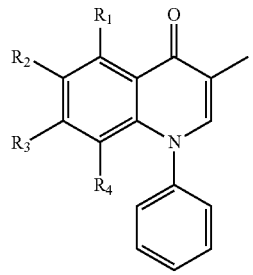
[Formula 1-21] 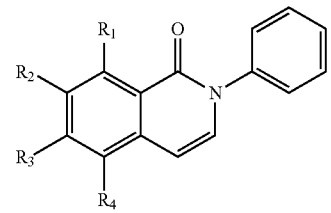
[Formula 1-22] 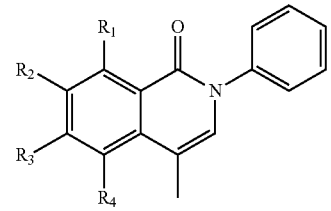

[Formula 1-23]

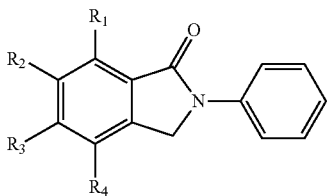

[Formula 1-24]

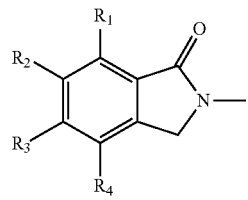

In Formulae 1-9 to 1-24, $R_1$ to $R_4$ are the same as described above.

In Formula 1, one of $R_2$ and $R_3$ may be represented by Formula 2 or 3, the remaining one of $R_2$ and $R_3$, $R_1$, and $R_4$ may be a hydrogen atom. In this case, the orbital separation between highest occupied molecular orbital (HOMO)-lowest unoccupied molecular orbital (LUMO) may be good, and decreasing effects of a difference value between singlet-triplet energy levels may be obtained.

In Formula 2 or 3, 1 may be a direct linkage. Thus, the polycyclic compound according to an example embodiment may include a structure in which an electron acceptor and an electron donor are directly combined. In another embodiment, the electron acceptor and the electron donor may be combined via a linker. For example, in Formula 2 or 3, L may be a substituted or unsubstituted arylene group having 6 to 20 carbon atoms forming a ring. In Formula 2 or 3, L may be phenylene. In Formula 2 or 3, L may be 1,4-phenylene.

In Formula 1, $R_1$ to $R_4$ may each independently be hydrogen, or represented by one of the above Formula 2, or the following Formulae 3-1 to 3-4.

[Formula 3-1]

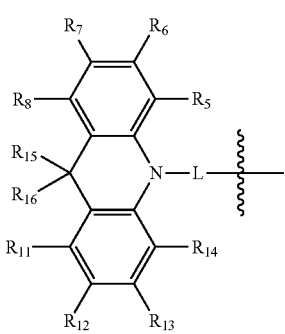

[Formula 3-2]

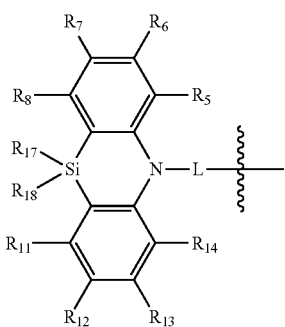

[Formula 3-3]

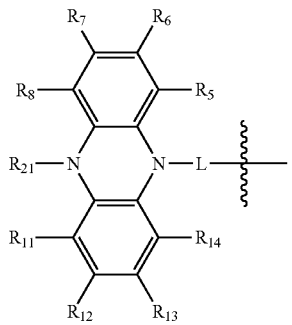

[Formula 3-4]

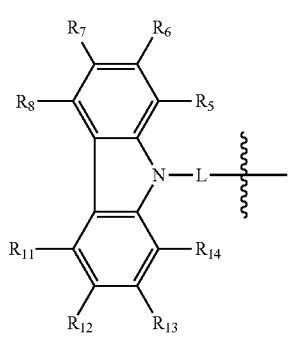

In Formulae 3-1 to 3-4, L, $R_5$ to $R_{18}$, and $R_{21}$ are the same as described above.

In Formula 1, $R_2$ or $R_3$ may be one represented by one of Formula 2, or Formulae 3-1 to 3-3.

In Formula 2, $R_5$ to $R_{14}$ may be a hydrogen atom. In Formula 2, $R_5$ to $R_{14}$ are each independently a hydrogen atom, halogen atom, trialkylsilyl group, diphenylamine group, methyl group phenyl group or carbazole group.

In Formula 3, X may be a direct linkage. When X is the direct linkage in Formula 3, Formula 3 is substituted or unsubstituted carbazole group represented by the above Formula 3-4.

In Formula 3, $R_5$ to $R_{14}$ may be a hydrogen atom. In Formula 3, $R_5$ to $R_{14}$ may each independently be a hydrogen atom, halogen atom, trialkylsilyl group, diphenylamine group, methyl group, phenyl group, or carbazole group.

In Formula 3-1, $R_{15}$ and $R_{16}$ may each be a phenyl group. In Formula 3-1, $R_{15}$ and $R_{16}$ may each be a phenyl group, and $R_{15}$ and $R_{16}$ may combine with each other to form a fluorenyl group. In Formula 3-1, $R_{15}$ and $R_{16}$ may each independently be a phenyl group, and $R_{15}$ and $R_{16}$ may combine with each other via a heteroatom. The heteroatom may be, for example, 0 or S, etc.

In Formula 3-1, at least one of $R_5$ to $R_8$ or $R_{11}$ to $R_{14}$ may be a halogen atom, substituted or unsubstituted silyl group, or substituted or unsubstituted alkyl group having 1 to 15 carbon atoms.

In Formula 3-1, $R_7$ and $R_{12}$ are each independently a halogen atom, substituted or unsubstituted silyl group, or substituted or unsubstituted alkyl having 1 to 15 carbon atoms. In Formula 3-1, $R_7$ and $R_{12}$ are each independently a fluorine atom, trimethylsilyl group, or methyl group.

In Formula 3-1, $R_5$ to $R_8$ and $R_{11}$ to $R_{14}$ may be a hydrogen atom.

In Formula 3-2, $R_{17}$ and $R_{18}$ may each be a phenyl group. In Formula 3-2, $R_{17}$ and $R_{18}$ may each be a phenyl group, and $R_{17}$ and $R_{18}$ may combine with each other to form a fluorenyl group.

In Formula 3-2, $R_5$ to $R_8$ and $R_{11}$ to $R_{14}$ may be a hydrogen atom.

In Formula 3-3, $R_{21}$ may be a phenyl group. In Formula 3-3, $R_5$ to $R_8$ and $R_{11}$ to $R_{14}$ may be a hydrogen atom. In Formula 3-3, at least one of $R_5$ to $R_8$ and $R_{11}$ to $R_{14}$ may be a halogen atom. In Formula 3-3, $R_7$ and $R_{12}$ may be a halogen atom.

In Formula 3-4, $R_5$ to $R_8$ and $R_{11}$ to $R_{14}$ may each independently be a hydrogen atom, substituted or unsubstituted arylamine group, or substituted or unsubstituted heteroaryl group having 2 to 30 carbon atoms forming a ring.

In Formula 3-4, $R_7$ and $R_{12}$ may each independently be a substituted or unsubstituted arylamine group, or substituted or unsubstituted heteroaryl group having 2 to 30 carbon atoms forming a ring. In Formula 3-4, $R_7$ and $R_{12}$ may each independently be a hydrogen atom, a diphenylamine group, or a carbazole group.

In Formula 1, $R_1$ to $R_4$ are each independently a hydrogen atom or a group represented by one of the above Formula 2 and the following Formulae 3-5 to 3-11.

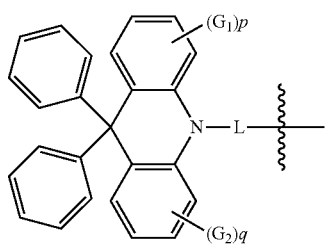

[Formula 3-5]

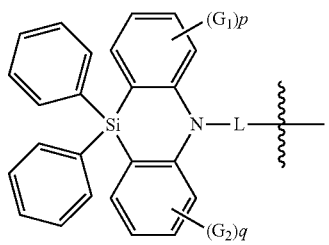

[Formula 3-6]

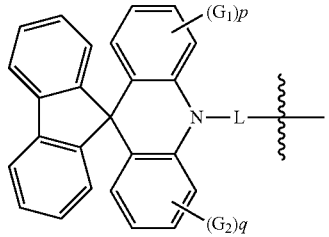

[Formula 3-7]

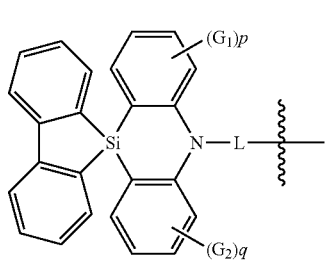

[Formula 3-8]

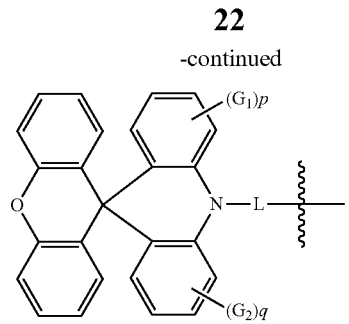

[Formula 3-9]

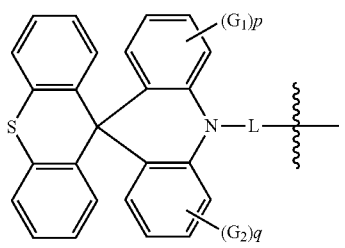

[Formula 3-10]

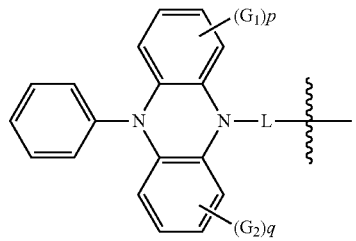

[Formula 11]

In Formulae 3-5 to 3-11, $G_1$ and $G_2$ are each independently a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring, p and q are each independently an integer of 0 to 4, and L is the same as described above.

When p is 1 or more, a plurality of $G_1$ are the same or different. When q is 1 or more, a plurality of $G_2$ are the same or different.

$G_1$ and $G_2$ may each independently be a hydrogen atom, fluorine atom, diphenylamine group, methyl group, phenyl group or carbazole group.

The polycyclic compound represented by Formula 1 may be, for example, one selected from the compounds represented in the following Compound Group 1.

[Compound Group 1]

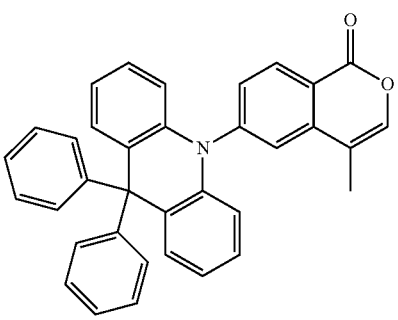

1

-continued
2
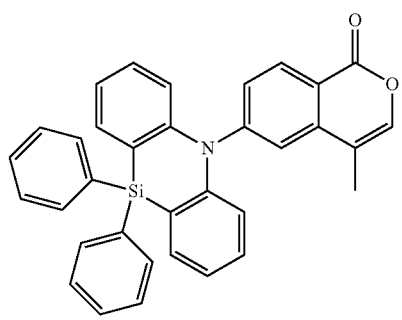
3
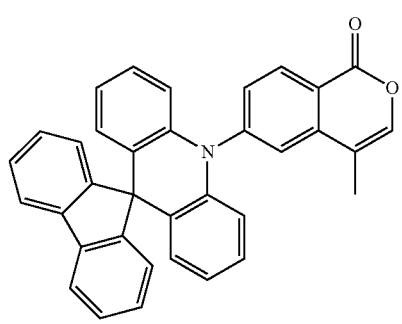
4
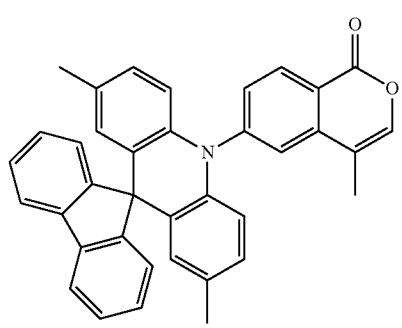
5
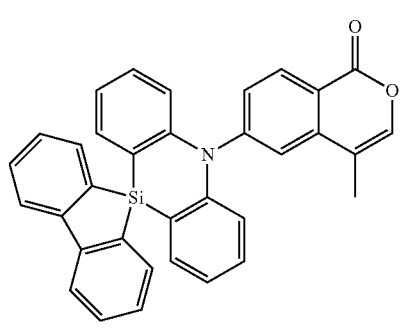
6
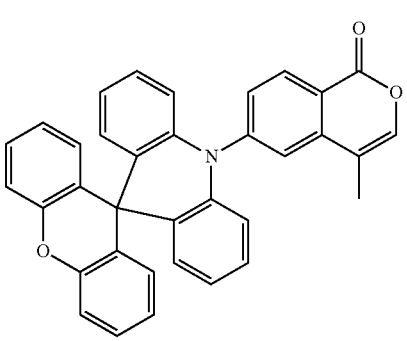
-continued
7
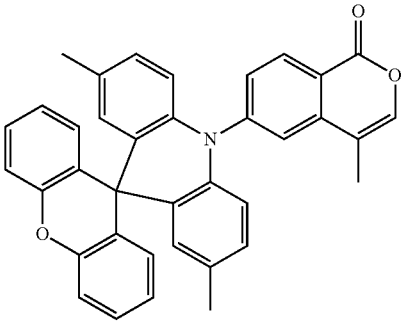
8
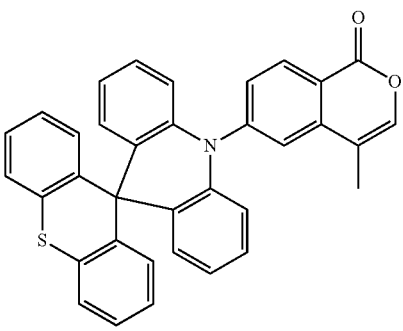
9
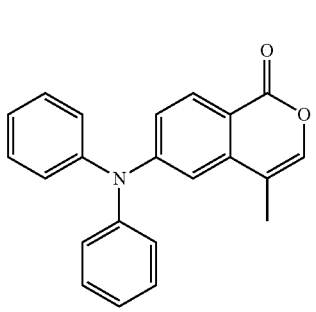
10
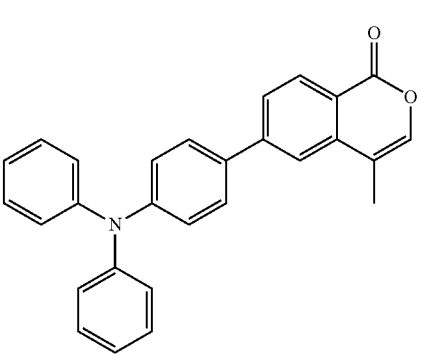
11
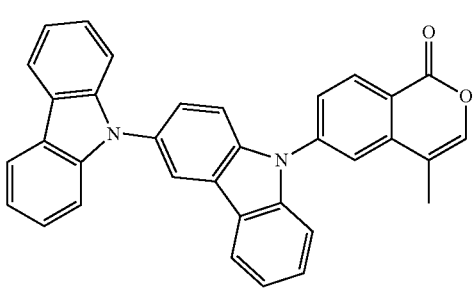

-continued
12
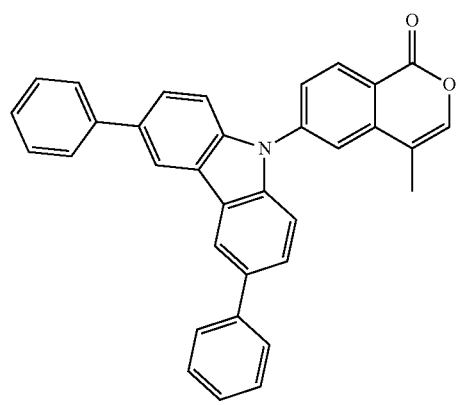
13
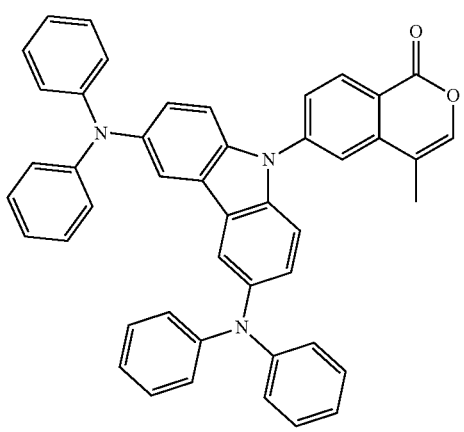
14
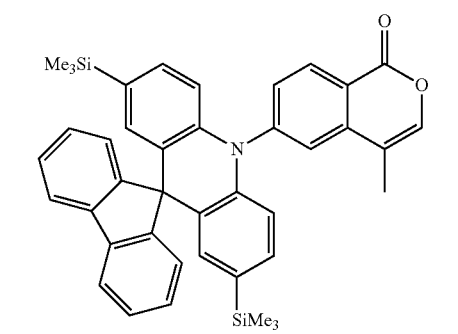
15
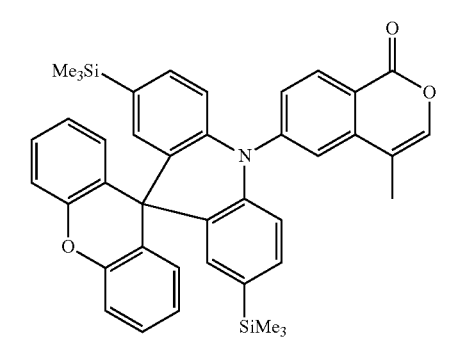
-continued
16
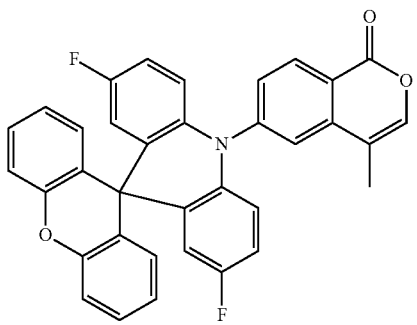
17
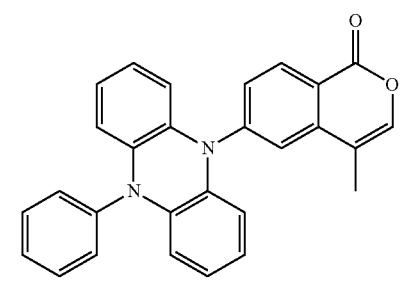
18
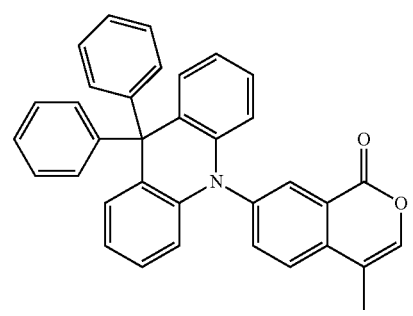
19
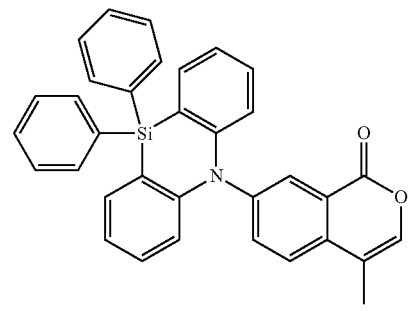
20
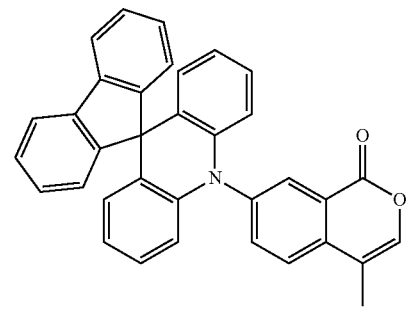

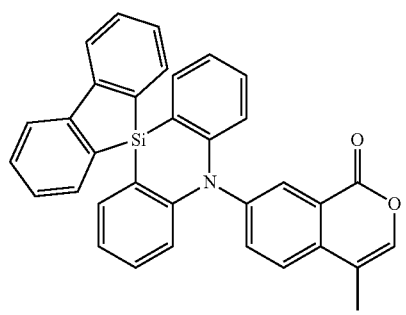
21
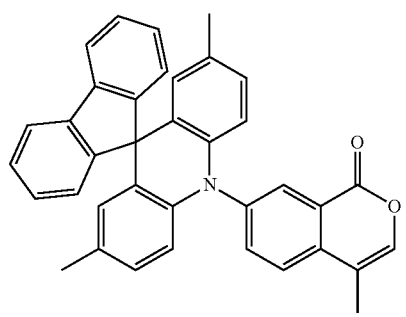
22
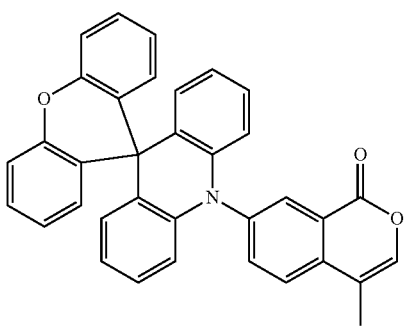
23
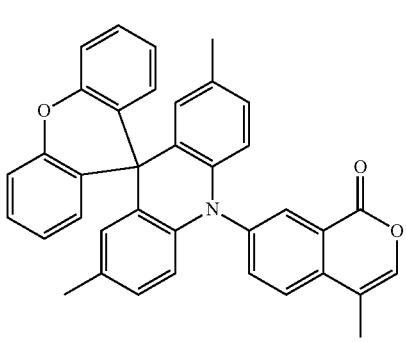
24
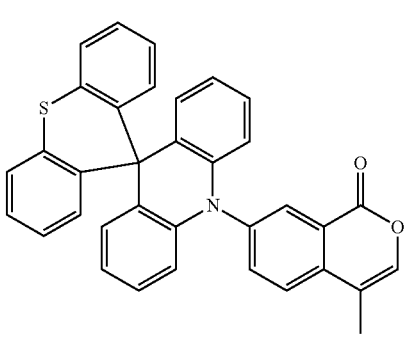
25
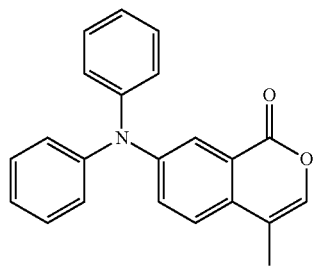
26
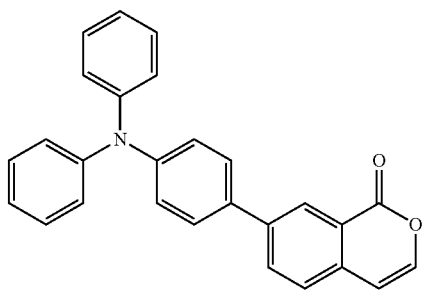
27
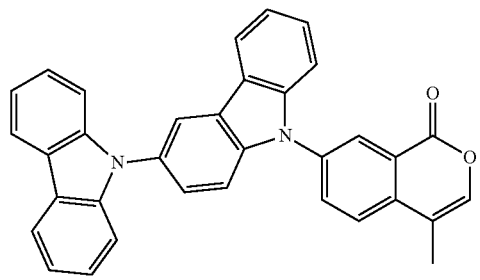
28
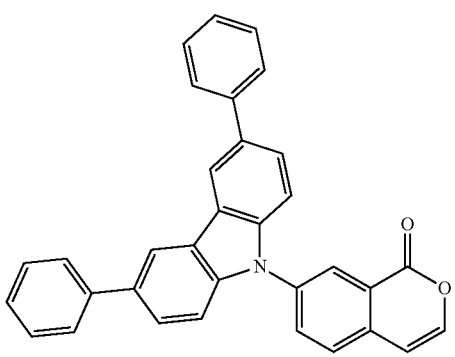
29
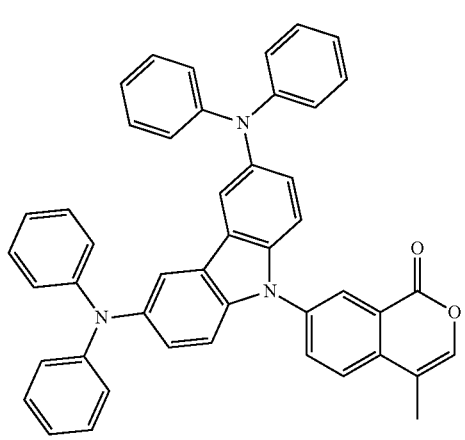
30

31
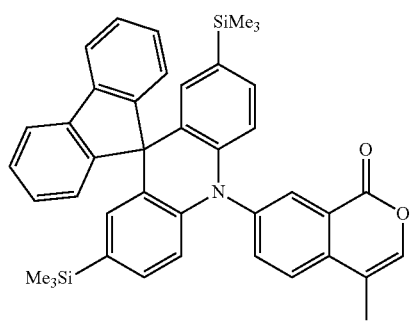
32
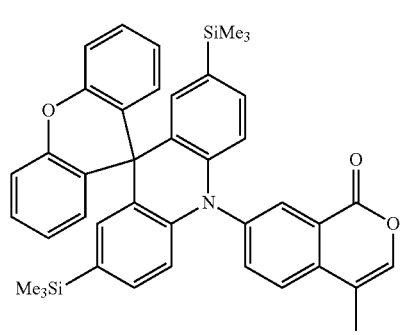
33
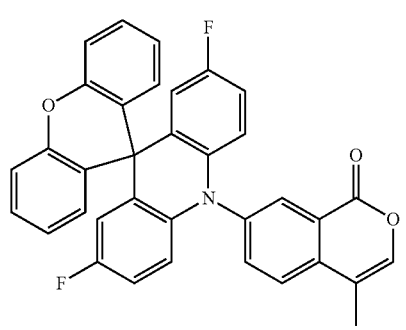
34
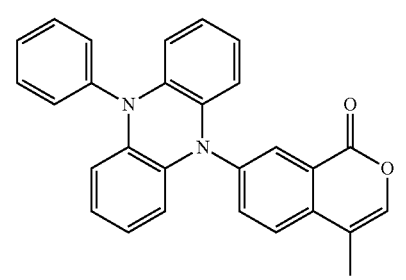
35
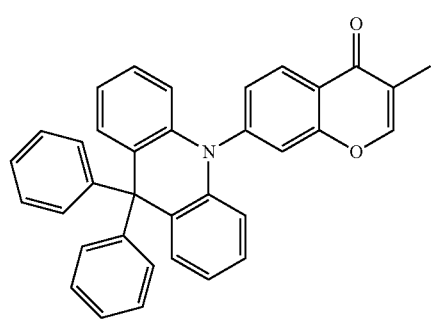
36
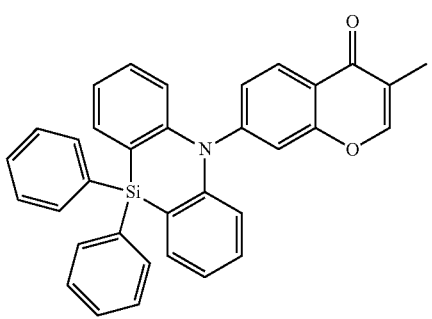
37
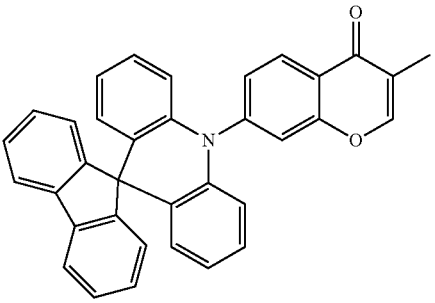
38
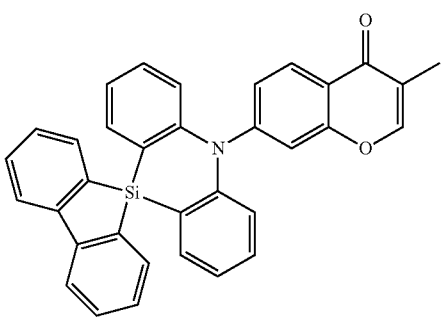
39
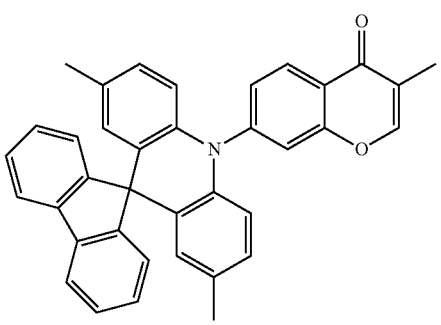
40
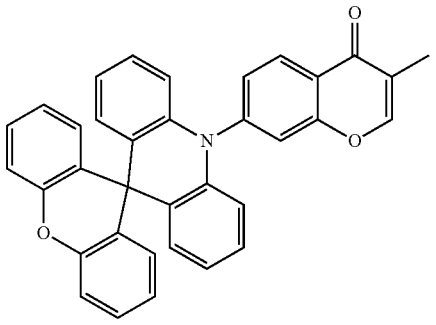

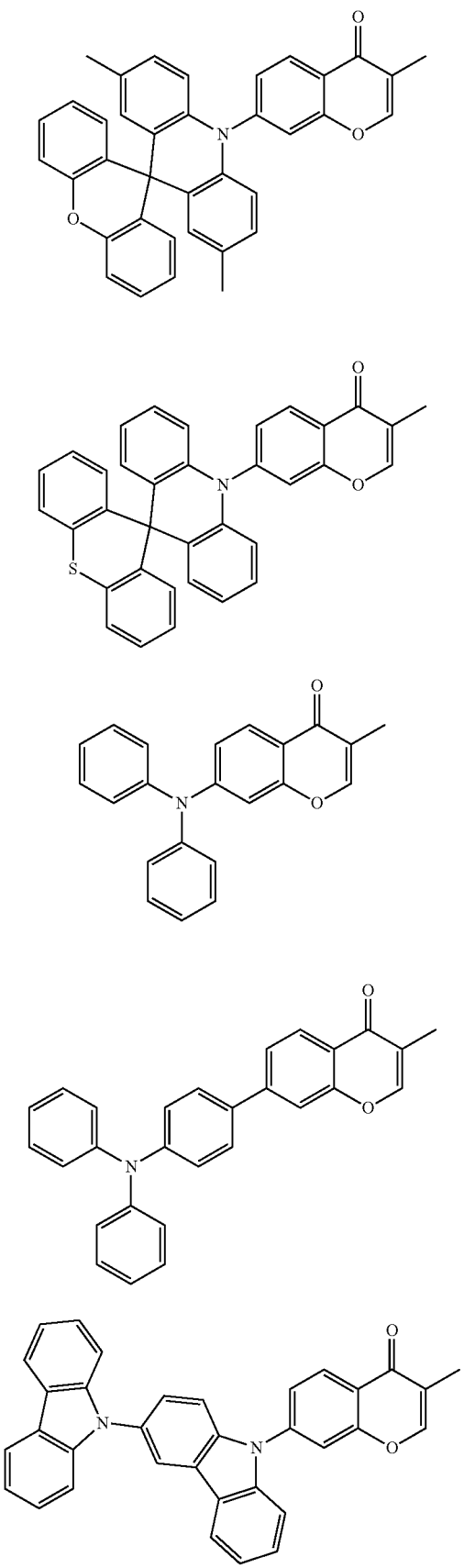
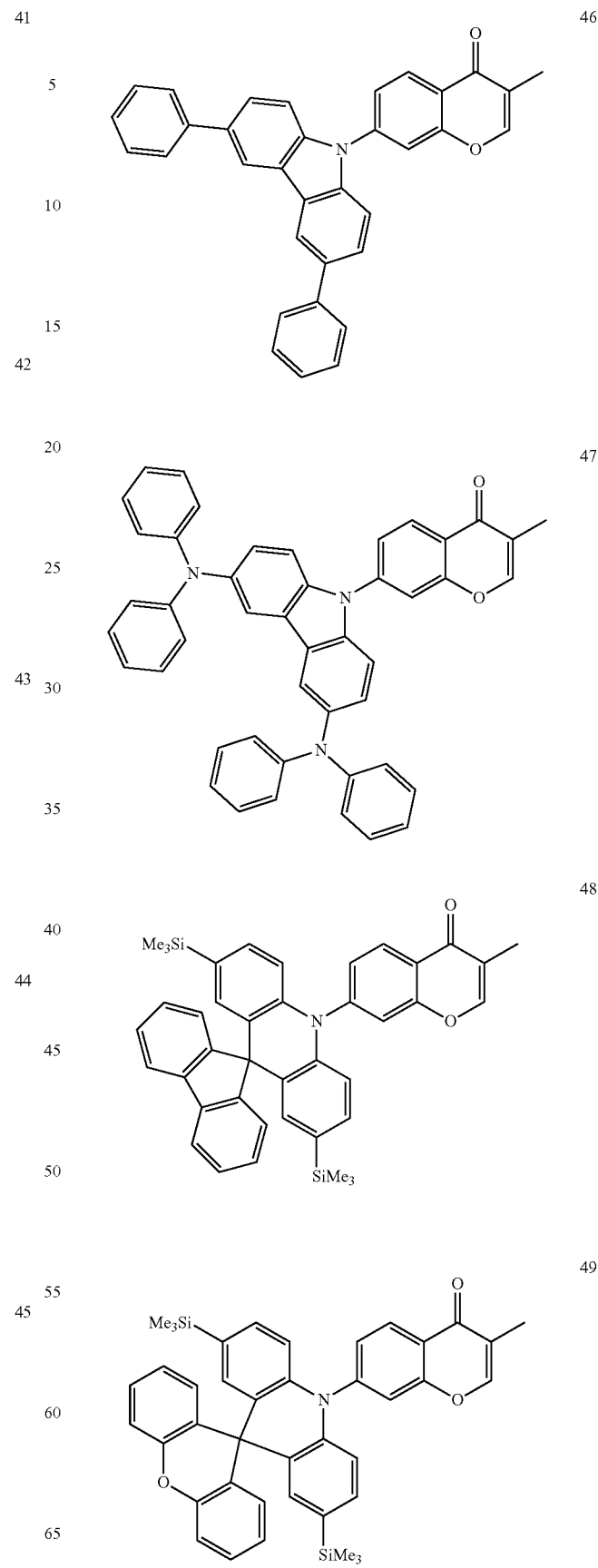

50
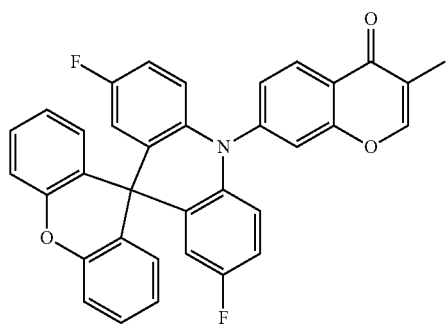
51
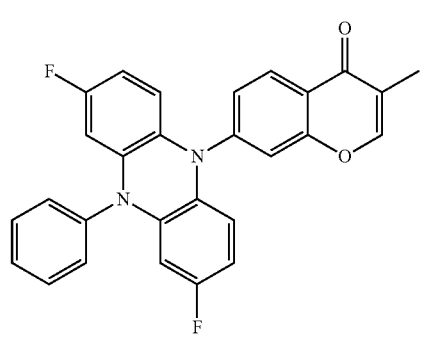
52
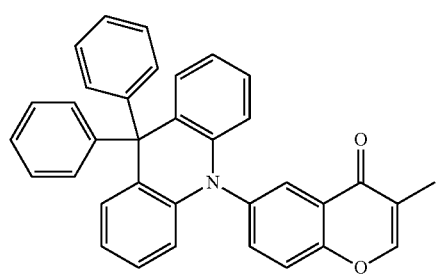
53
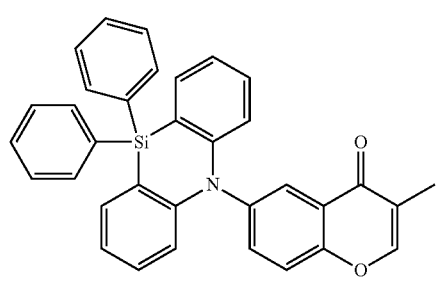
54
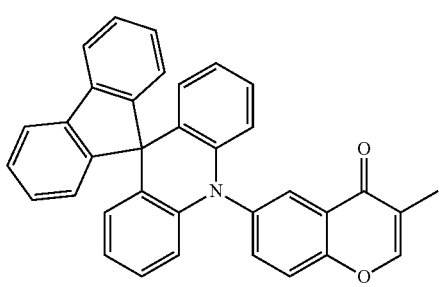
55
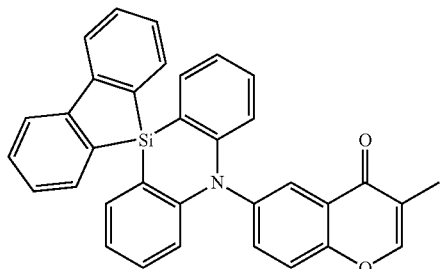
56
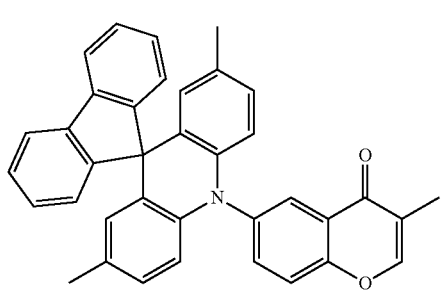
57
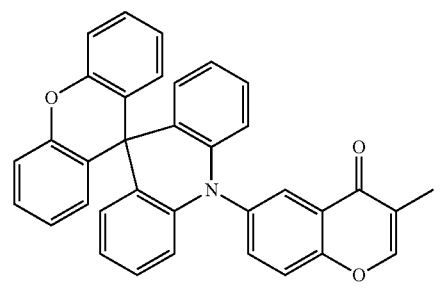
58
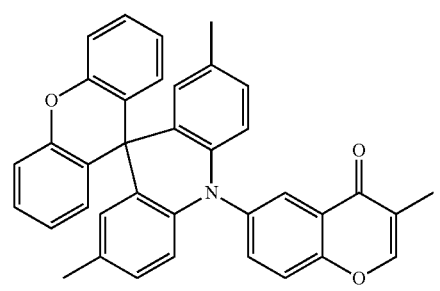
59
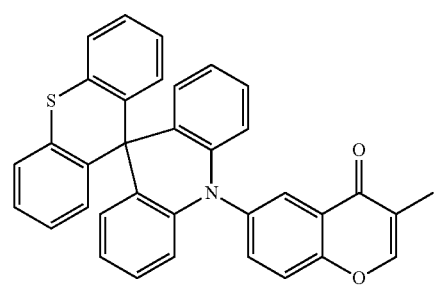

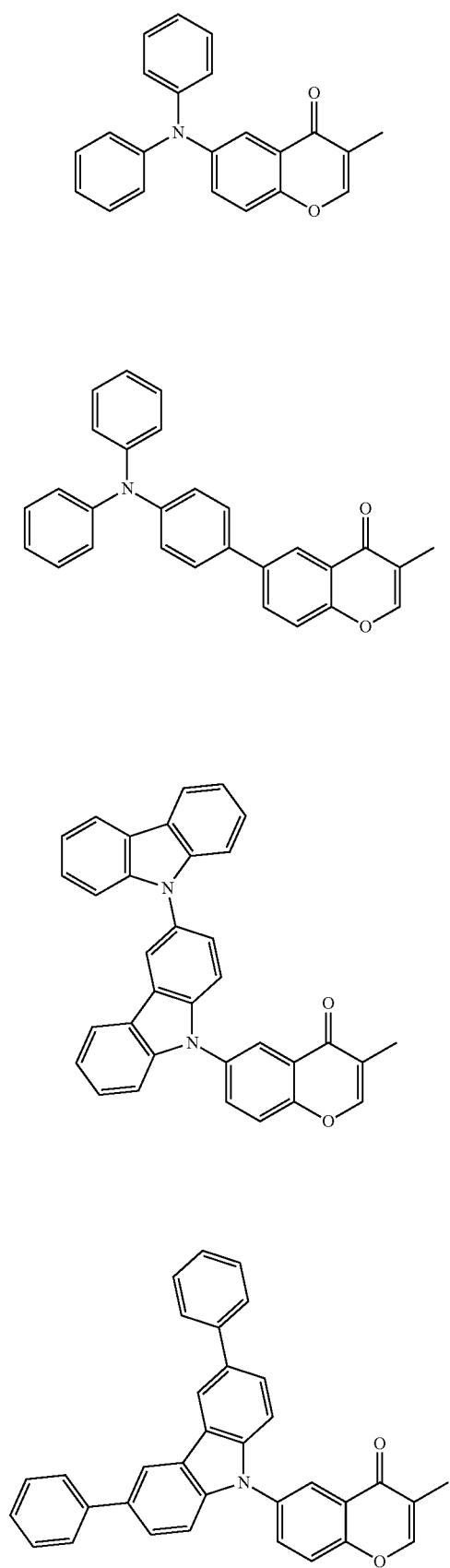
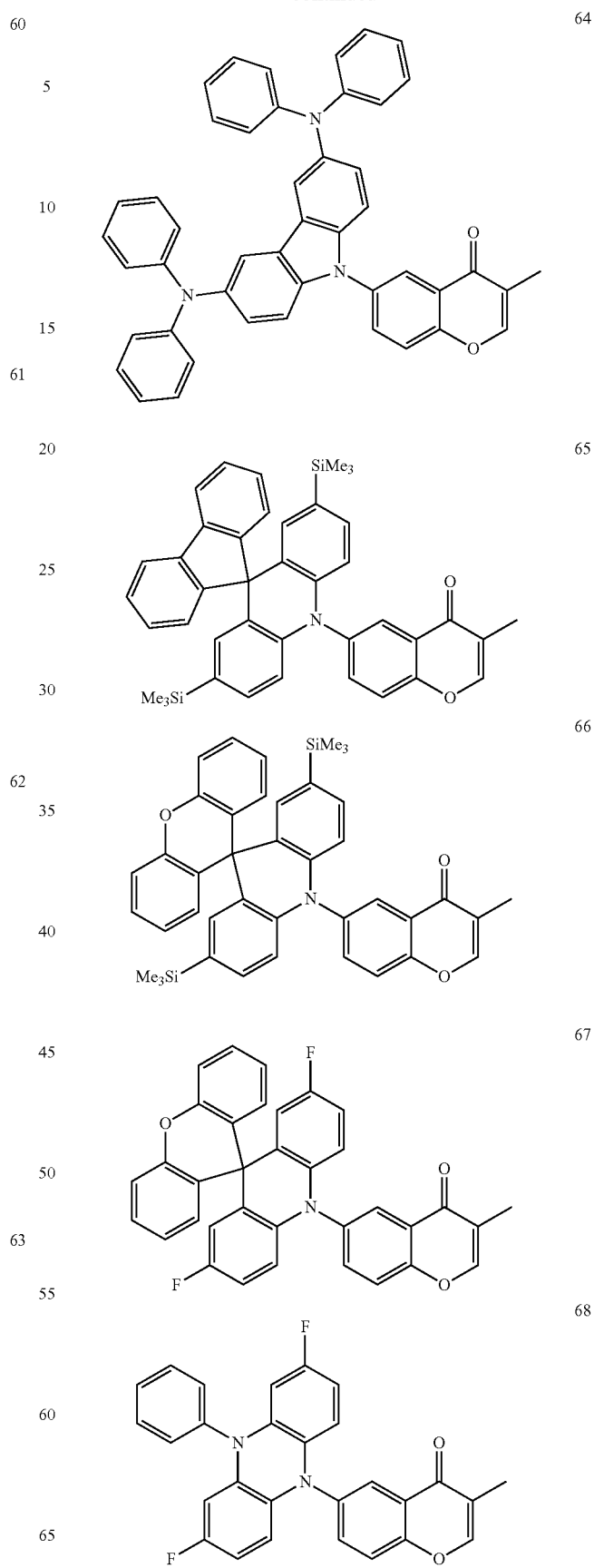

69
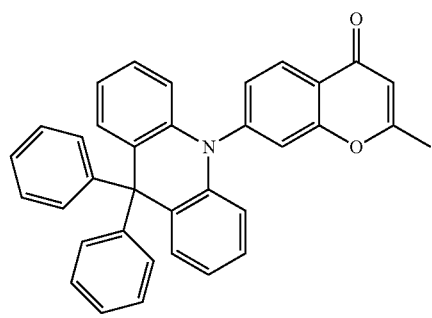
70
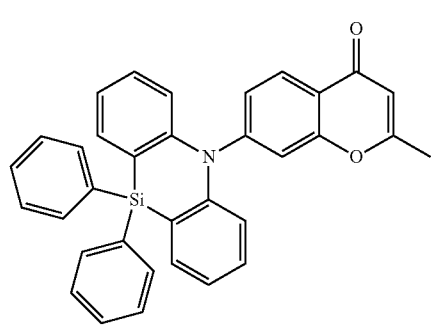
71
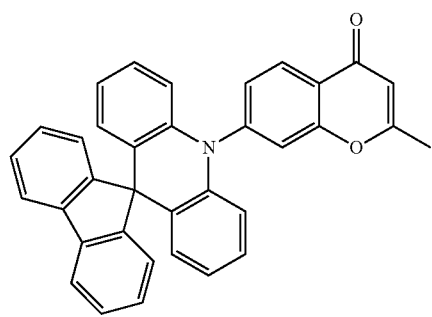
72
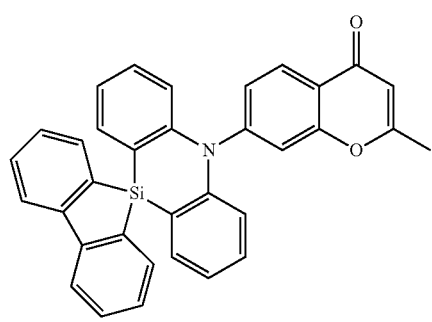
73
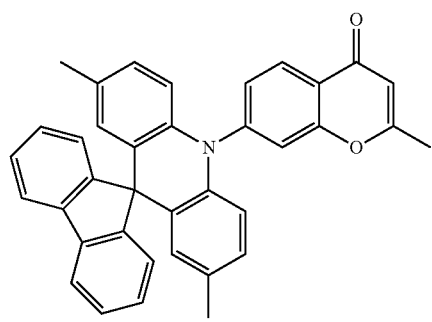
74
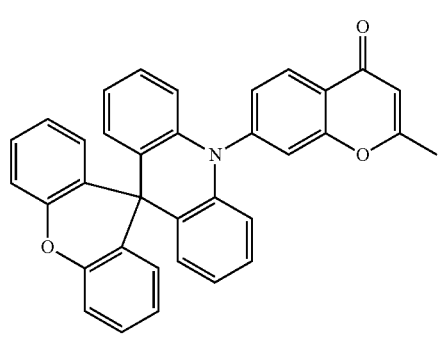
75
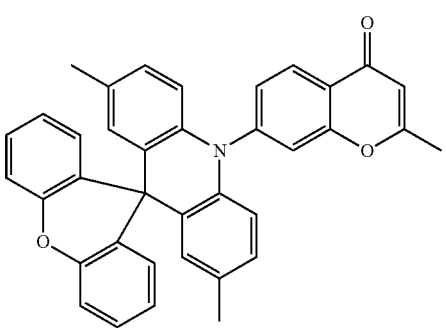
76
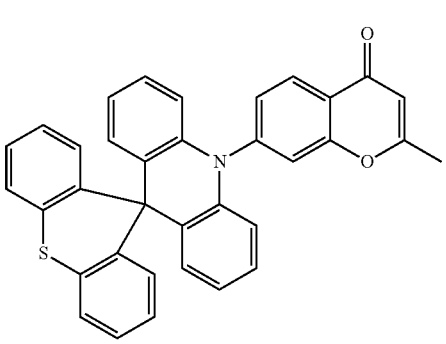
77
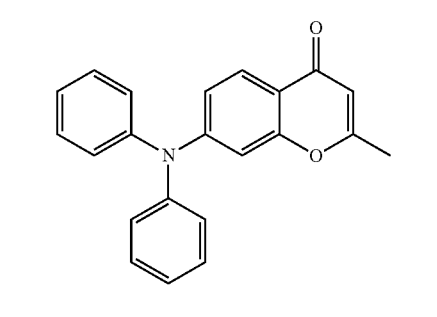
78
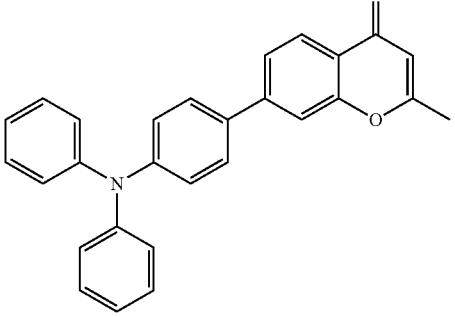

-continued
79
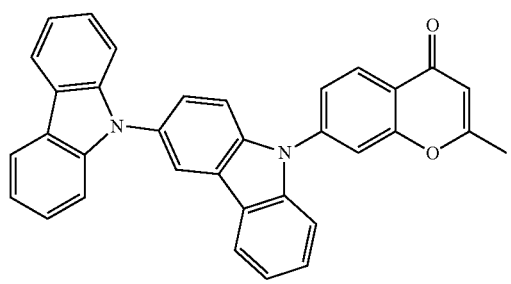
80
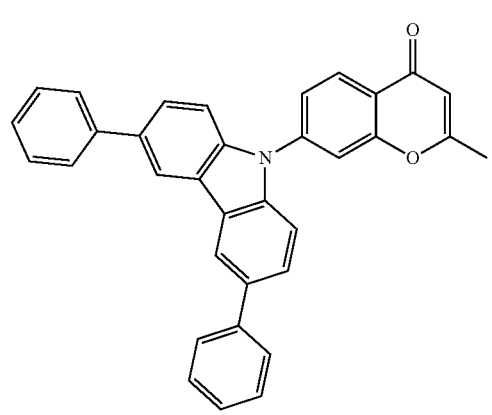
81
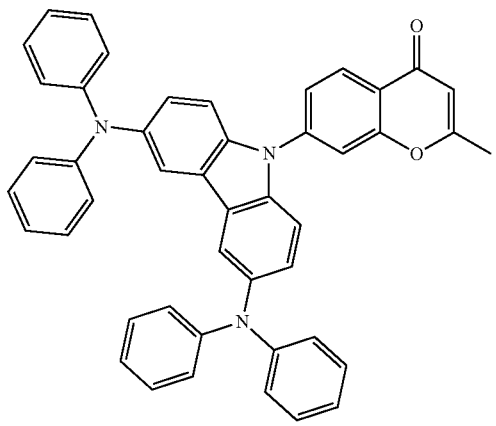
82
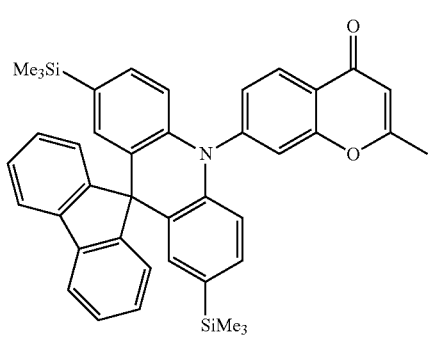
-continued
83
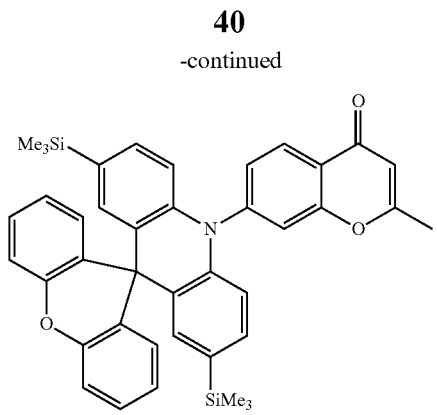
84
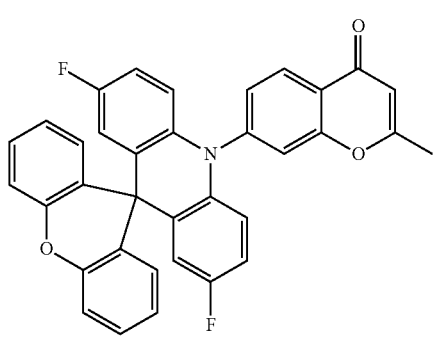
85
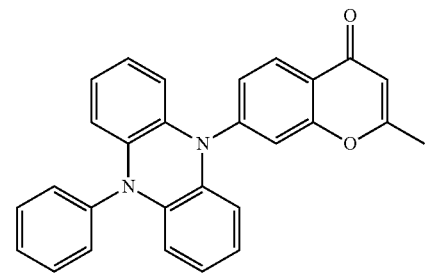
86
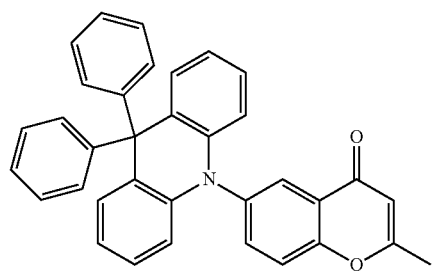
87
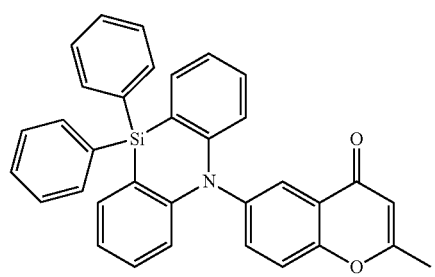

-continued
88
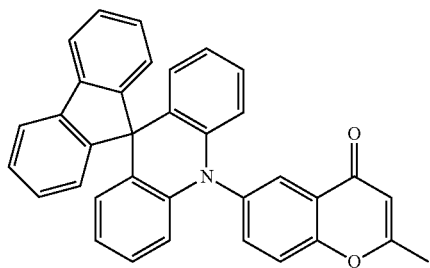
89
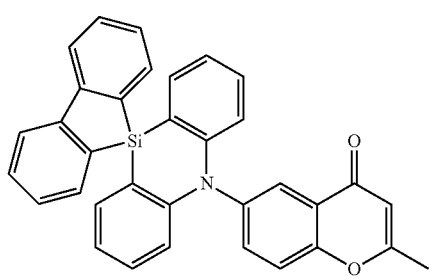
90
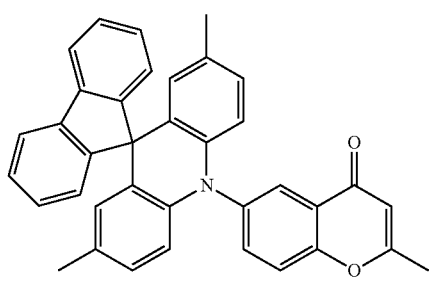
91
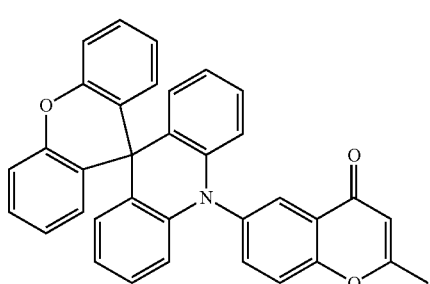
92
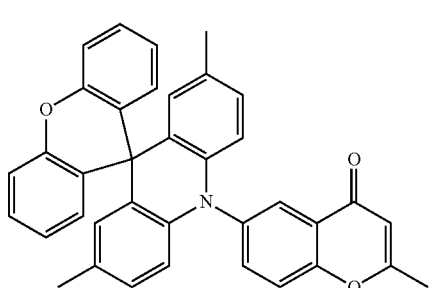
-continued
93
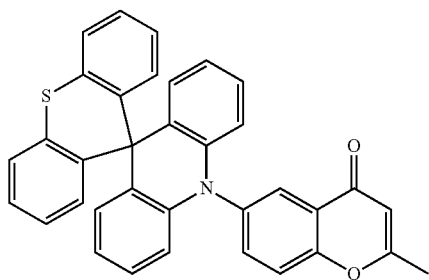
94
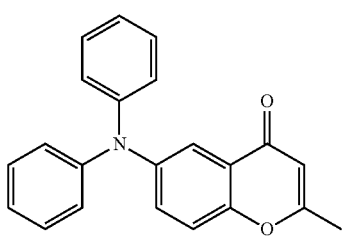
95
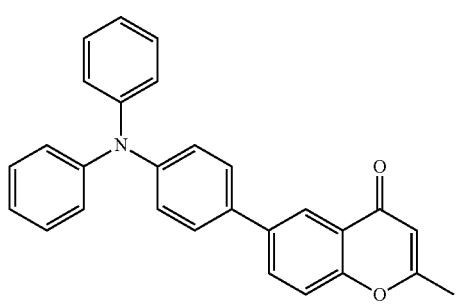
96
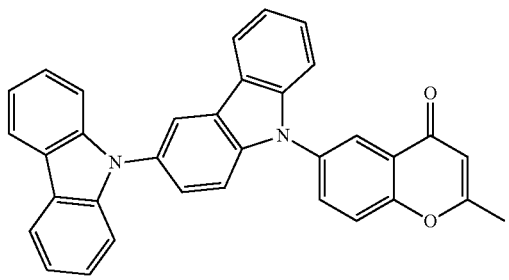
97
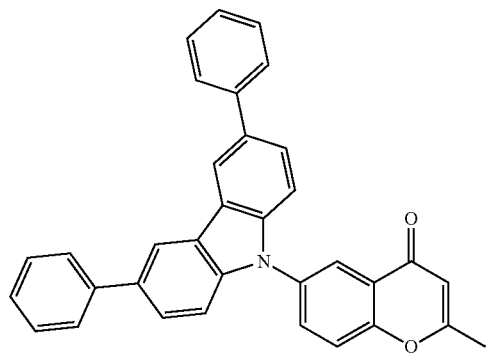

98
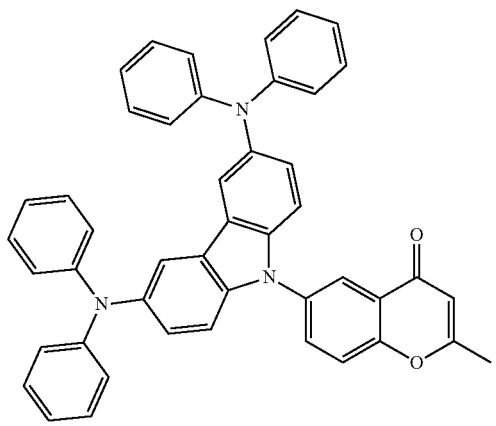
99
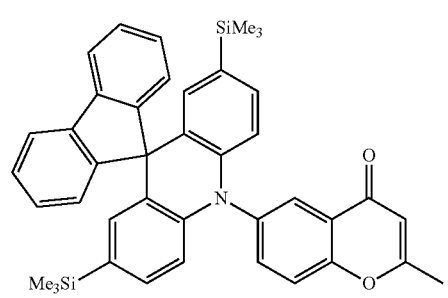
100
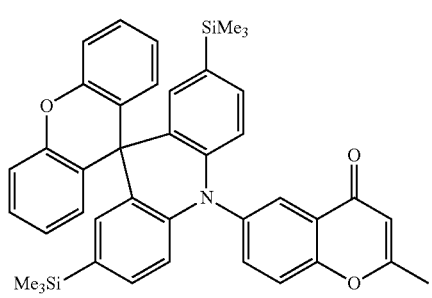
101
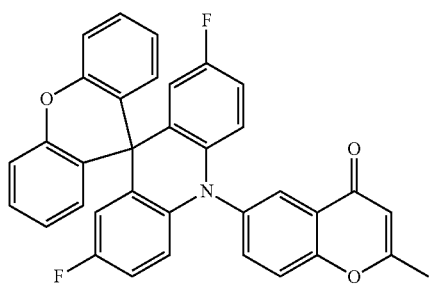
102
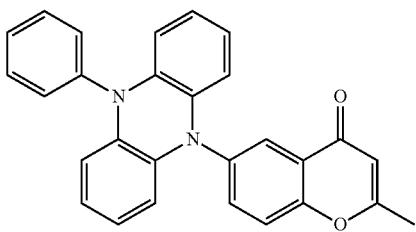
103
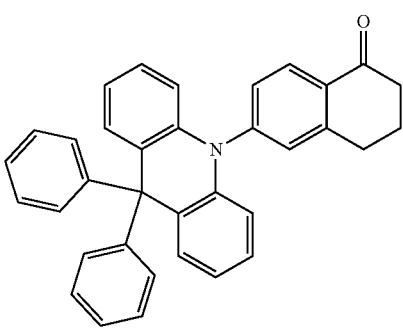
104
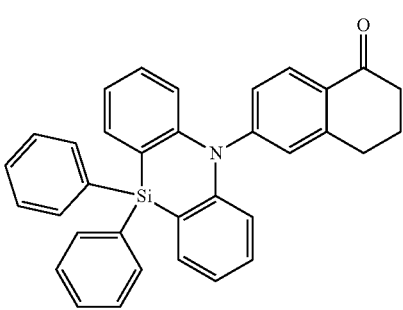
105
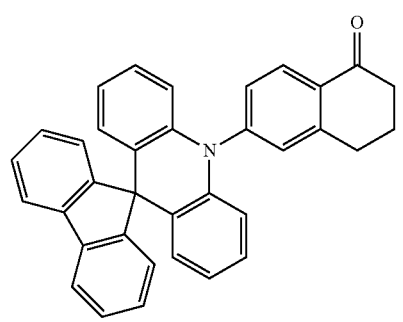
106
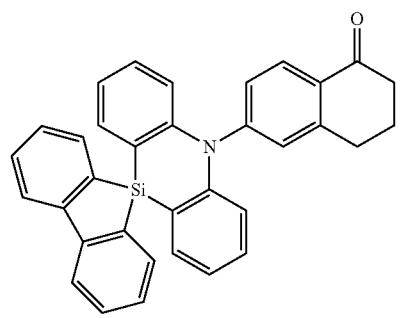
107
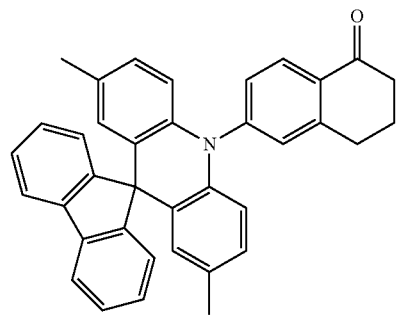

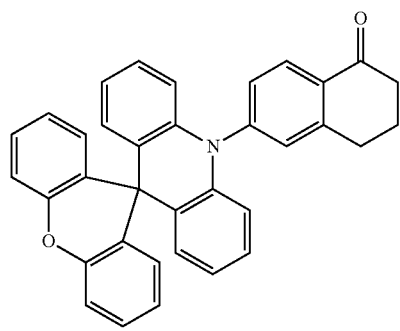
108
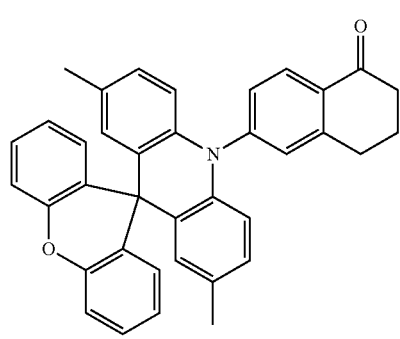
109
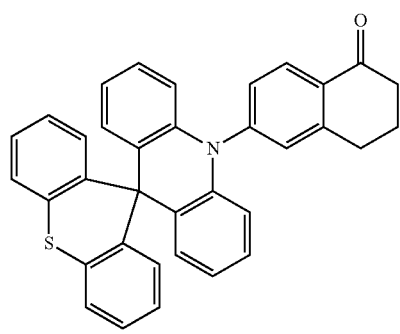
110
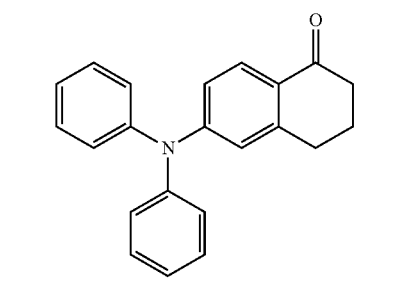
111
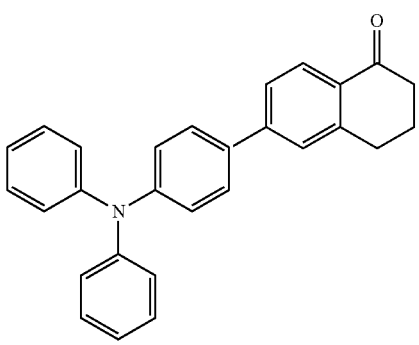
112
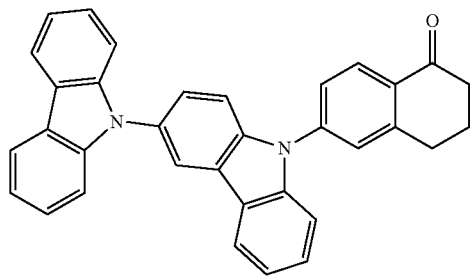
113
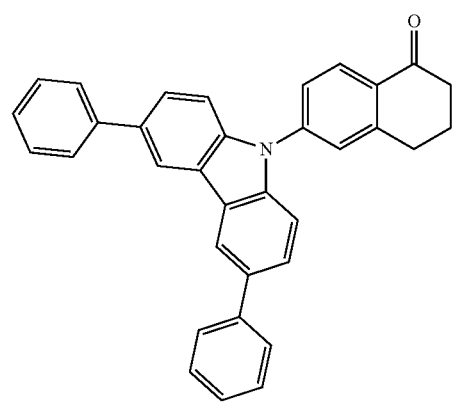
114
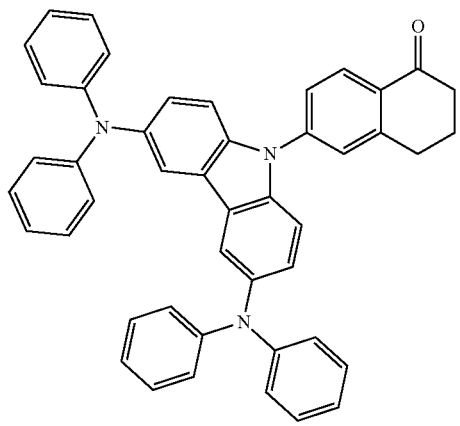
115
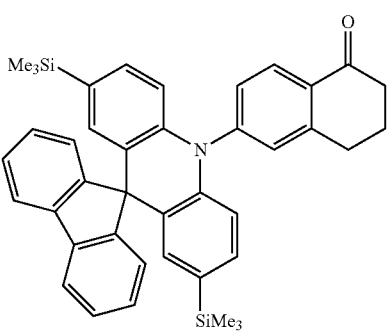
116

117
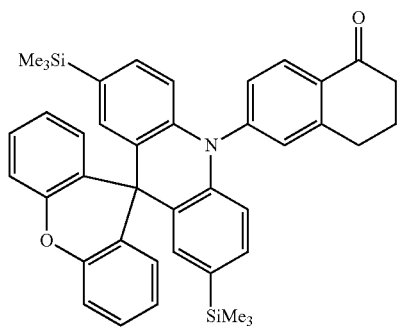
118
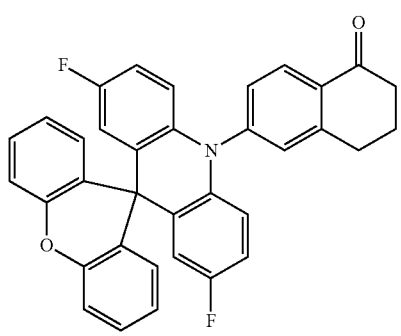
119
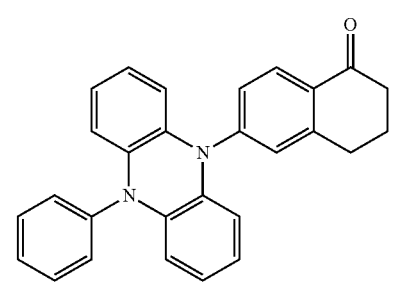
120
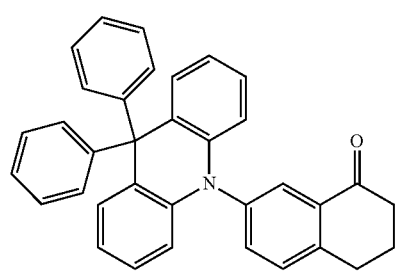
121
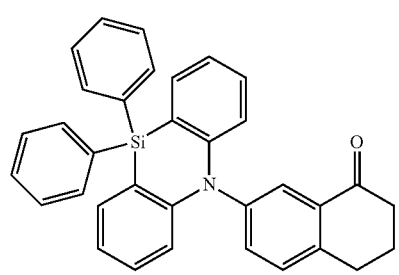
122
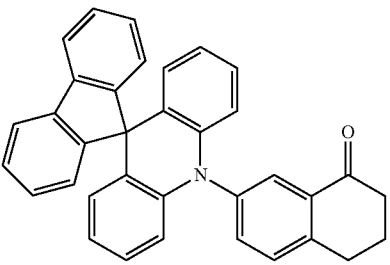
123
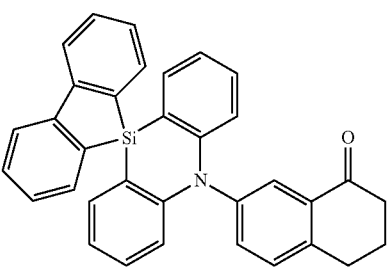
124
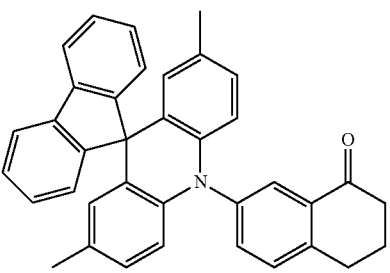
125
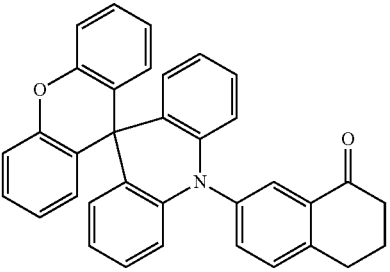
126
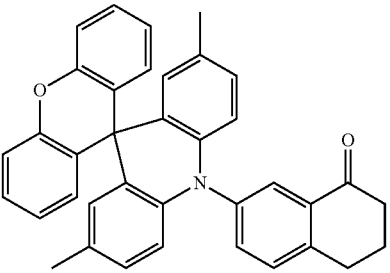

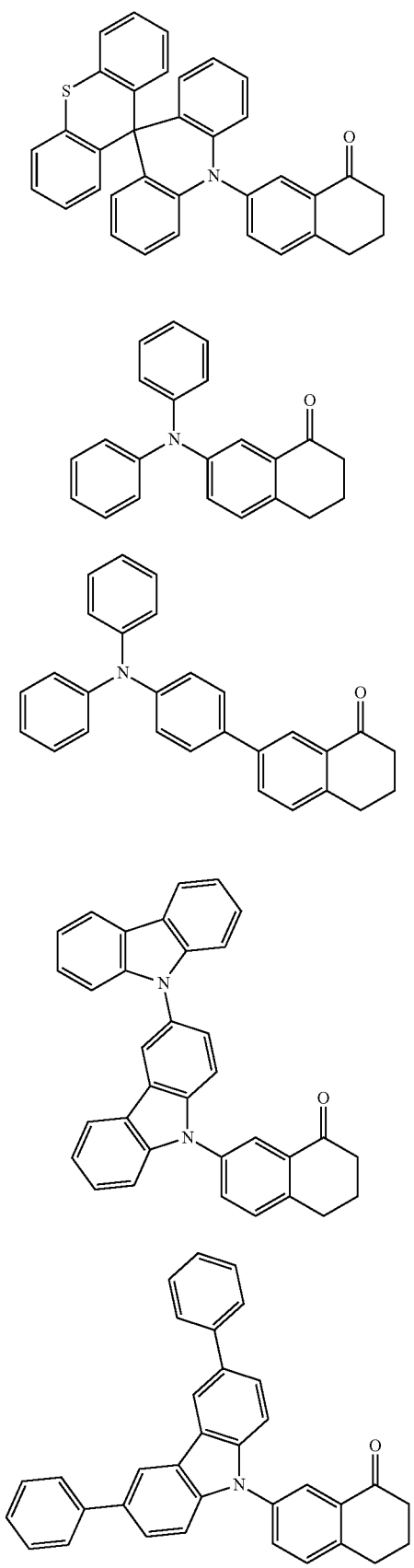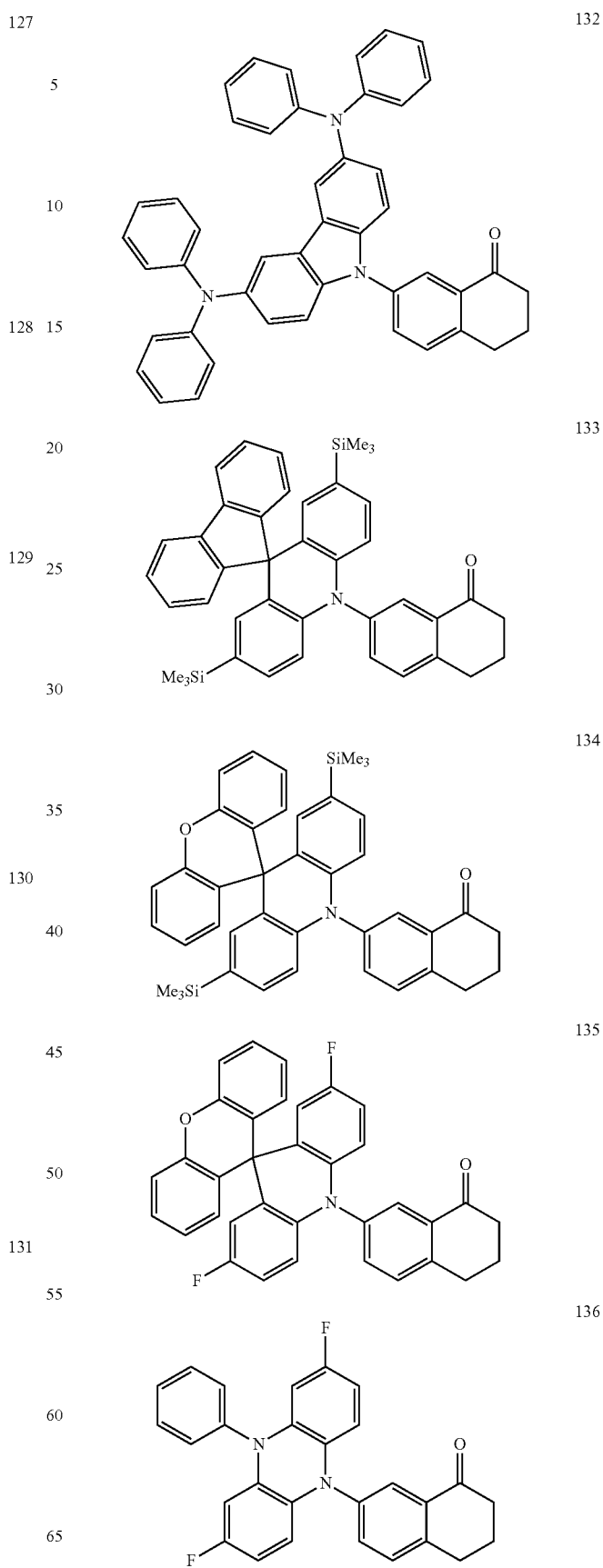

137 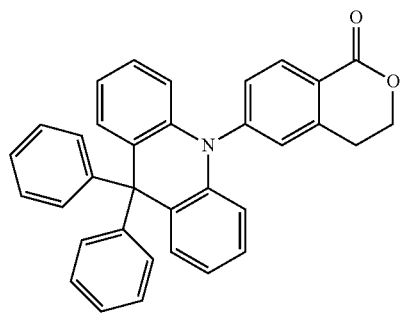
138 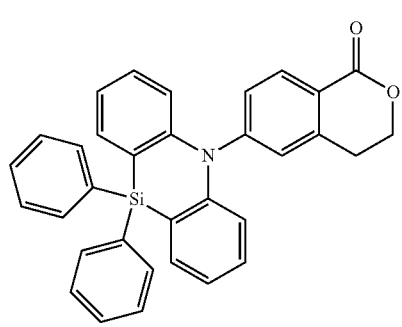
139 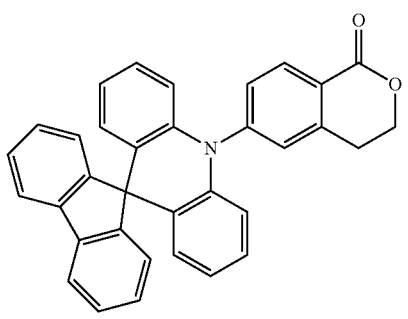
140 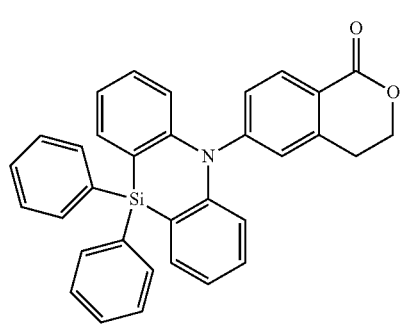
141 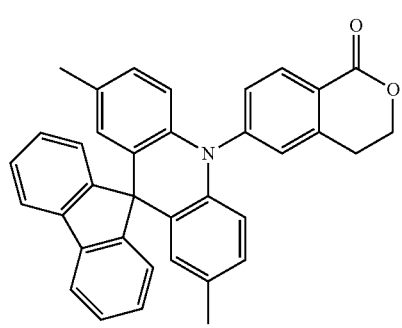
142 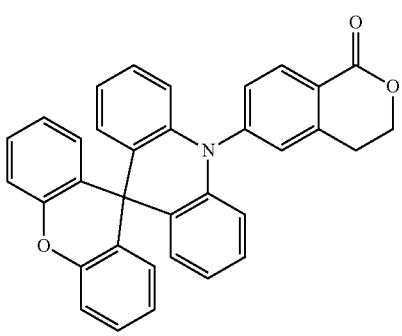
143 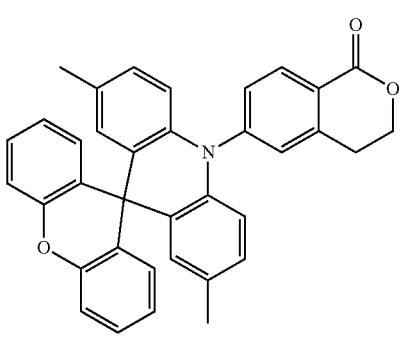
144 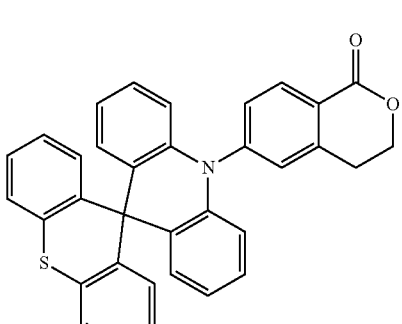
145 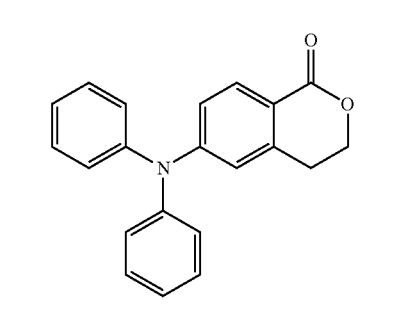
146 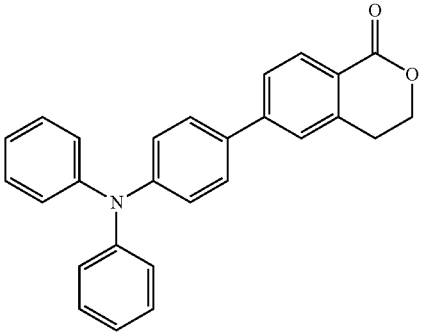

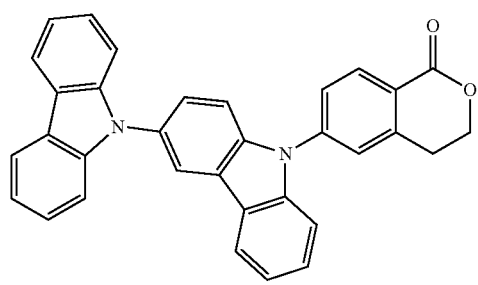
147
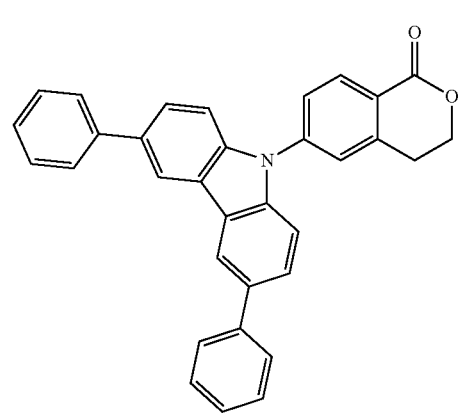
148
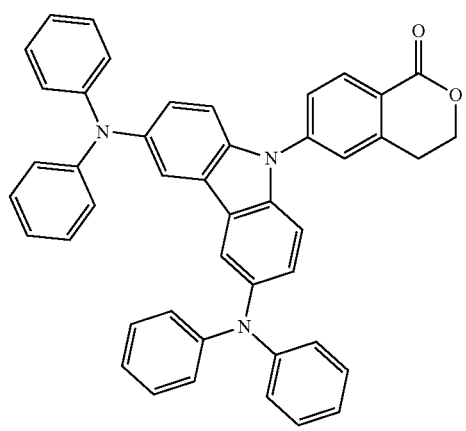
149
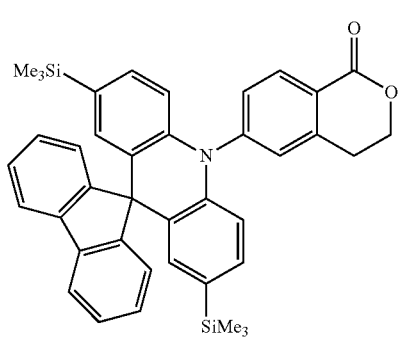
150
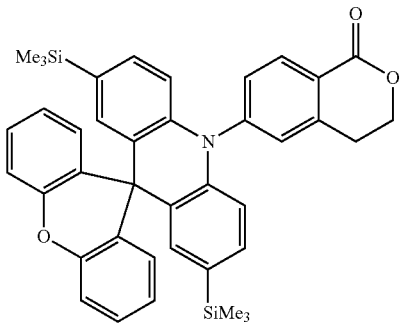
151
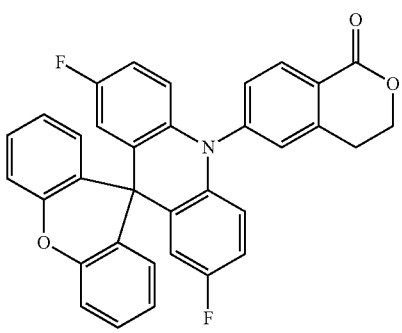
152
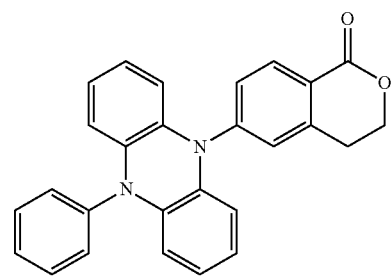
153
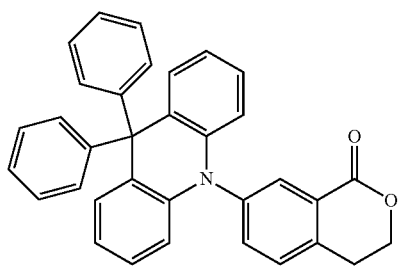
154
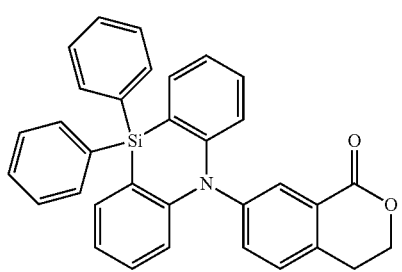
155

156
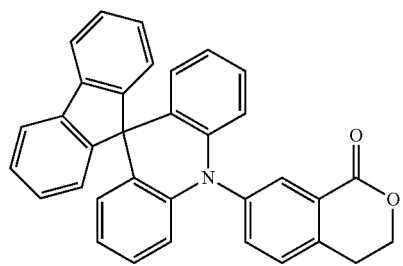
157
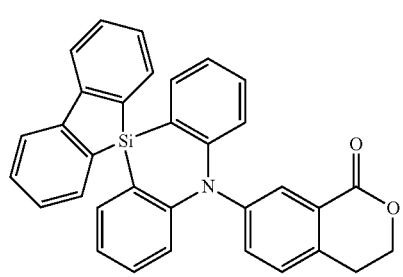
158
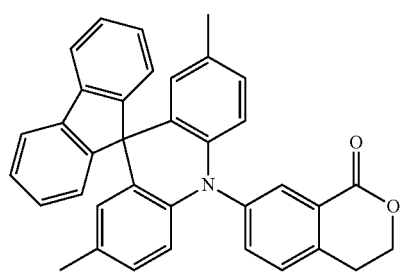
159
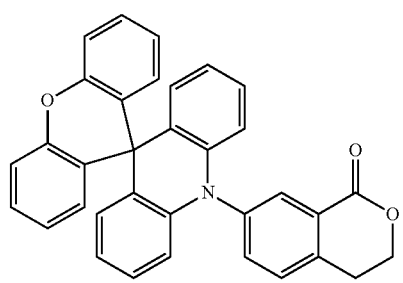
160
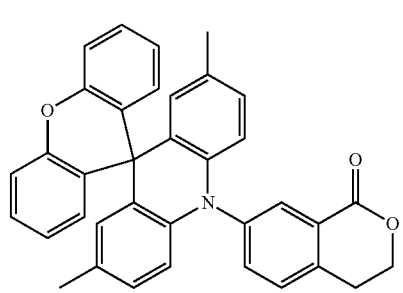
161
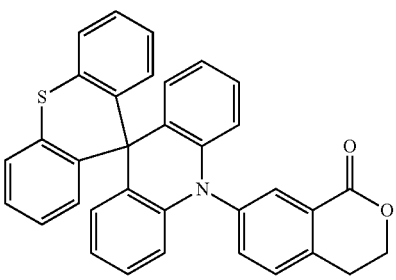
162
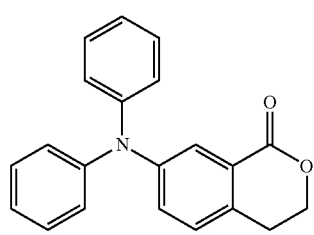
163
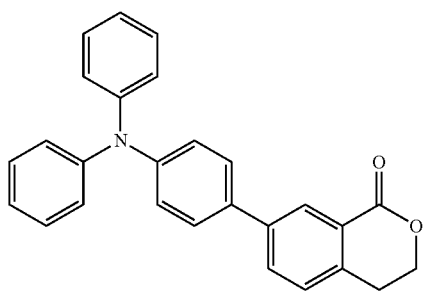
164
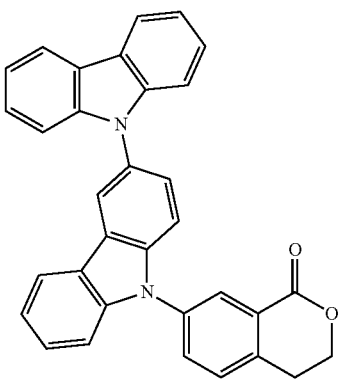
165
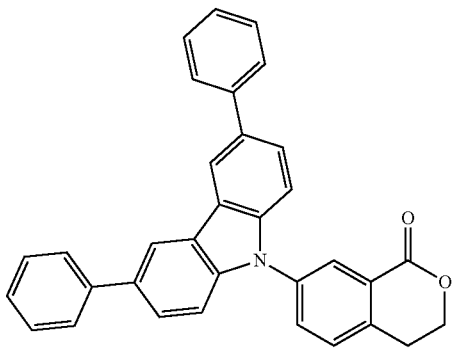

-continued
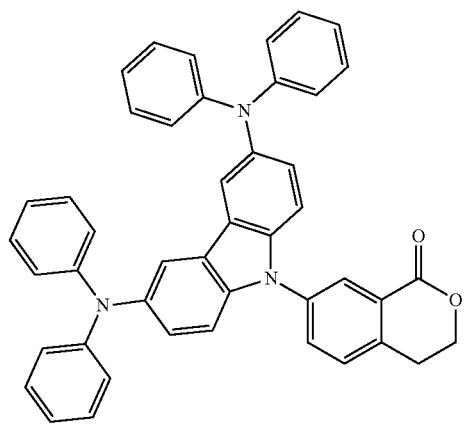
166
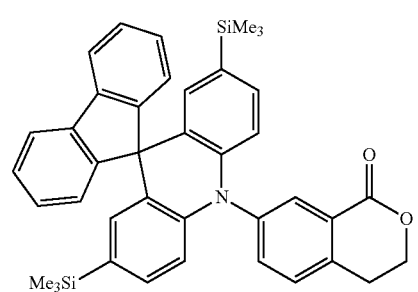
167
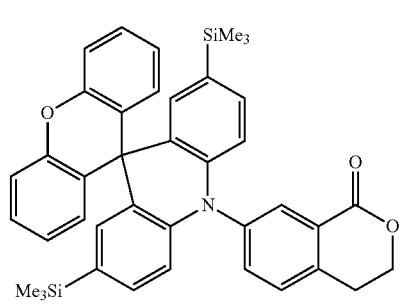
168
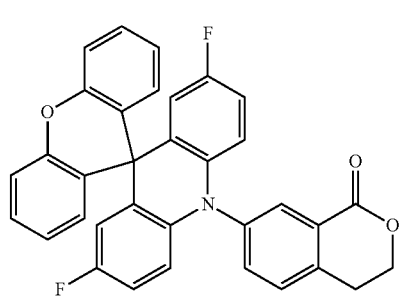
169
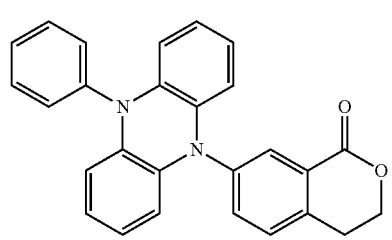
170
-continued
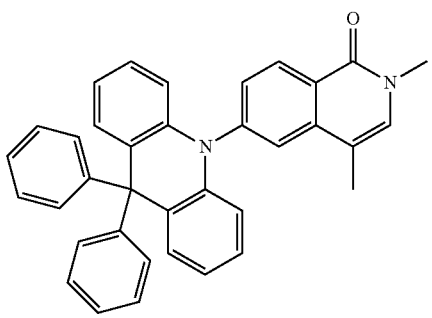
171
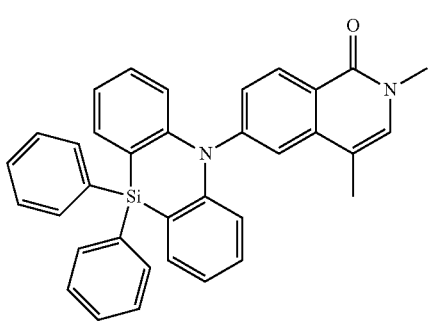
172
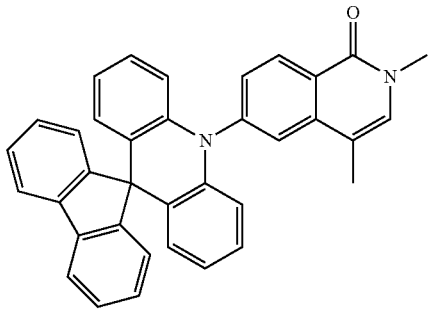
173
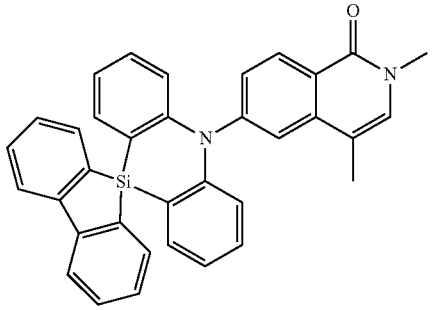
174
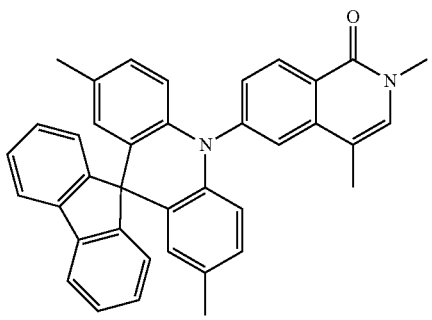
175

176 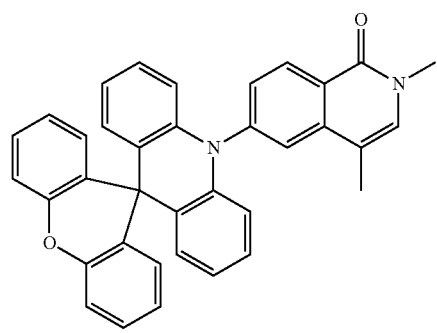
177 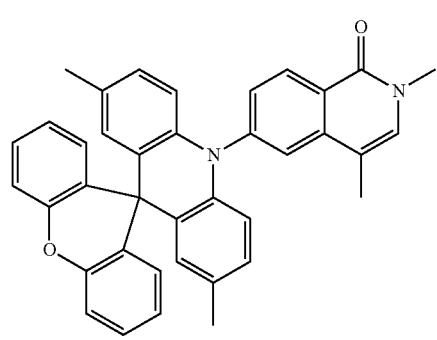
178 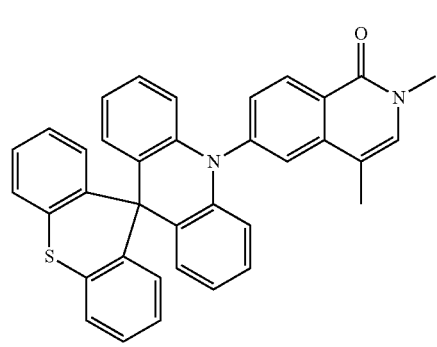
179 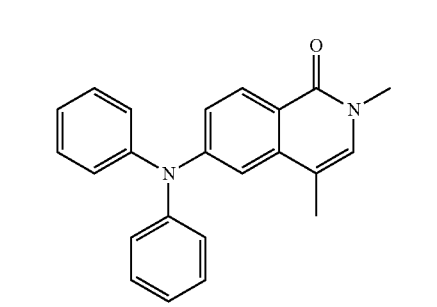
180 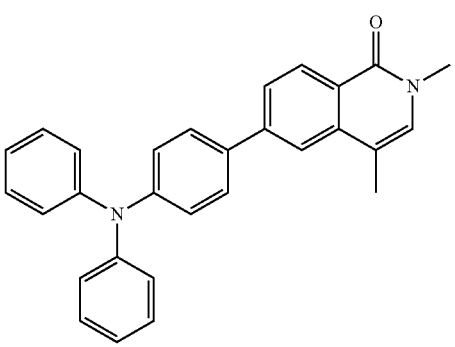
181 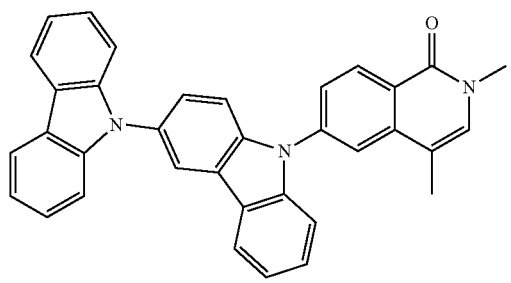
182 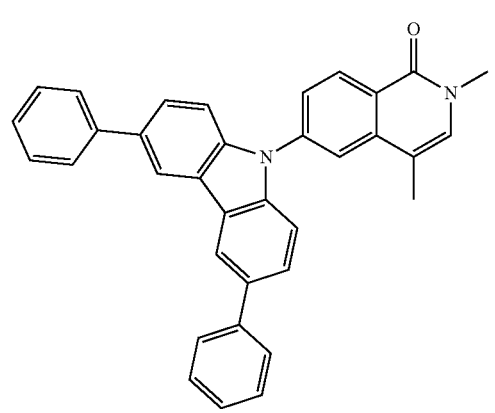
183 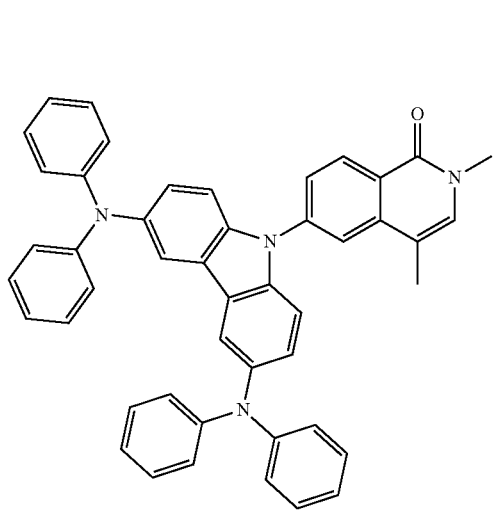
184 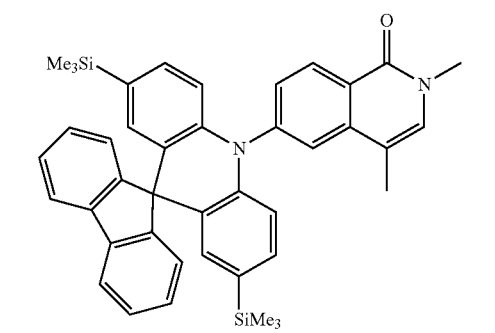

185
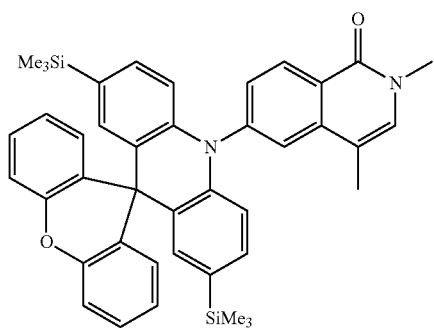
186
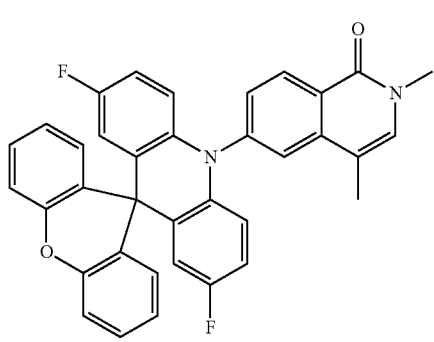
187
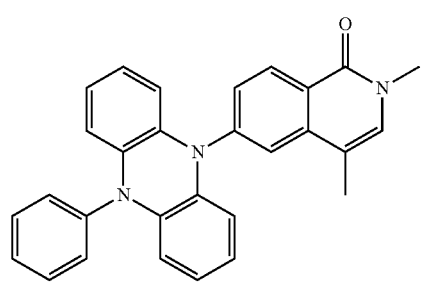
188
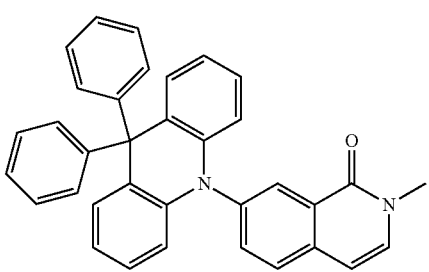
189
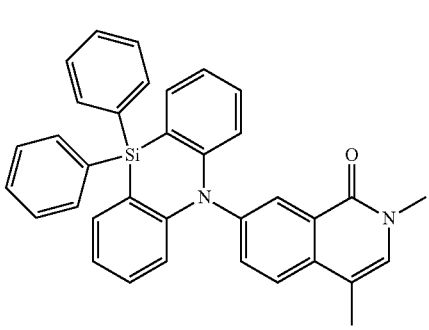
190
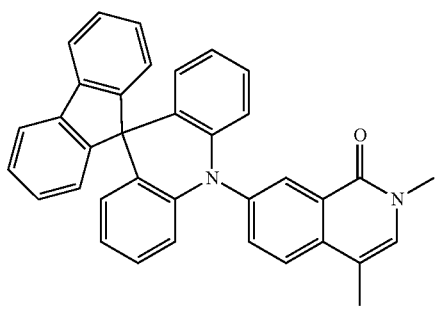
191
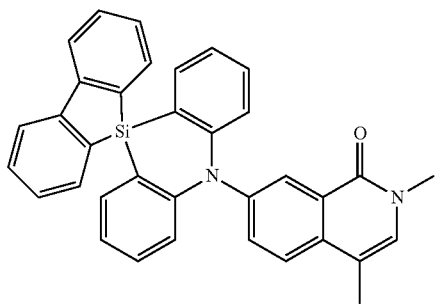
192
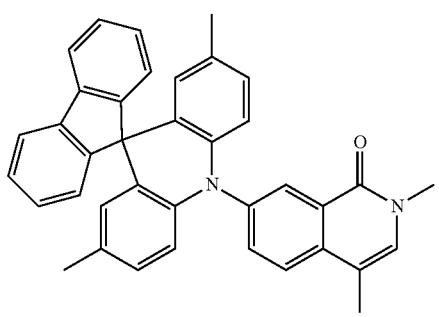
193
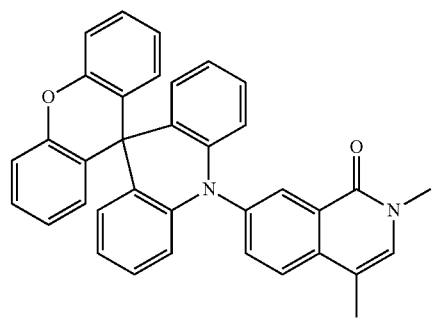
194
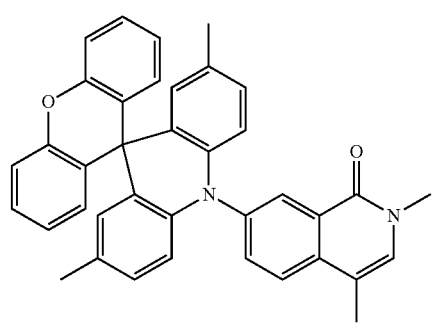

195 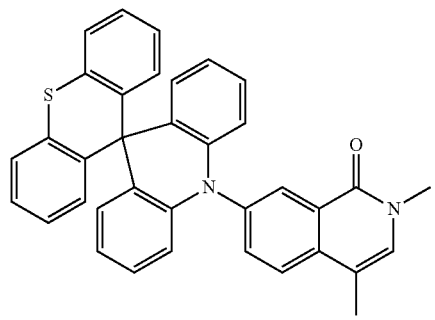
196 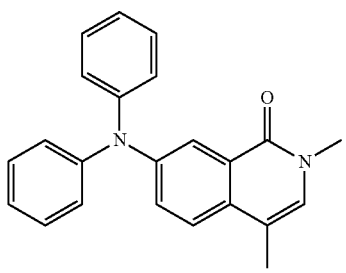
197 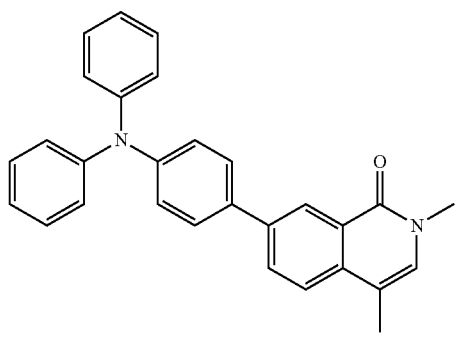
198 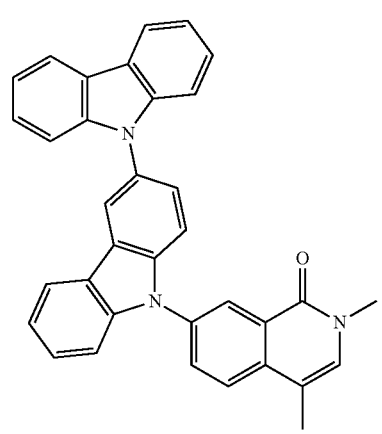
199 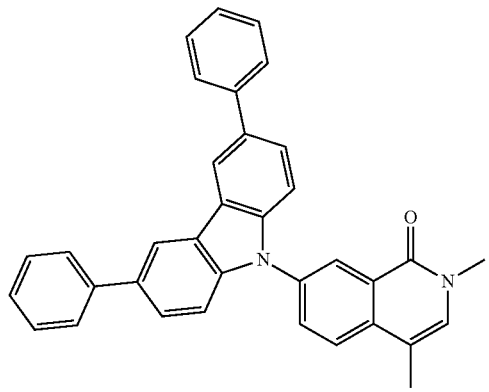
200 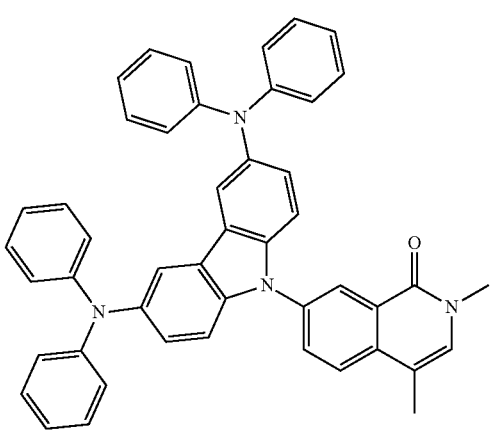
201 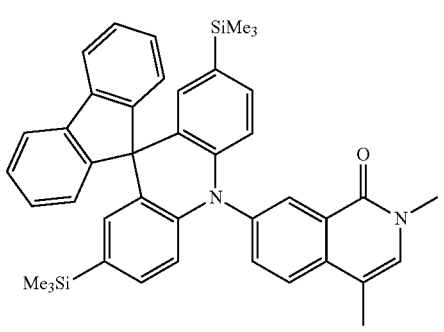
202 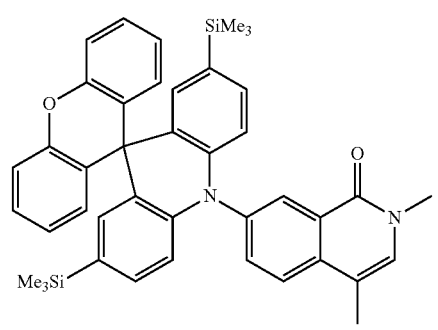

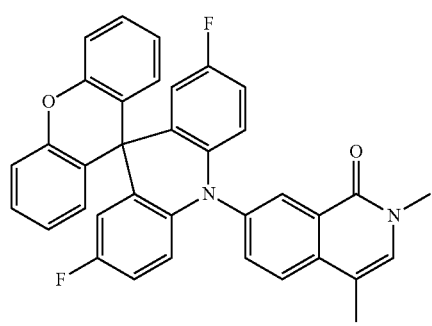
203
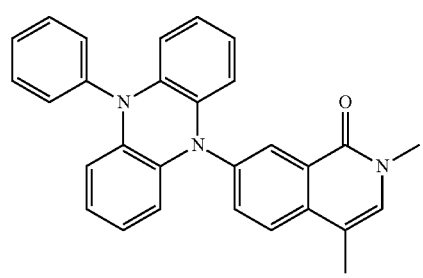
204
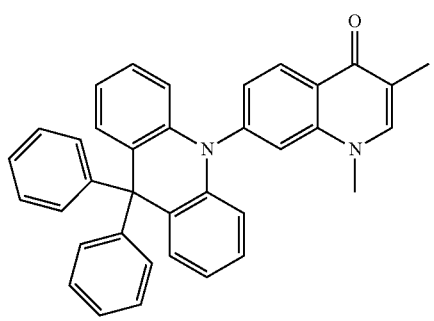
205
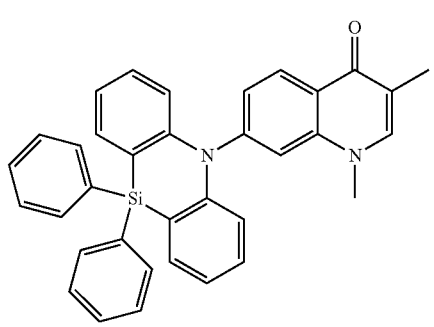
206
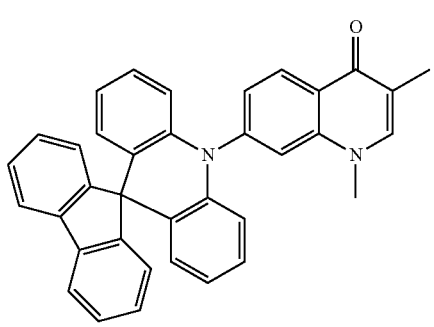
207
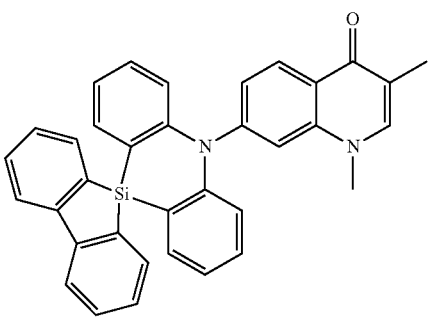
208
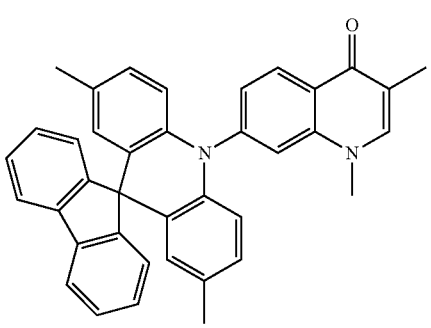
209
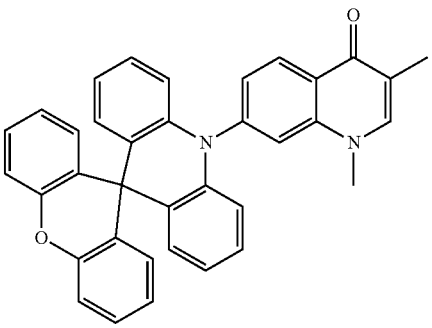
210
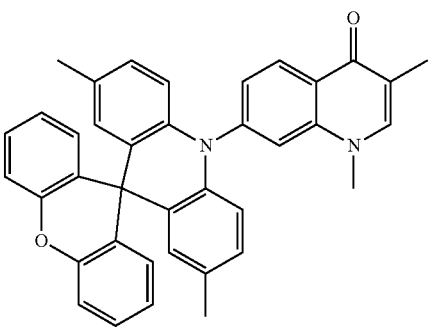
211
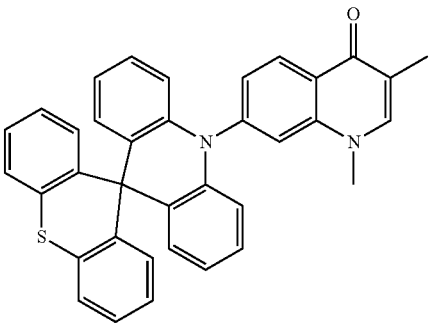
212

213 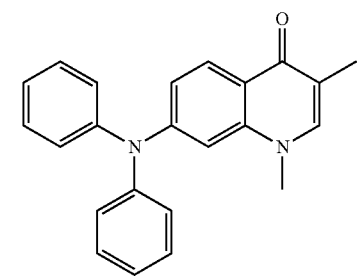
214 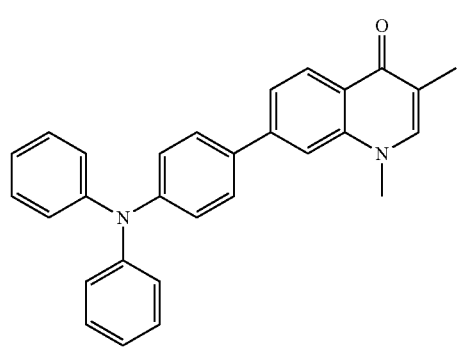
215 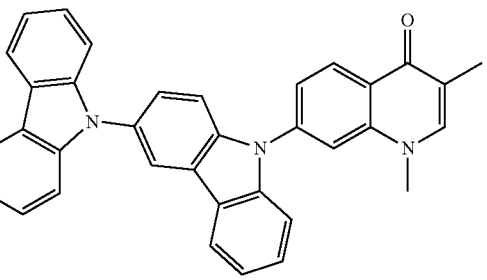
216 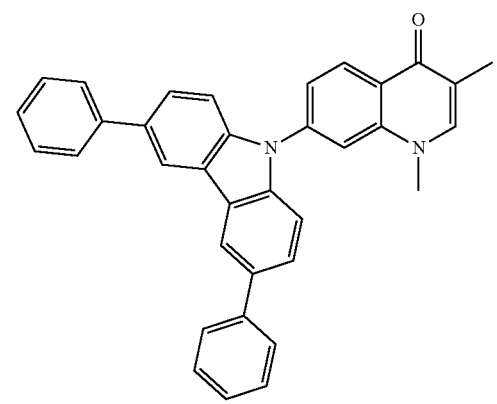
217 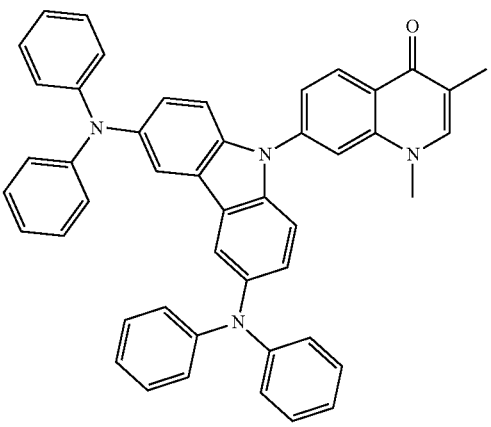
218 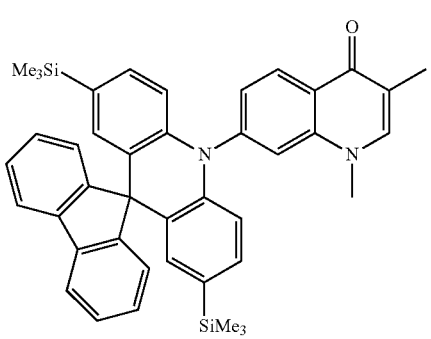
219 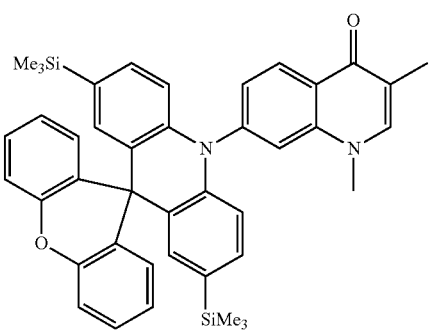
220 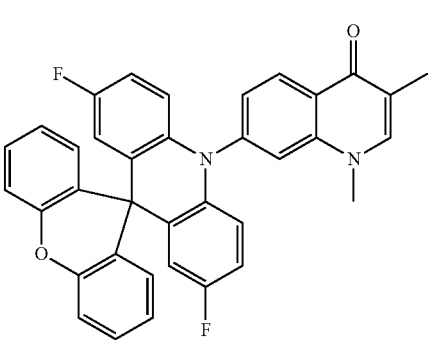

221
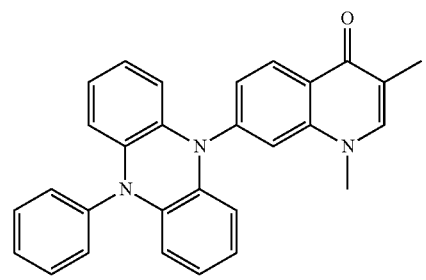
222
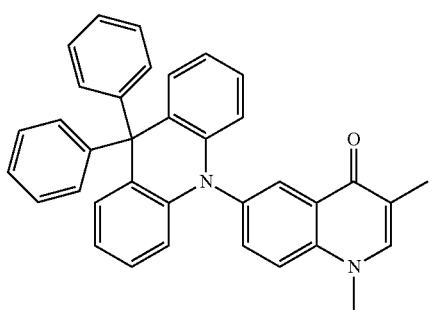
223
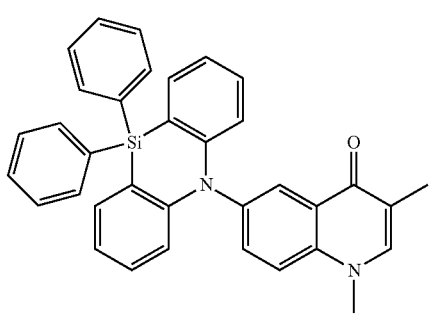
224
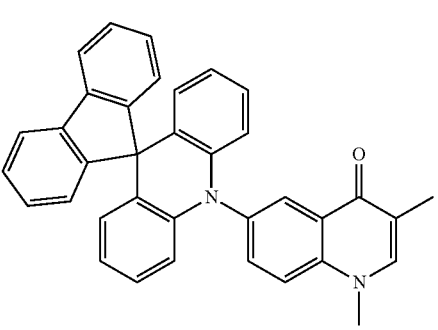
225
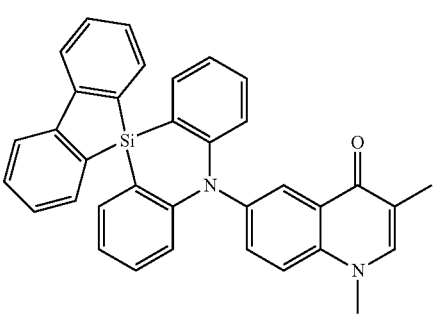
226
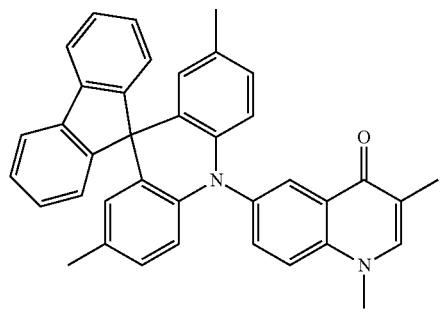
227
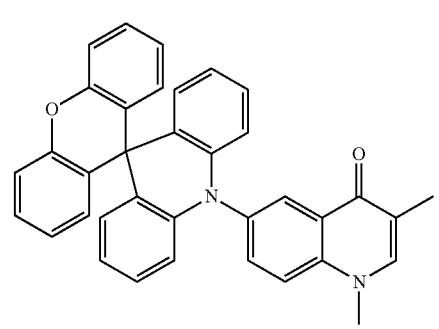
228
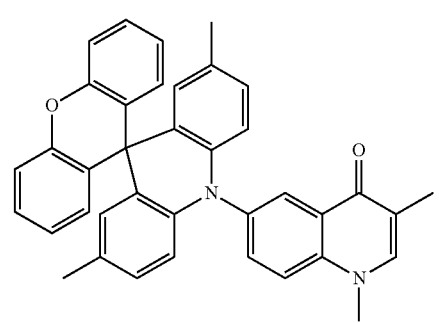
229
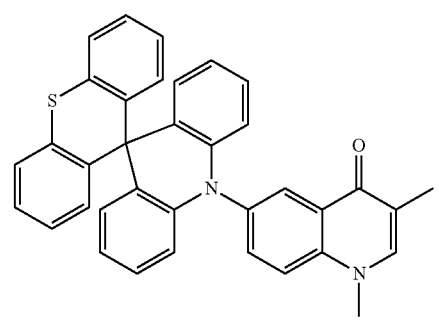
230
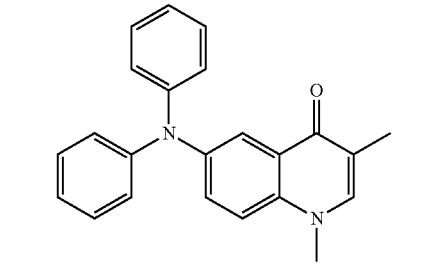

231
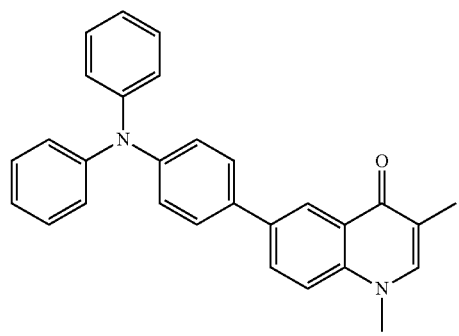
232
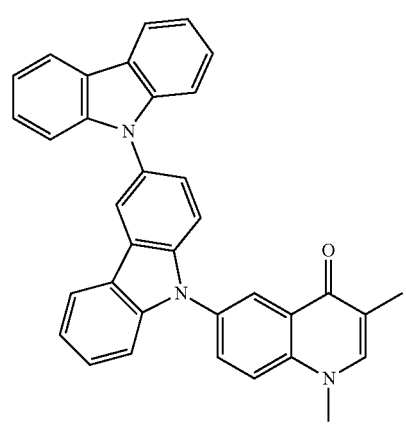
233
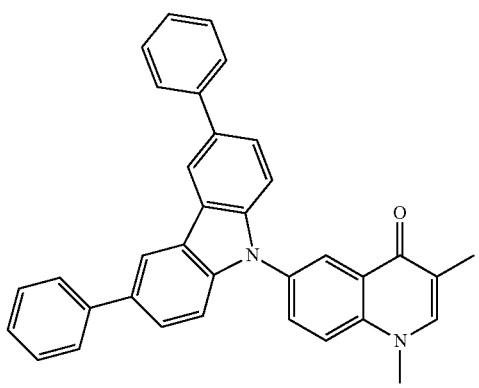
234
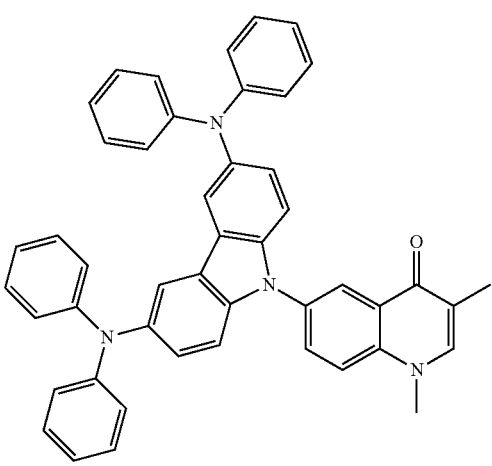
235
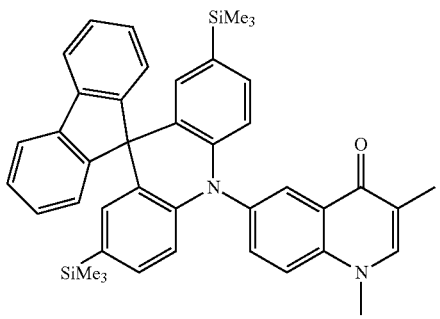
236
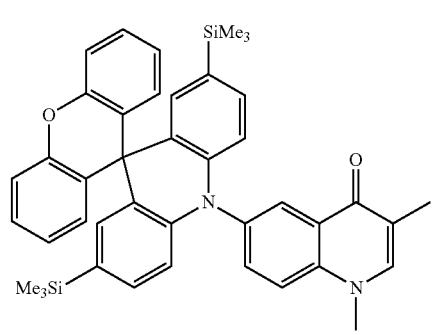
237
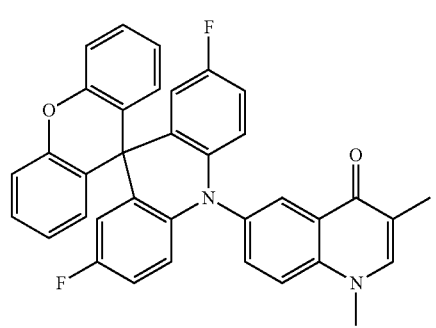
238
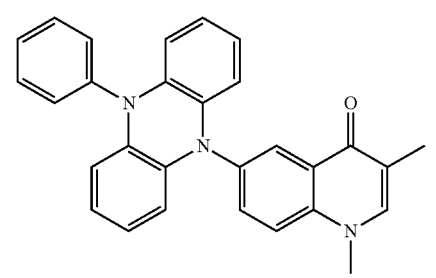
239
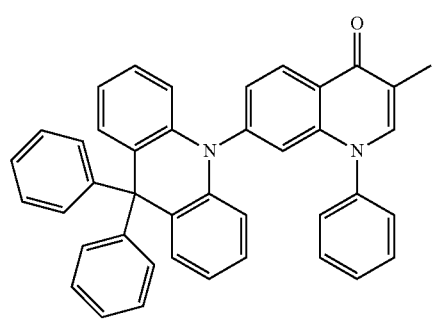

240
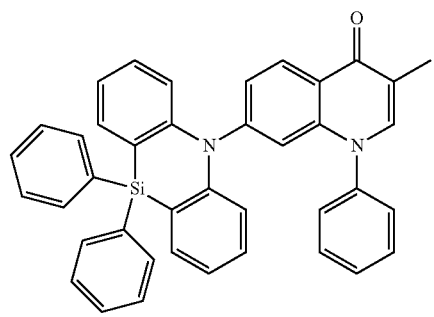
241
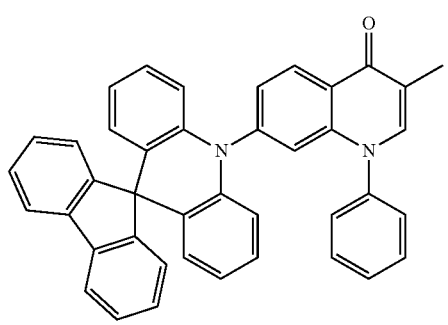
242
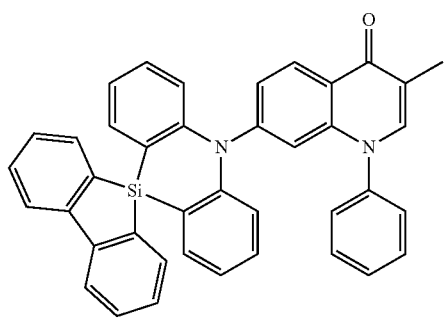
243
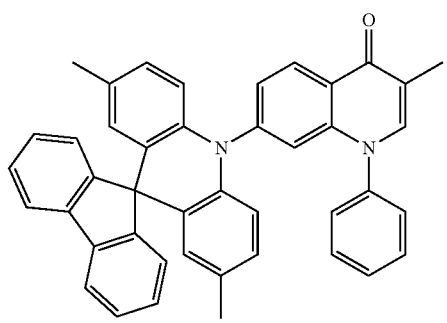
244
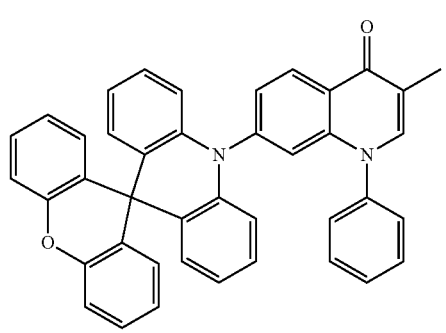
245
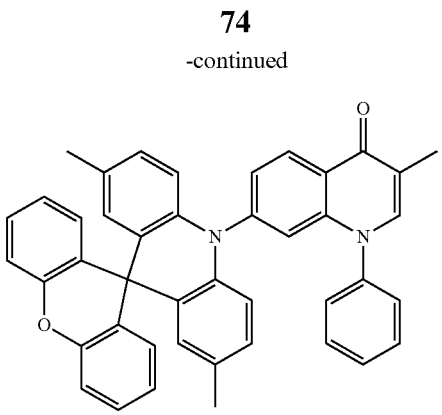
246
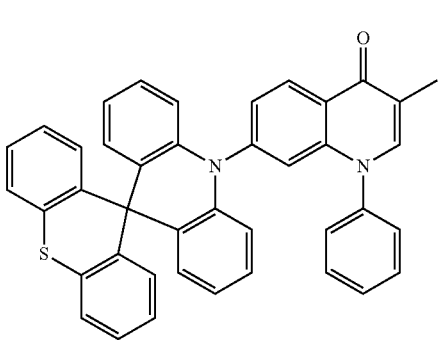
247
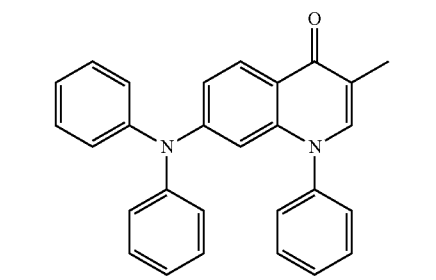
248
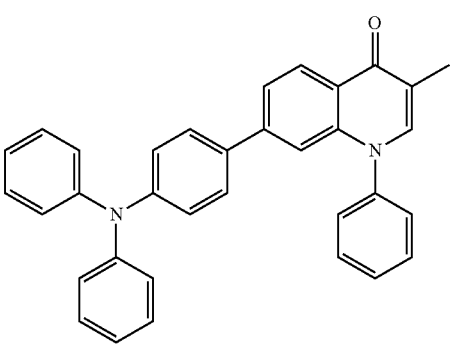
249
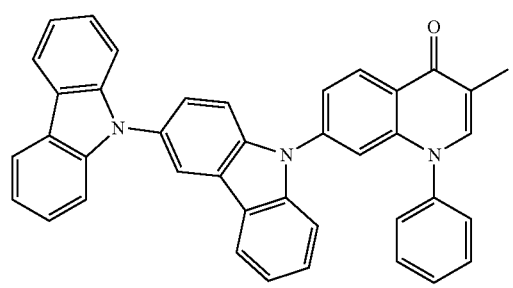

250 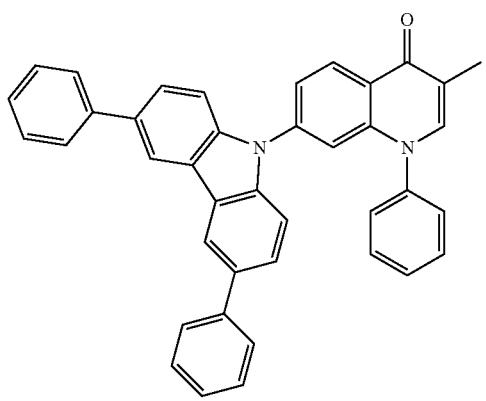
251 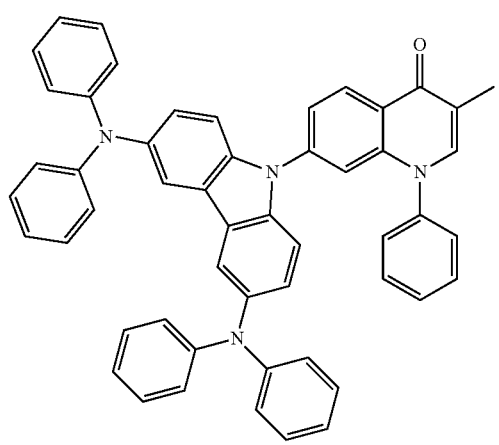
252 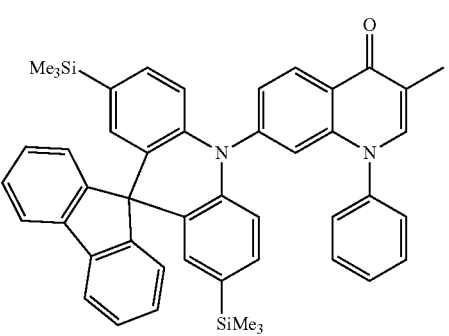
253 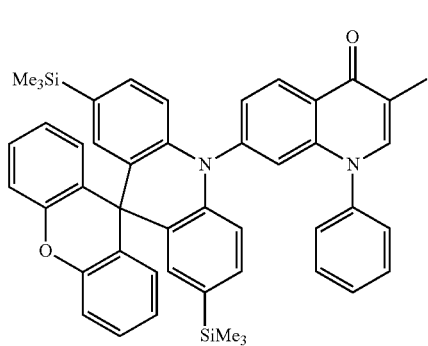
254 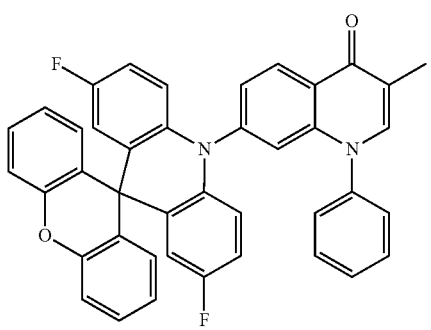
255 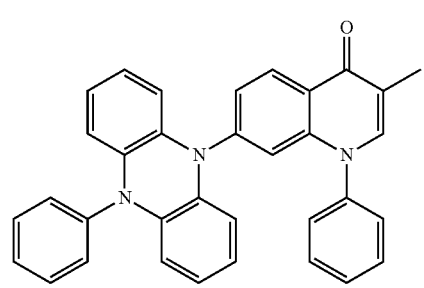
256 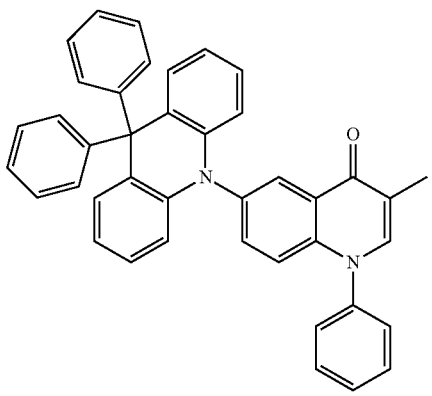
257 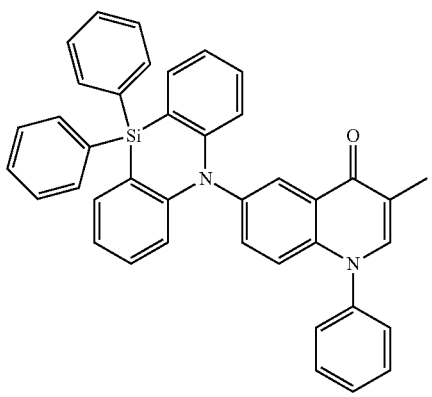

-continued
258
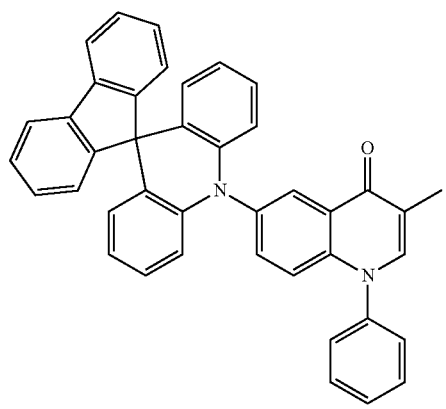
259
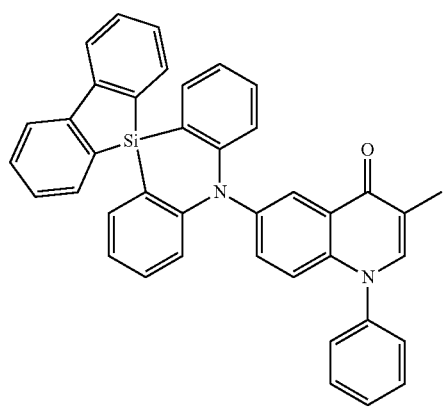
260
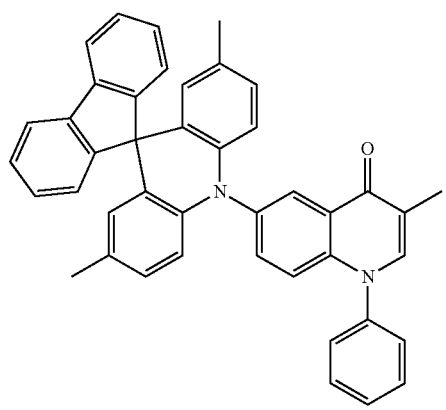
261
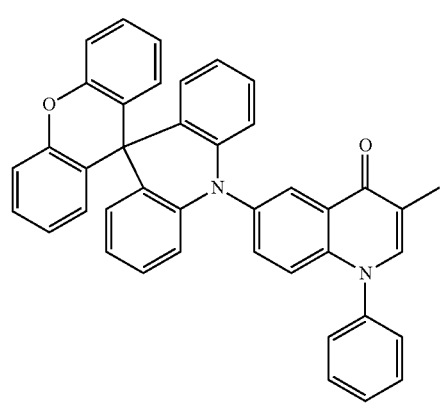
-continued
262
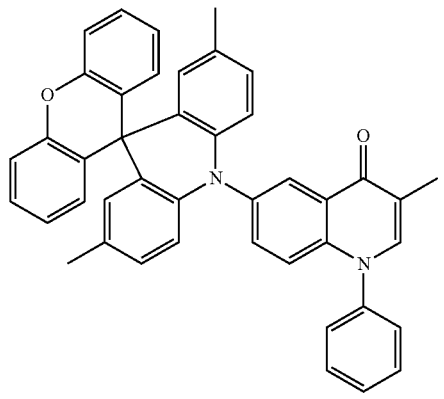
263
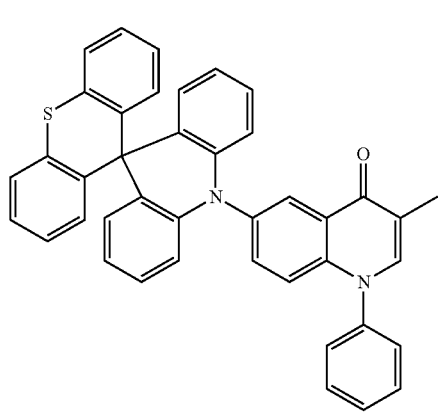
264
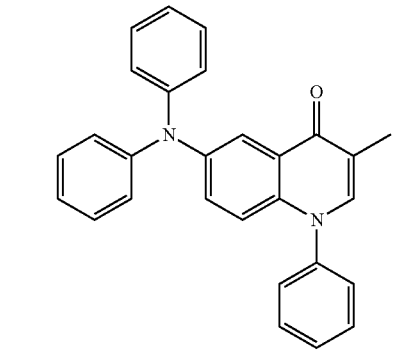
265
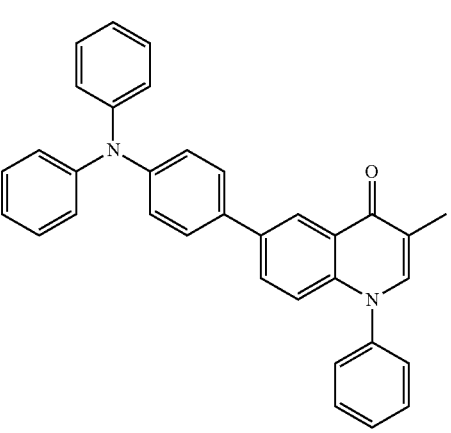

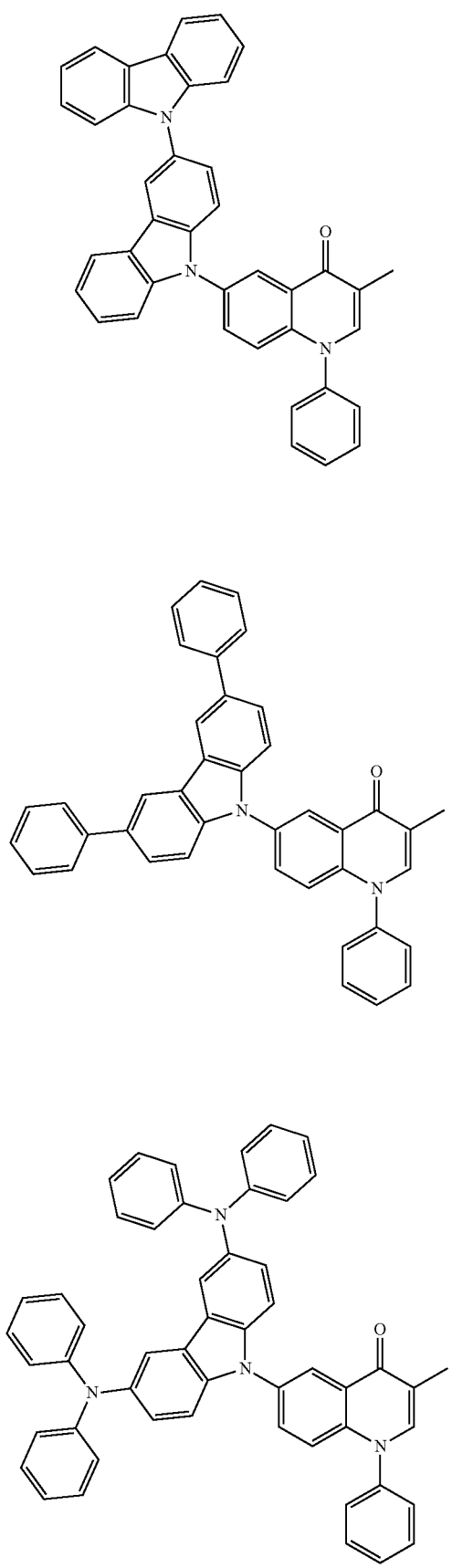
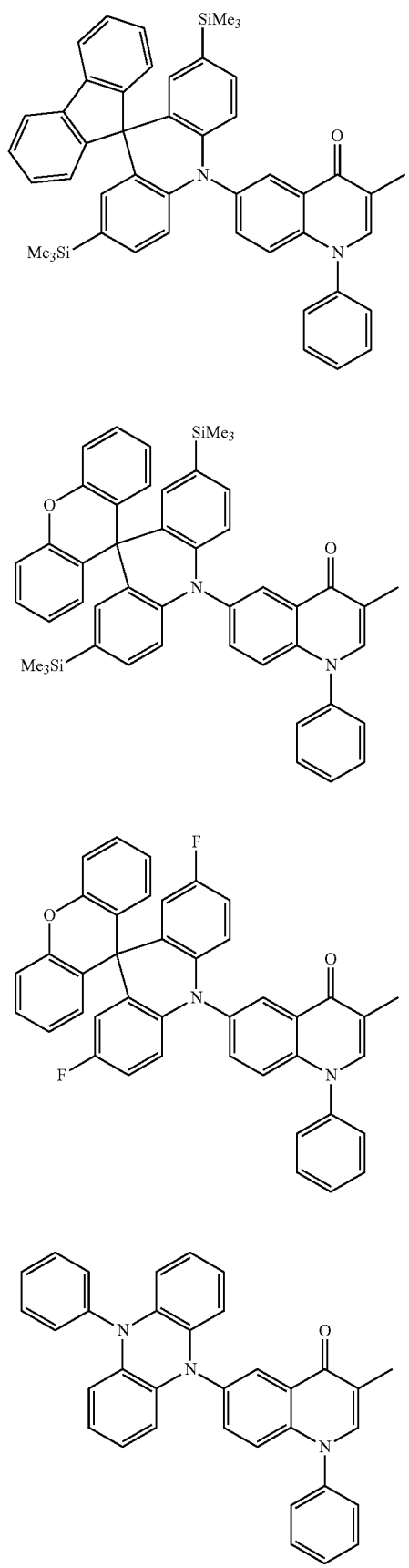

273
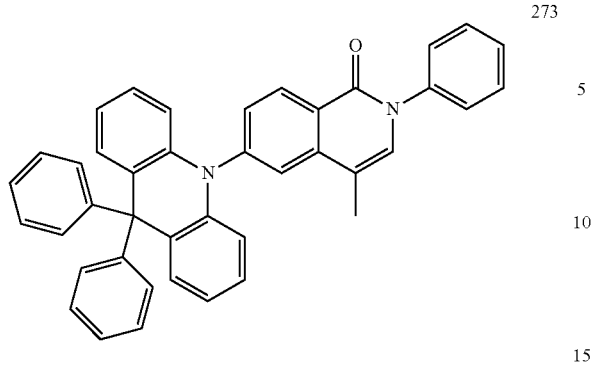
277
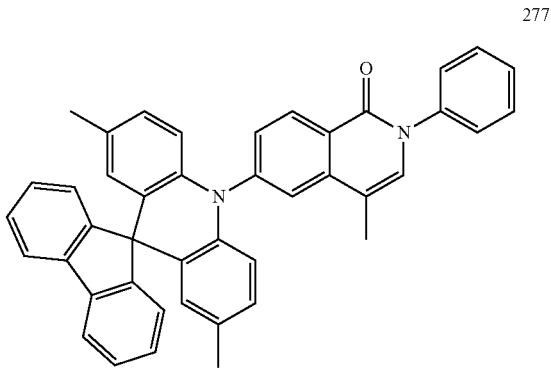
274
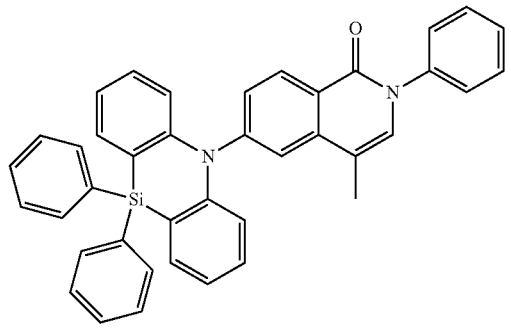
278
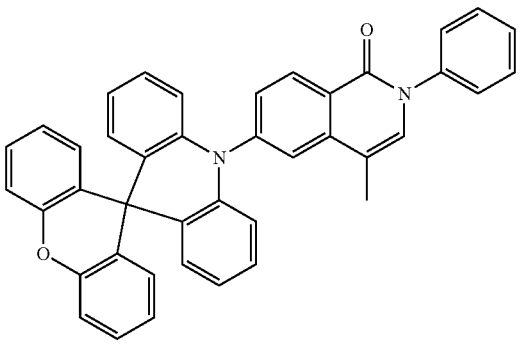
275
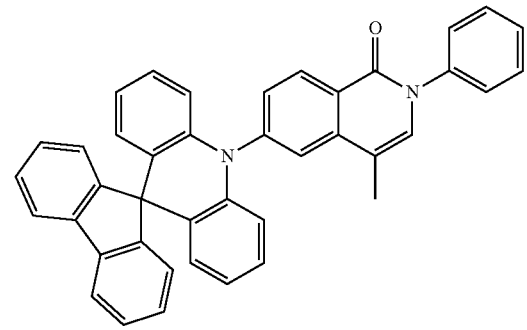
279
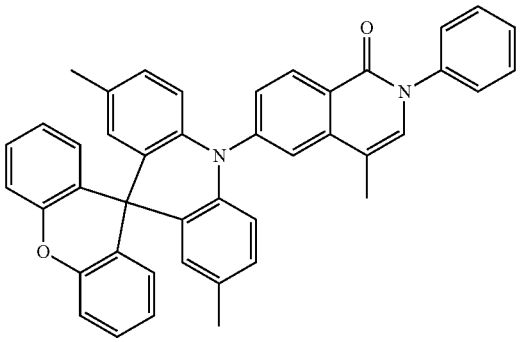
276
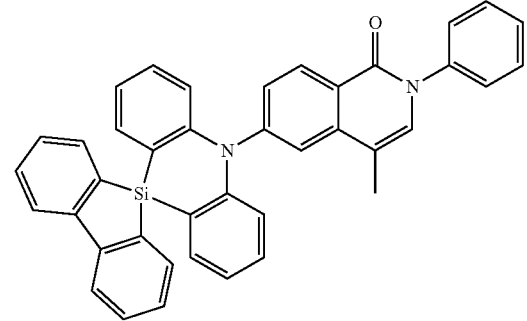
280
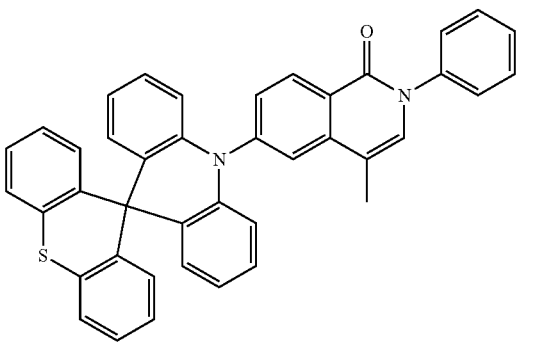

-continued
281
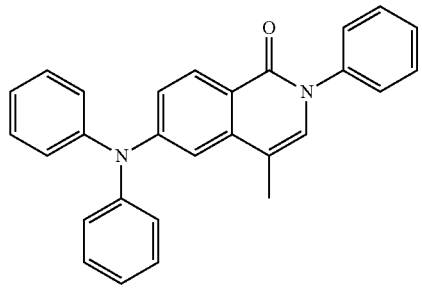
282
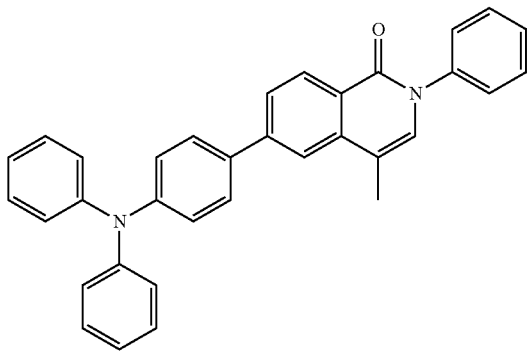
283
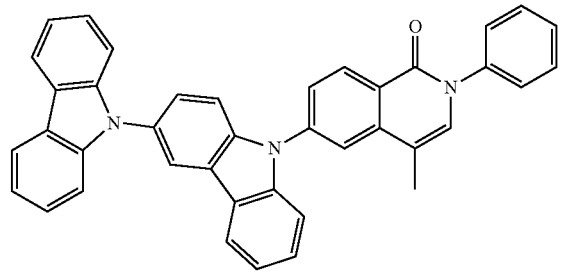
284
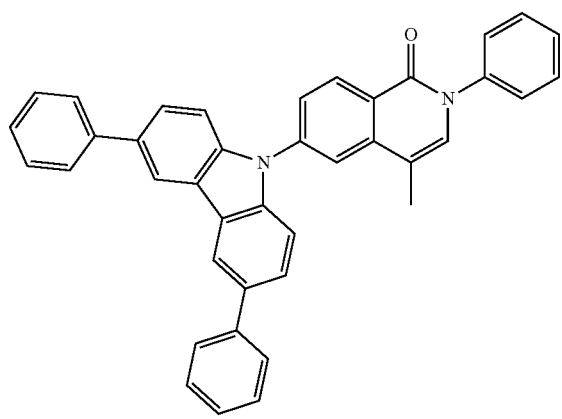
-continued
285
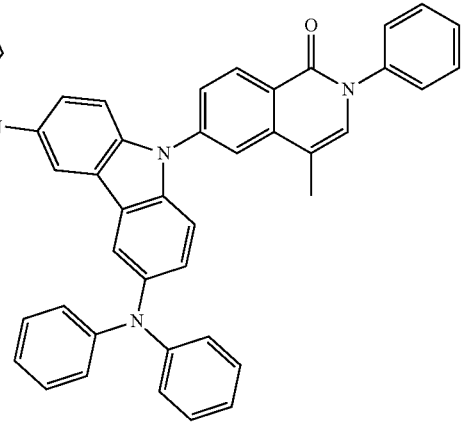
286
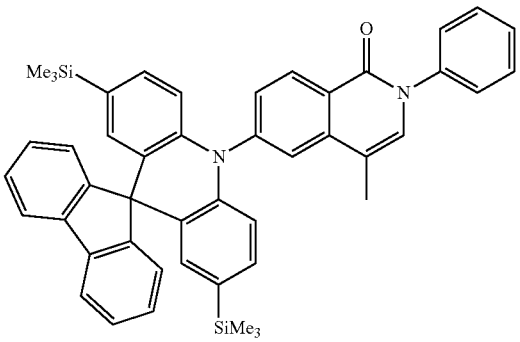
287
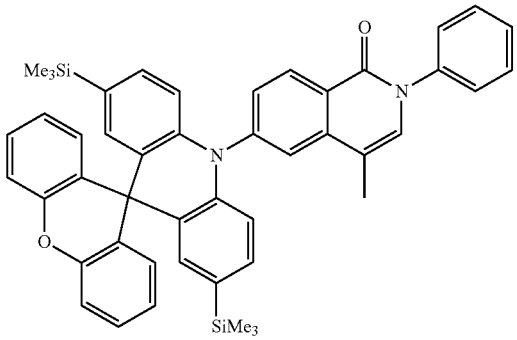
288
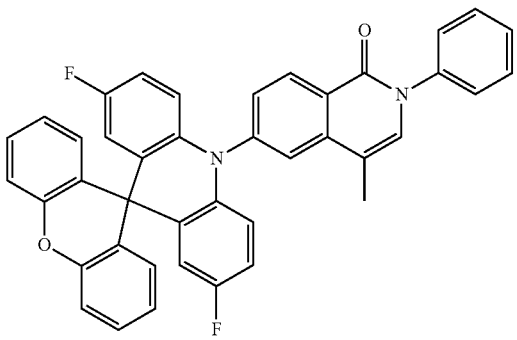

289
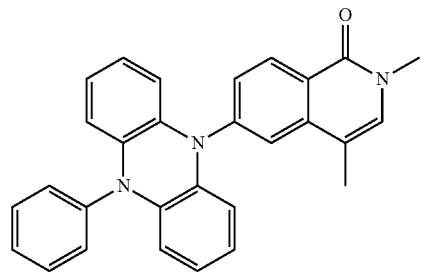
290
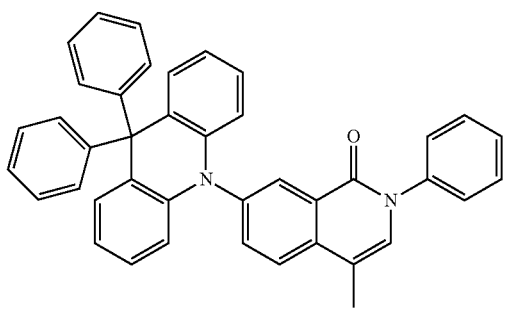
291
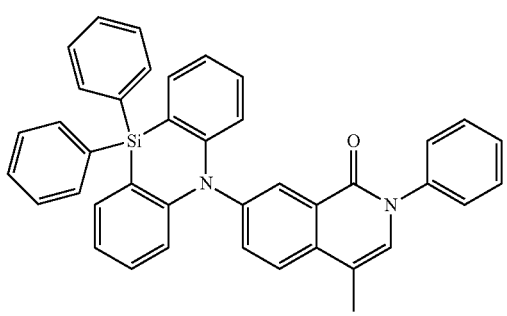
292
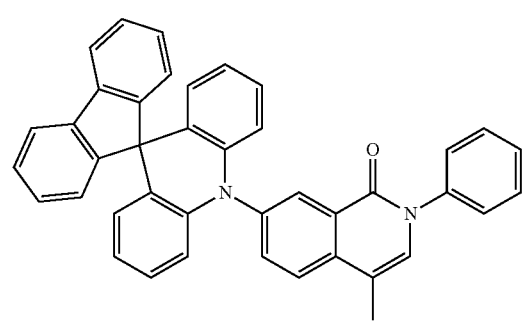
293
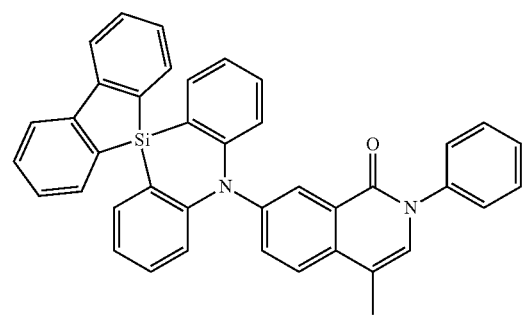
294
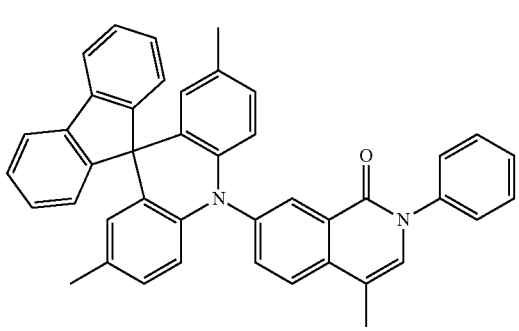
295
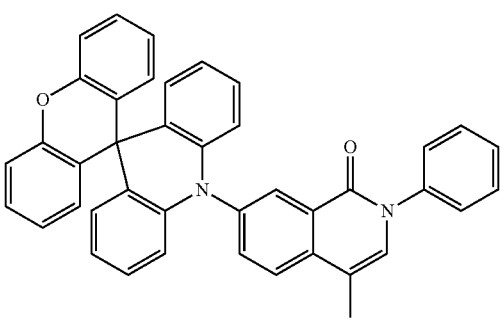
296
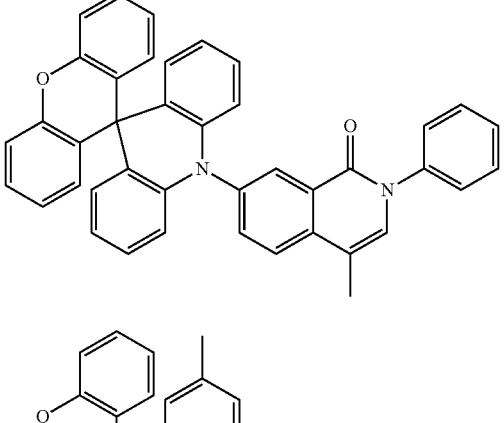
297
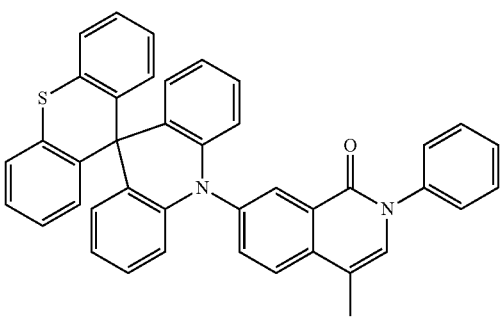
298
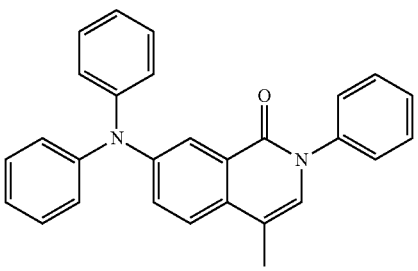

299
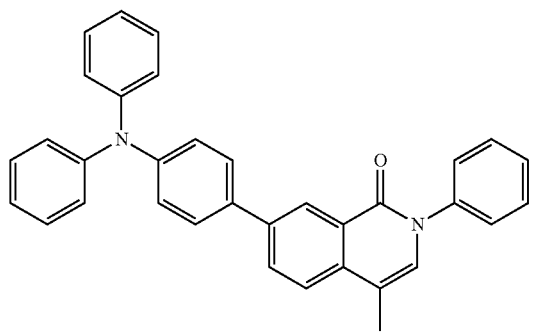
300
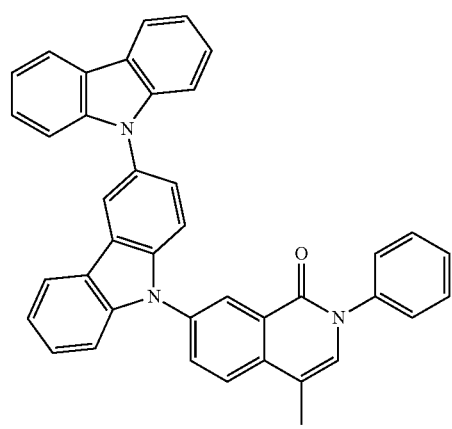
301
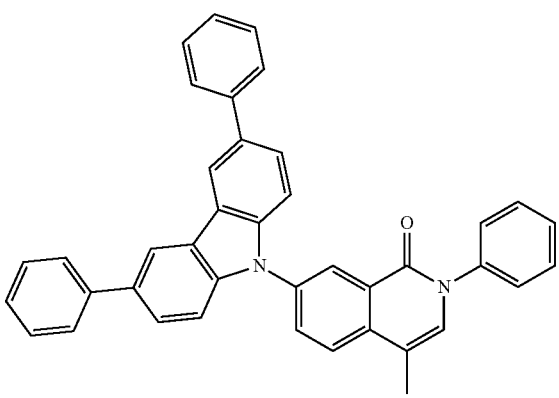
302
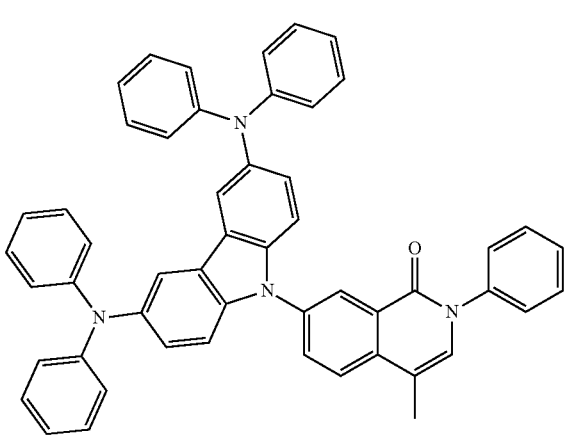
303
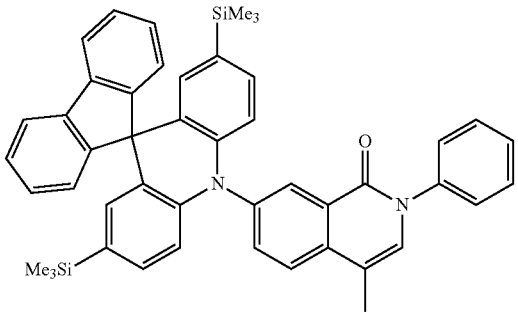
304
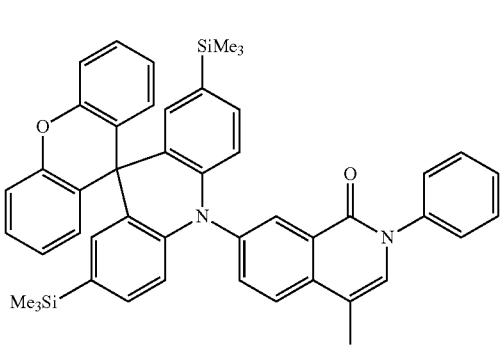
305
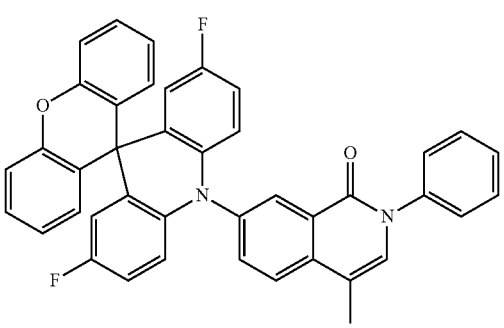
306
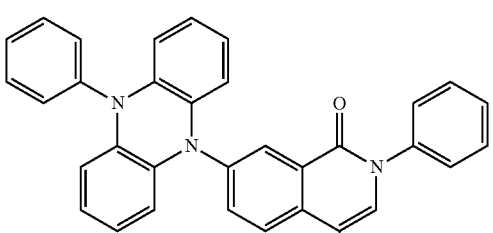
307
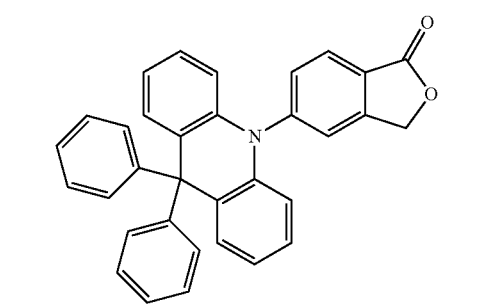

US 10,714,693 B2
-continued
308 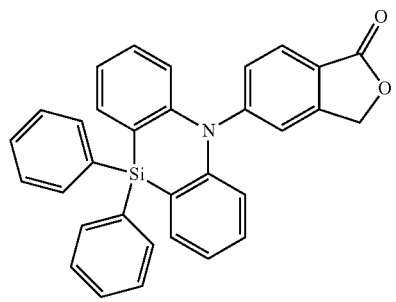
309 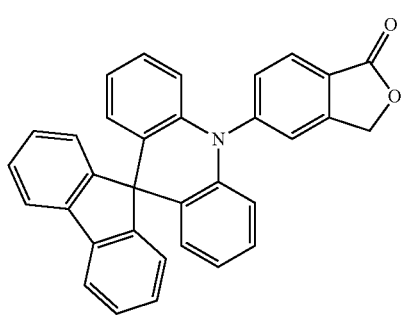
310 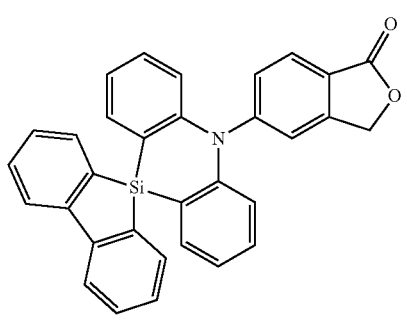
311 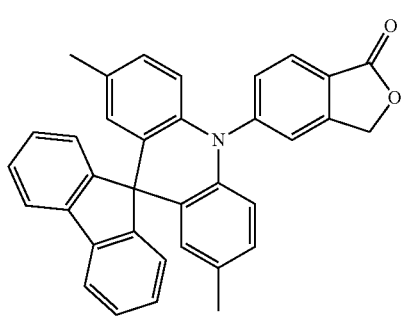
312 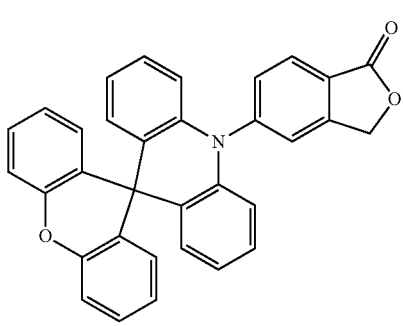
-continued
313 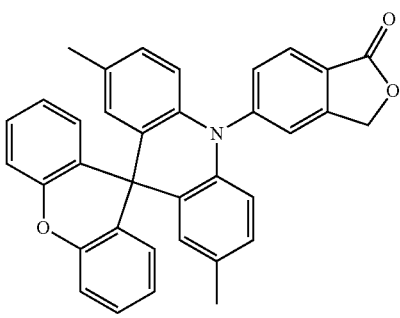
314 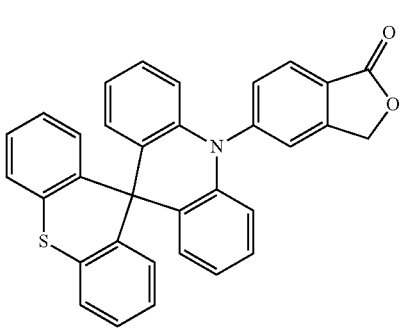
315 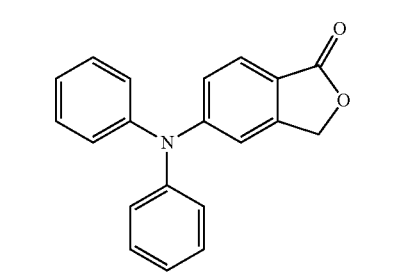
316 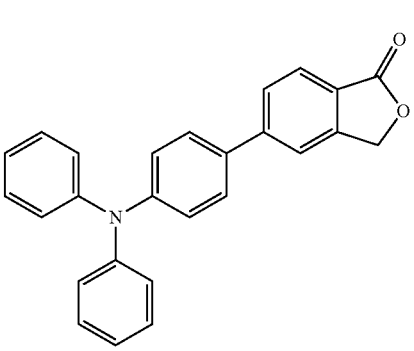
317 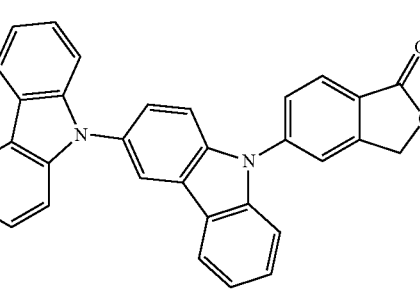

-continued
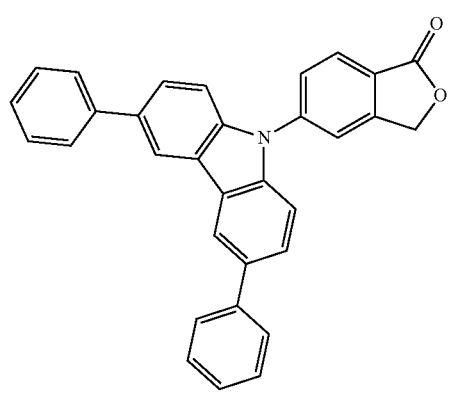
318
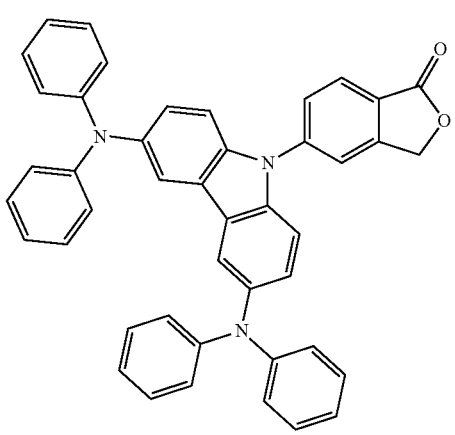
319
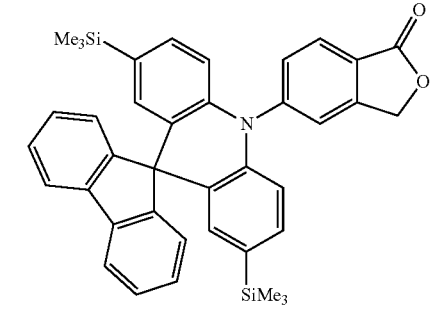
320
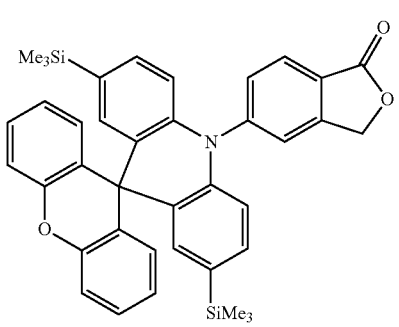
321
-continued
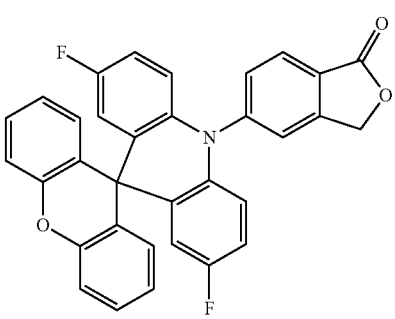
322
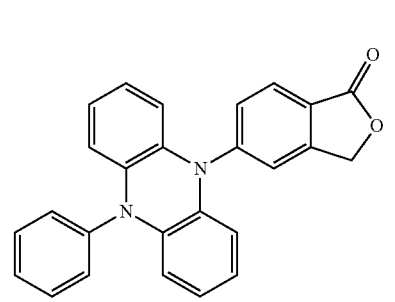
323
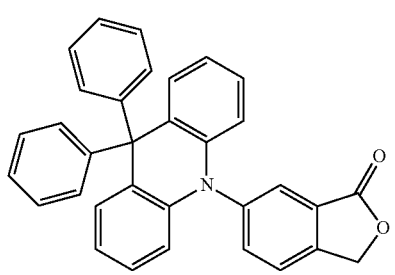
324
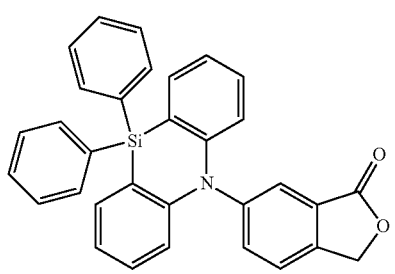
325
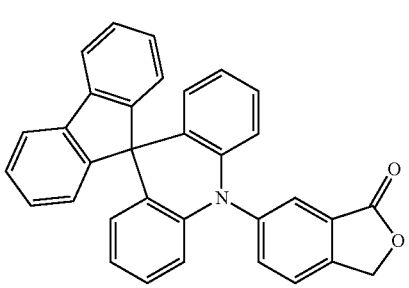
326

327
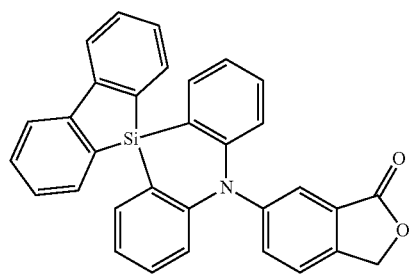
328
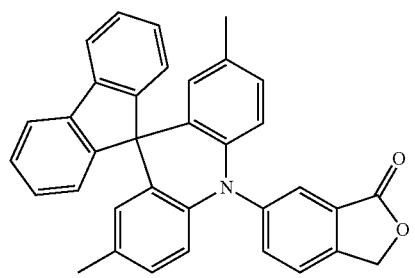
329
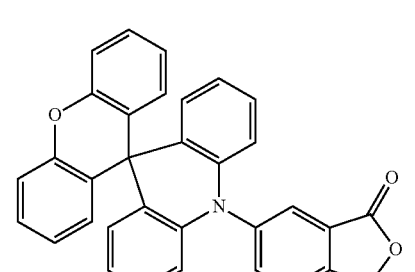
330
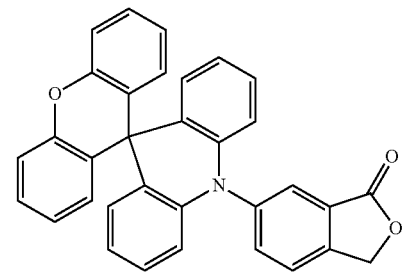
331

332
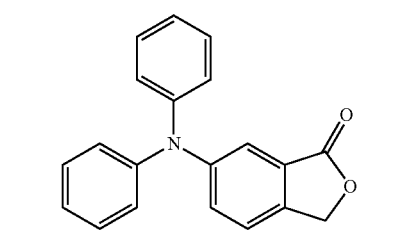
333
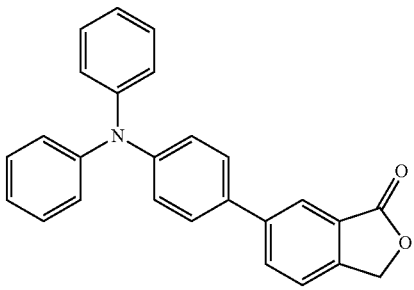
334
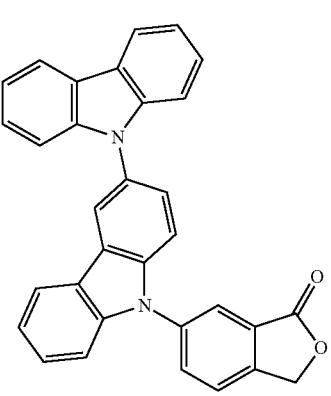
335
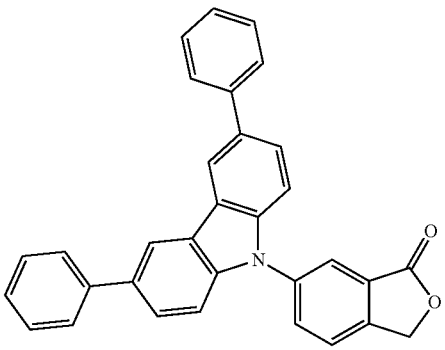
336
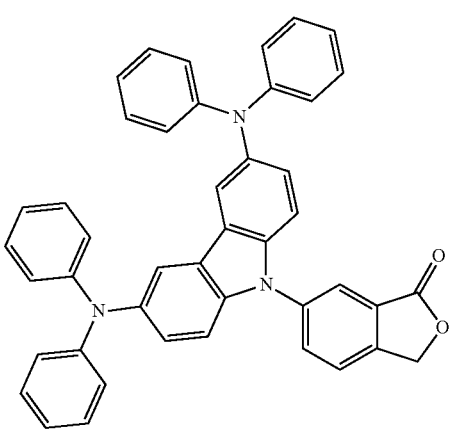

337
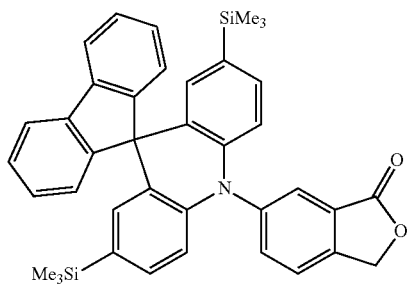
338
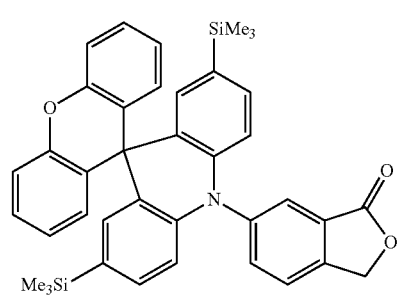
339
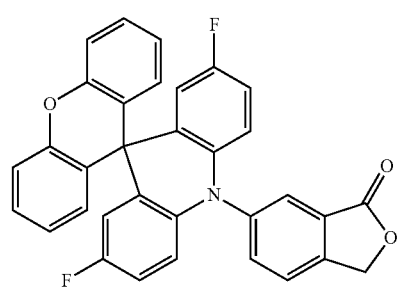
340
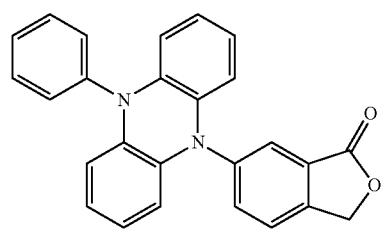
341
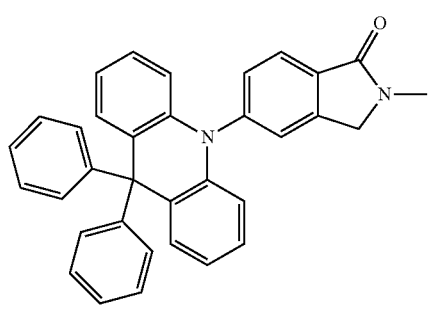
342
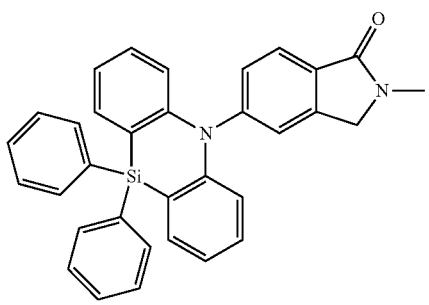
343
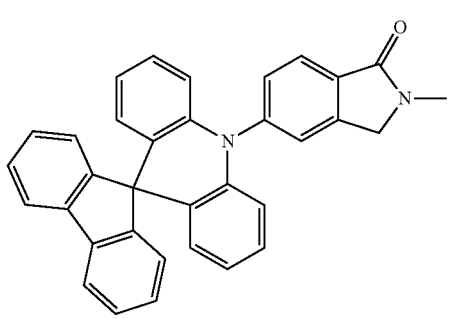
344
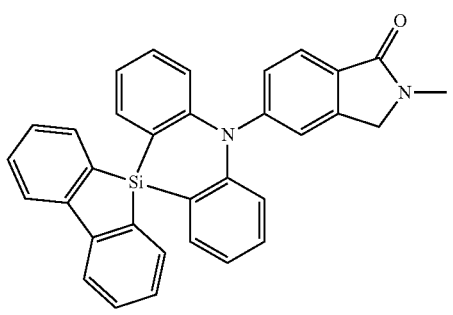
345
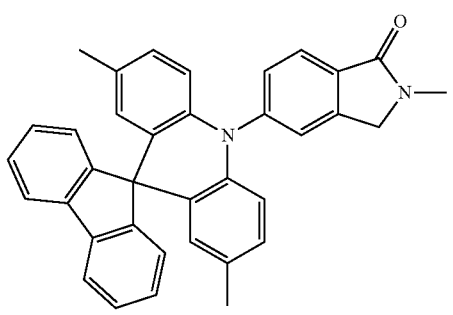
346
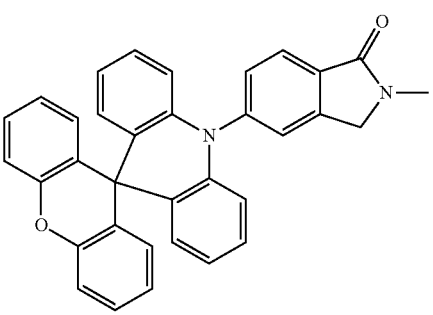

347
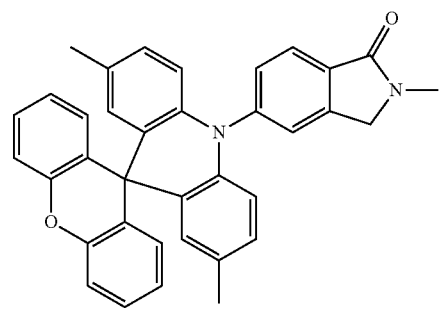
348
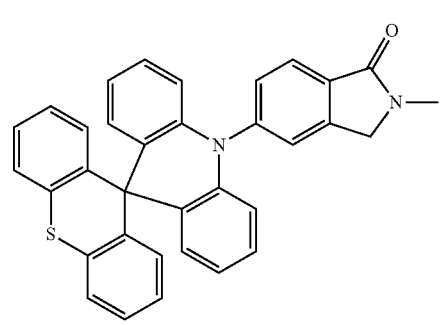
349
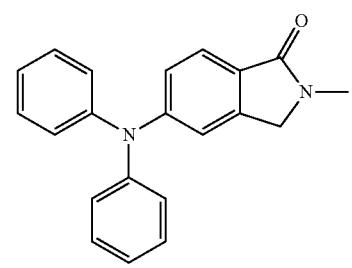
350
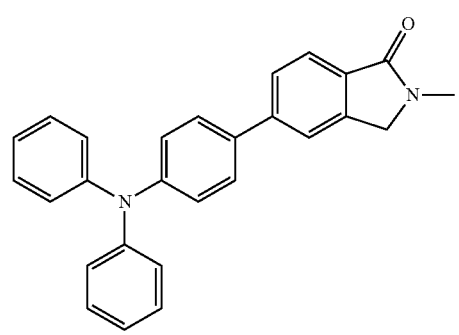
351
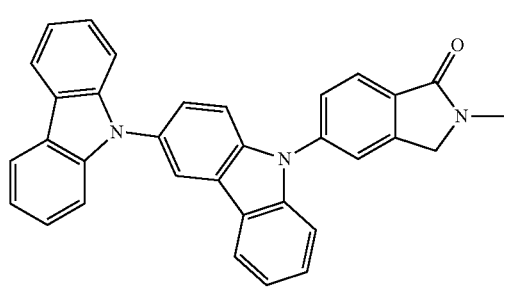
352
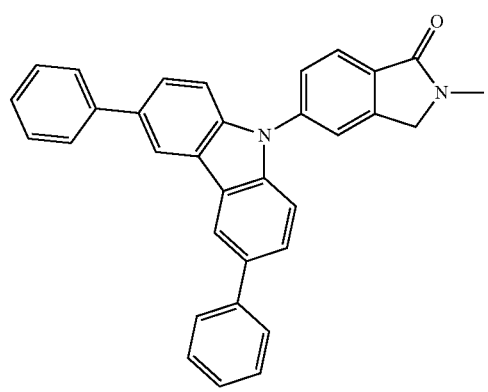
353
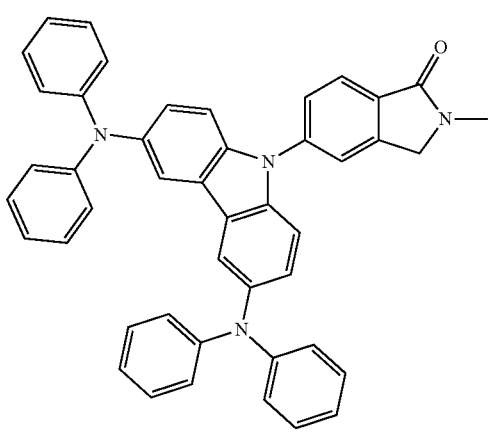
354
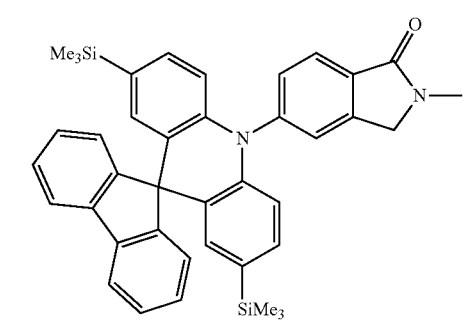
355
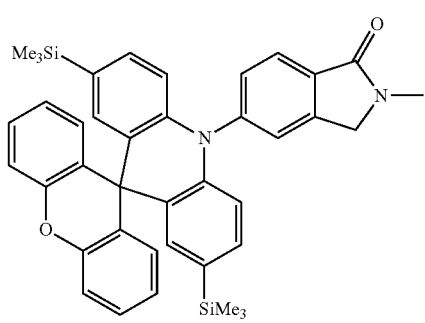

356
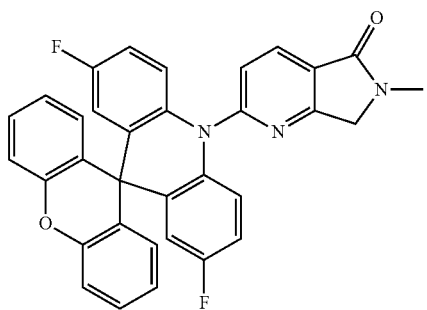
357
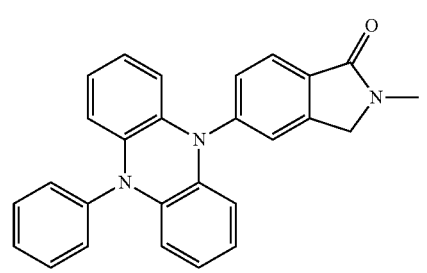
358
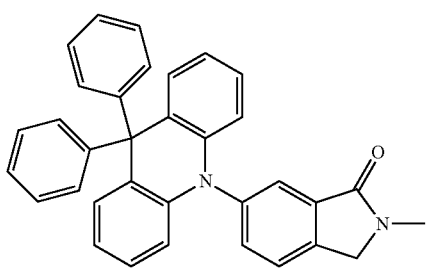
359
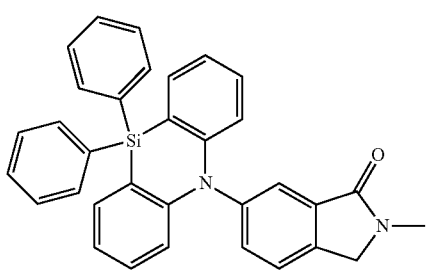
360
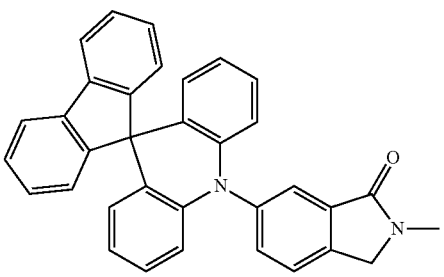
361
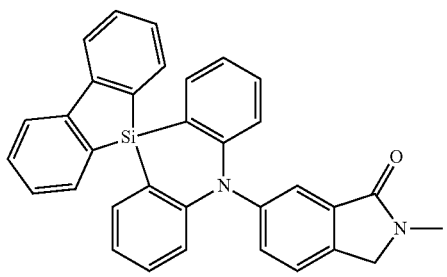
362
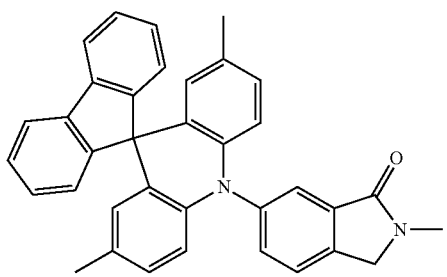
363
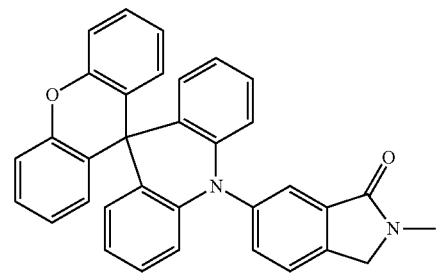
364
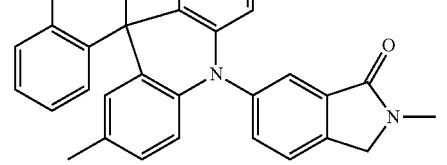
365
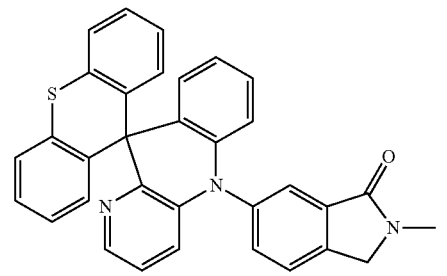
366

-continued
367 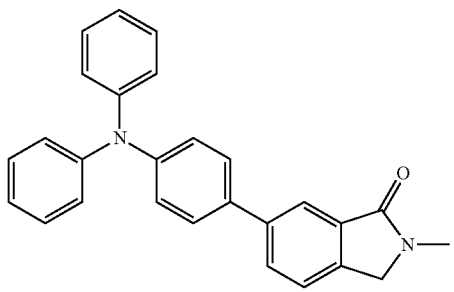
368 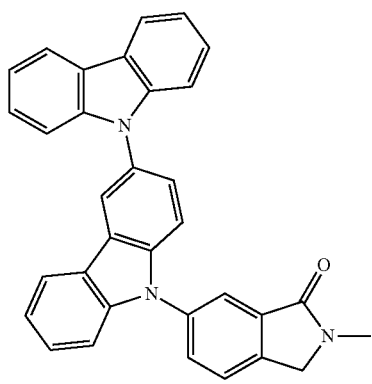
369 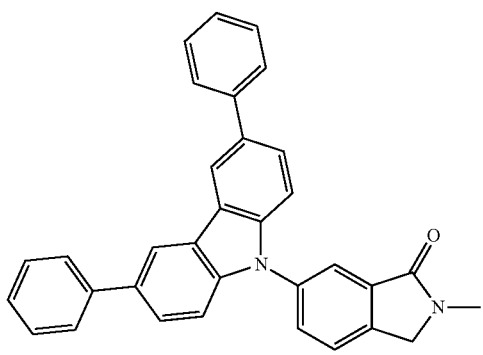
370 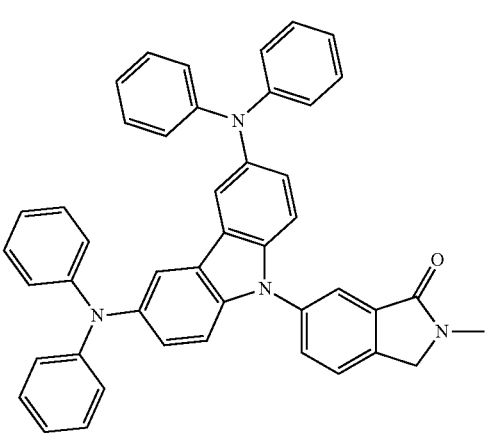
-continued
371 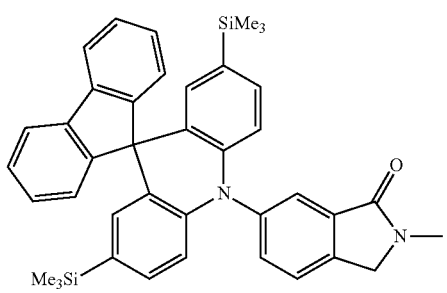
372 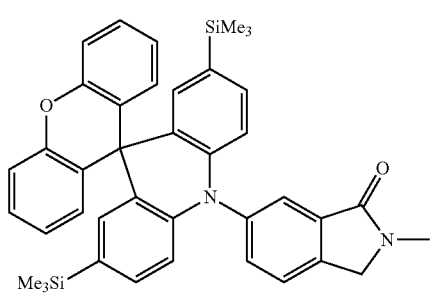
373 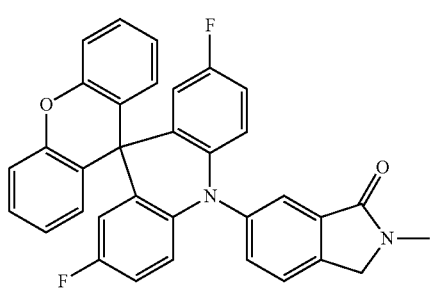
374
375 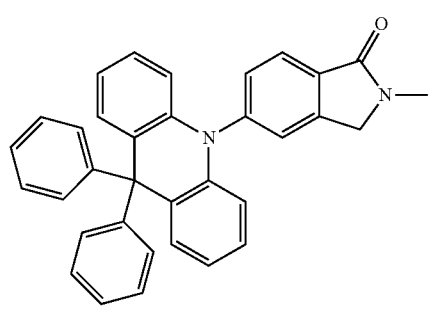

376
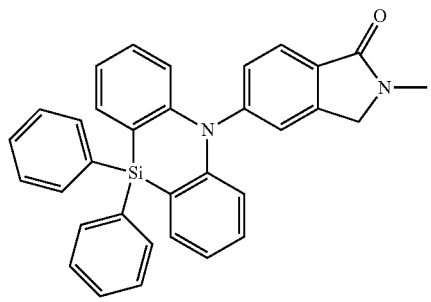
377
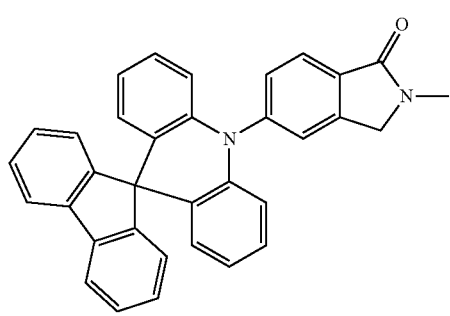
378
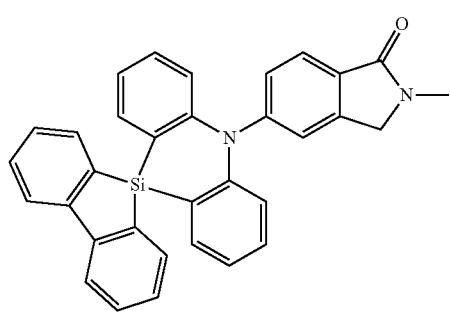
379
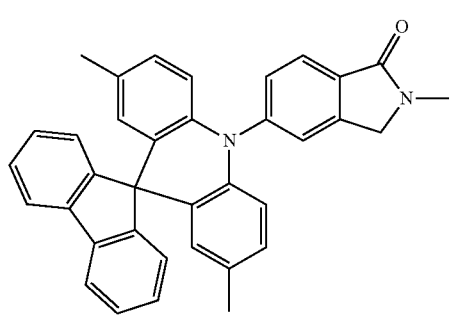
380
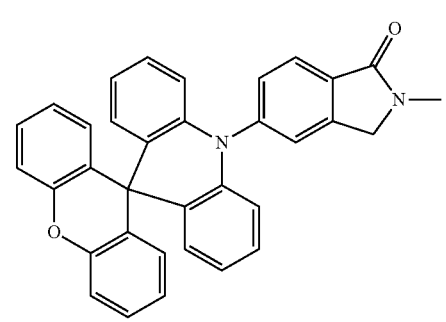
381
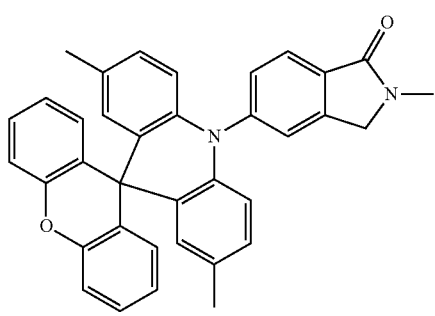
382
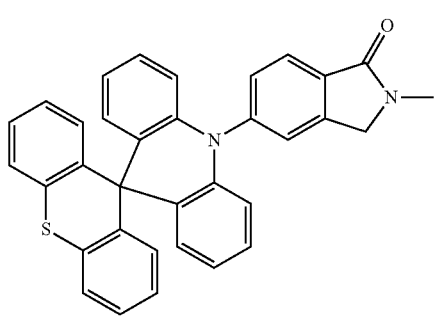
383
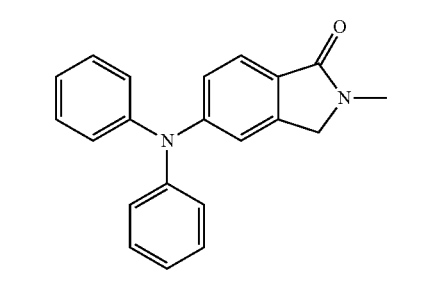
384
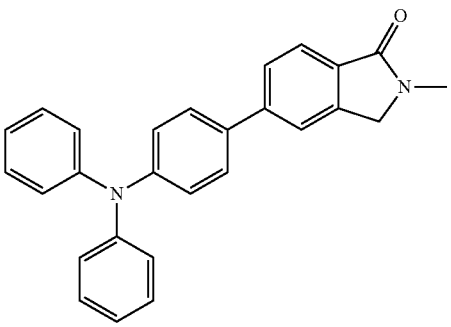
385
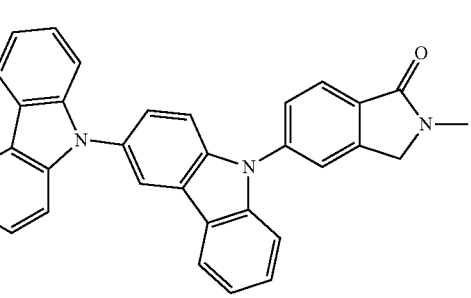

386
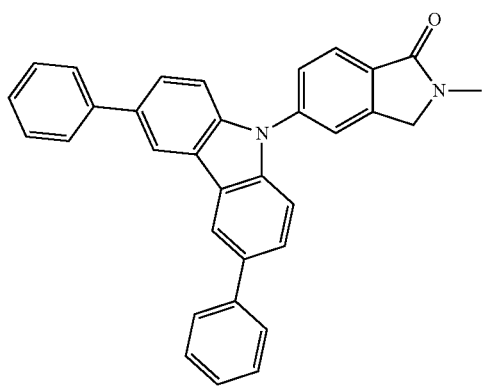
387
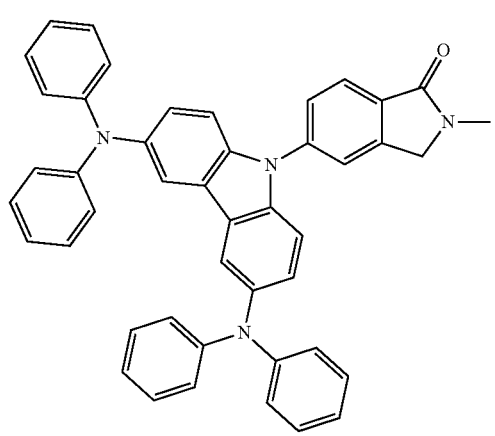
388
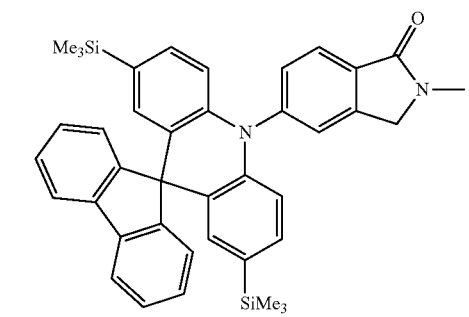
389
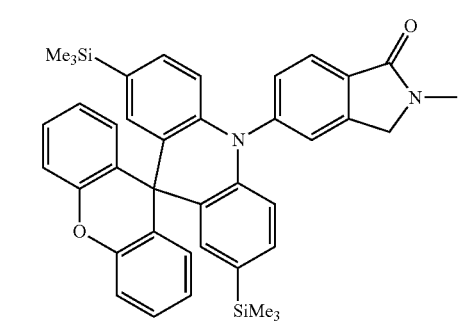
390
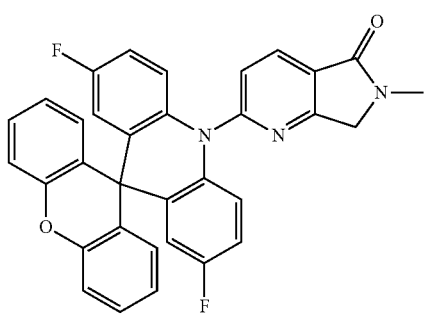
391
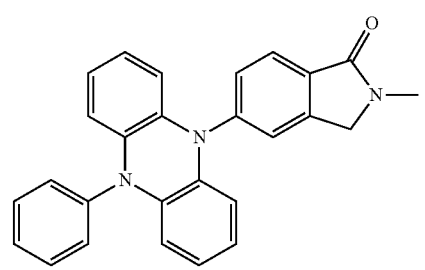
392
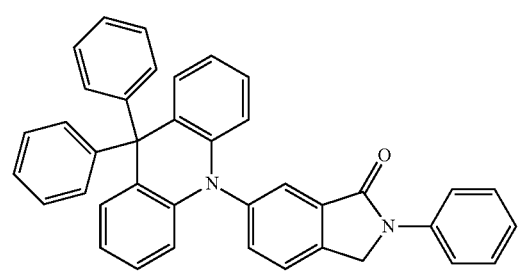
393
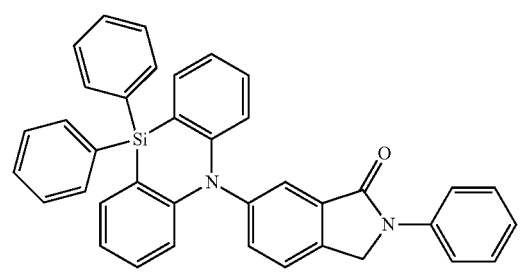
394
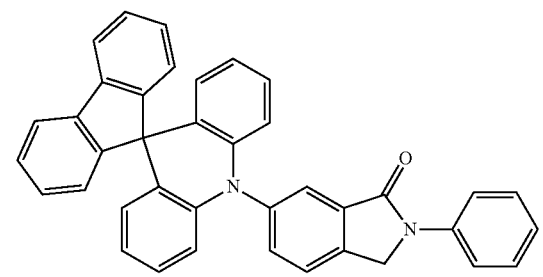

395
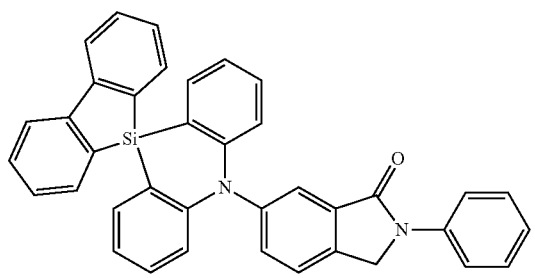
396
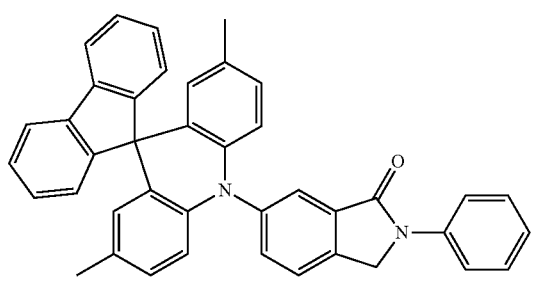
397
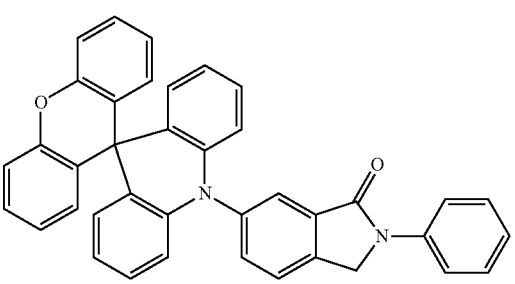
398
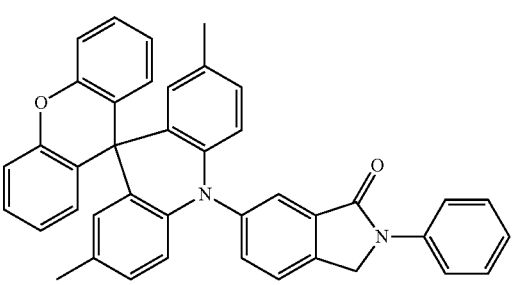
399
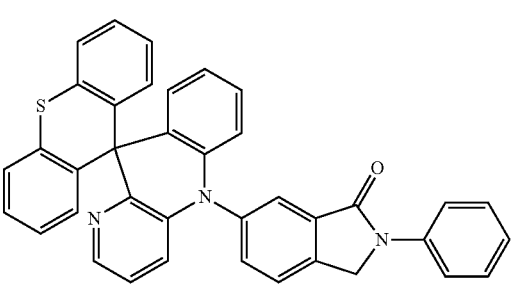
400
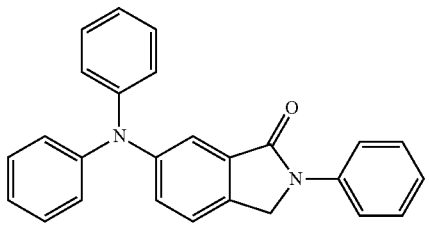
401
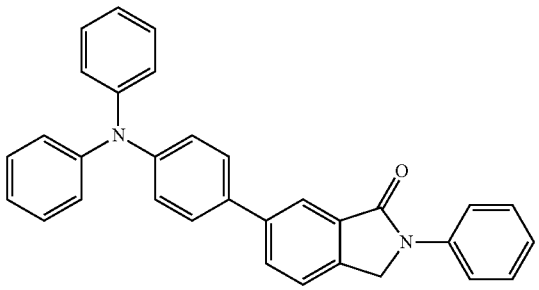
402
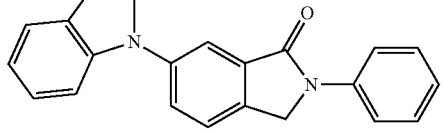
403
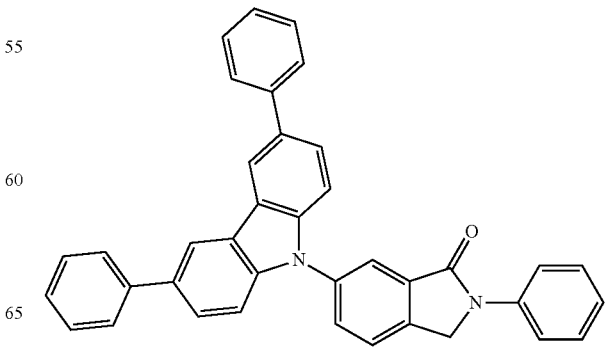

404
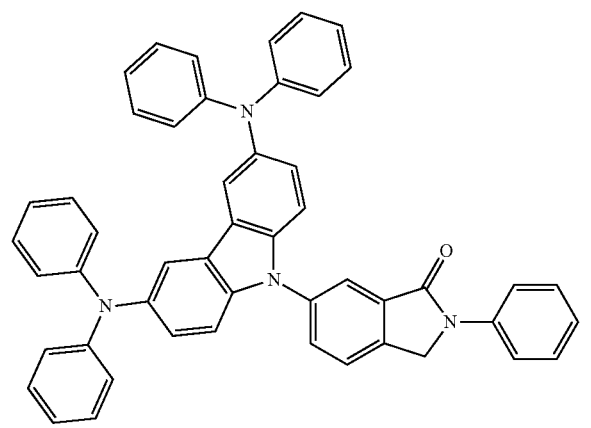
405
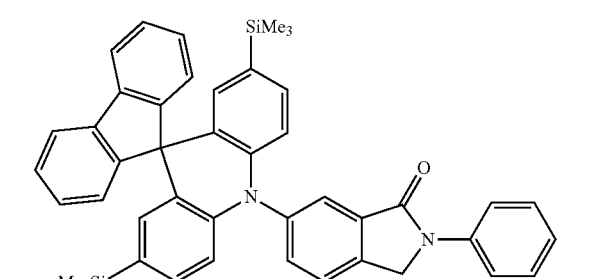
406
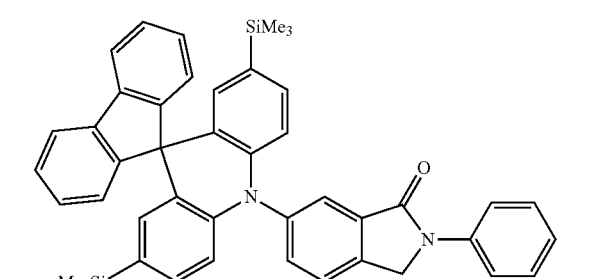
407
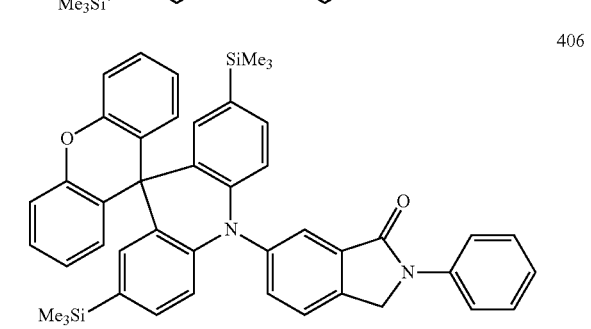
408
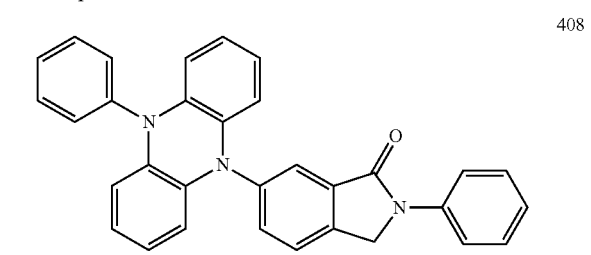
409
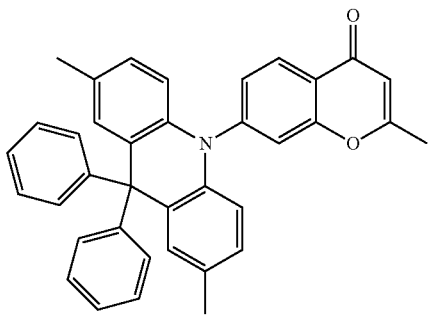
410
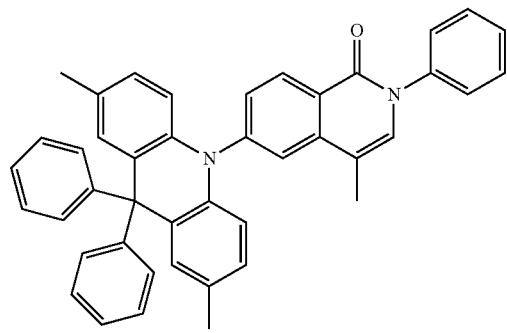
411
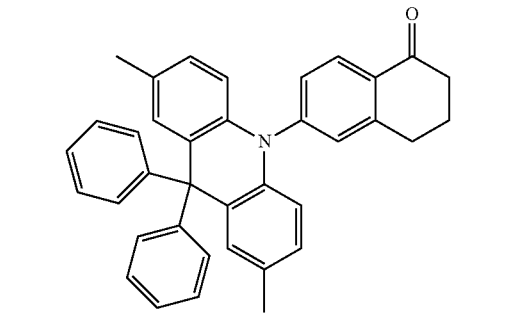
412
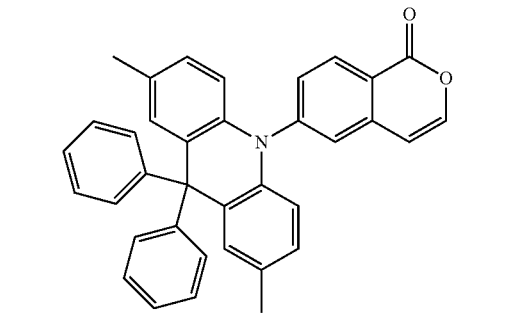
413
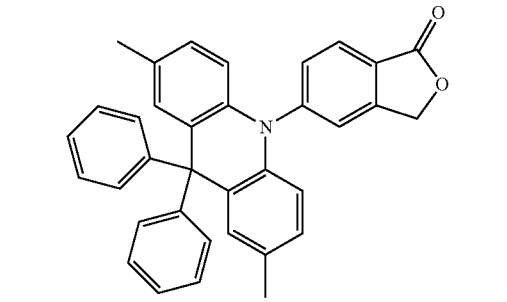

-continued

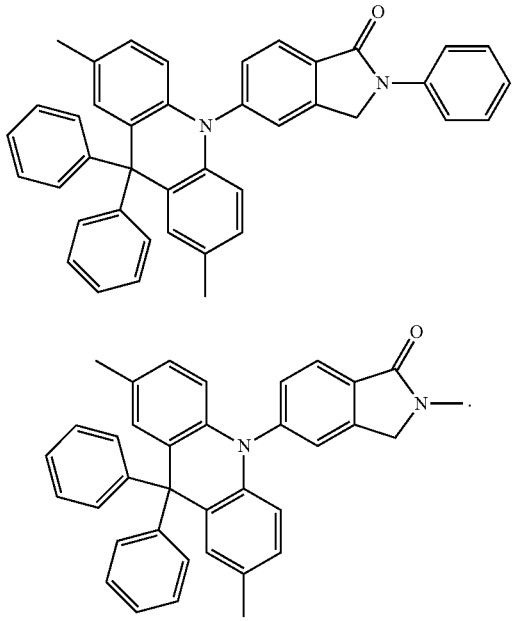

414

415

Hereinafter, an organic electroluminescence device according to an example embodiment will be described. The following description will be mainly with respect to the difference in the polycyclic compound according to an example embodiment, and any undescribed part will follow the above-description on the polycyclic compound according to an example embodiment.

The organic electroluminescence device according to an example embodiment includes the above-described polycyclic compound according to an example embodiment.

Figure 2:
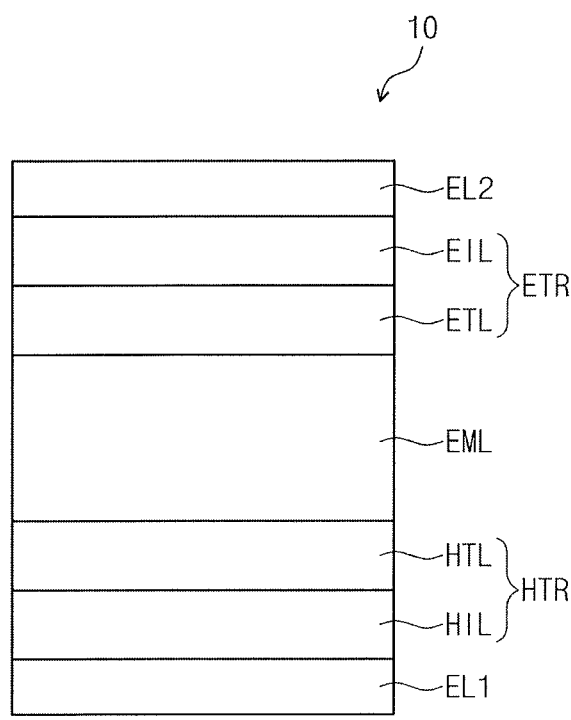
FIG. 2 illustrates a schematic cross-sectional view of an organic electroluminescence device according to an example embodiment.

FIG. 1 is a schematic cross-sectional view of an organic electroluminescence device according to an example embodiment. FIG. 2 is a schematic cross-sectional view of an organic electroluminescence device according to an example embodiment.

Referring to FIGS. 1 and 2, an organic electroluminescence device 10 according to an example embodiment may include a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. When the first electrode EL1 is the transmissive electrode, the first electrode EL1 may be formed using a transparent metal oxide such as indium tin oxide (ITO), indium zinc oxide (IZO), zinc oxide (ZnO), or indium tin zinc oxide (ITZO). When the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed using the above materials, or a transparent layer formed using ITO, IZO, ZnO, or ITZO.

The hole transport region HTR may be provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 200 Å to about 2,500 Å.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL and a hole transport layer HTL, or may have a structure of a single layer formed using a hole injection material and a hole transport material. In addition, the hole transport region HTR may have a structure of a single layer formed using a plurality of different materials, or a structure laminated from the first electrode EL1 of hole injection layer HIL/hole transport layer HTL, hole injection layer HIL/hole transport layer HTL/buffer layer, hole injection layer HIL/hole buffer layer, hole transport layer HTL/hole buffer layer, or hole injection layer HIL/hole transport layer HTL/electron blocking layer, etc.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-dinaphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, etc.

The hole transport layer HTL may include, for example, a carbazole derivative such as N-phenyl carbazole, and polyvinyl carbazole, a fluorine-based derivative, N,N'-bis(3-methylphenyl)-N,N'-diphenyl-[1,1-biphenyl]-4,4'-diamine (TPD), a triphenylamine-based derivative such as 4,4',4"-tris(N-carbazolyl)triphenylamine (TCTA), N,N'-di(1-naphthyl)-N,N'-diphenylbenzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, for example, from about 100 Å to about 1,000 Å. When the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. When the thicknesses of the hole transport region HTR, the hole injection layer HIL, and the hole transport layer HTL satisfy the above-described ranges, satisfactory hole transport properties may be obtained without a substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of a quinone derivative, a metal oxide, or a cyano group-containing compound, etc. For example, non-limiting examples of the p-dopant may include a quinone derivative such as tetracyanoquinodimethane (TCNQ), and 2,3,5,6-tetrafluoro-tetracyanoquinodimethane (F4-TCNQ), a metal oxide such as tungsten oxide, and molybdenum oxide, etc.

As described above, the hole transport region HTR may further include one of the hole buffer layer or the electron blocking layer other than the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR to the hole transport region HTR.

The emission layer EML may be provided on the hole transport region HTR. The thickness of the emission layer EML may be, for example, from about 100 Å to about 1,000 Å. The emission layer EML may have a single layer formed using a single material, a single layer formed using a plurality of different materials, or a multilayer structure having a plurality of layers formed using a plurality of different materials.

Hereinafter, an example embodiment is described in which the polycyclic compound according to an example embodiment is included in an emission layer EML. In other embodiments, the polycyclic compound according to an example embodiment may be included in at least one organic layer provided between the first electrode EL1 and the second electrode EL2. For example, the polycyclic compound according to an example embodiment may be included in the hole transport region HTR. For example, the polycyclic compound according to an example embodiment may be included in the electron transport layer ETL.

The emission layer EML may include the polycyclic compound according to an example embodiment. For example, the emission layer EML may include a polycyclic compound represented by the following Formula 1. The polycyclic compound represented by Formula 1 may be used as the dopant material of the emission layer EML.

[Formula 1]

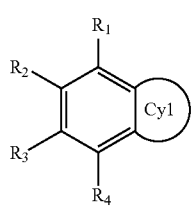

Particular explanation on $R_1$ to $R_4$, and Cy1 are the same as described above and will not be repeated.

The emission layer EML may include at least one kind of the polycyclic compound represented by Formula 1. The emission layer EML may further include a general material other than the polycyclic compound represented by Formula 1. For example, the emission layer EML may further include a fluorescent material including one selected from the group of spiro-DPVBi, 2,2',7,7'-tetrakis(biphenyl-4-yl)-9,9'-spiro-bifluorene (spiro-6P, spiro-sexiphenyl), distyryl-benzene (DSB), distyryl-arylene (DSA), a polyfluorene (PFO)-based polymer, and a poly(p-phenylene vinylene) (PPV)-based polymer, etc.

The polycyclic compound according to an example embodiment may be a material included in the emission layer EML and radiating delayed fluorescence. Thus, the polycyclic compound represented by Formula 1 is a delayed fluorescence material. The polycyclic compound represented by Formula 1 is a TADF (thermally activated delayed fluorescence) material.

The polycyclic compound according to an example embodiment may be a TADF material emitting blue light. The polycyclic compound according to an example embodiment is a TADF material emitting deep blue light. The polycyclic compound according to an example embodiment may emit blue light having a wavelength region from about 440 nm to about 480 nm, from about 440 nm to about 475 nm, from about 440 nm to about 470 nm, or from about 440 nm to about 460 nm.

The polycyclic compound according to an example embodiment may have an absolute difference of about 0.2 eV or less between a singlet energy level and a triplet energy level. By controlling the singlet-triplet energy gap small, the TADF may be efficiently emitted.

The emission layer EML may further include a host. The host may include commonly used materials, for example, tris(8-hydroxyquinolino)aluminum (Alq3), 4,4'-bis(N-carbazolyl)-1,1'-biphenyl (CBP), poly(n-vinylcarbazole) (PVK), 9,10-di(naphthalene-2-yeanthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl] ether oxide (DPEPO), hexaphenyl cyclotriphosphazene (CP1), 1,4-bis(triphenylsilyl)benzene (UGH2), hexaphenylcyclotrisiloxane (DPSiO3), octaphenylcyclotetra siloxane (DPSiO4), 2,8-bis(diphenylphosphoryl)dibenzofuran (PPF), etc.

The emission layer EML may have a thickness, for example, from about 100 Å to about 1,000 Å.

The electron transport region ETR may be provided on the emission layer EML. The electron transport region ETR may include at least one of an electron blocking layer, an electron transport layer ETL, or an electron injection layer EIL, etc.

The electron transport region ETR may have a single layer formed using a single material, a single layer formed using a plurality of different materials, or a multilayer structure including a plurality of layers formed using a plurality of different materials. For example, the electron transport region ETR may include only the electron transport layer ETL.

For example, the electron transport region ETR may have the structure of a single layer such as the electron injection layer EIL or the electron transport layer ETL, or a single layer structure formed using an electron injection material and an electron transport material. In addition, the electron transport region ETR may have a single layer structure formed using a plurality of different materials, or a structure laminated from the first electrode EL1 of electron transport layer ETL/electron injection layer EIL, or hole blocking layer (exciton blocking layer)/electron transport layer ETL/electron injection layer EIL, etc. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

When the electron transport region ETR includes the electron transport layer ETL, the electron transport region ETR may include tris(8-hydroxyquinolinato)aluminum (Alq3), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebq2), 9,10-di(naphthalene-2-yl) anthracene (ADN), or a mixture thereof, etc. The thickness of the electron transport layer ETL may be from about 100 Å to about 1,000 Å, for example, from about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include, for example, LiF, lithium quinolate (LiQ), Li$_2$O, BaO, NaCl, CsF, a metal in lanthanides such as Yb, or a metal halide such as RbCl and RbI, etc. The electron injection layer EIL also may be formed using a mixture material of an electron transport material and an insulating organo metal salt. The organo metal salt may be a material having an energy band gap of about 4 eV or more. For example, the organo metal salt may include, for example, a metal acetate, a metal benzoate, a metal acetoacetate, a metal acetylacetonate, or a metal stearate. The thickness of the electron injection layer EIL may be from about 1 Å to about 100 Å, and from about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen), etc.

The second electrode EL2 may be provided on the electron transport region ETR. The second electrode EL2 may be a common electrode or a cathode. The second electrode EL2 may be a transmissive electrode, a transflective electrode or a reflective electrode. When the second electrode EL2 is the transmissive electrode, the second electrode EL2 may include a transparent metal oxide, for example, ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials or a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may decrease.

In the organic electroluminescence device 10, voltages are applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, and the excitons may emit light via transition from an excited state to a ground state.

When the organic electroluminescence device 10 is a top emission type, the first electrode EL1 may be a reflective electrode, and the second electrode EL2 may be a transmissive electrode or a transflective electrode. When the organic electroluminescence device 10 is a bottom emission type, the first electrode EL1 may be the transmissive electrode or the transflective electrode, and the second electrode EL2 may be the reflective electrode.

The organic electroluminescence device according to an example embodiment includes the polycyclic compound represented by Formula 1, thereby attaining high emission efficiency. For example, the polycyclic compound represented by Formula 1 may emit light via a TADF process. Accordingly, the organic electroluminescence device according to an example embodiment may accomplish high efficiency. More For example, the organic electroluminescence device according to an example embodiment may emit blue light via the TADF process and attain high efficiency. In addition, the organic electroluminescence device according to an example embodiment may be a blue emitting organic electroluminescence device with high efficiency, etc.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthetic Example

1. Synthesis of Compound 69

Compound 69, which is a polycyclic compound according to an example embodiment, may be synthesized, for example, by the following reaction.

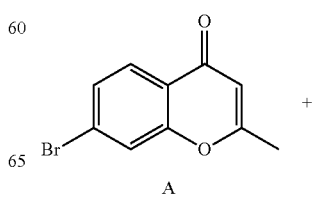

-continued

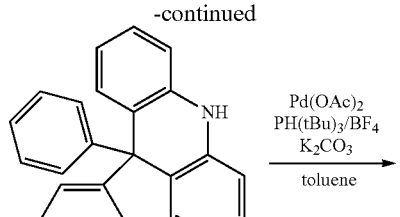

B

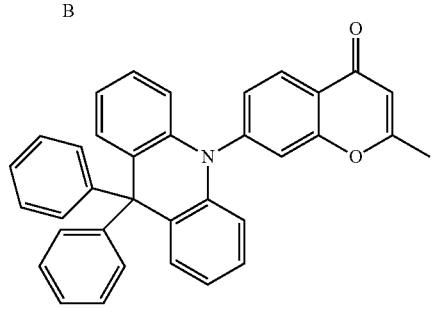

69

Under a nitrogen (N₂) atmosphere, 1.67 g of Compound B, 1.00 g of Compound A, 0.03 g of palladium acetate, 0.18 g of tri-tert-butylphosphonium tetrafluoroborate (PH(t-Bu)₃/BF₄, and 1.39 g of potassium carbonate (K₂CO₃) were added to a 100 mL, three-necked flask, followed by heating and refluxing in 30 mL of a toluene solvent (90° C.) for five days. The crude product thus obtained was separated by silica gel column chromatography (using a mixture solvent of ethyl acetate and hexane), and recrystallized using a mixture solvent of chloroform/methanol to produce 0.87 g (yield 42%) of a white solid.

The chemical shift values (δ) of the white solid compound measured by ¹H NMR were ¹H NMR (400 MHz, CDCl₃, δ): 8.28 (d, J=8.4 Hz, 1H), 7.28-7.23 (m, 6H), 7.13 (d, J=2.0 Hz, 1H), 7.10-7.06 (m, 3H), 6.99-6.96 (m, 4H), 6.94-6.93 (m, 4H), 6.49 (d, J=8.0 Hz, 2H), 6.21 (d, J=0.8 Hz, 1H), 2.38 (s, 3H). From the results, the white solid was identified as Compound 69.

2. Synthesis of Compound 74

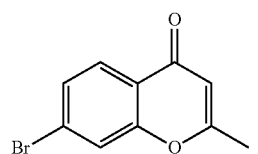

A

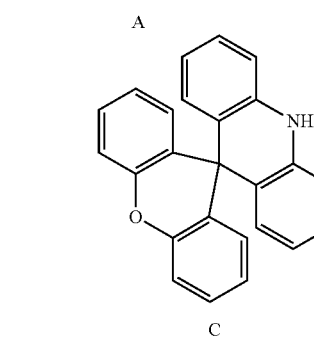

C

-continued

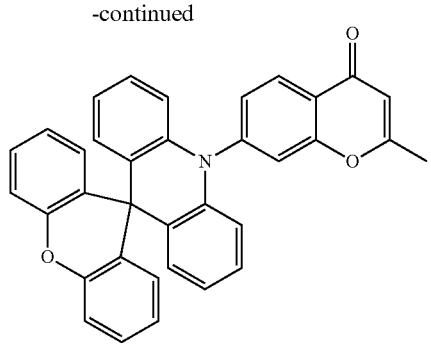

74

Under a nitrogen (N₂) atmosphere, 1.74 g of Compound C, 1.00 g of Compound A, 0.03 g of palladium acetate, 0.18 g of PH(t-Bu)₃/BF₄, and 1.39 g of potassium carbonate (K₂CO₃) were added to a 100 mL, three-necked flask, followed by heating and refluxing in 30 mL of a toluene solvent (90° C.) for five days. The crude product thus obtained was separated by silica gel column chromatography (using a mixture solvent of ethyl acetate and hexane), and recrystallized using a mixture solvent of dichloromethane/methanol to produce 1.05 g (yield 50%) of a white solid.

The chemical shift values (δ) of the white solid compound measured by ¹H NMR were ¹HNMR (400 MHz, CDCl₃, δ): 8.51 (d, J=8.4 Hz, 1H), 7.60 (d, J=2.0 Hz, 1H), 7.48 (dd, J=8.2 Hz, 1.8 Hz, 1H), 7.21-7.13 (m, 6H), 6.99-6.95 (m, 2H), 6.92-6.87 (m, 4H), 6.72 (td, J=7.4 Hz, 1.3 Hz, 2H), 6.30-6.26 (m, 3H), 2.45 (s, 3H). From the results, the white solid was identified as Compound 74.

3. Synthesis of Compound 108

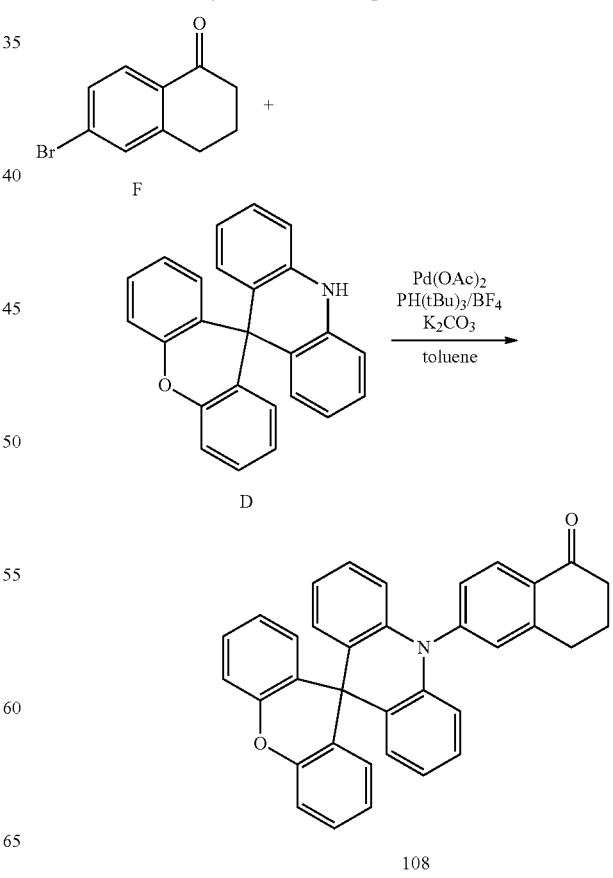

108

Under a nitrogen (N₂) atmosphere, 0.64 g of Compound D, 0.70 g of Compound F, 0.01 g of palladium acetate, 0.08 g of PH(t-Bu)₃/BF₄, and 0.61 g of potassium carbonate (K₂CO₃) were added to a 100 mL, three-necked flask, followed by heating and refluxing in 30 mL of a toluene solvent (90° C.) for three days. The crude product thus obtained was separated by silica gel column chromatography (using a mixture solvent of ethyl acetate and hexane), and recrystallized using a mixture solvent of dichloromethane/methanol to produce 0.5 g (yield 55%) of a white solid.

The chemical shift values (δ) of the white solid compound measured by ¹H NMR were ¹H NMR (400 MHz, CDCl₃, δ): 8.37 (d, J=8.4 Hz, 1H), 7.42-7.38 (m, 2H), 7.17-7.13 (m, 6H), 6.95-6.87 (m, 6H), 6.71-6.69 (m, 2H), 6.27 (d, J=8.0 Hz, 2H), 3.10 (s, 2H), 2.78 (m, 2H), 2.27 (s, 2H). From the results, the white solid was identified as Compound 74.

4. Synthesis of Compound 313

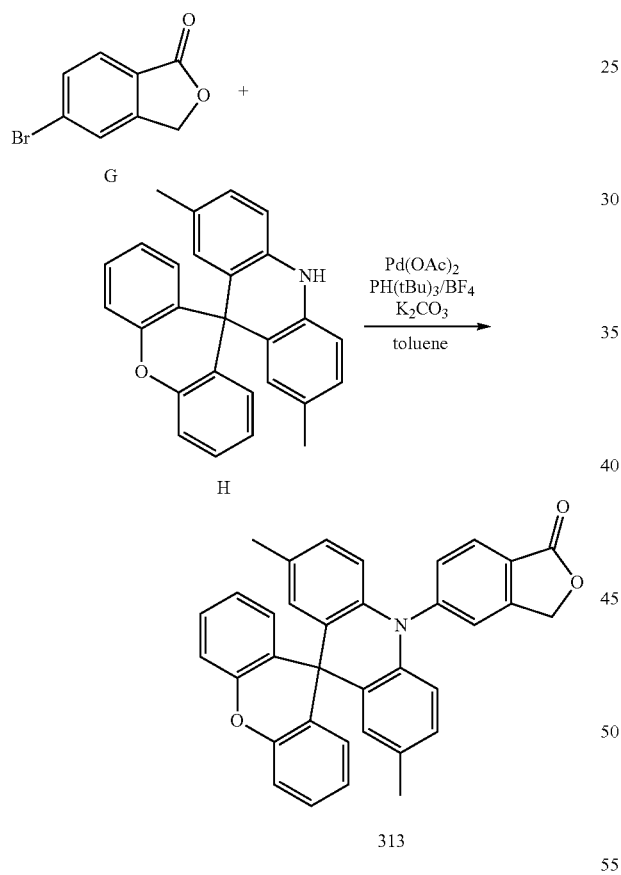

Under a nitrogen (N₂) atmosphere, 4.76 g of Compound H, 2.70 g of Compound G, 0.09 g of palladium acetate, 0.55 g of PH(t-Bu)₃/BF₄, and 5.26 g of potassium carbonate (K₂CO₃) were added to a 300 mL, three-necked flask, followed by heating and refluxing in 150 mL of a toluene solvent (90° C.) for five days. The crude product thus obtained was separated by silica gel column chromatography (using a mixture solvent of chloroform, ethyl acetate and hexane), and recrystallized using a mixture solvent of chloroform/hexane to produce 3.79 g (yield 59%) of a white solid.

The chemical shift values (δ) of the white solid compound measured by ¹H NMR were ¹H NMR (400 MHz, DMSO-d₆, δ): 8.21 (d, J=8.0 Hz, 1H), 7.90 (s, 1H), 7.70 (d, J=8.0 Hz, 1H), 7.28-7.22 (m, 4H), 7.12-7.09 (m, 2H), 7.05-7.00 (m, 2H), 6.73 (dd, J=8.8 Hz, 2.0 Hz, 2H), 6.47 (d, J=1.6 Hz, 2H), 6.11 (d, J=8.4 Hz, 2H) 5.56 (s, 2H), 1.95 (s, 6H). From the results, the white solid was identified as Compound 313.

Device Manufacturing Examples

As described in further detail below, organic electroluminescence devices of Examples 1 to 3 were manufactured using Compounds 74, 312, and 313 as dopant materials in an emission layer.

Example Compounds

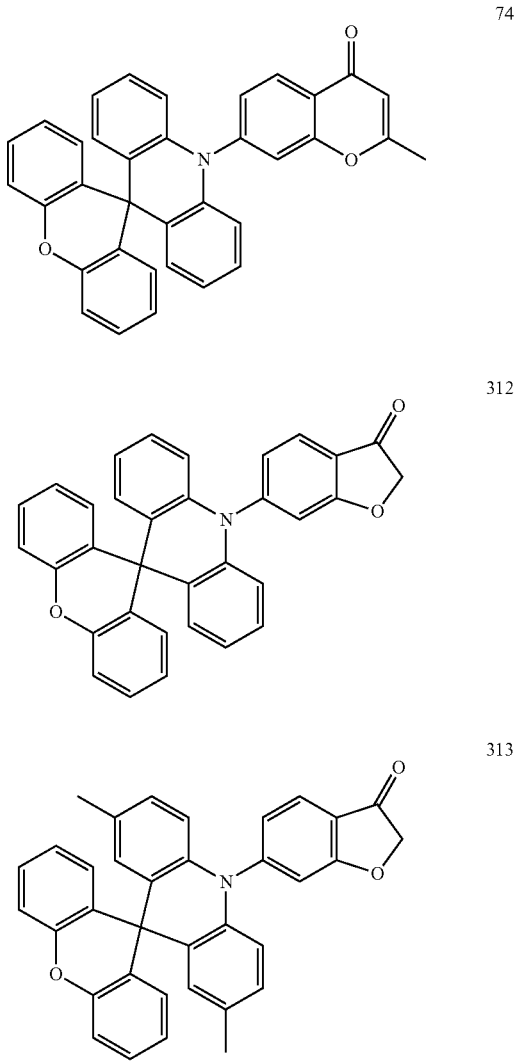

Organic electroluminescence devices of Comparative Examples 1 and 2 were manufactured using Comparative Compounds X1 and X2 as dopant materials in an emission layer.

Comparative Compounds

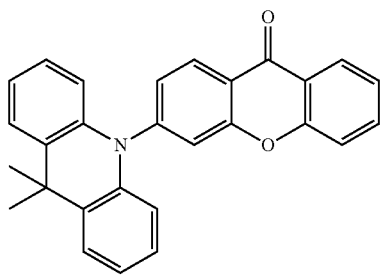
X-1

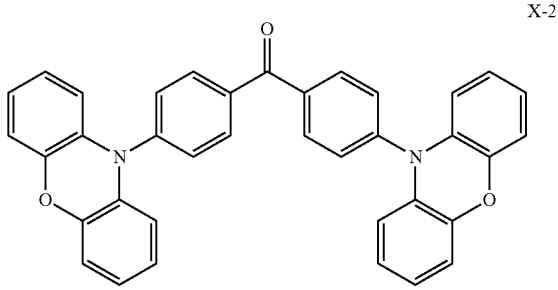
X-2

The organic electroluminescence devices of Examples 1 to 3 and Comparative Examples 1 and 2 were manufactured as follows. On a glass substrate, ITO (first electrode) with a thickness of about 150 nm was patterned, washed with ultrapure water, and treated with UV-ozone for about 10 minutes. After that, a hole injection layer with a thickness of about 10 nm was formed using [2,3-f: 2',3'-h]quinoxaline-2,3,6,7,10,11-hexacarbonitrile (HAT-CN), a hole transport layer with a thickness of about 80 nm was formed using N,N'-di(naphthalene-1-yl)-N,N'-diphenyl-benzidine (NPB), an emission layer doped with 18% bis{2-[di-(phenyl)phosphino]phenyl} ether oxide (DPEPO) and having a layer thickness of about 20 nm was formed, an electron transport layer with a thickness of about 30 nm was formed using 1,3,5-tris(1-phenyl-1H-benzimidazol-2-yl)benzene (TPBi), an electron injection layer with a thickness of about 0.5 nm was formed using lithium fluoride (LiF), and a second electrode with a thickness of about 100 nm was formed using aluminum (Al). Each layer and the second electrode were formed by a resistance heating method.

After that, the maximum emission wavelength and external quantum efficiency of the organic electroluminescence devices thus manufactured were measured. The evaluation results are shown in the following Table 1.

The maximum emission wavelength was obtained using a deposited specimen of a target compound for measuring on a quartz glass plate by measuring the maximum emission wavelength of an emission spectrum at room temperature (about 300K).

The current density of a device was measured using Source Meter 2400 Series (Keithley Instruments), the voltage was measured using a CS-200 luminance colorimeter (Konica Minolta Holdings Co., Ltd.), and the external quantum efficiency was measured using C9920-12 (HAMAMATSU Photonics Co.).

TABLE 1

| Device manufacturing examples | Dopant materials in emission layer | Maximum emission wavelength λmax (nm) | External quantum efficiency EQE (%) |
|---|---|---|---|
| Example 1 | Compound 74 | 443 | 13.9 |
| Example 2 | Compound 312 | 440 | 7.4 |
| Example 3 | Compound 313 | 460 | 12.9 |
| Comparative Example 1 | Comparative Compound X-1 | 510 | 8.5 |
| Comparative Example 2 | Comparative Compound X-2 | 550 | 10.7 |

In Table 1, λmax is the maximum emission wavelength, and EQE is the external quantum efficiency.

Referring to the results in Table 1, the organic electroluminescence devices of Examples 1 to 3 using the polycyclic compounds according to example embodiments emitted deep blue light with a maximum emission wavelength of 470 nm or less, and had high external quantum efficiency.

In Comparative Compound X-1 used in Comparative Example 1, an electron acceptor has a tricyclic structure and has a broader π conjugation system than the polycyclic compound according to an example embodiment. Comparative Compound X-2 used in Comparative Example 2 has an electron acceptor including a carbonyl group; however is different from the polycyclic compounds according to an example embodiment in that a carbonyl group is not substituted in a ring. Comparative Examples 1 and 2 are different from the polycyclic compound according to an example embodiment in exhibiting high external quantum efficiency and emitting light in sky blue to green region.

Through the above-described results, it is found that the organic electroluminescence device using the polycyclic compound according to an present disclosure may attain blue emission and high efficiency, simultaneously.

By way of summation and review, as an organic electroluminescence device, an organic device including, for example, a first electrode, a hole transport layer disposed on the first electrode, an emission layer disposed on the hole transport layer, an electron transport layer disposed on the emission layer, and a second electrode disposed on the electron transport layer may be used. Holes are injected from the first electrode, and the injected holes move via the hole transport layer and are injected to the emission layer. Meanwhile, electrons are injected from the second electrode, and the injected electrons move via the electron transport layer and are injected to the emission layer. The holes and electrons injected to the emission layer recombine to produce excitons in the emission layer. The organic electroluminescence device emits light using light generated by the excitons.

The development of various fluorescent materials to attain an organic electroluminescence device with high efficiency is being conducted. For example, a technique aiming to attain the high efficiency of a fluorescent device based on triplet-triplet annihilation (TTA) producing singlet excitons due to the collision of triplet excitons may be used. According to the technique, the fluorescence emission efficiency may be improved to about twice to three times that of the conventional fluorescent device; however, the theoretical singlet production ratio of TTA is about 40%.

Fluorescent emission by thermally activated delayed fluorescence (TADF) has theoretical production efficiency of singlet excitons of about 100%, and is expected to be a method for rapidly increasing the emission efficiency. In particular, various TADF materials exhibiting red, green color have been considered. However, TADF materials exhibiting blue color with high efficiency present a challenge in molecular designing. For the application to a full color device, the creation of a blue emitting device using the TADF is important.

For example, for a TADF material having an electron acceptor part including a cyclic carbonyl group may be selected green emission may be provided but blue emission may be easily obtained. For example, a TADF material with sky blue emission including pyridine as an electron acceptor may be selected; however a material attaining blue emission with shorter wavelength is desired.

As described above, embodiments may provide a polycyclic compound and an organic electroluminescence device including the same. Embodiments may provide a polycyclic compound for a TADF material accomplishing blue emission and an organic electroluminescence device including the same. Embodiments may provide a polycyclic compound for a TADF material accomplishing blue emission, which uses a it polycyclic compound that is a weak acceptor with a decreased 7E conjugation system, and an organic electroluminescence device including the same.

A compound according to an example embodiment may be used as a material for an organic electroluminescence device.

A compound according to an example embodiment may improve emission efficiency of the organic electroluminescence device. A compound according to an example embodiment may have small difference between singlet and triplet energy levels, and have short retardant life, improved roll-off, and high efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A polycyclic compound represented by the following Formula 1:

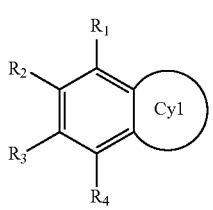

[Formula 1]

wherein in Formula 1,

Cy1 is a substituted or unsubstituted five- or six-membered cyclic hydrocarbon containing a single carbonyl-group, or a substituted or unsubstituted five- or six-membered heterocycle containing a single carbonyl-group, and $R_1$ to $R_4$ are each independently a hydrogen atom or a group represented by one of the following Formula 2 or 3,

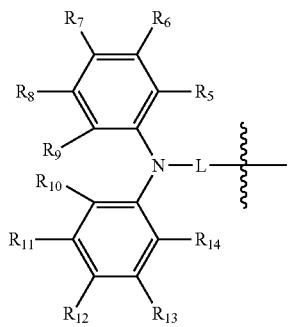

[Formula 2]

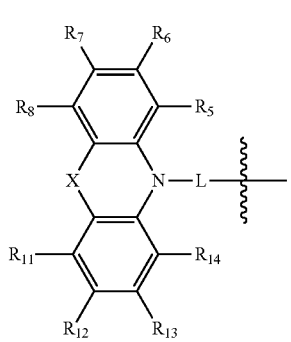

[Formula 3]

wherein in Formulae 2 and 3,

L is a direct linkage or substituted or unsubstituted arylene group having 6 to 30 carbon atoms forming a ring, $R_5$ to $R_{14}$ are each independently a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring, X is a direct linkage, $CR_{15}R_{16}$, $SiR_{17}R_{18}$, $GeR_{19}R_{20}$, $NR_{21}$, O, or S, and $R_{15}$ to $R_{21}$ are each independently a substituted or unsubstituted aryl group having 6 to 12 carbon atoms forming a ring, where the aryl group may combine with an adjacent group to form a ring, wherein a substituent of the substituted five- or six-membered cyclic hydrocarbon containing a single carbonyl-group, and a substituent of the substituted five- or six-membered heterocycle containing a single carbonyl-group are each independently a deuterium atom, halogen atom, cyano group, nitro group, amino group, silyl group, boron group, arylamine group, phosphine oxide group, phosphine sulfide group, alkyl group, alkenyl group, aryl group, or heteroaryl group.

2. The polycyclic compound as claimed in claim 1, wherein the polycyclic compound represented by Formula 1 is represented by the following Formula 1-1 or 1-2:

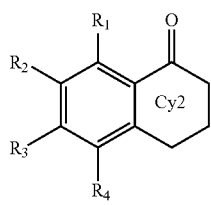

[Formula 1-1]

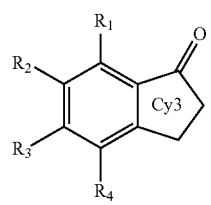

[Formula 1-2]

wherein in Formulae 1-1 and 1-2,

Cy2 and Cy3 are each independently a substituted or unsubstituted cyclic hydrocarbon or substituted or unsubstituted heterocycle, and $R_1$ to $R_4$ are the same as defined in claim 1.

3. The polycyclic compound as claimed in claim 1, wherein the polycyclic compound represented by Formula 1 is represented by the following Formula 1-3 or 1-4:

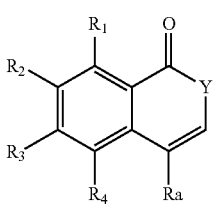

[Formula 1-3]

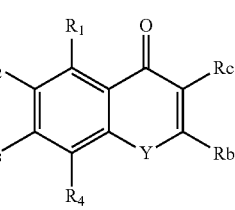

[Formula 1-4]

wherein in Formulae 1-3 and 1-4,

Y is O or $NR_{22}$, $R_{22}$ is a hydrogen atom, substituted or unsubstituted alkyl group having 1 to 15 carbon atoms, or substituted or unsubstituted aryl group having 6 to 30 carbon atoms forming a ring, Ra to Rc are each independently a hydrogen atom or substituted or unsubstituted alkyl group having 1 to 15 carbon atoms, and $R_1$ to $R_4$ are the same as defined in claim 1.

4. The polycyclic compound as claimed in claim 1, wherein the polycyclic compound represented by Formula 1 is represented by the following Formula 1-5 or 1-6:

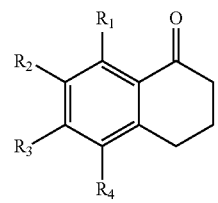

[Formula 1-5]

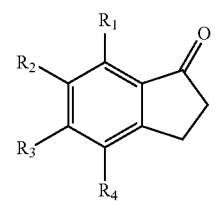

[Formula 1-6]

wherein in Formulae 1-5 and 1-6, $R_1$ to $R_4$ are the same as defined in claim 1.

5. The polycyclic compound as claimed in claim 1, wherein the polycyclic compound represented by Formula 1 is represented by the following Formula 1-7:

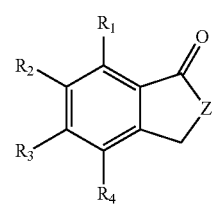

[Formula 1-7]

wherein in Formula 1-7,

Z is O or $NR_{23}$, $R_{23}$ is hydrogen atom, substituted or unsubstituted alkyl group having 1 to 15 carbon atoms, or substituted or unsubstituted aryl group having 6 to 30 carbon atoms forming a ring, and $R_1$ to $R_4$ are the same as defined in claim 1.

6. The polycyclic compound as claimed in claim 1, wherein the polycyclic compound represented by Formula 1 is represented by the following Formula 1-8:

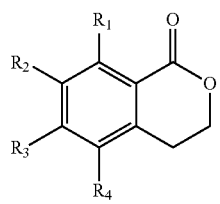

[Formula 1-8]

wherein in Formula 1-8, $R_1$ to $R_4$ are the same as defined in claim 1.

7. The polycyclic compound as claimed in claim 1, wherein the polycyclic compound represented by Formula 1 is represented by one of the following Formulae 1-9 to 1-24:

[Formula 1-9]
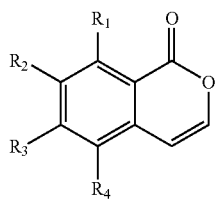
[Formula 1-10]
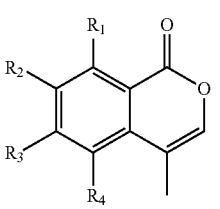
[Formula 1-11]
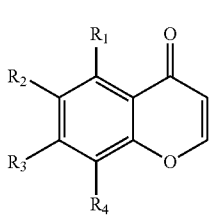
[Formula 1-12]
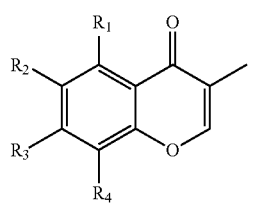
[Formula 1-13]
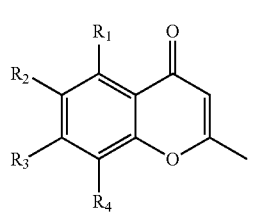
[Formula 1-14]
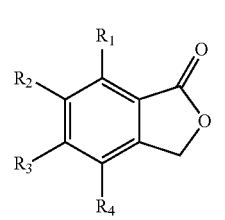
[Formula 1-15]
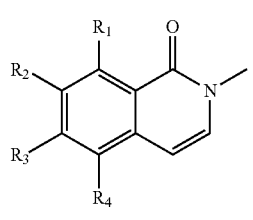
[Formula 1-16]
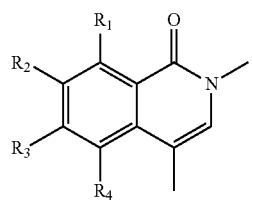
[Formula 1-17]
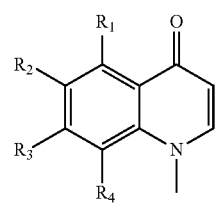
[Formula 1-18]
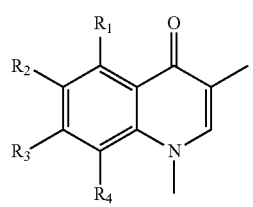
[Formula 1-19]
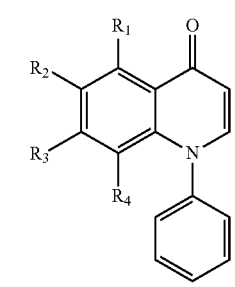
[Formula 1-20]
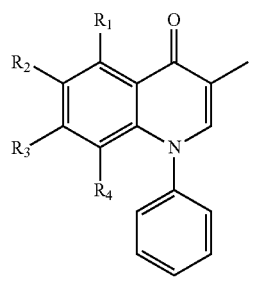
[Formula 1-21]
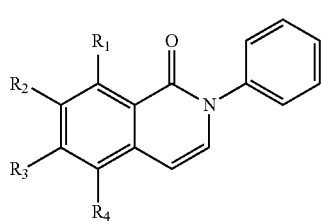
[Formula 1-22]
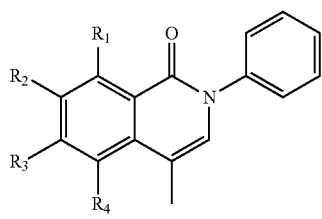

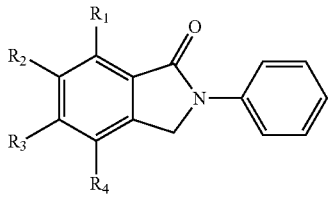
[Formula 1-23]

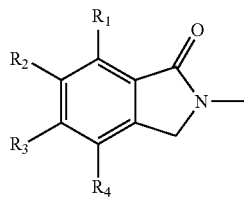
[Formula 1-24]

wherein in Formulae 1-9 to 1-24, $R_1$ to $R_4$ are the same as defined in claim 1.

8. The polycyclic compound as claimed in claim 1, wherein one of $R_2$ and $R_3$ is represented by Formula 2 or 3, and the other one of $R_2$ and $R_3$, $R_1$, and $R_4$ are a hydrogen atom.

9. The polycyclic compound as claimed in claim 1, wherein L is a direct linkage.

10. The polycyclic compound as claimed in claim 1, wherein $R_1$ to $R_4$ are each independently a hydrogen atom or a group represented by one of Formula 2 and the following Formulae 3-1 to 3-4:

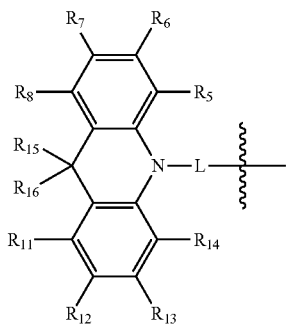
[Formula 3-1]

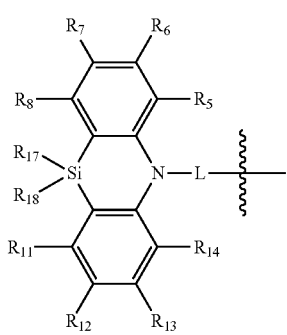
[Formula 3-2]

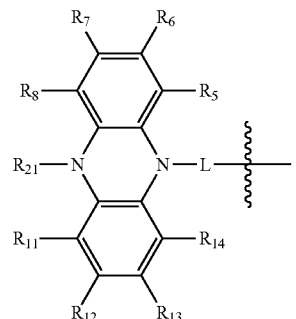
[Formula 3-3]

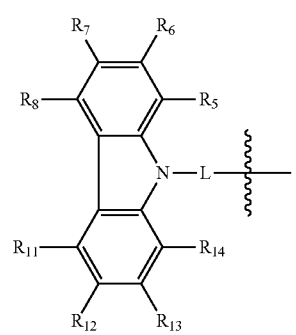
[Formula 3-4]

wherein in Formulae 3-1 to 3-4,

L, $R_5$ to $R_{18}$, and $R_{21}$ are the same as defined in claim 1.

11. The polycyclic compound as claimed in claim 1, wherein $R_1$ to $R_4$ are each independently a hydrogen atom or one of Formula 2 and the following Formulae 3-5 to 3-11:

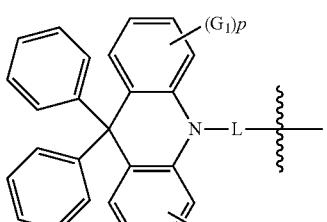
[Formula 3-5]

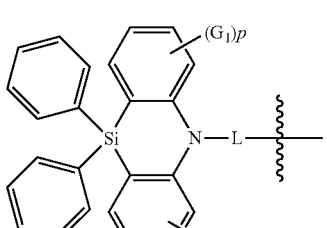
[Formula 3-6]

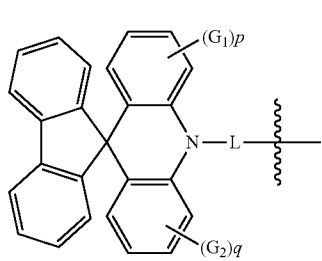
[Formula 3-7]

-continued

[Formula 3-8]

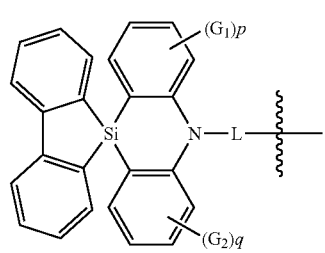

[Formula 3-9]

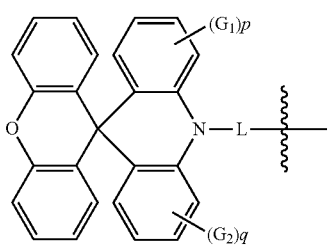

[Formula 3-10]

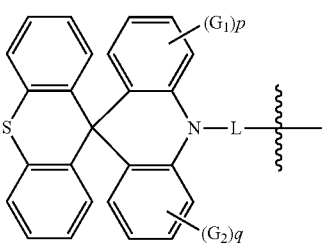

[Formula 3-11]

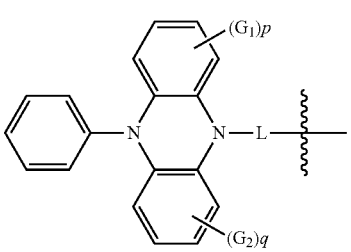

wherein, in Formulae 3-5 to 3-11, $G_1$ and $G_2$ are each independently a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring, p and q are each independently an integer of 0 to 4, and L is the same as defined in claim 1.

12. The polycyclic compound as claimed in claim 1, wherein $R_5$ to $R_{14}$ are each independently a hydrogen atom, halogen atom, trialkylsilyl group, diphenylamine group, methyl group, phenyl group, or carbazole group.

13. The polycyclic compound as claimed in claim 1, wherein the polycyclic compound represented by Formula 1 is one of compounds represented in the following Compound Group 1:

1

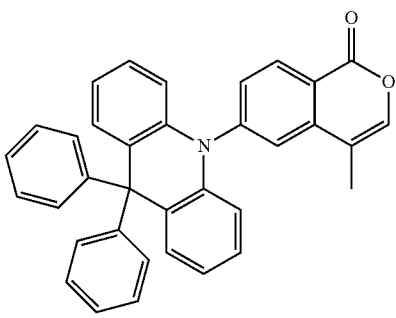

2

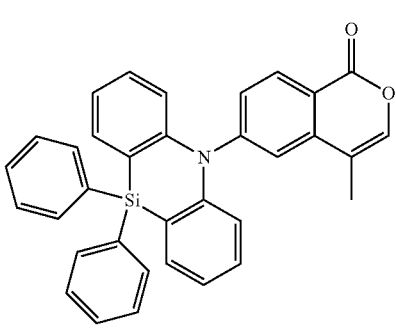

3

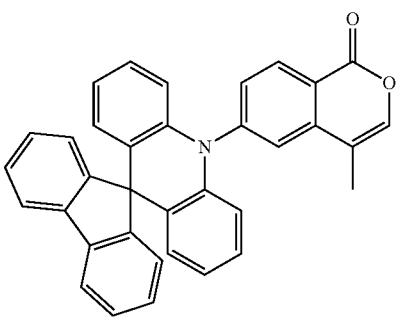

4

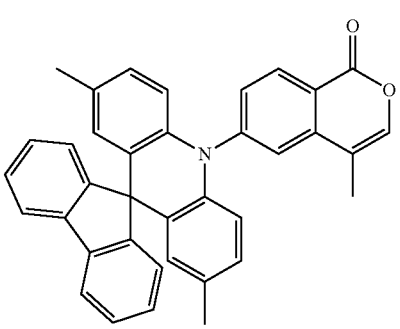

5

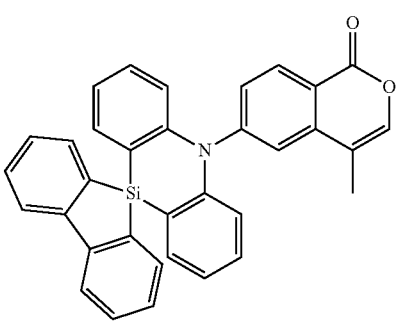

-continued
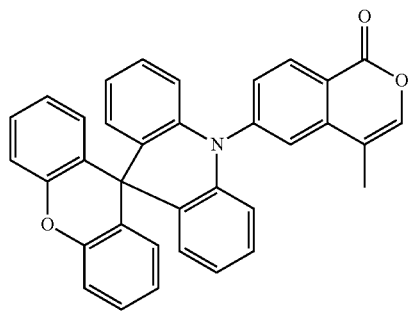
6
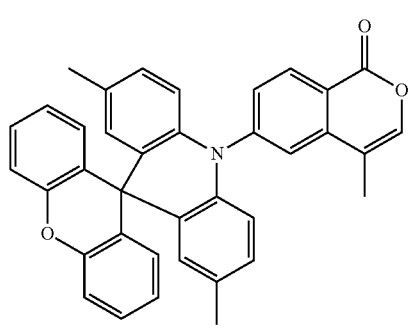
7
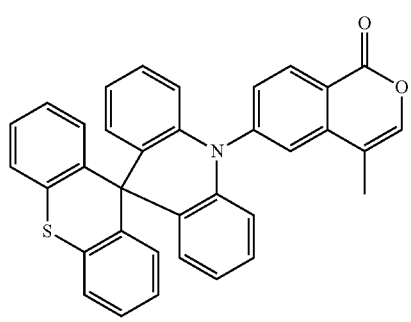
8
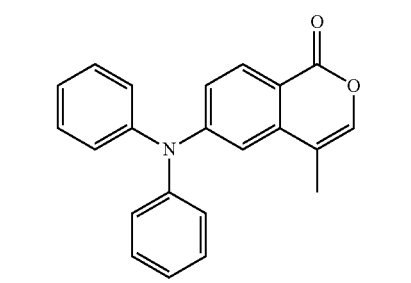
9
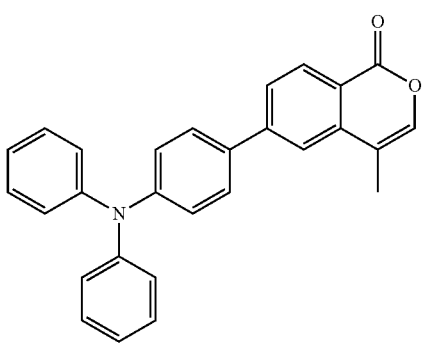
10
-continued
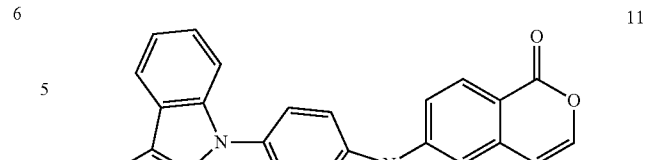
11
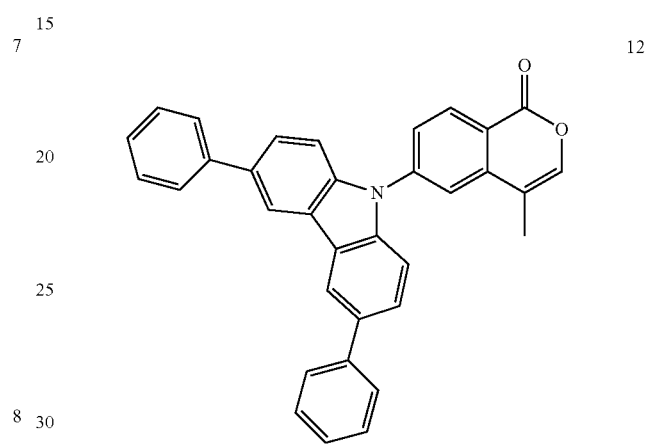
12
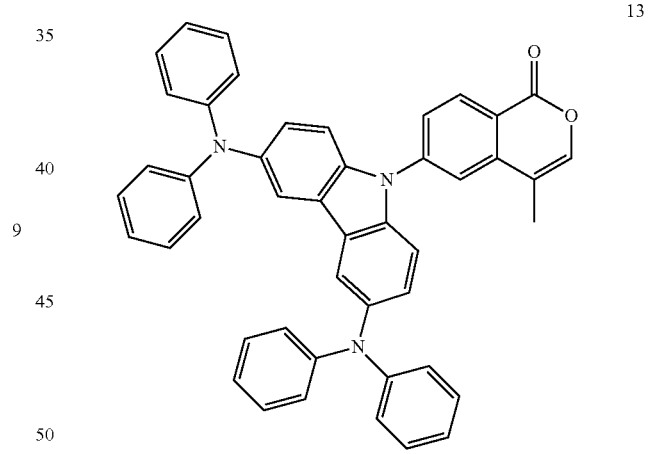
13
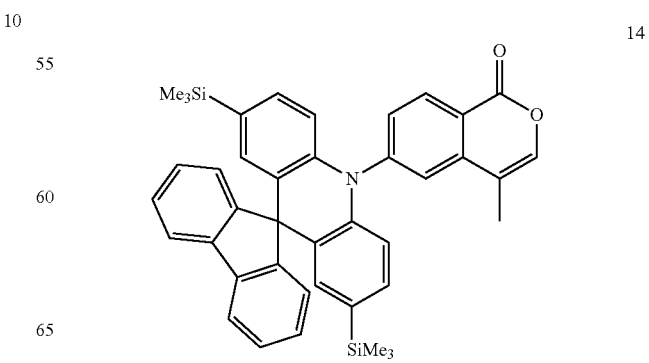
14

135
-continued
15
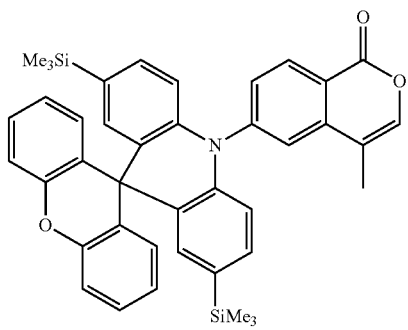
16
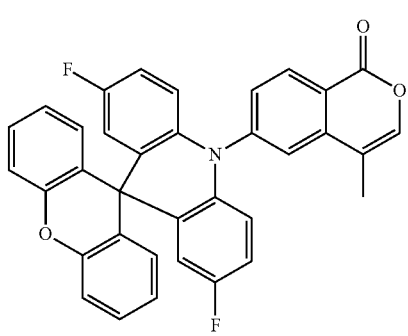
17
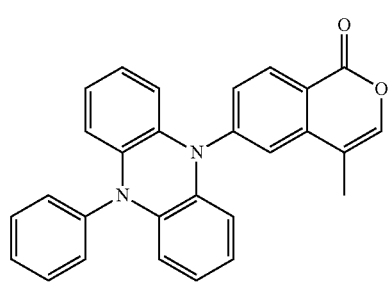
18
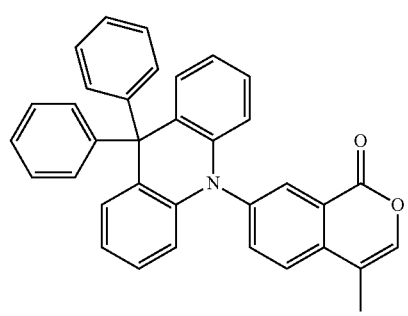
19
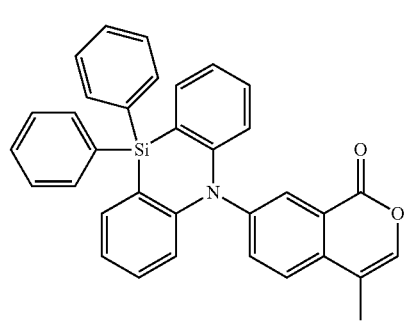
136
-continued
20
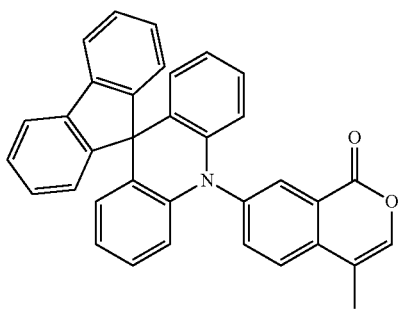
21
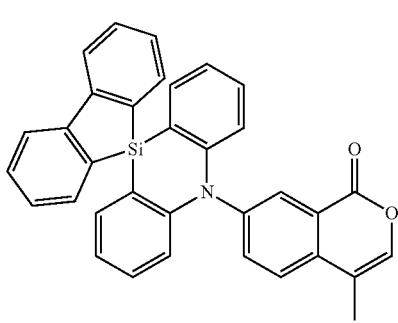
22
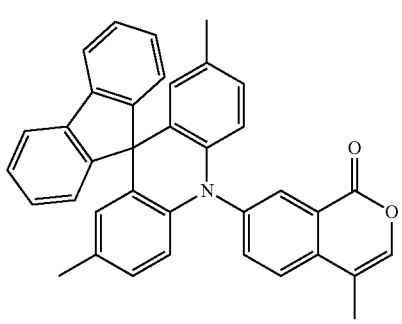
23
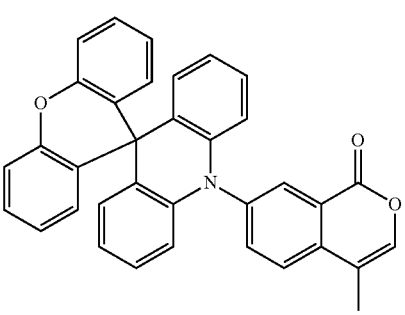
24
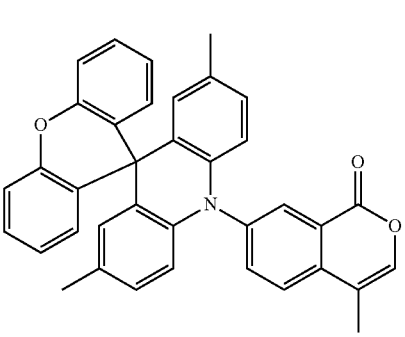

25
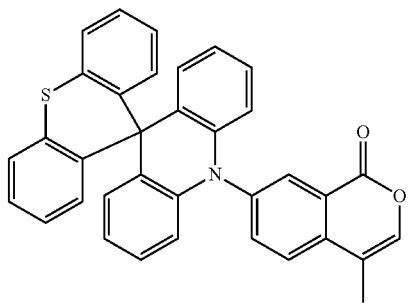
26
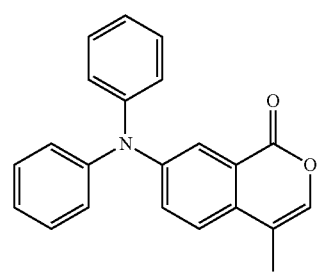
27
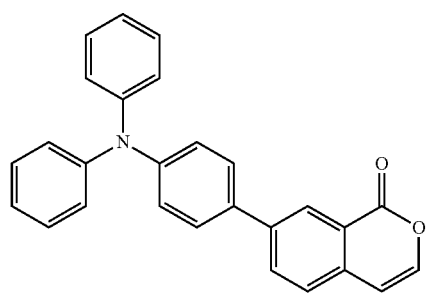
28
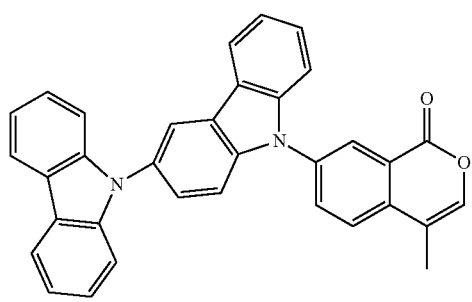
29
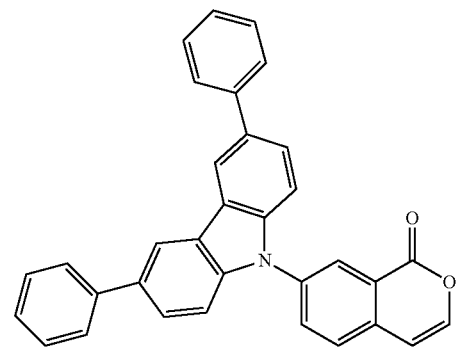
30
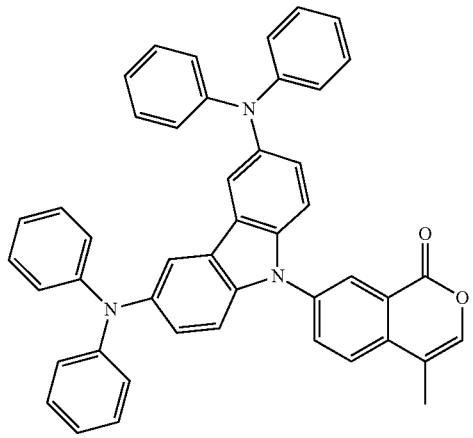
31
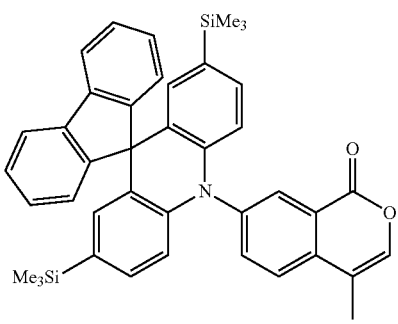
32
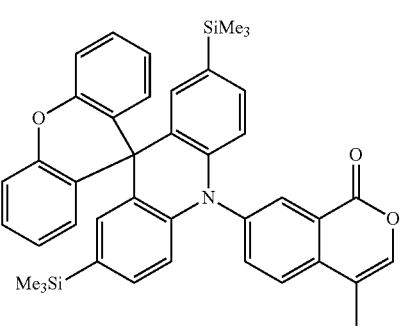
33
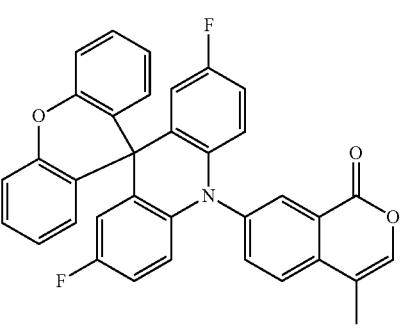

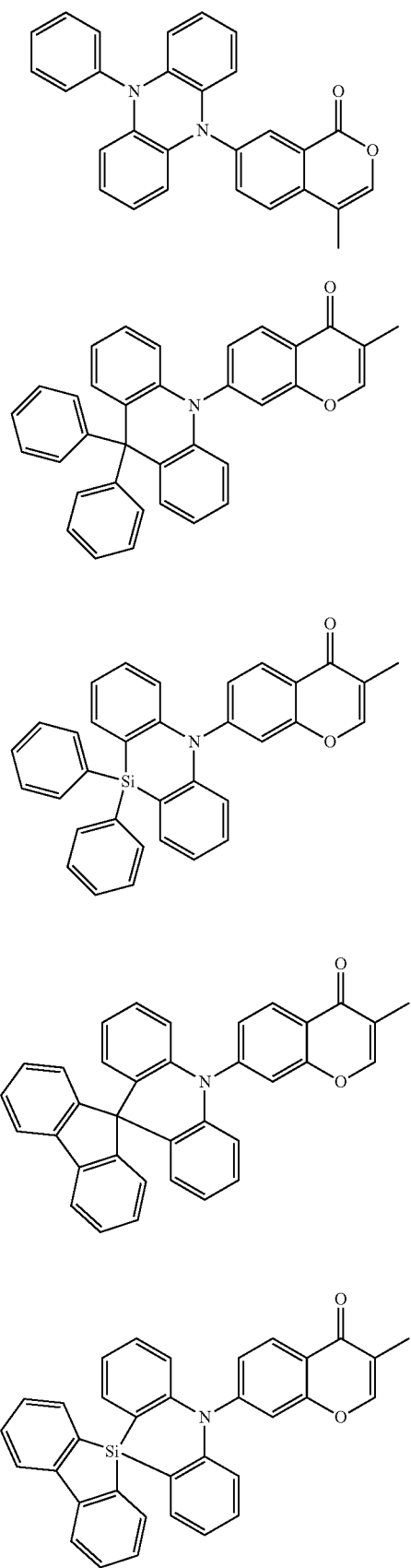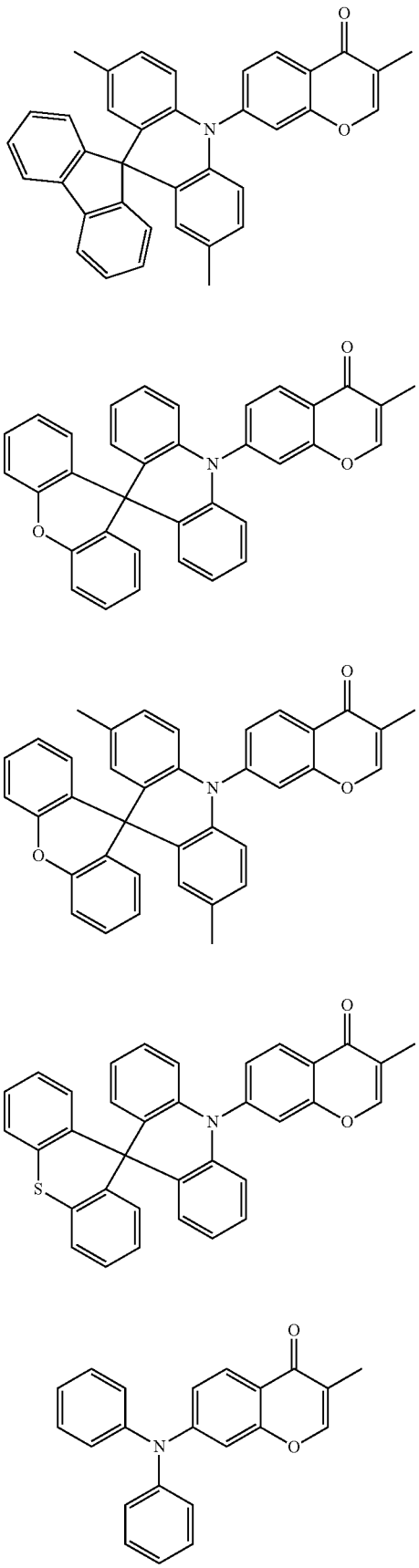

44
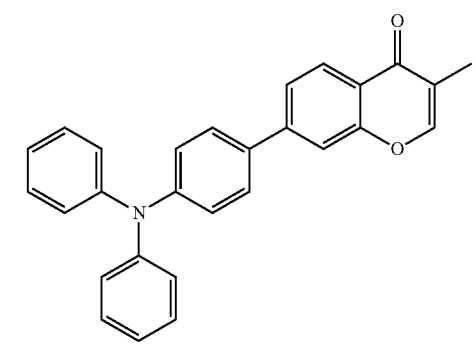
45
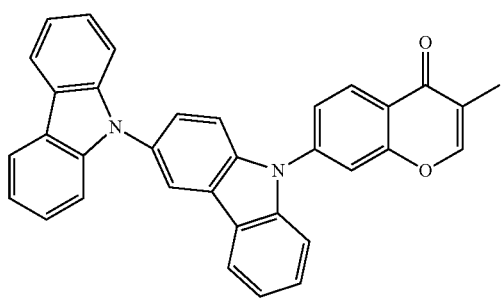
46
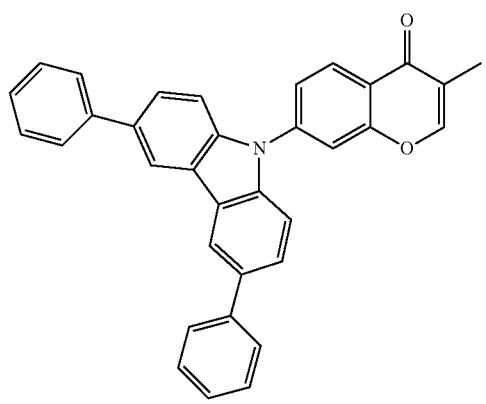
47
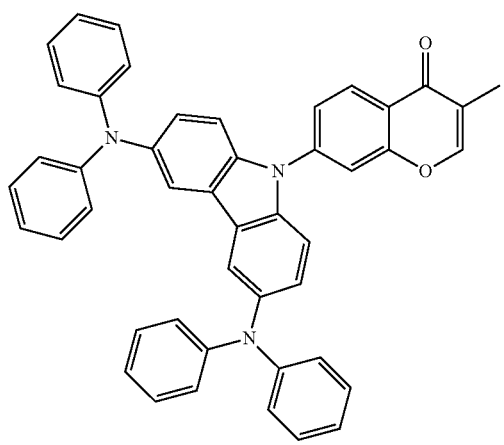
48
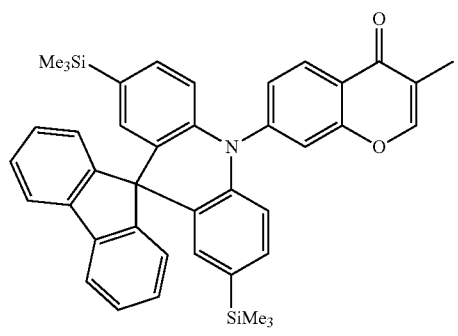
49
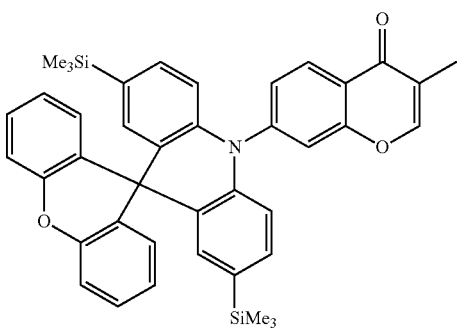
50
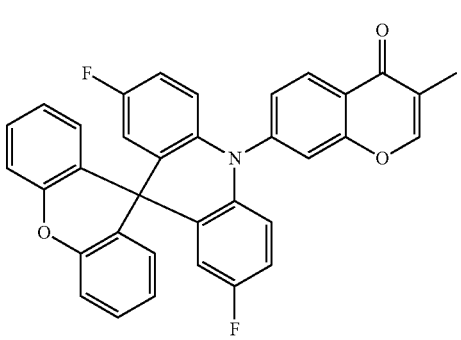
51
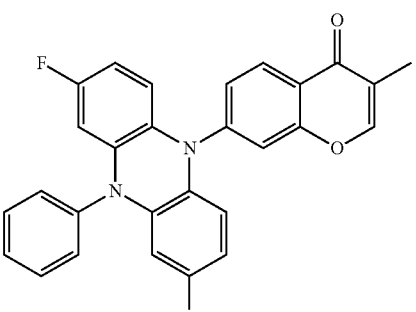
52
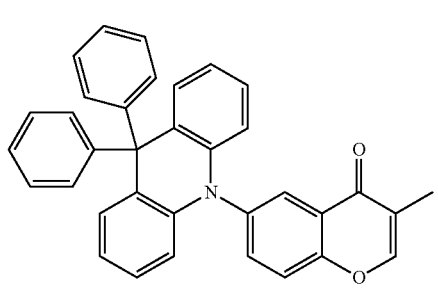

53
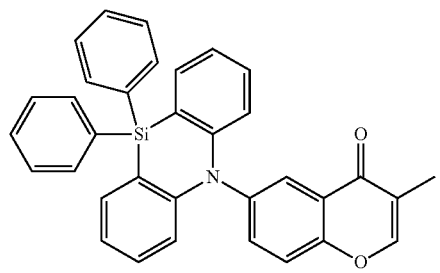
54
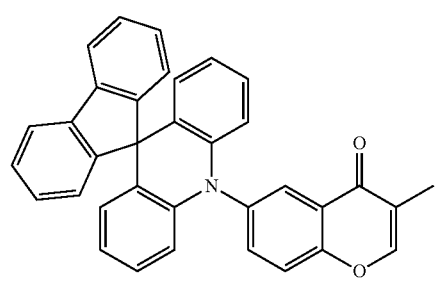
55
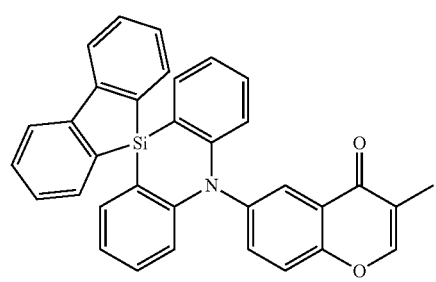
56
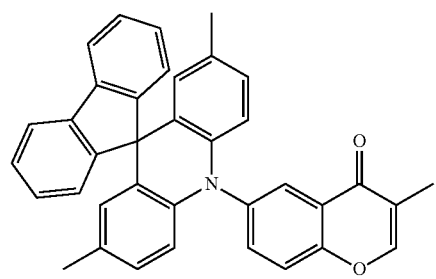
57
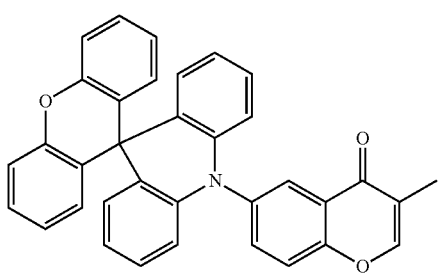
58
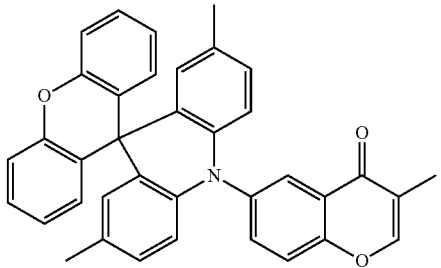
59
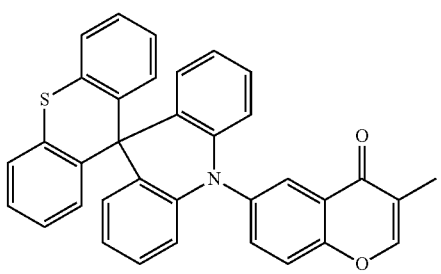
60
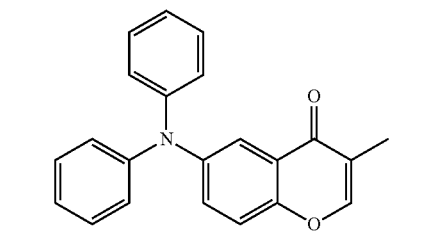
61
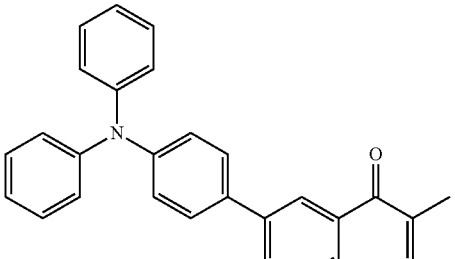
62
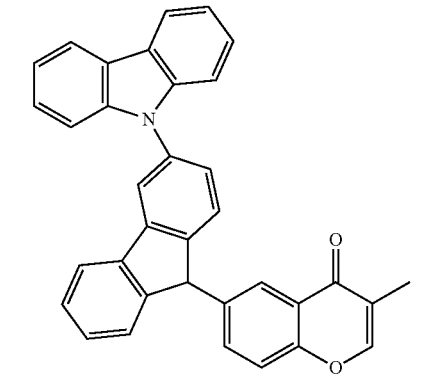

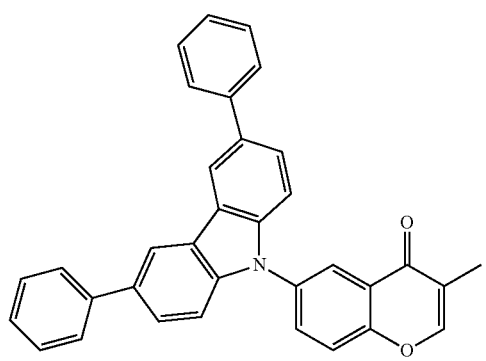
63
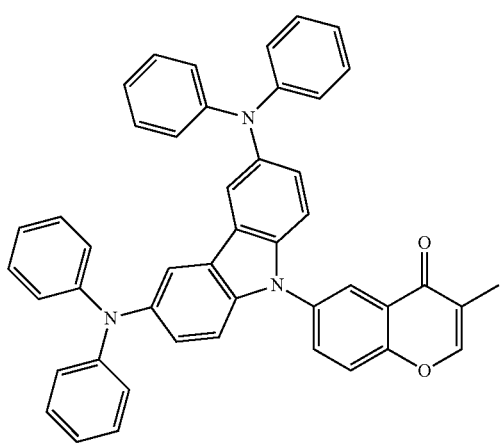
64
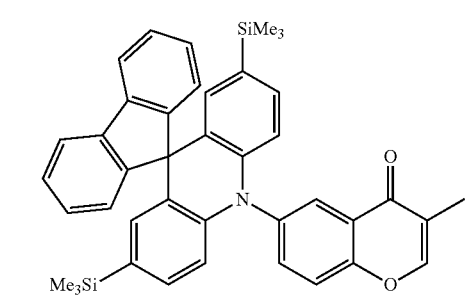
65
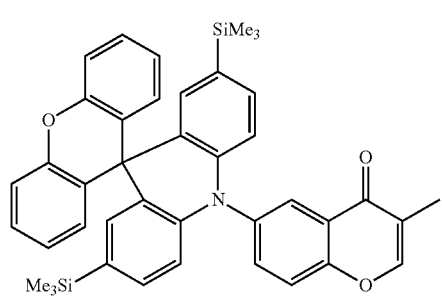
66
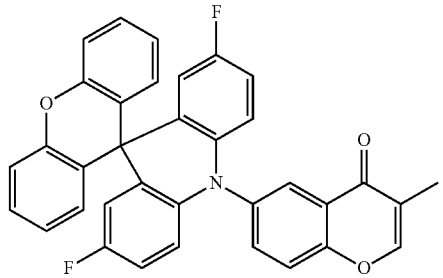
67
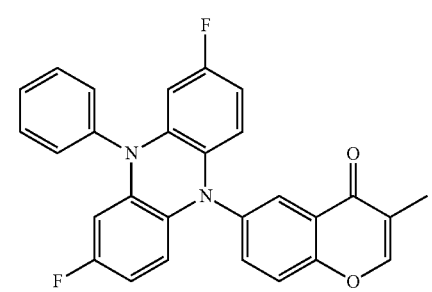
68
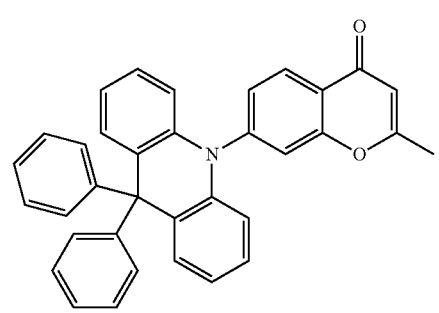
69
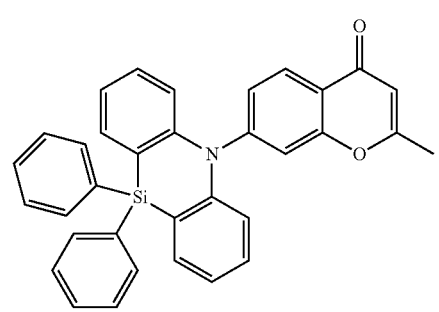
70
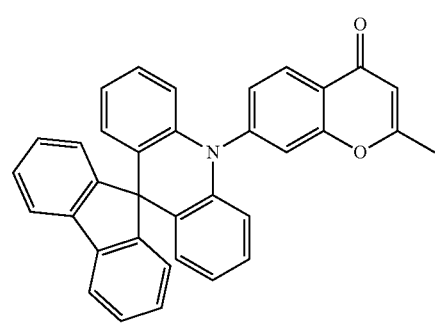
71

72
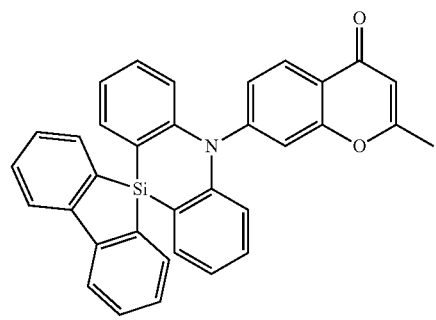
73
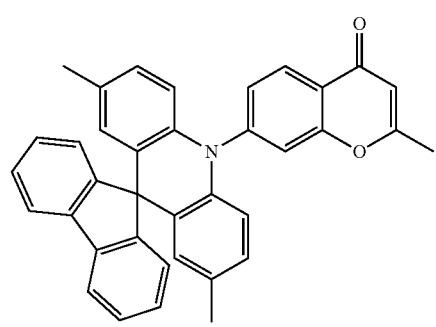
74
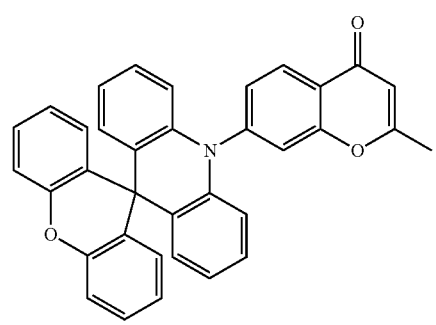
75
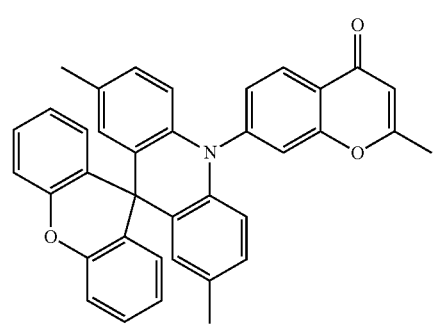
76
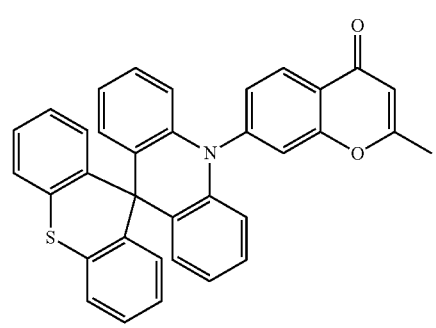
77
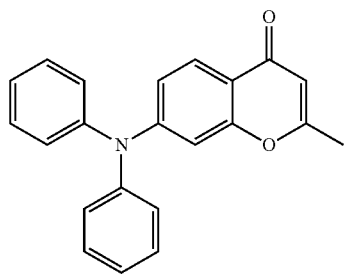
78
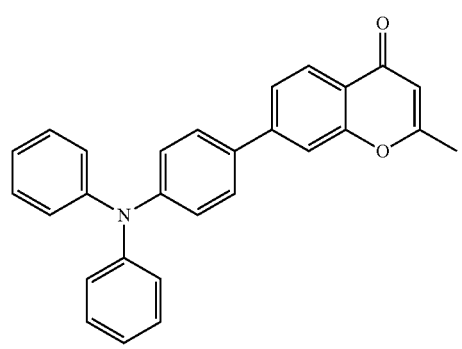
79
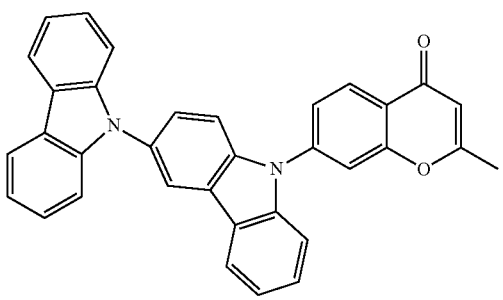
80
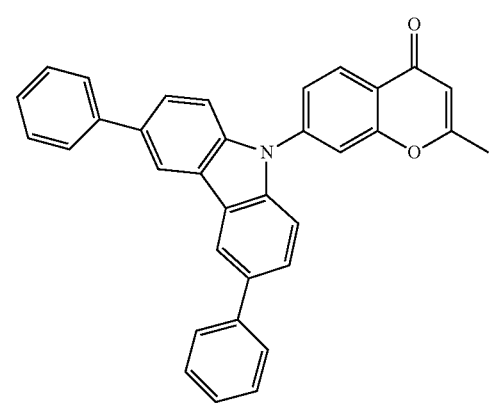

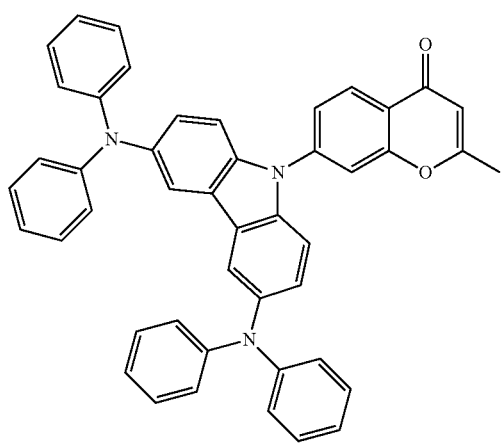
81
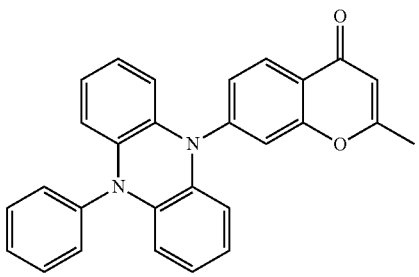
85
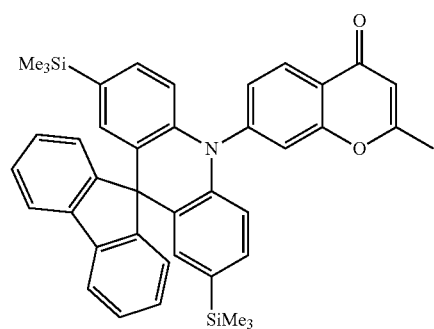
82
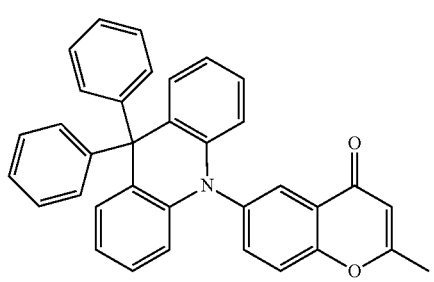
86
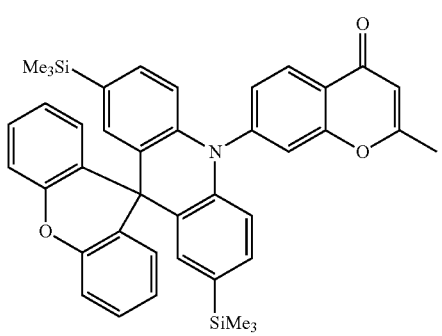
83
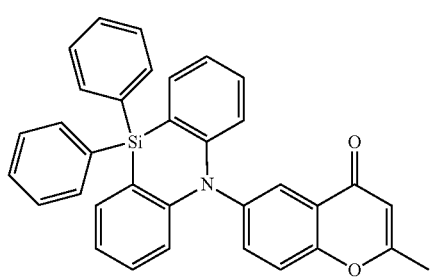
87
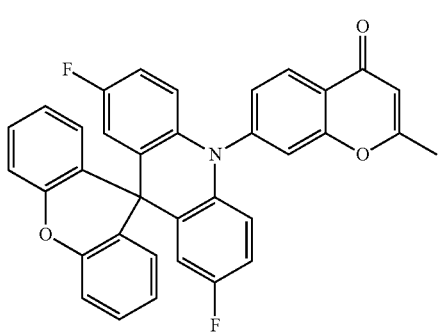
84
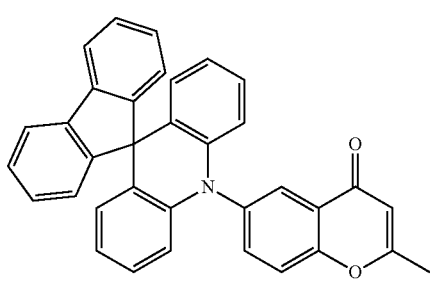
88
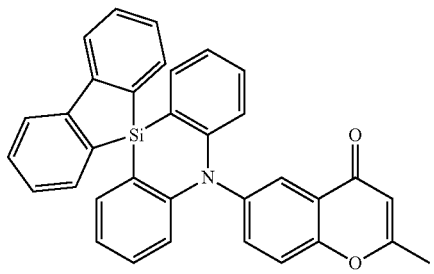
89

90
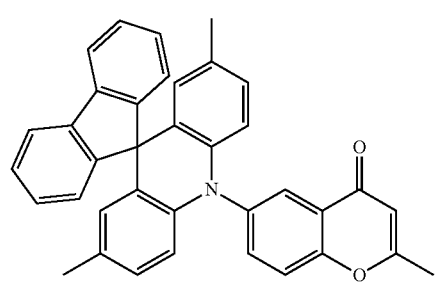
91
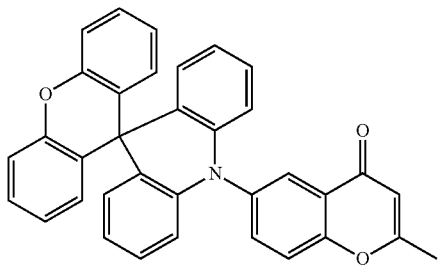
92
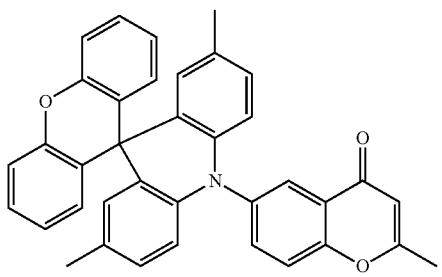
93
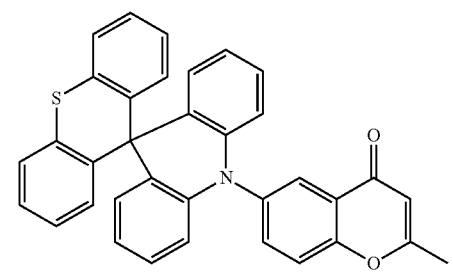
94
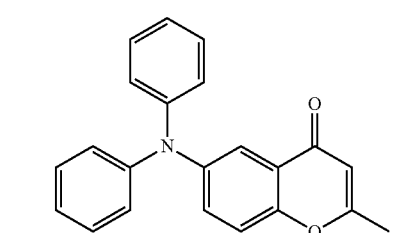
95
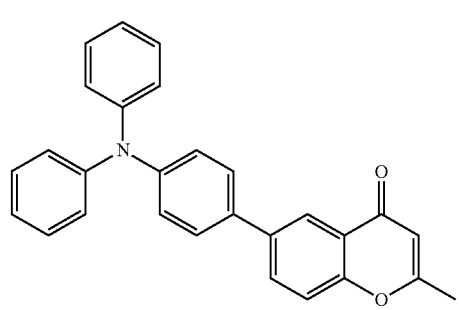
96
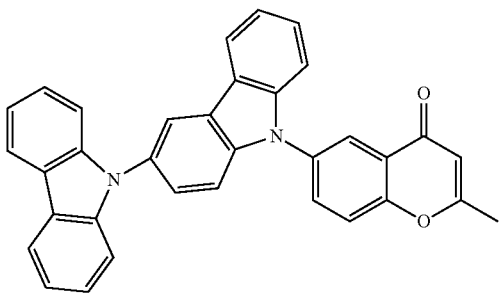
97
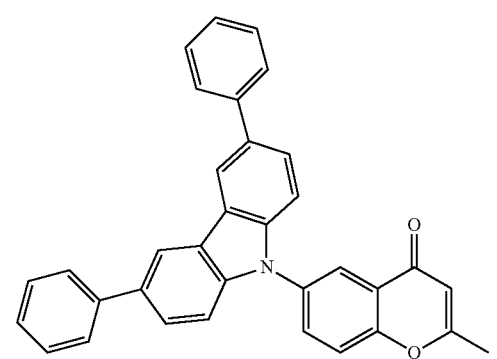
98
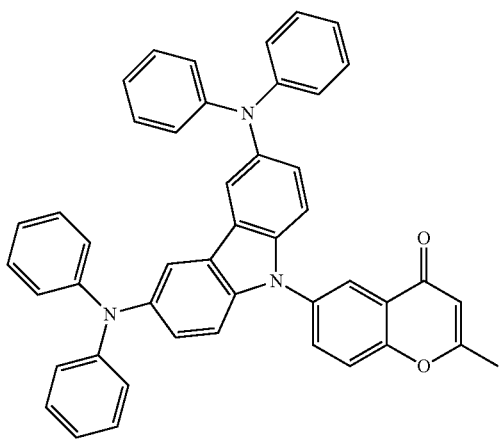
99
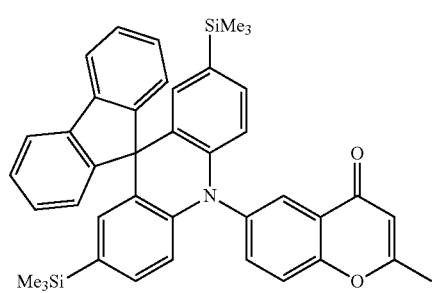

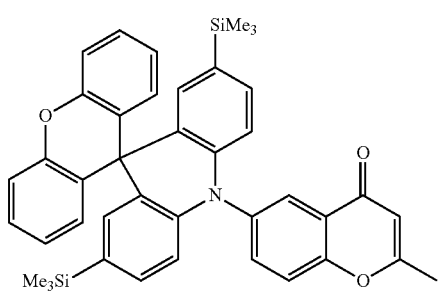
100
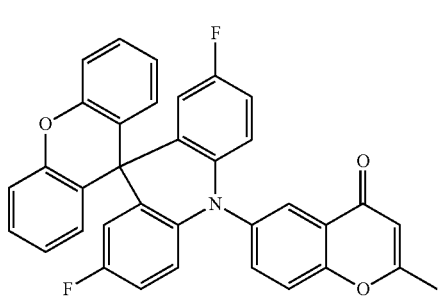
101
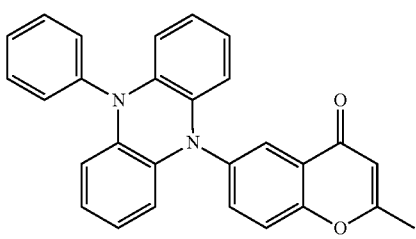
102
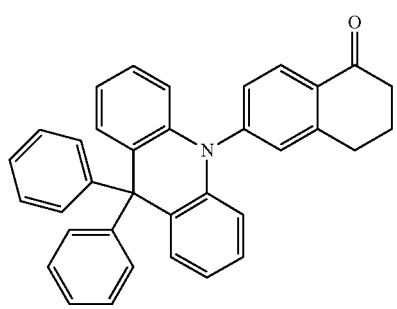
103
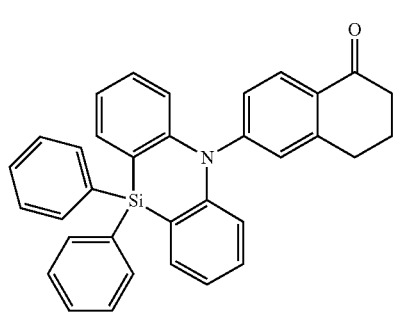
104
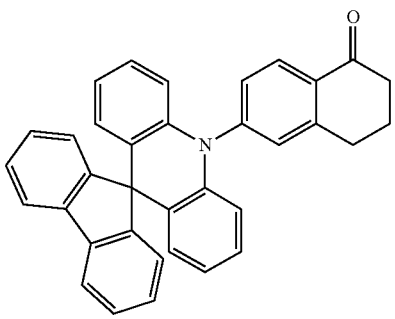
105
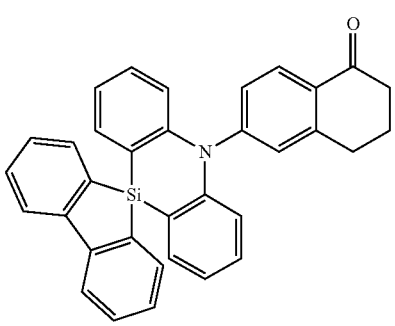
106
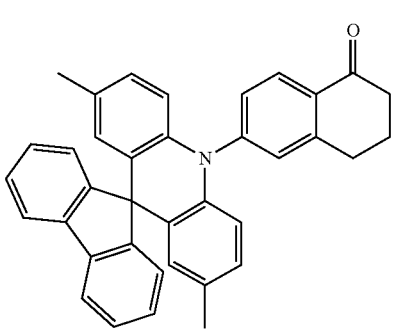
107
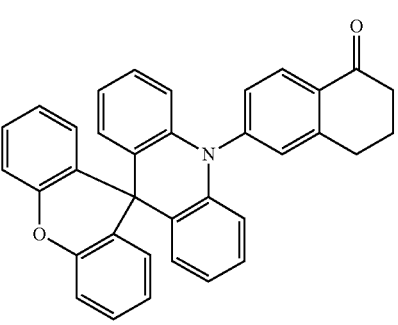
108
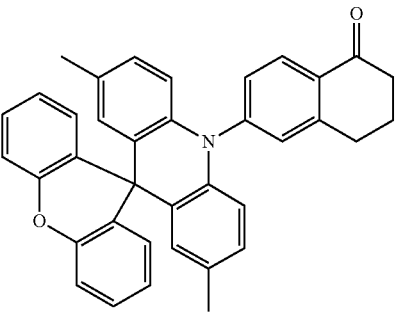
109

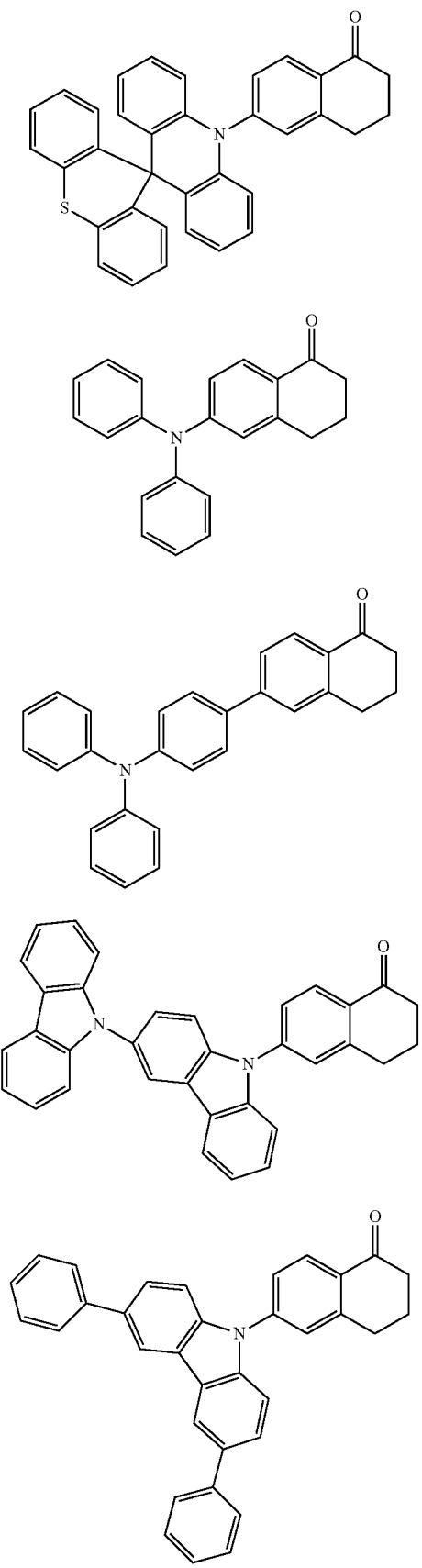
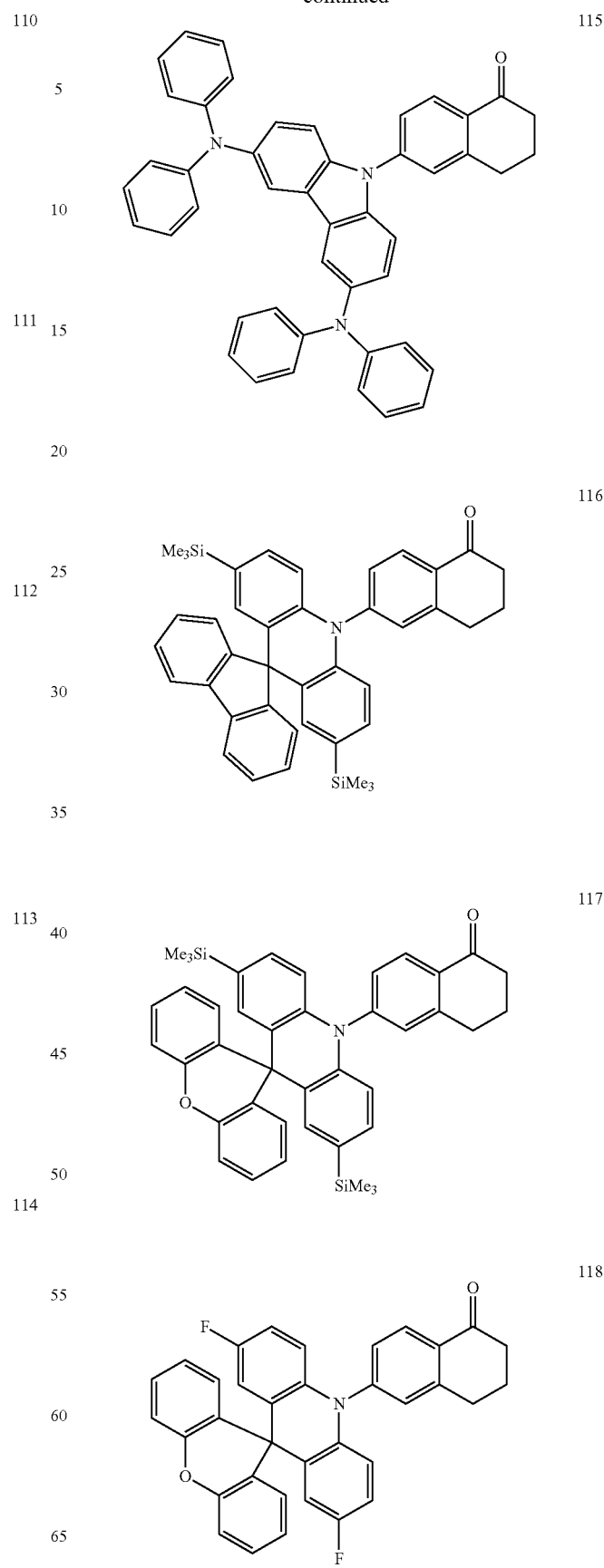

119
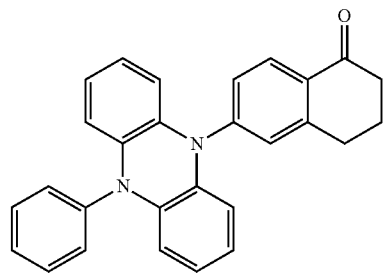
120
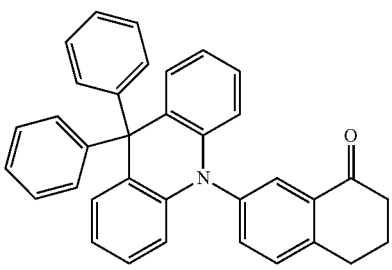
121
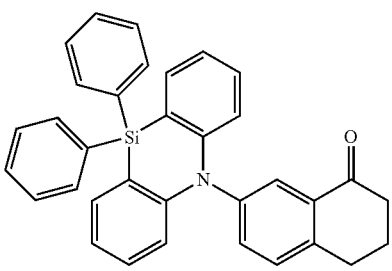
122
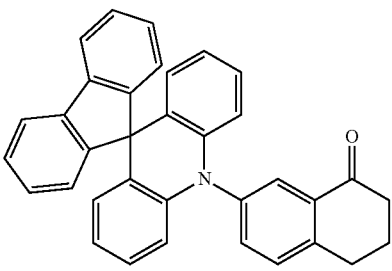
123
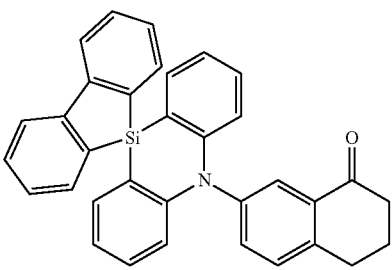
124
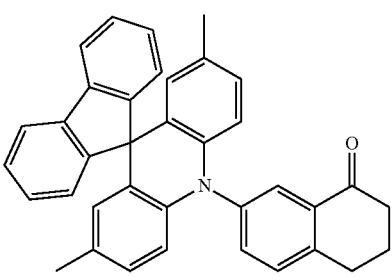
125
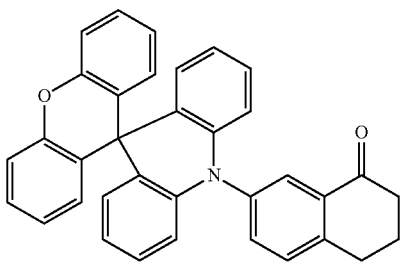
126
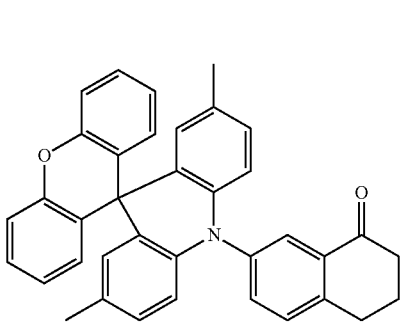
127
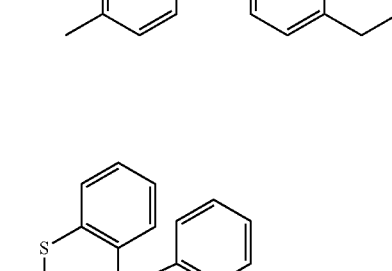
128
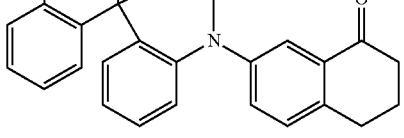
129
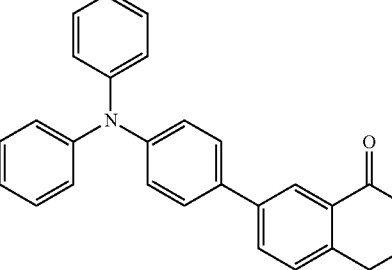

-continued
130
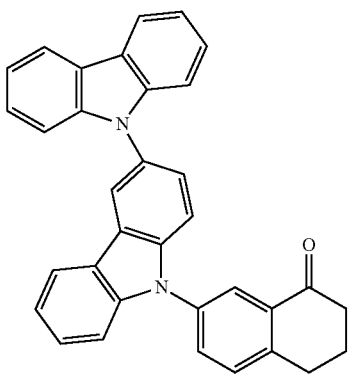
131
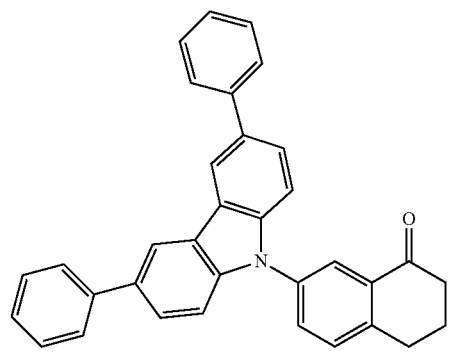
132
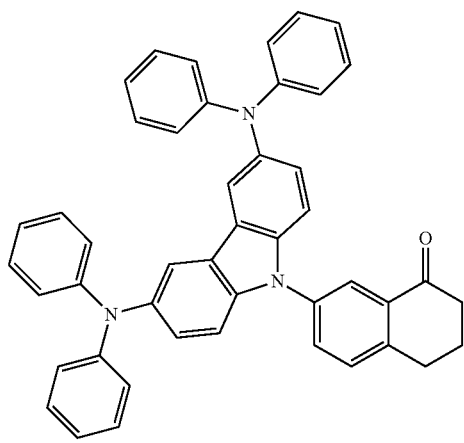
133
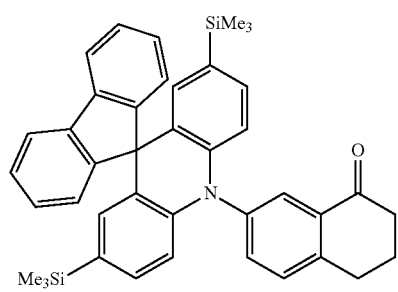
-continued
134
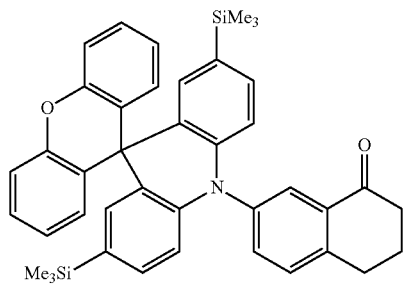
135
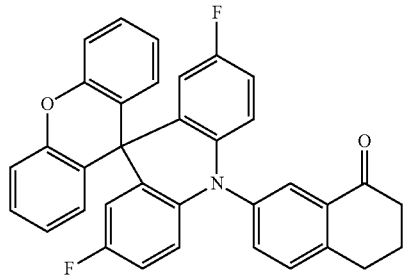
136
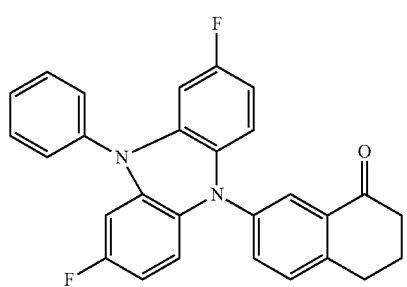
137
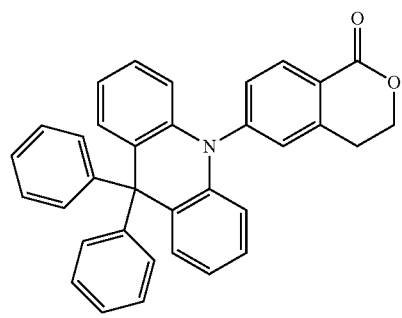
138
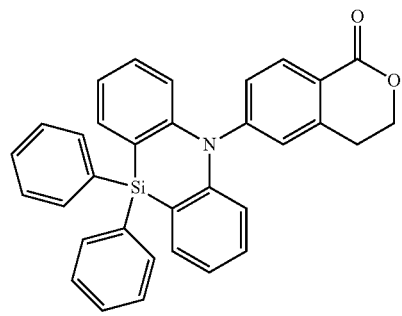

139
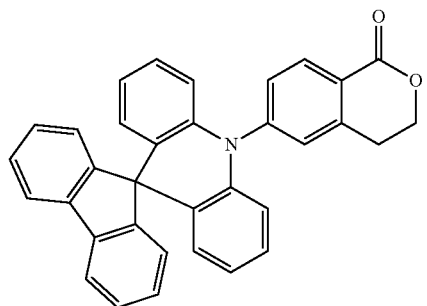
140
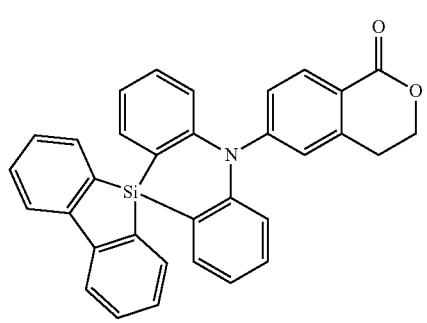
141
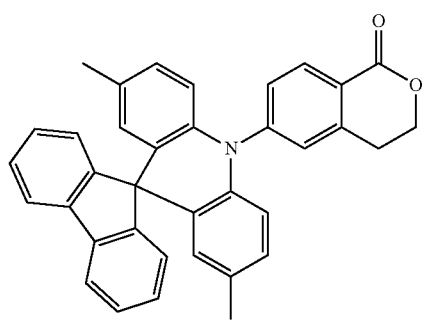
142
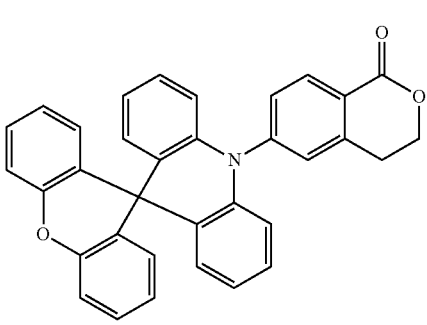
143
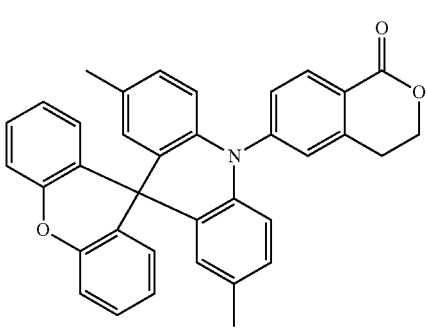
144
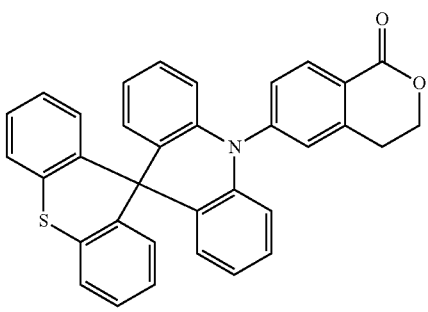
145
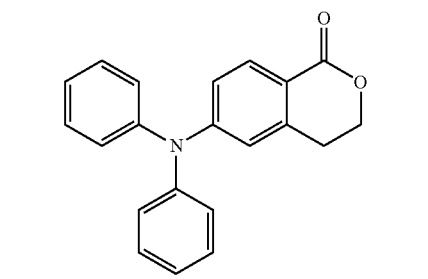
146
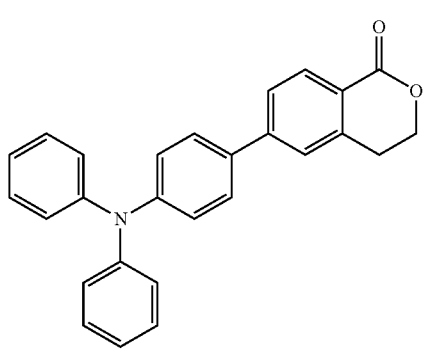
147
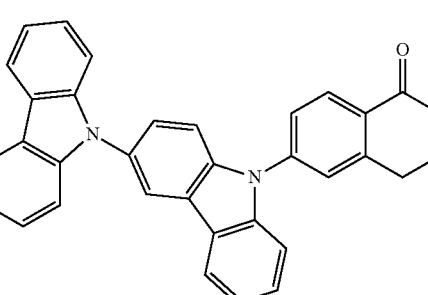
148
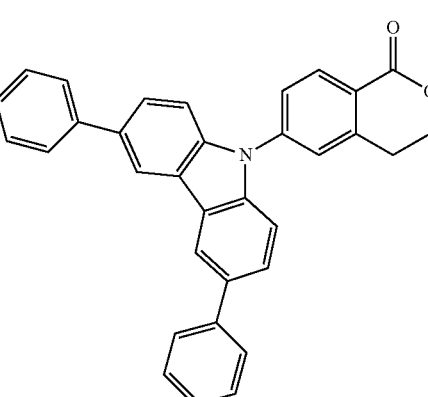

149
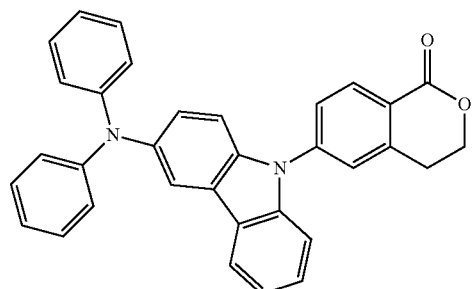
150
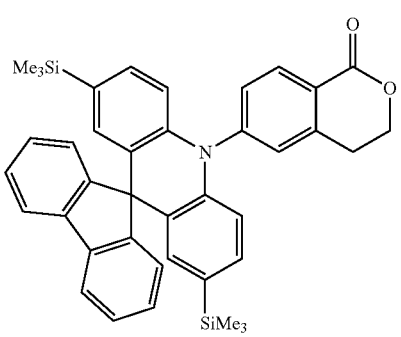
151
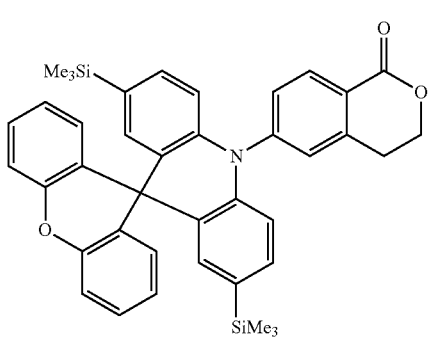
152
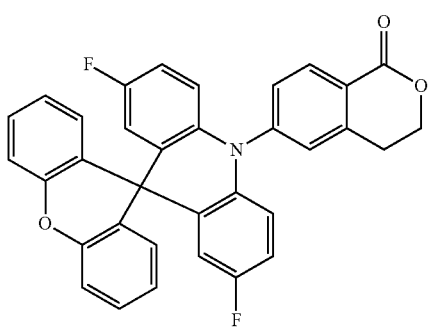
153
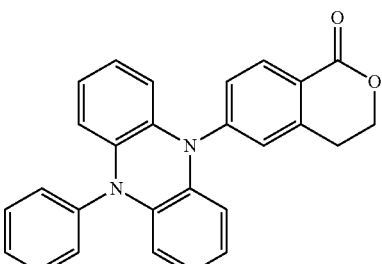
154
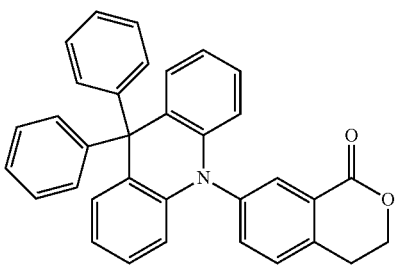
155
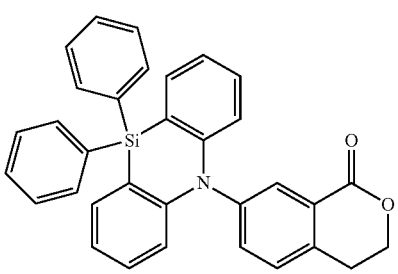
156
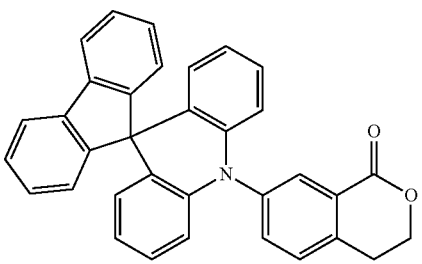
157
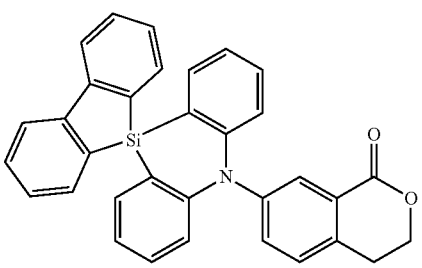
158
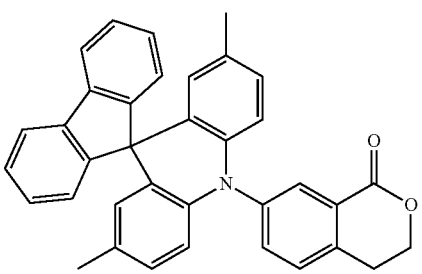

-continued
159
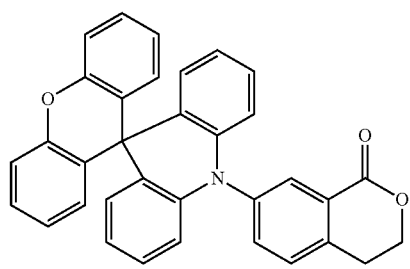
160
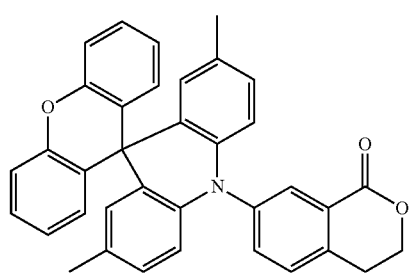
161
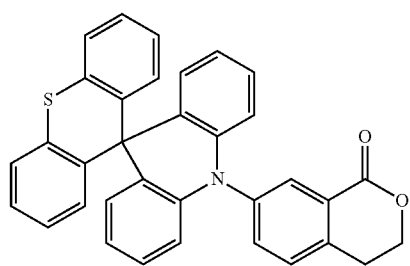
162
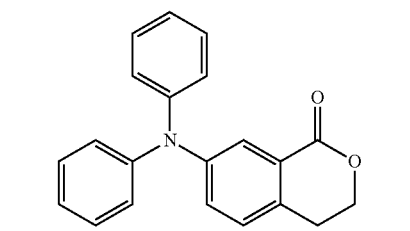
163
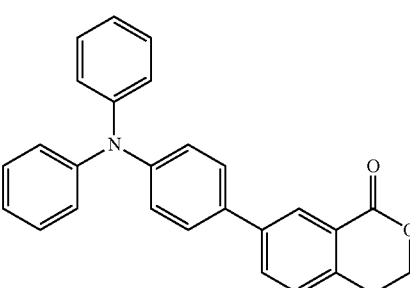
-continued
164
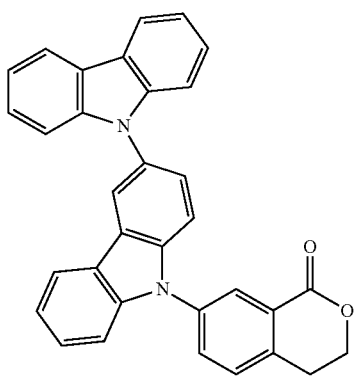
165
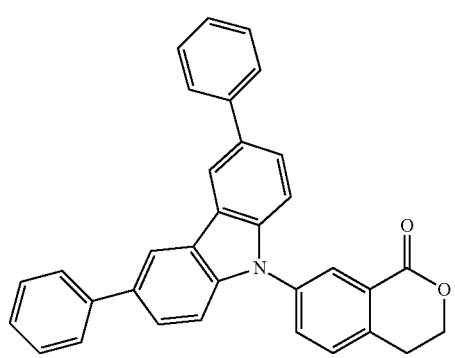
166
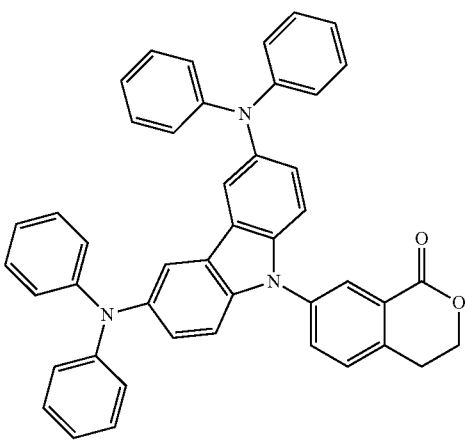
167
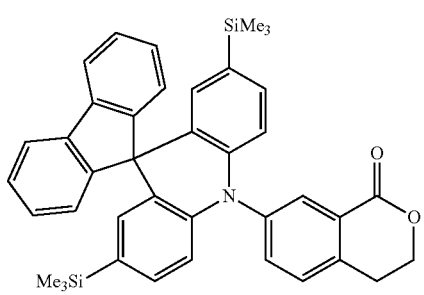

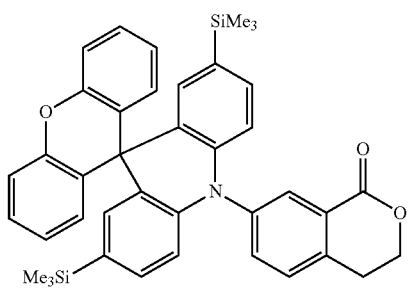
167
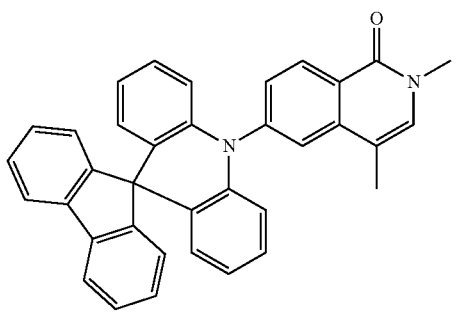
168
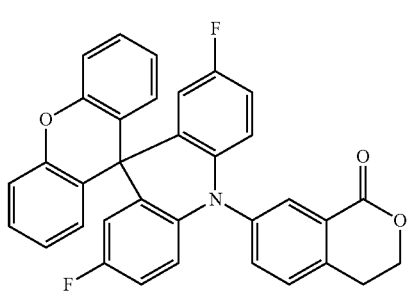
169
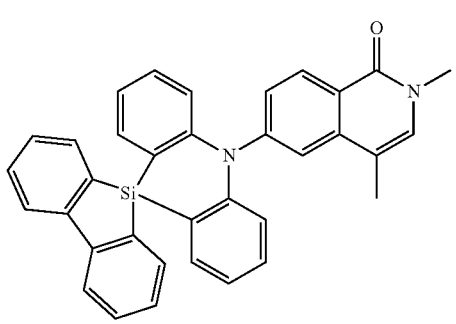
174
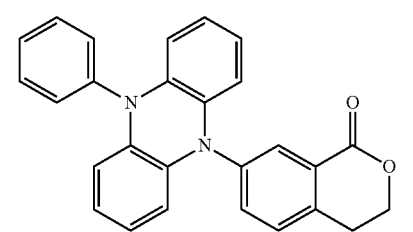
170
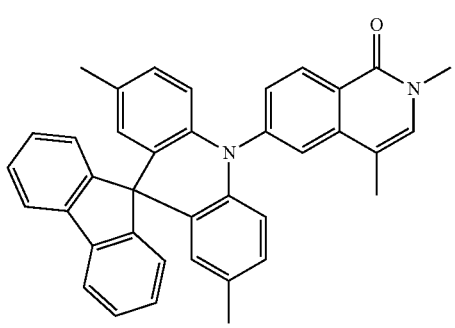
175
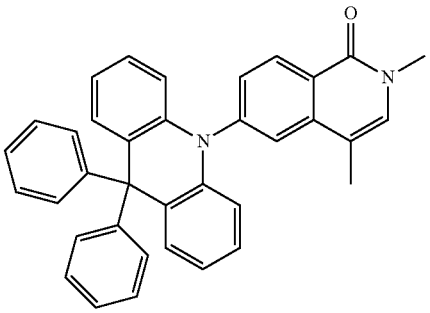
171
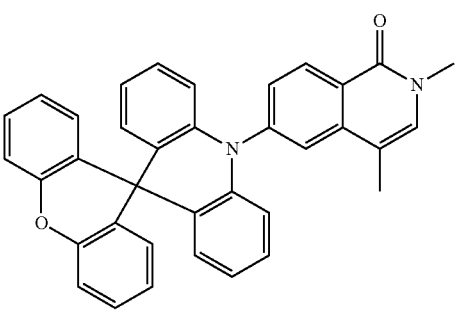
176
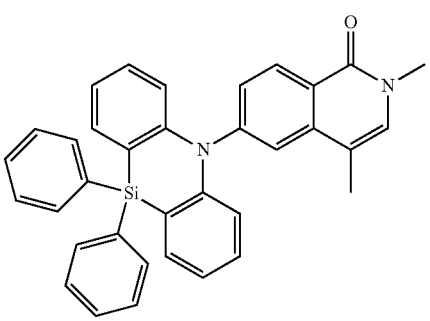
172
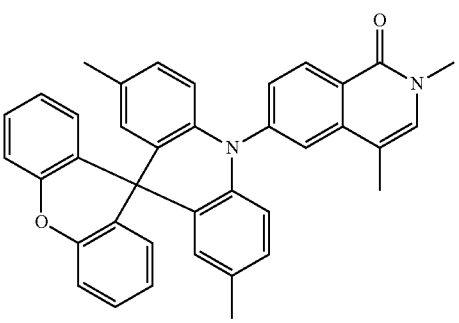
177

169
-continued
178
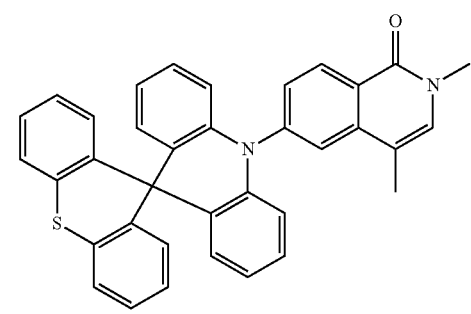
179
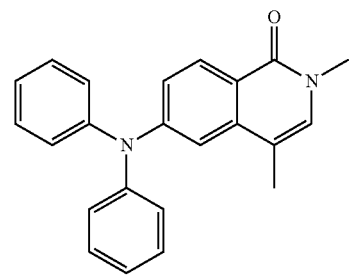
180
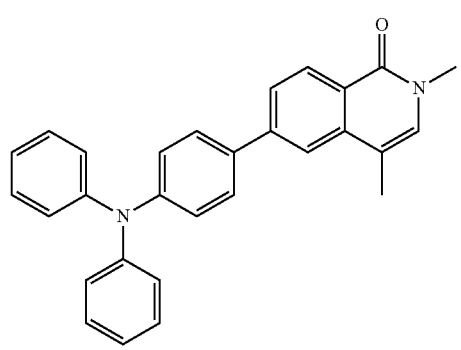
181
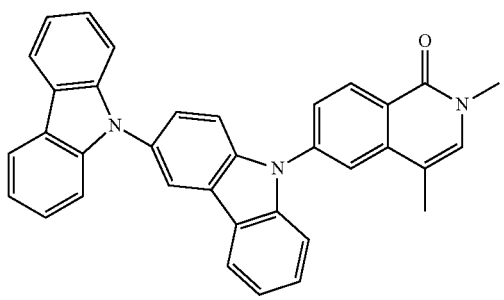
182
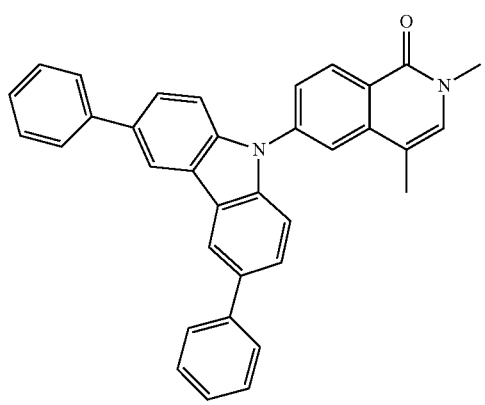
170
-continued
183
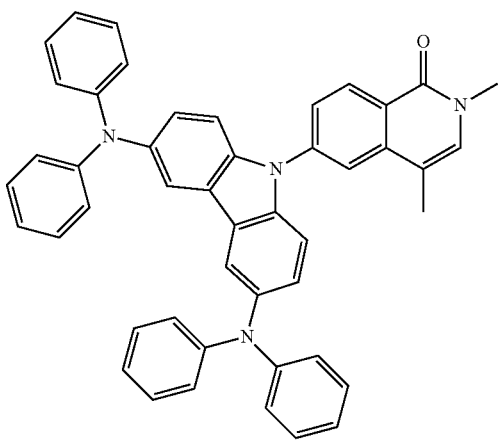
184
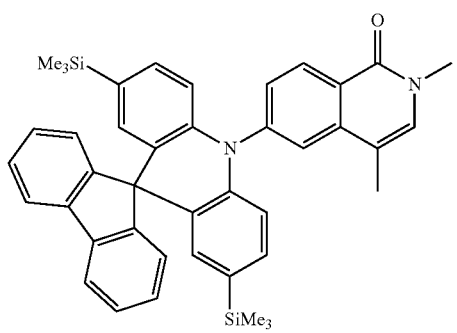
185
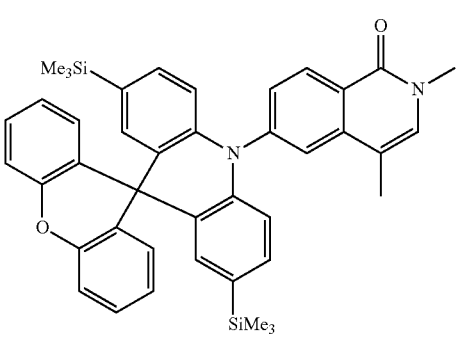
186
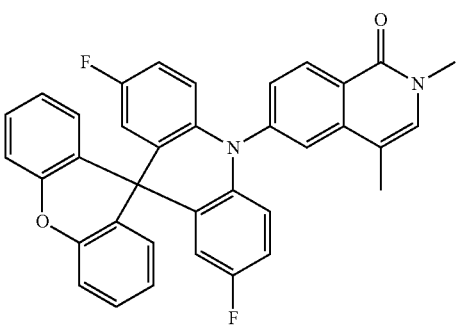

187
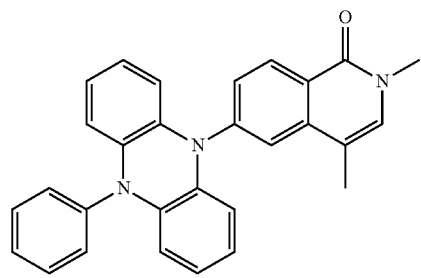
188
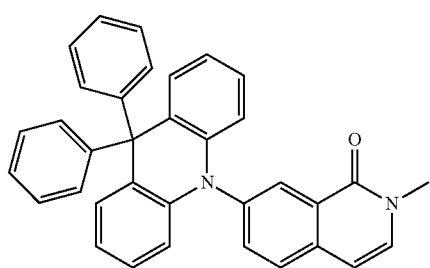
189
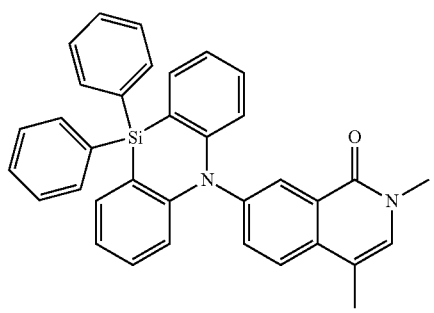
190
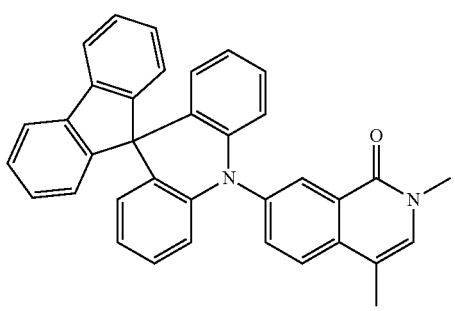
191
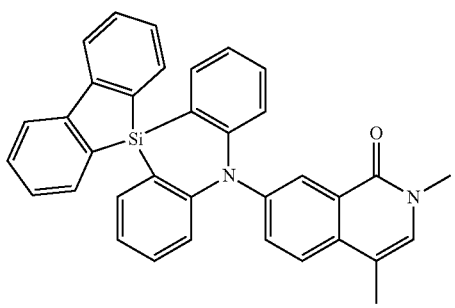
192
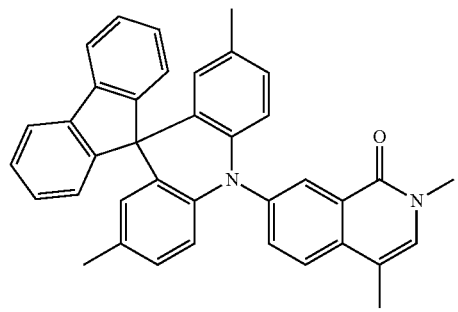
193
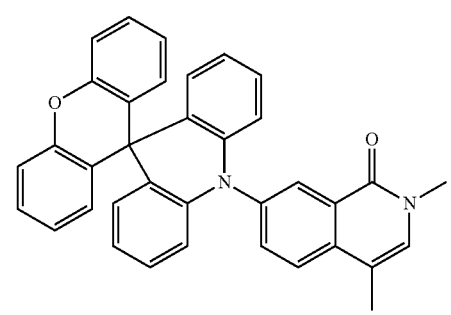
194
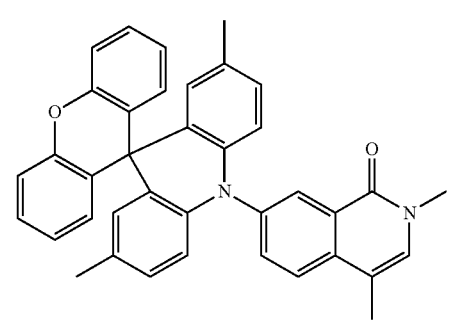
195
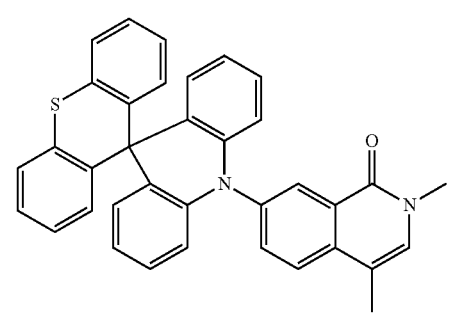
196
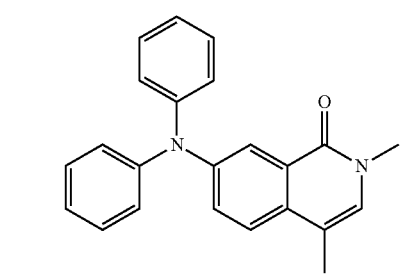

197
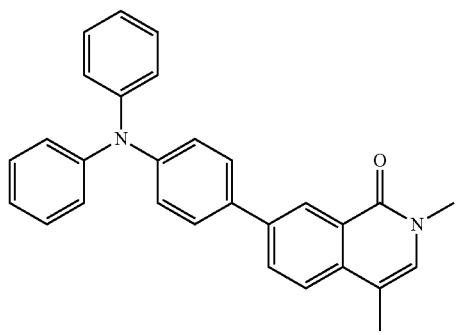
198
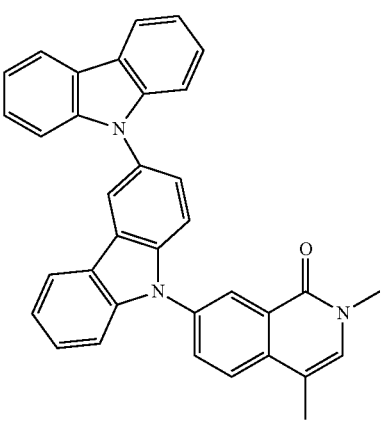
199
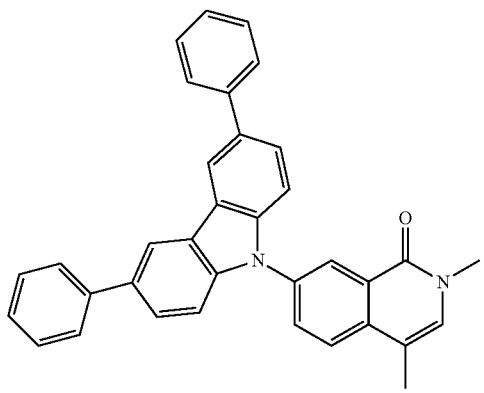
200
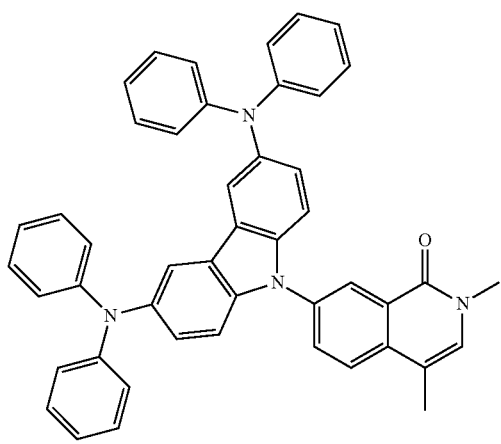
201
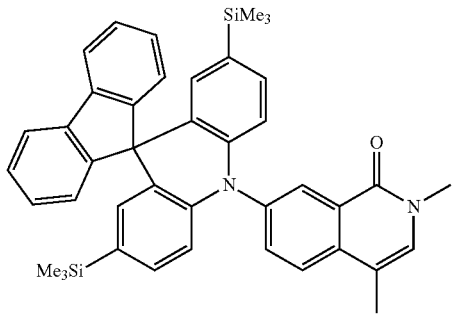
202
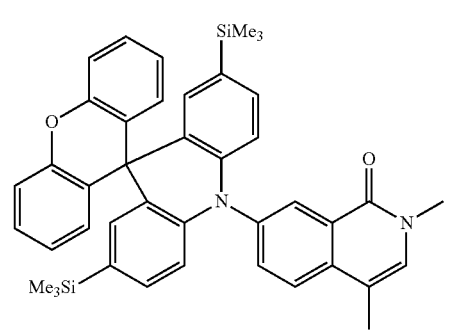
203
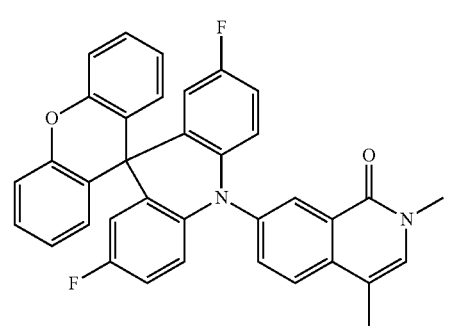
204
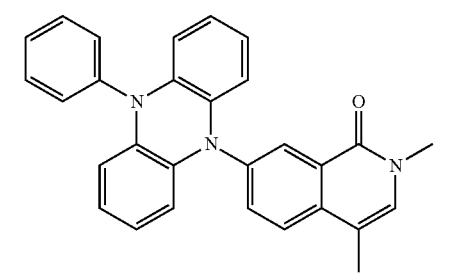
205
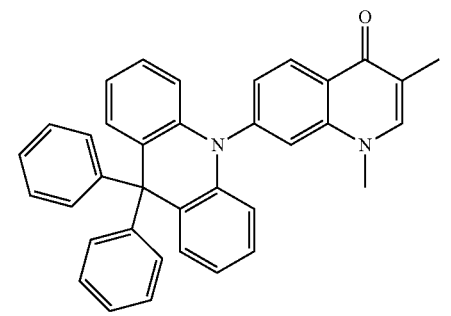

206 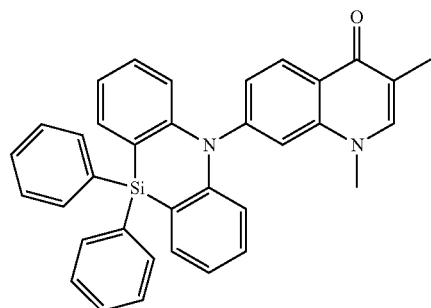
207 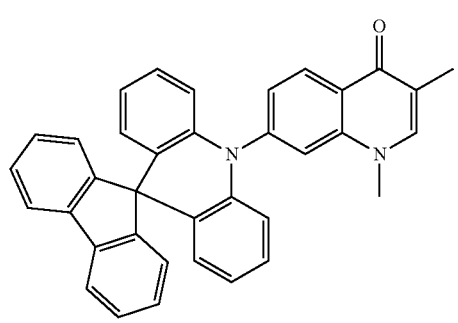
208 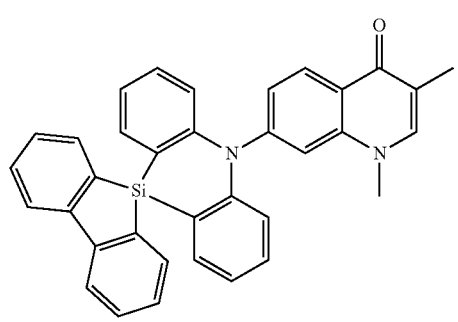
209 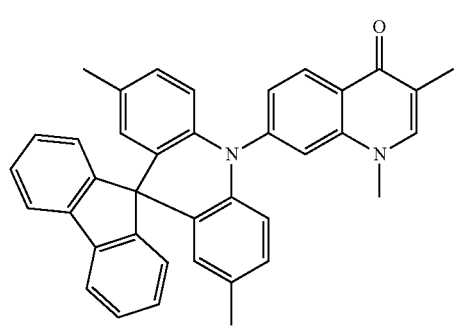
210 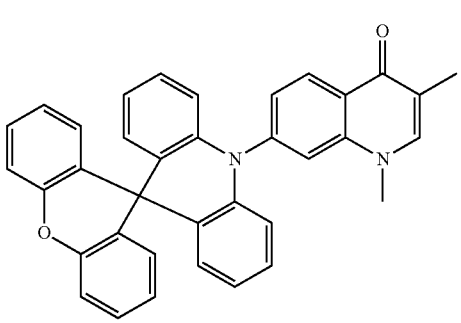
211 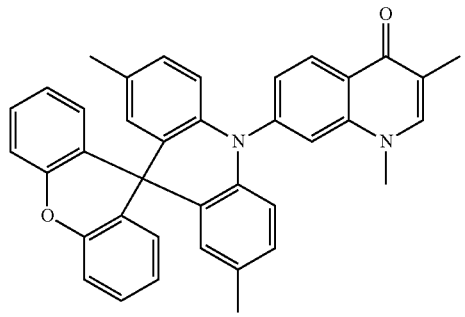
212 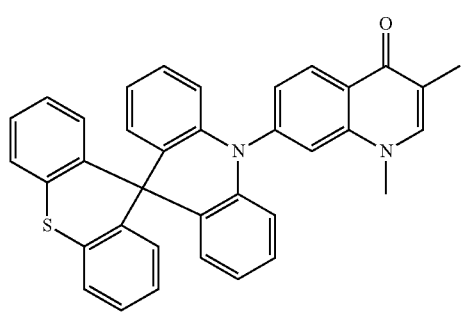
213 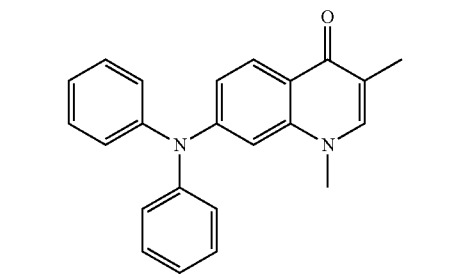
214 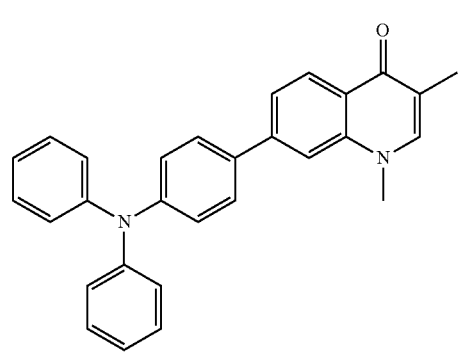
215 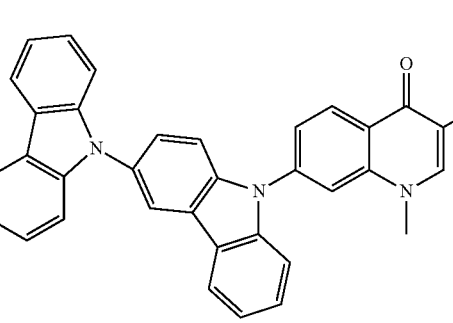

216
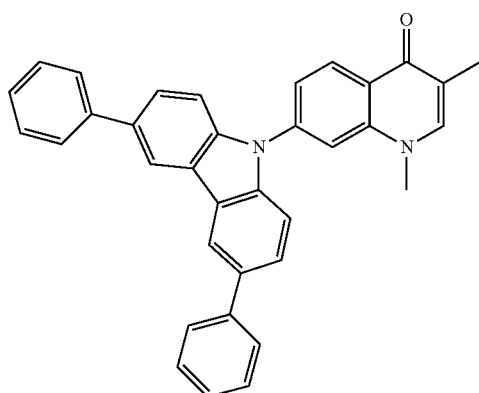
217
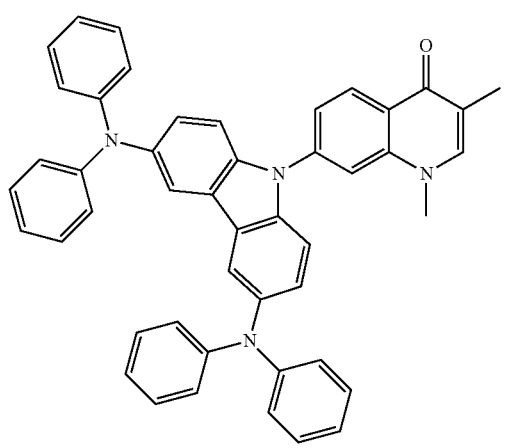
218
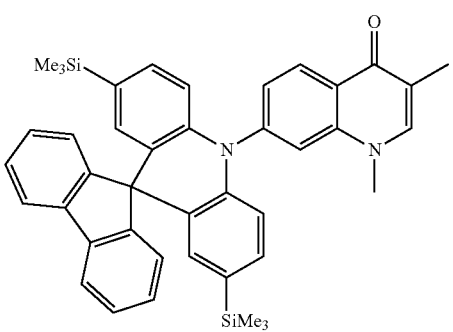
219
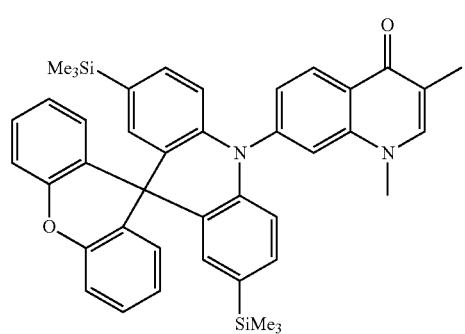
220
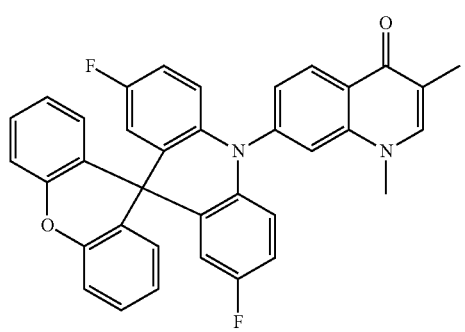
221
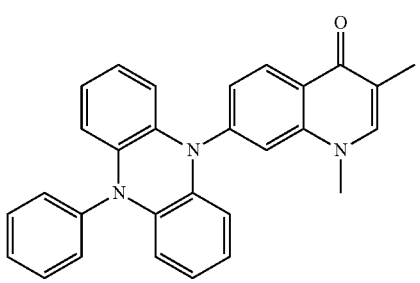
222
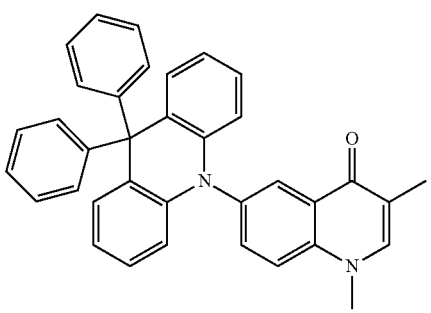
223
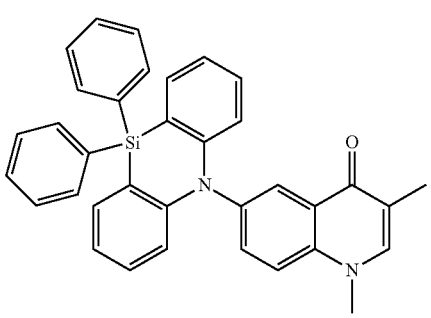
224
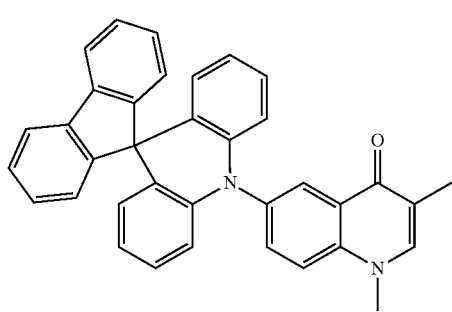

225
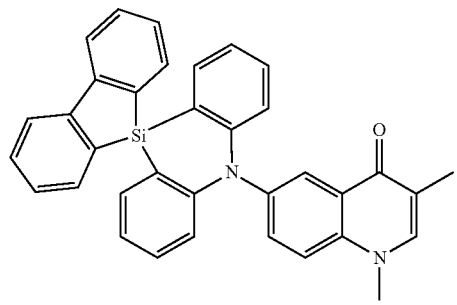
226
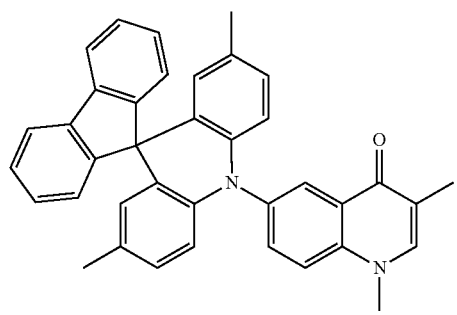
227
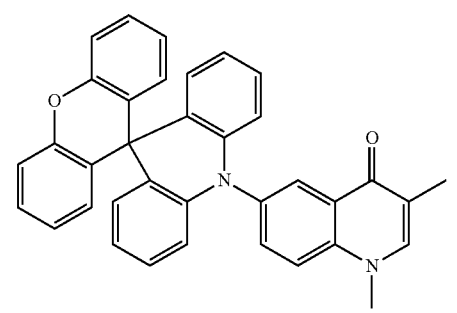
228
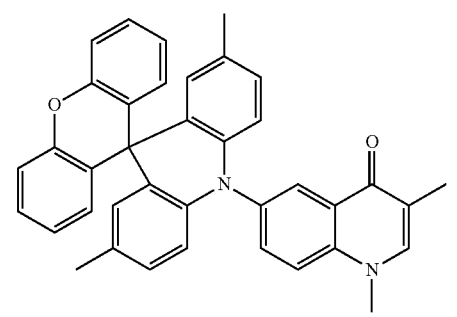
229
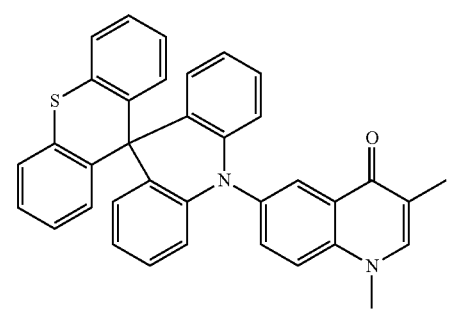
230
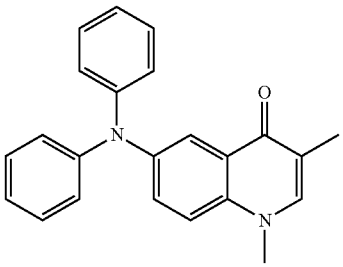
231
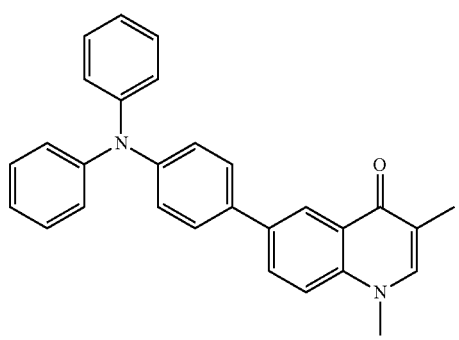
232
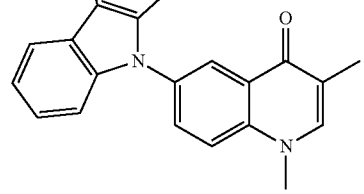
233
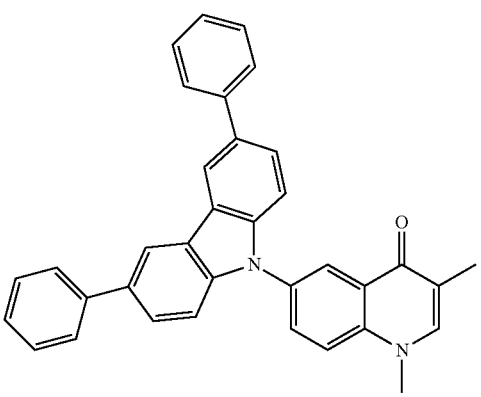

234
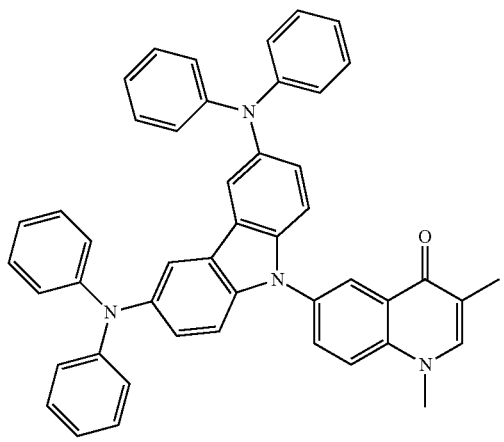
235
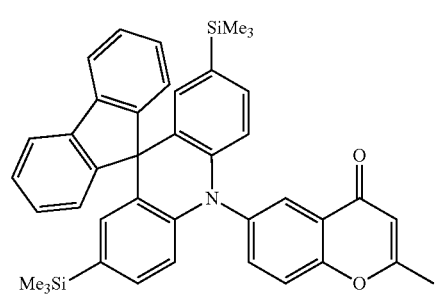
235
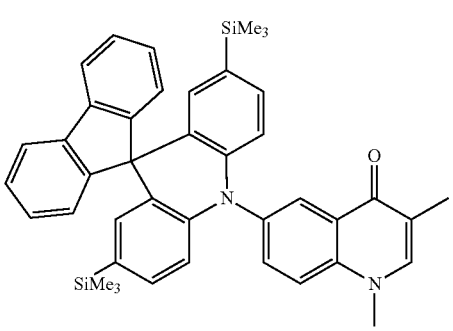
236
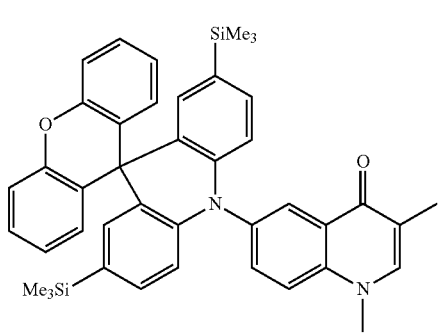
237
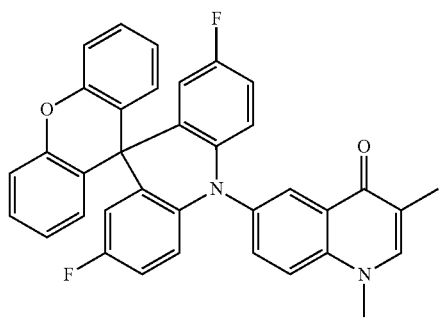
238
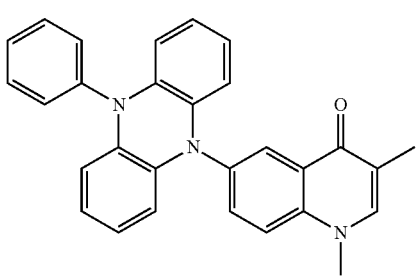
239
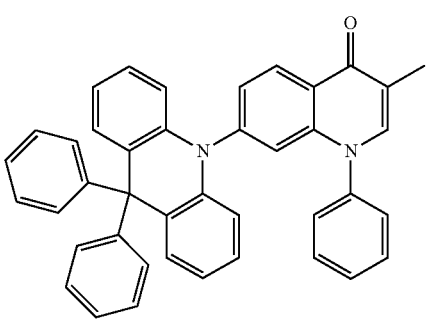
240
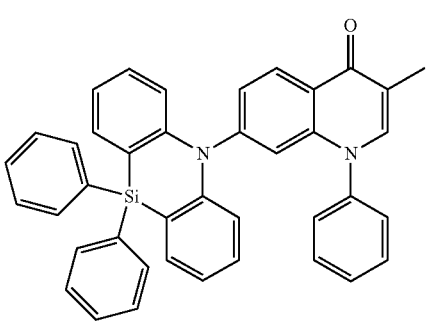
241
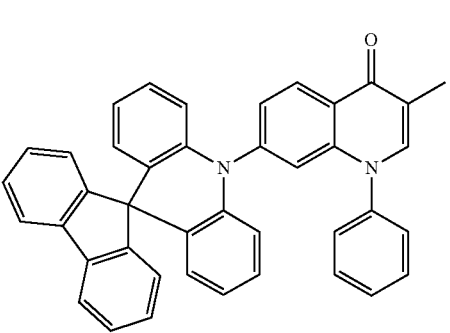

-continued
242
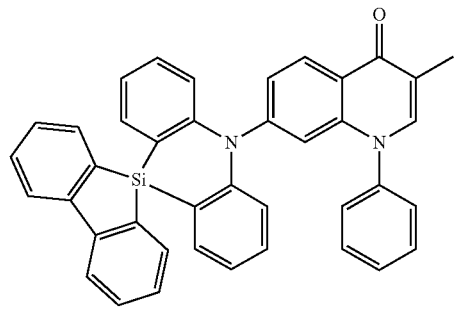
243
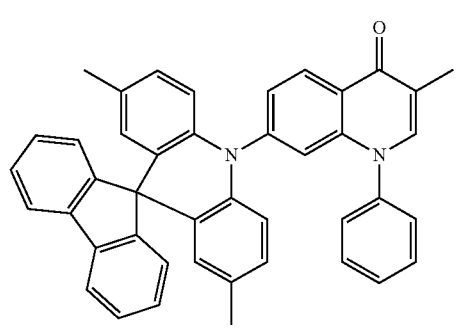
244
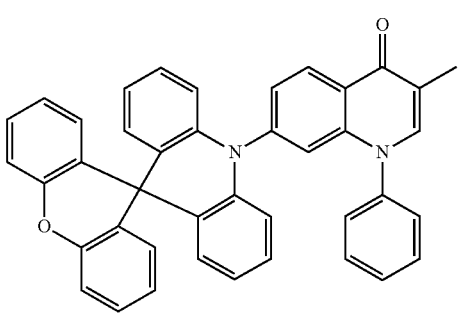
245
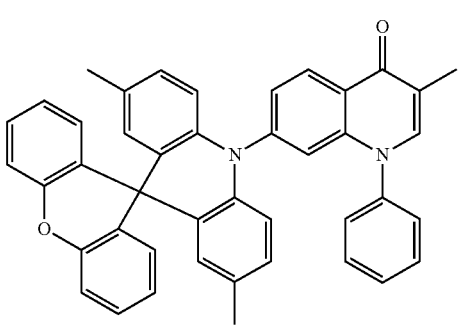
246
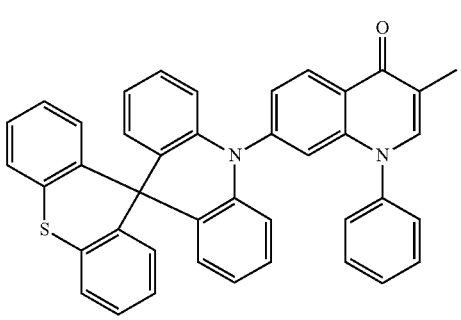
-continued
247
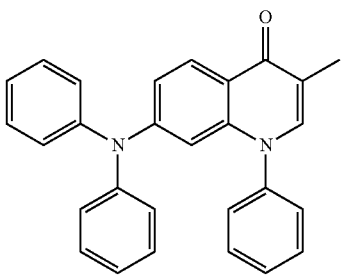
248
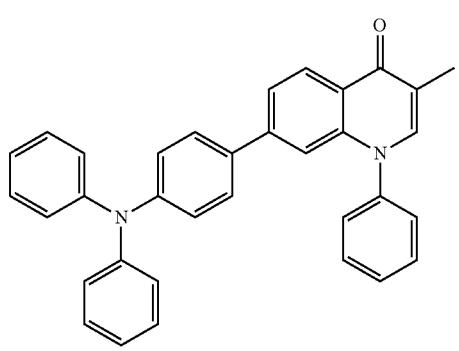
249
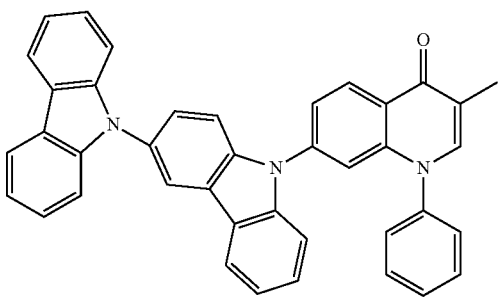
250
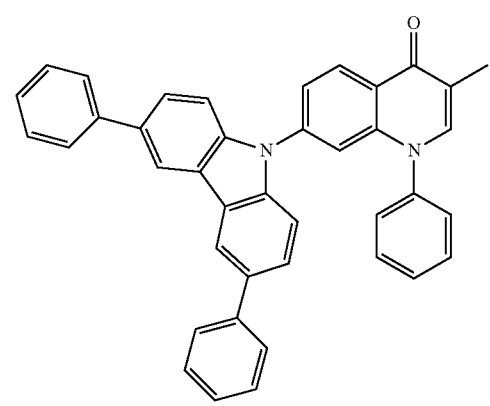

-continued
251
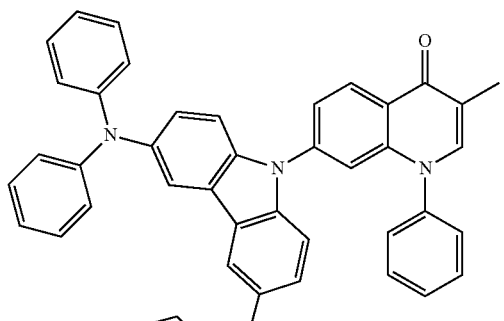
252
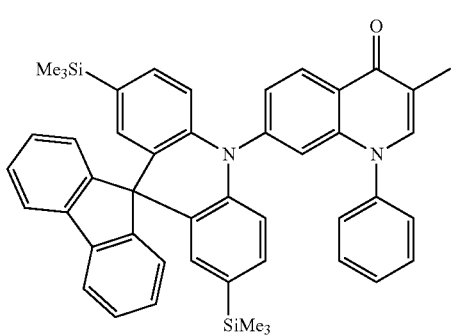
253
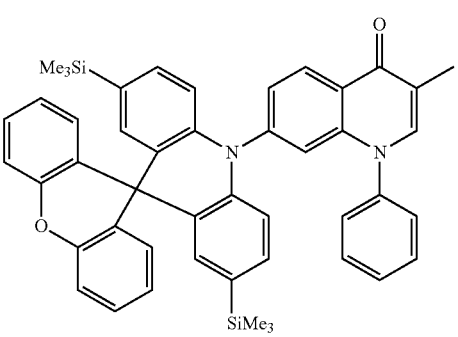
254
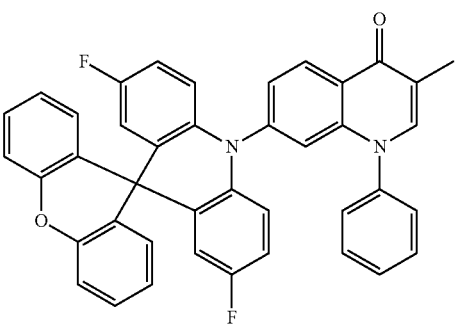
-continued
255
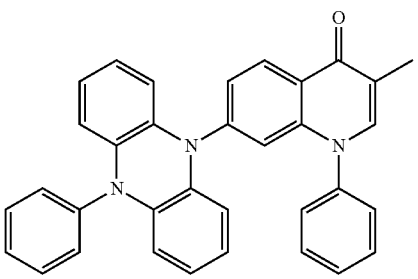
256
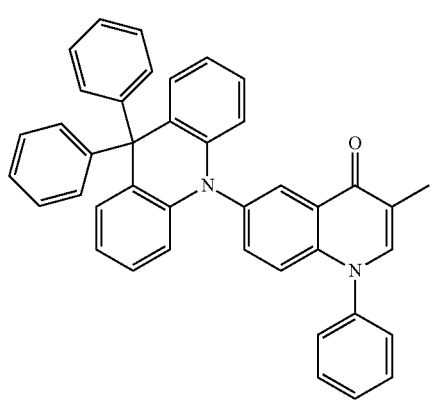
257
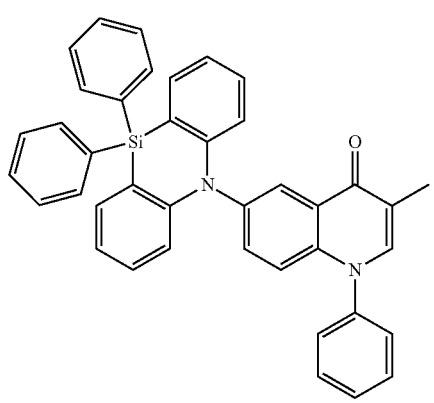
258
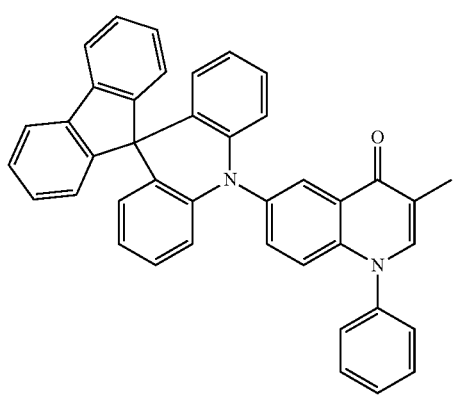

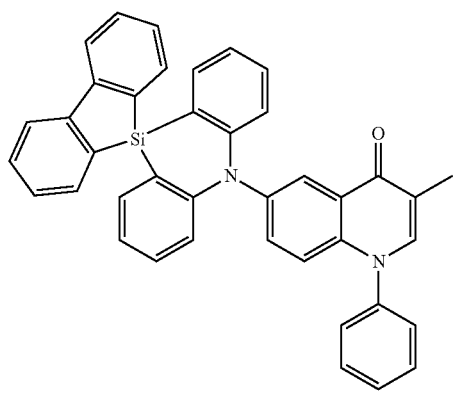
259
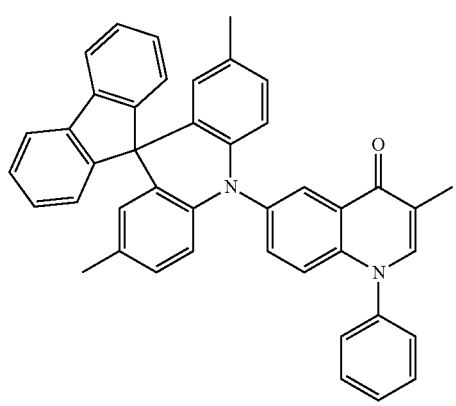
260
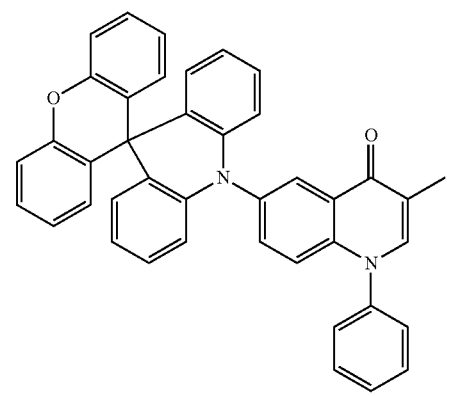
261
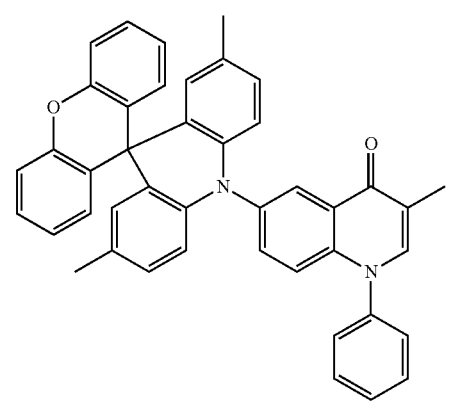
262
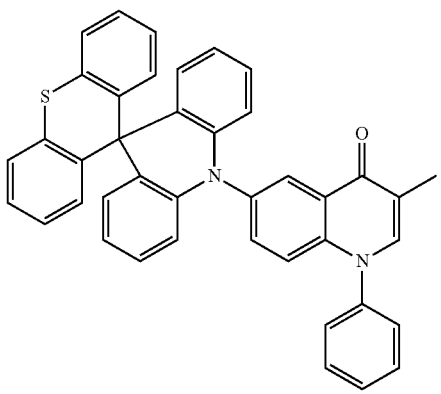
263
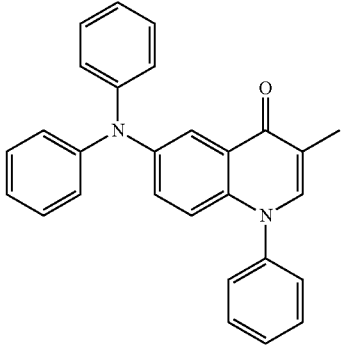
264
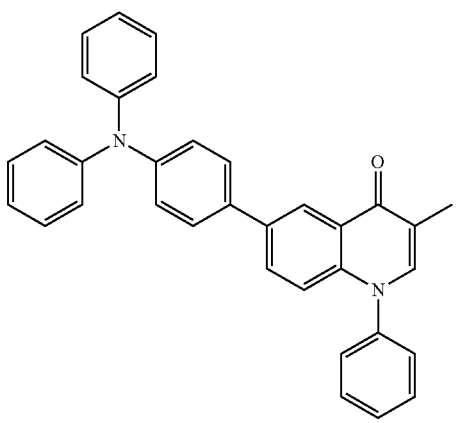
265
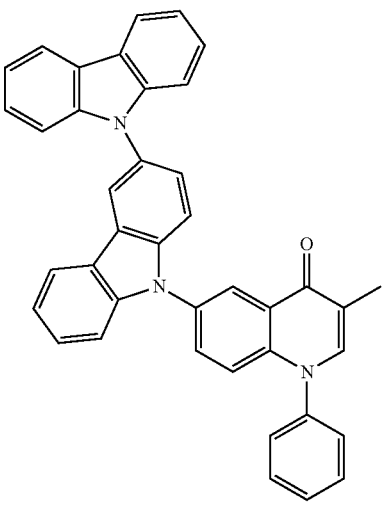
266

-continued
267
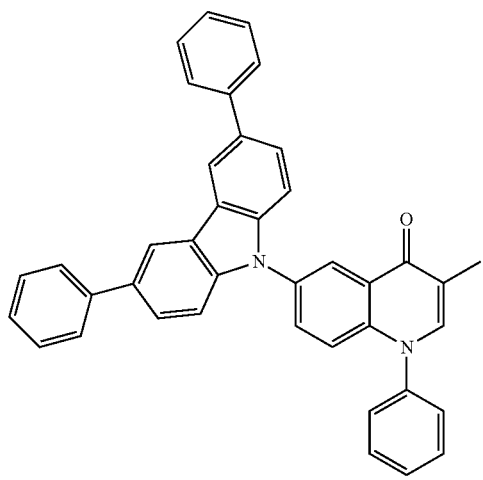
268
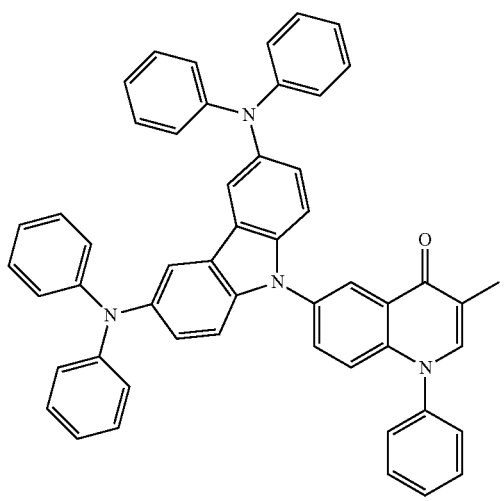
269
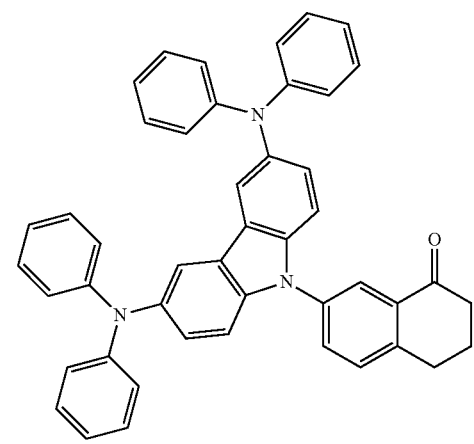
-continued
269
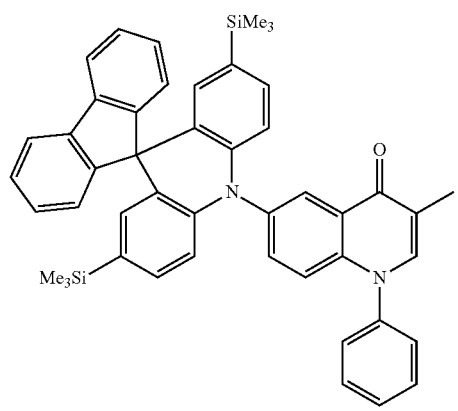
270
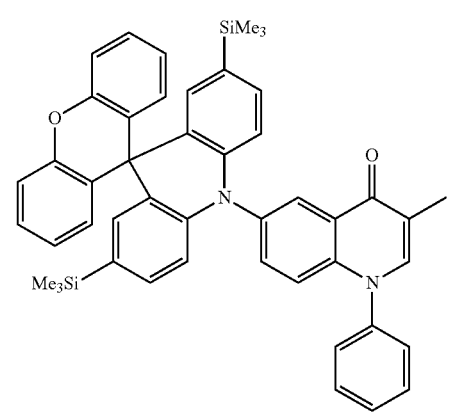
271
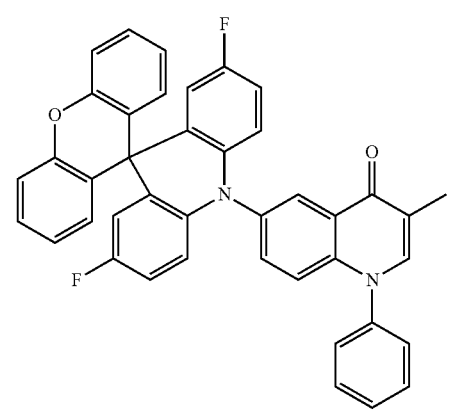
272
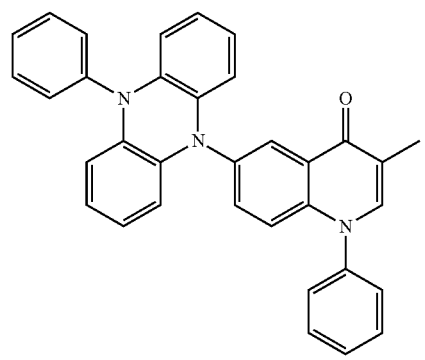

-continued
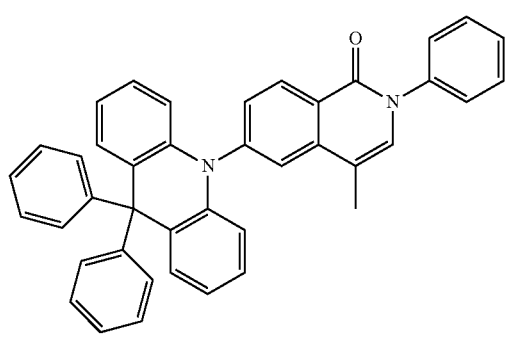
273
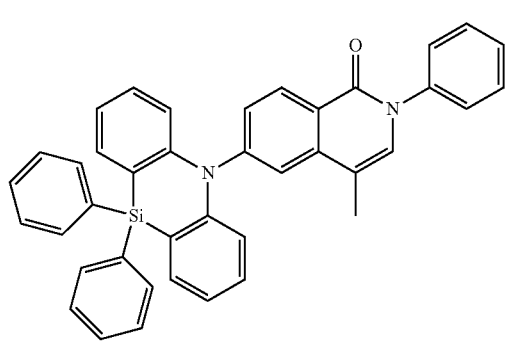
274
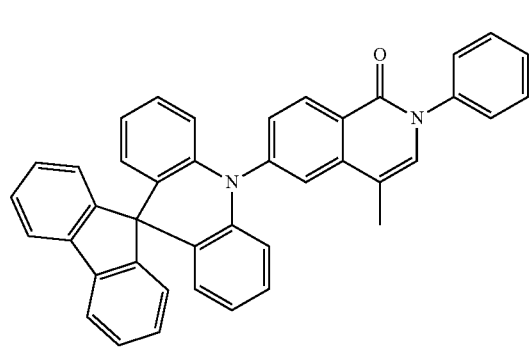
275
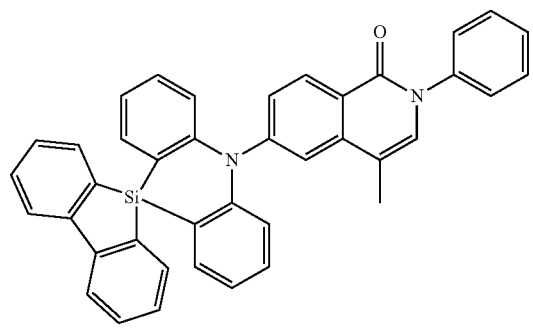
276
-continued
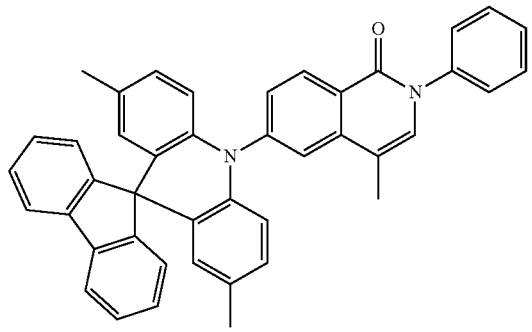
277
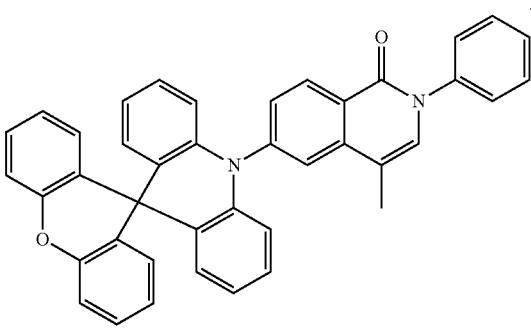
278
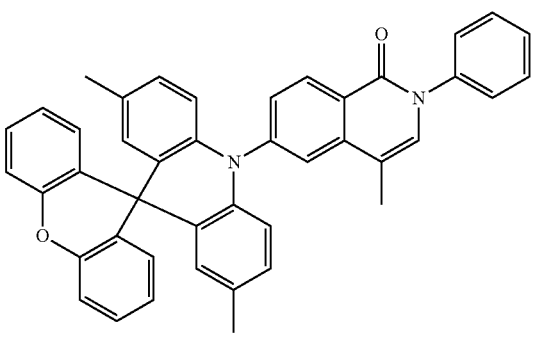
279
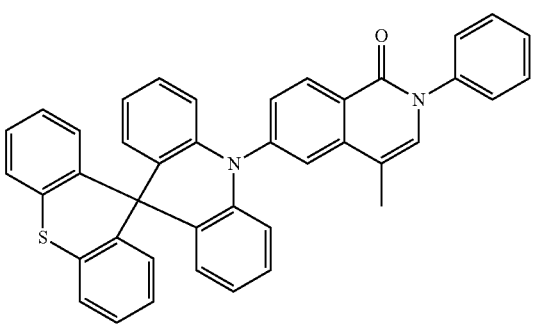
280

281
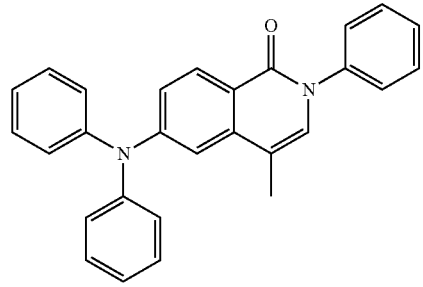
282
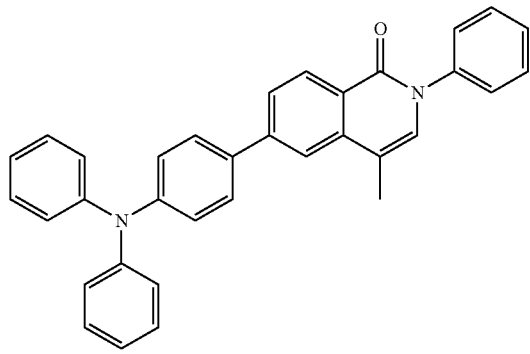
283
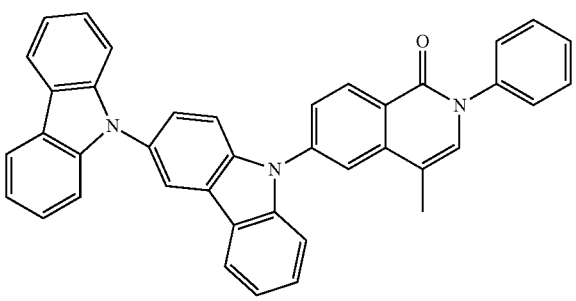
284
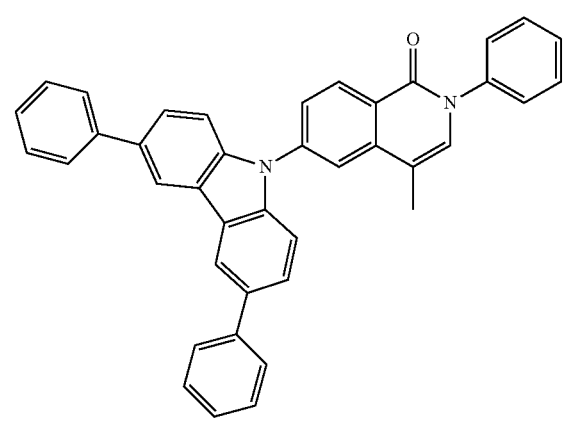
285
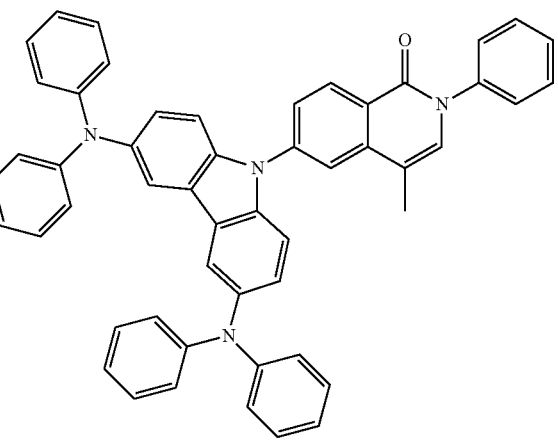
286
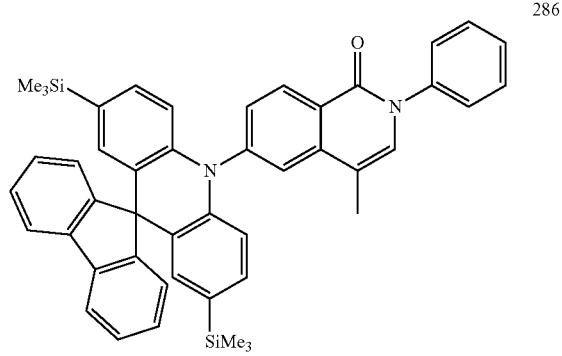
287
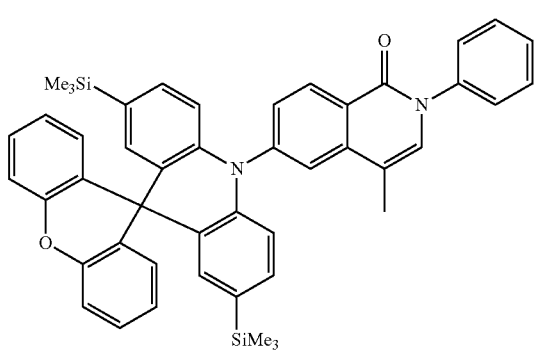
288
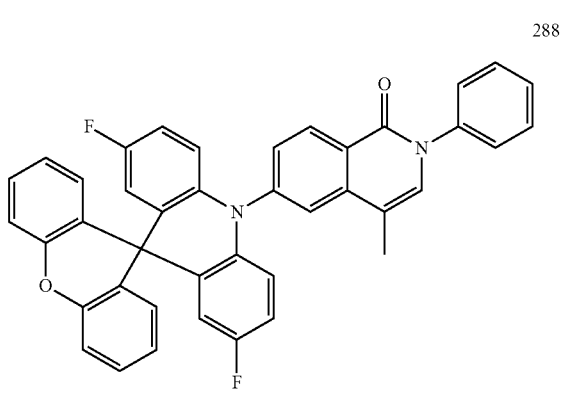

-continued
289
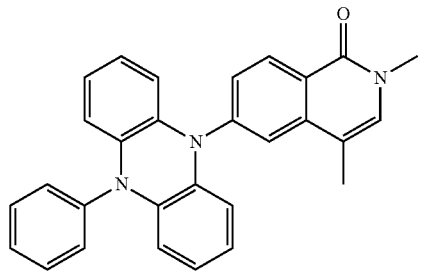
290
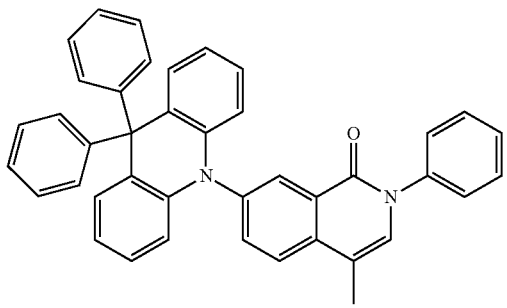
291
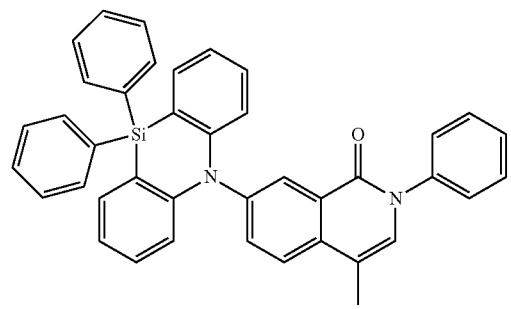
292
293
-continued
294
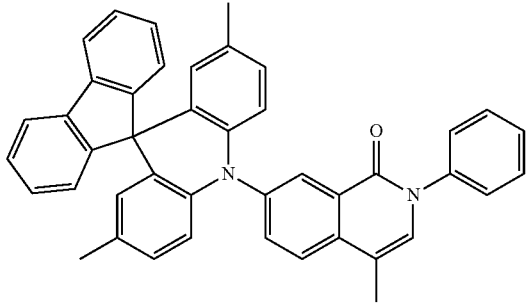
295
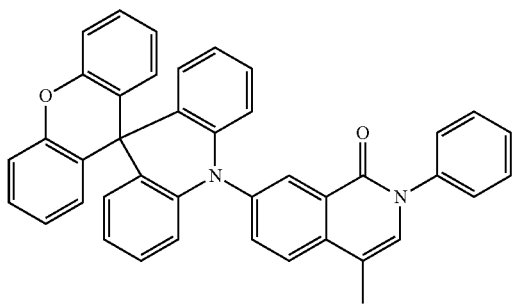
296
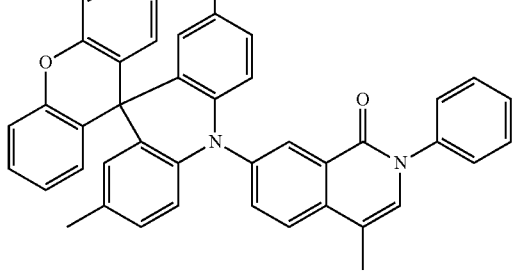
297
298
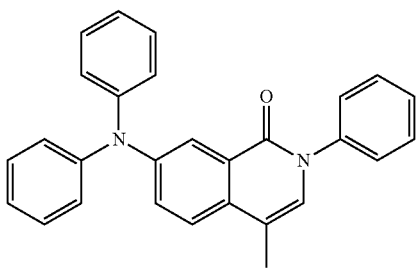

299
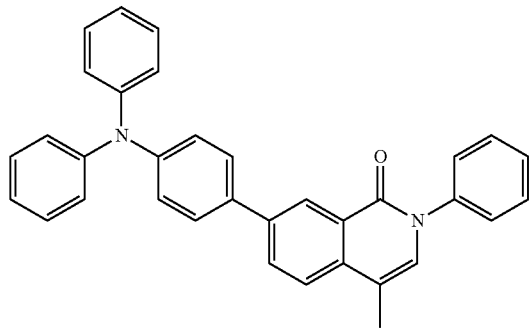
300
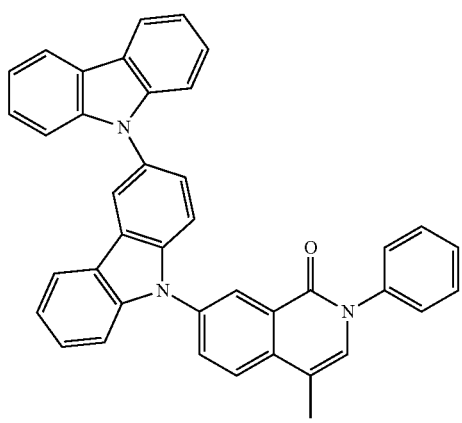
301
303
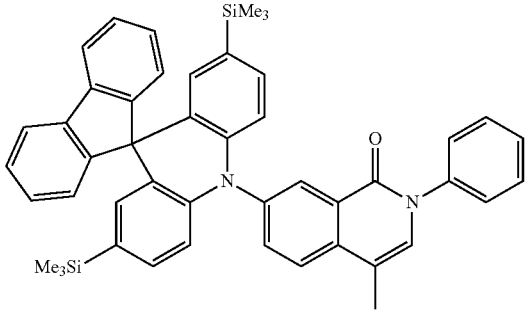
304
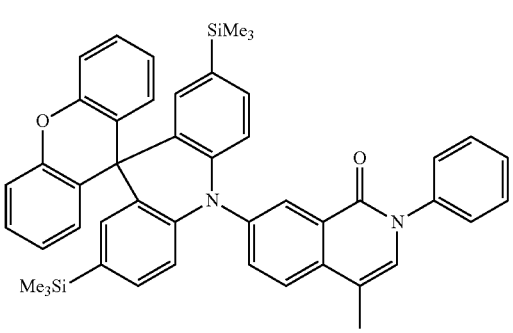
305
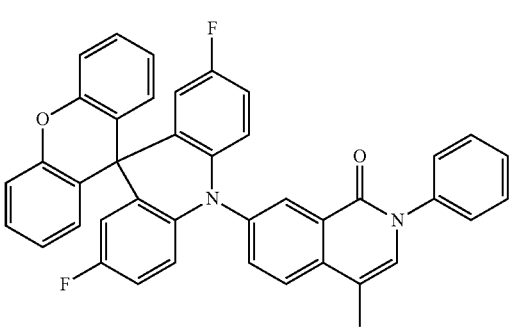
306
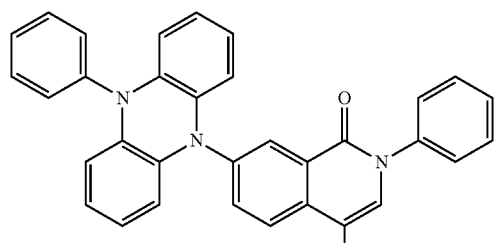
307
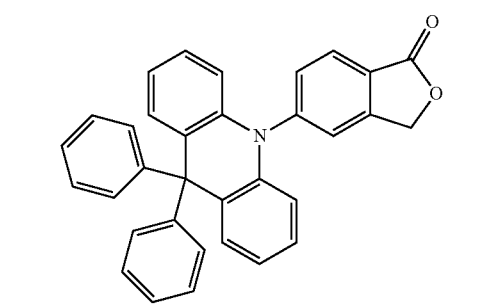

| | |
|---|---|
| 308 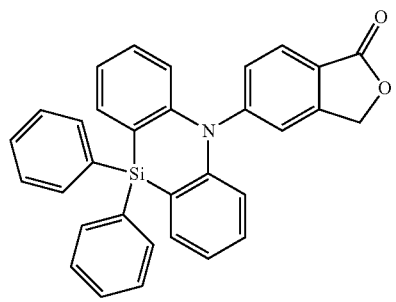 | 313 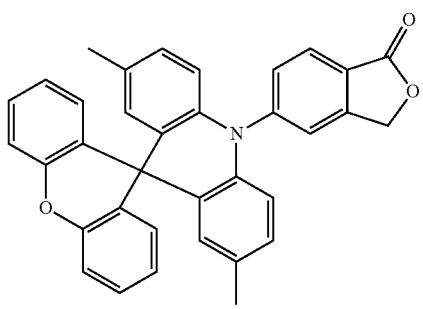 |
| 309 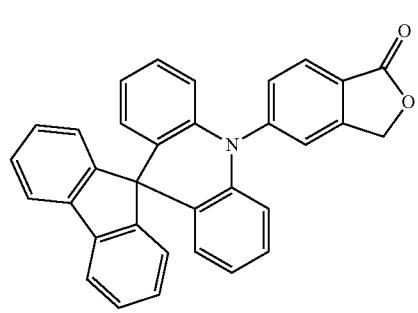 | 314 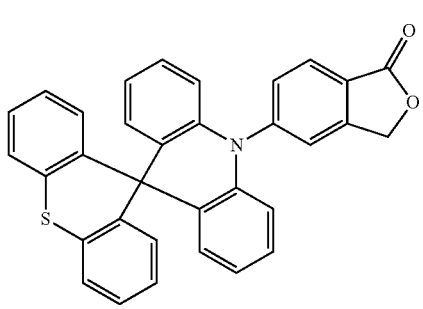 |
| 310 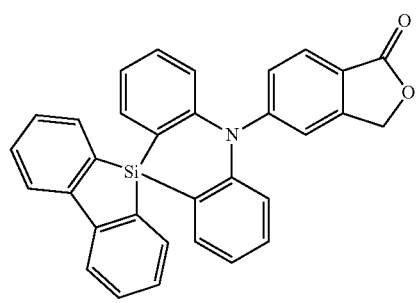 | 315 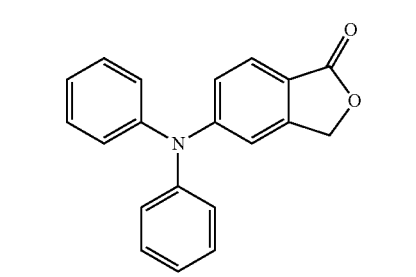 |
| 311 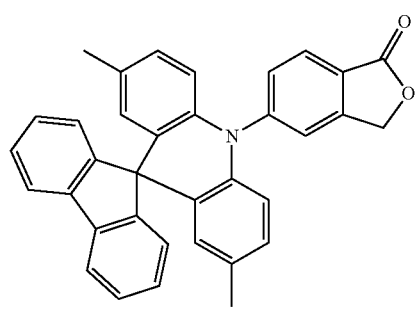 | 316 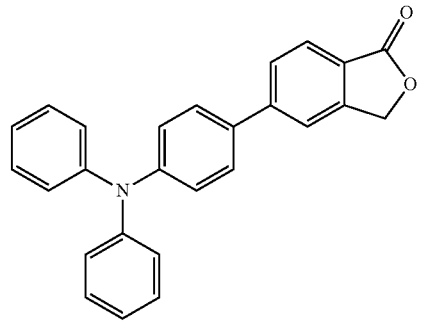 |
| 312 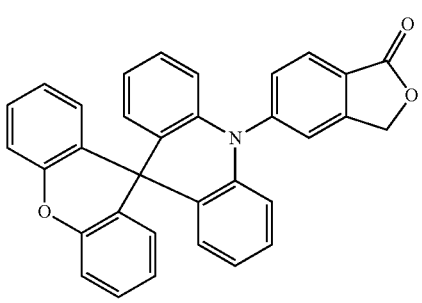 | 317 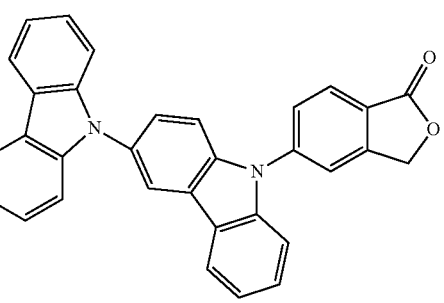 |

318
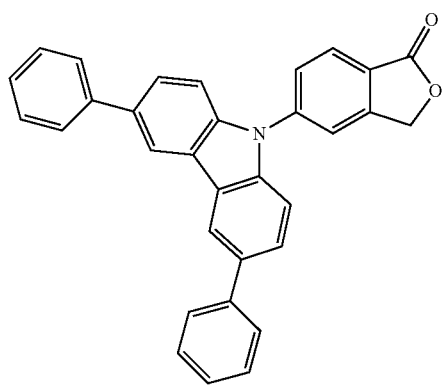
319
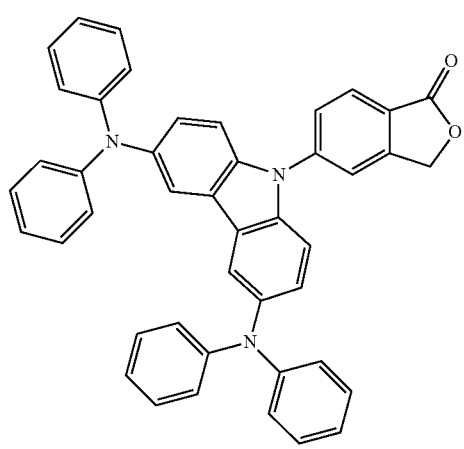
320
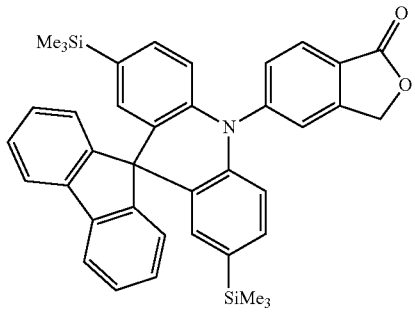
321
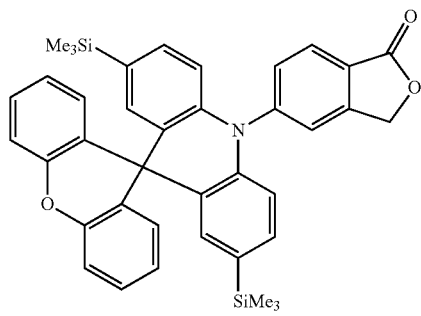
322
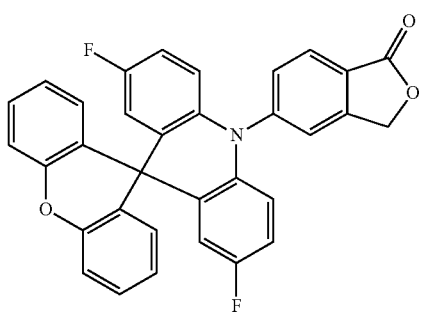
323
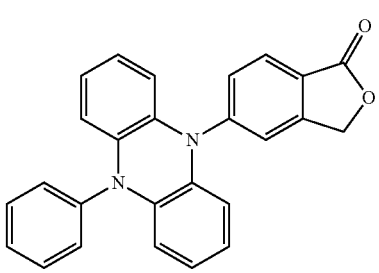
324
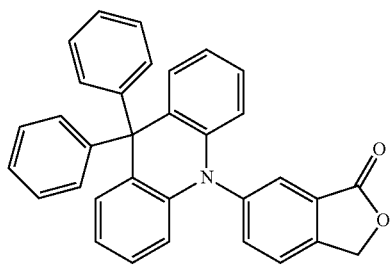
325
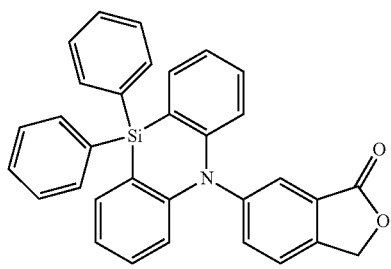
326
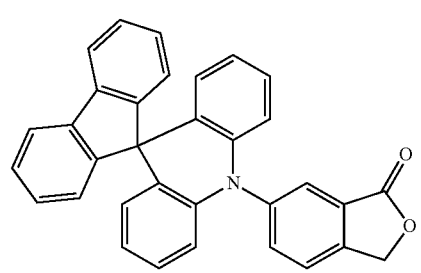

203
-continued
327
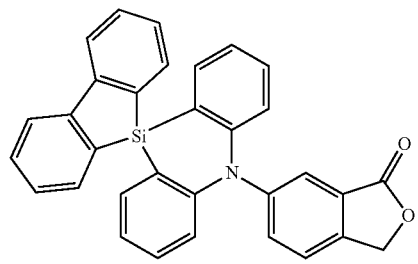
328
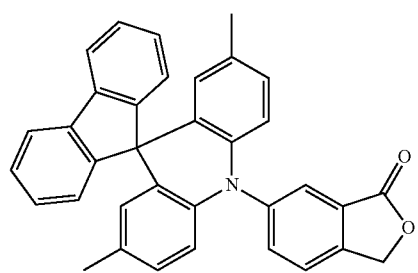
329
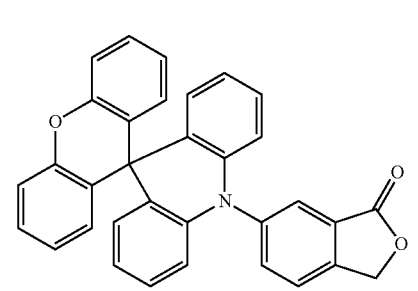
330
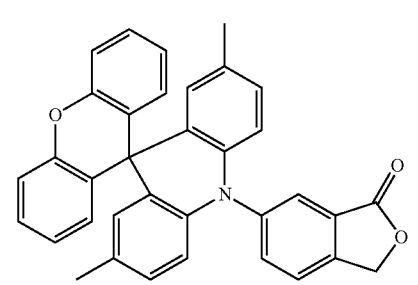
331
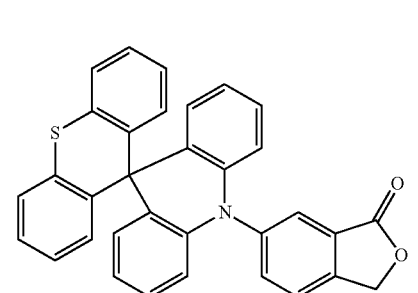
332
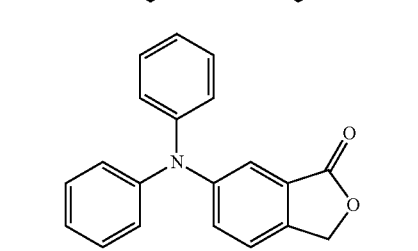
204
-continued
333
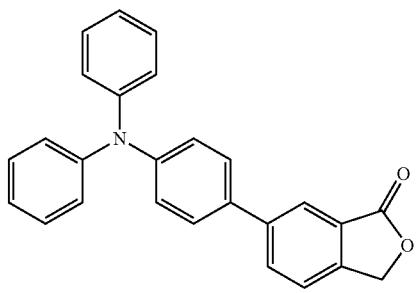
334
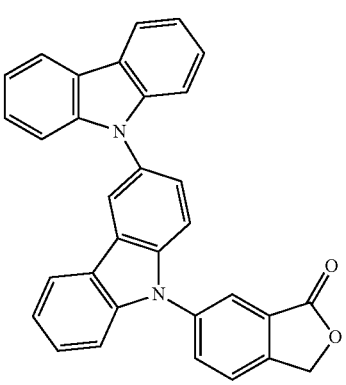
335
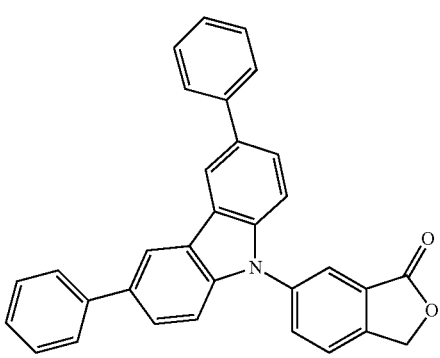
336
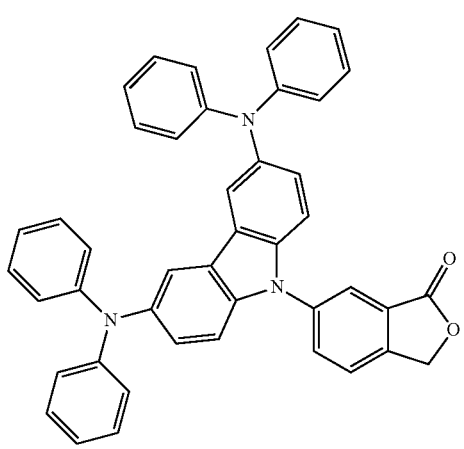

| | |
|---|---|
| 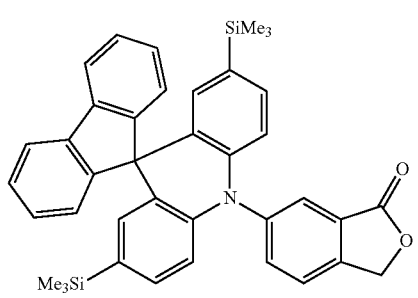 337 | 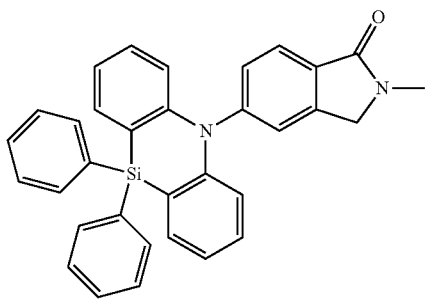 342 |
| 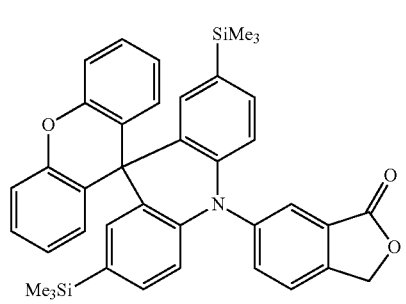 338 | 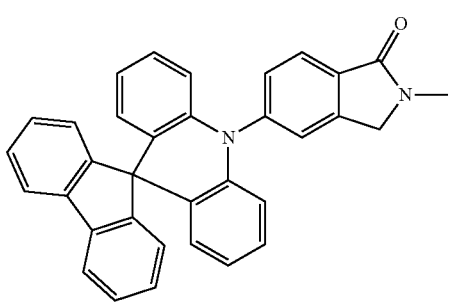 343 |
| 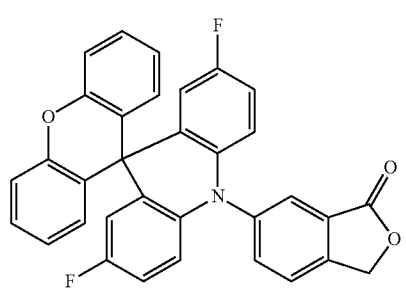 339 | 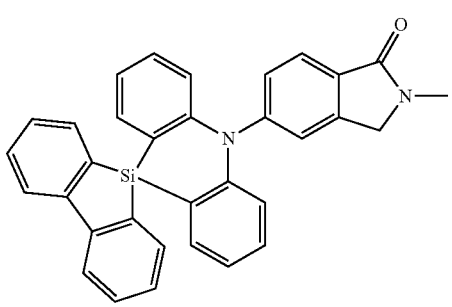 344 |
| 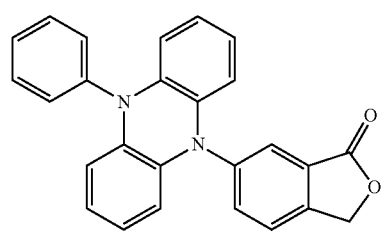 340 | 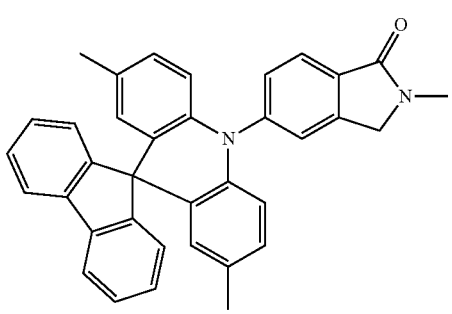 345 |
| 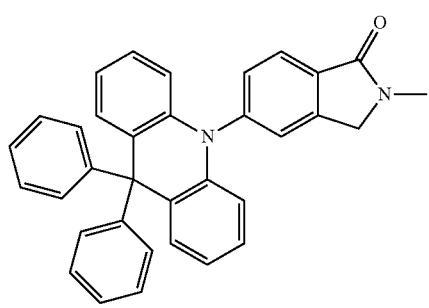 341 | 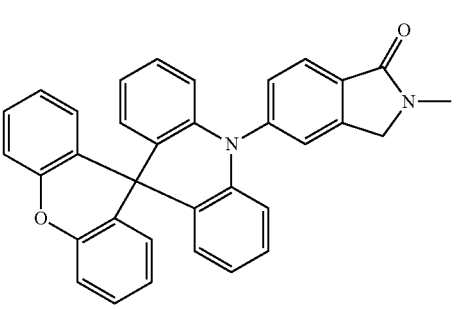 346 |

-continued
347
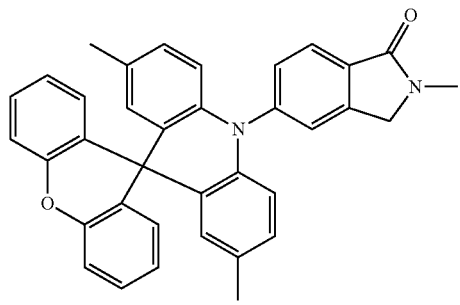
348
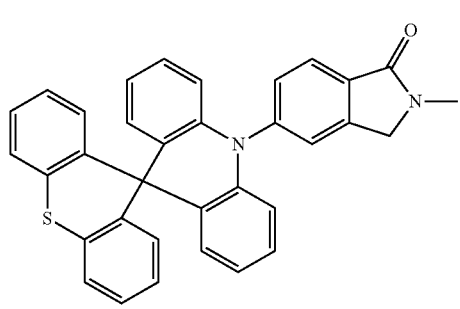
349
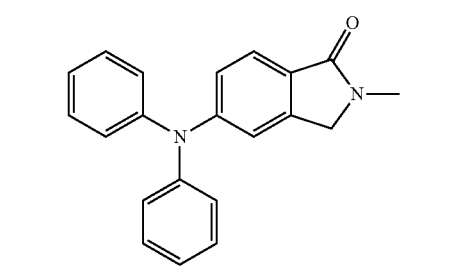
350
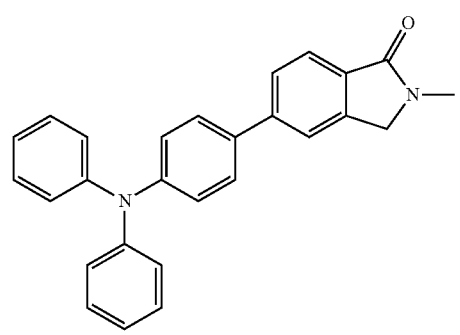
351
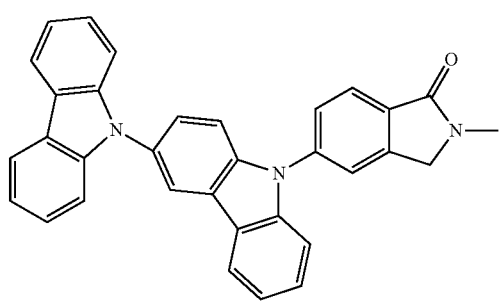
-continued
352
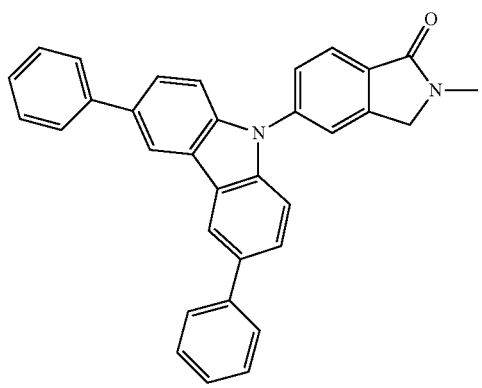
353
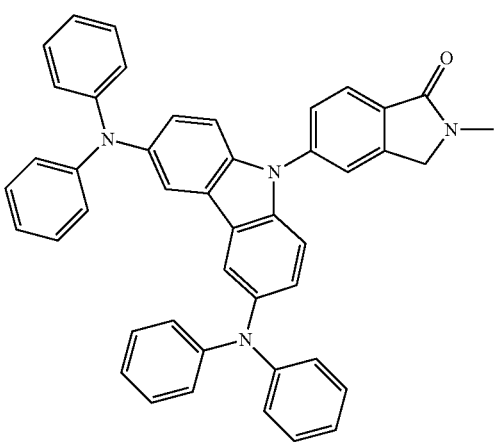
354
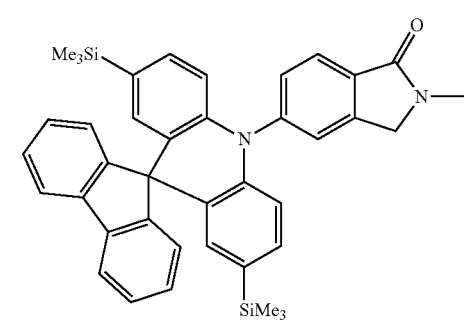
355
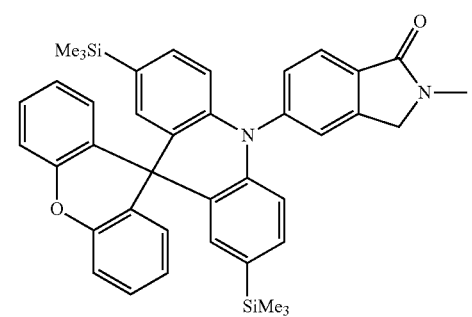

| | |
|---|---|
| 356 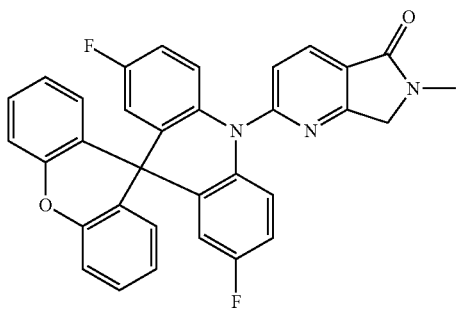 | 361 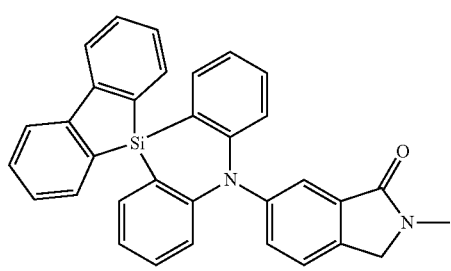 |
| 357 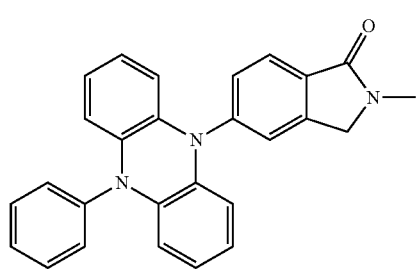 | 362 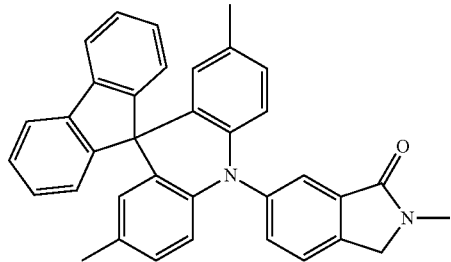 |
| 358 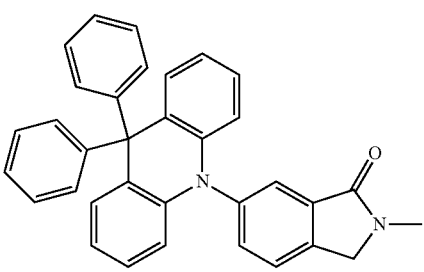 | 363 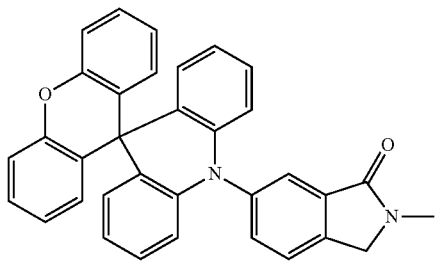 |
| | 364 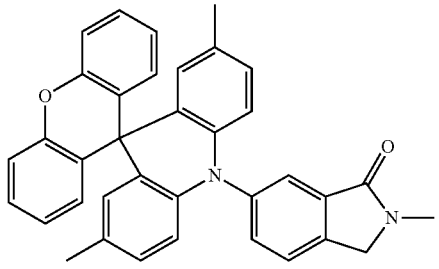 |
| 359 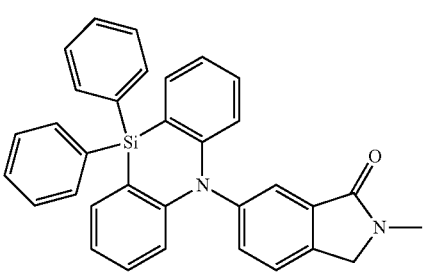 | 365 |
| 360 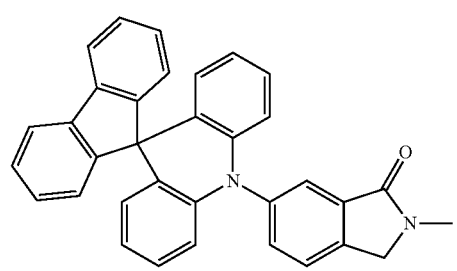 | 366 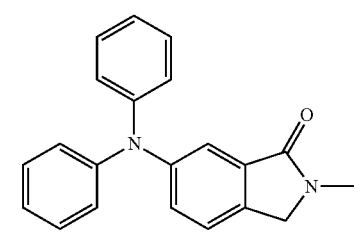 |

211
-continued
367
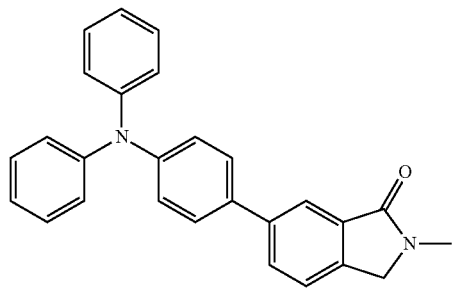
368
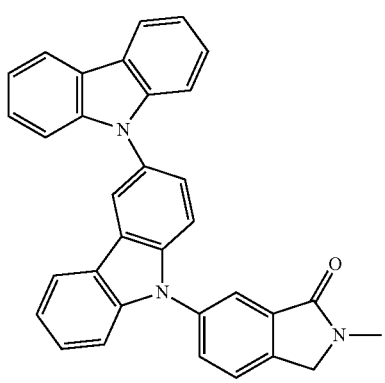
369
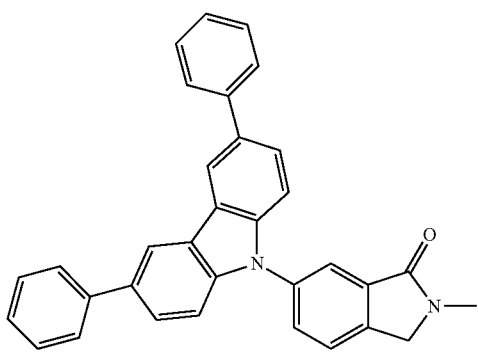
370
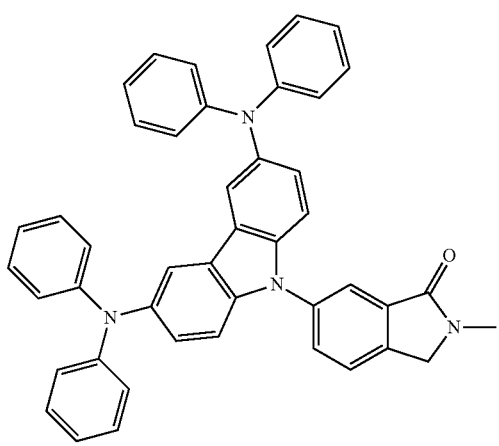
212
-continued
371
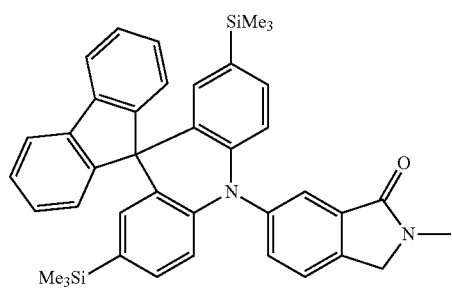
372
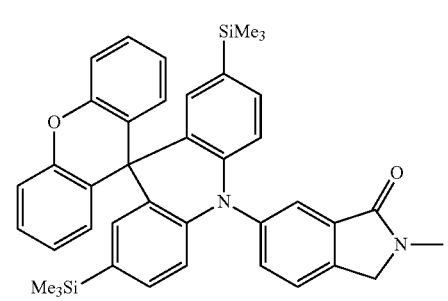
373
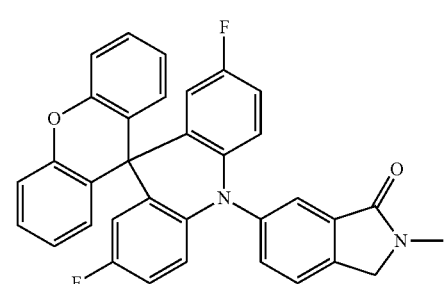
374
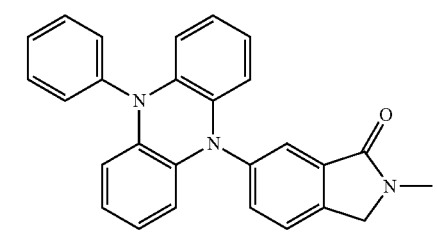
375
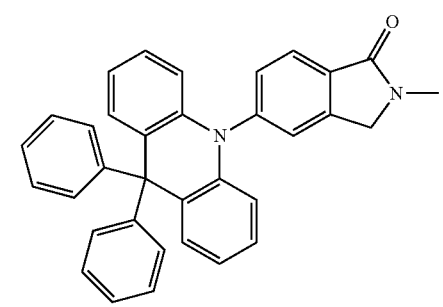

376 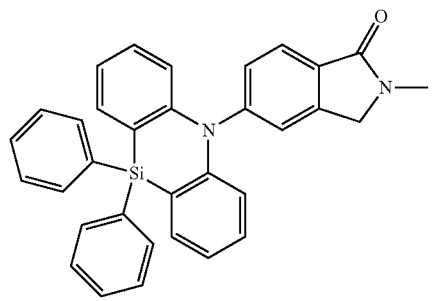
377 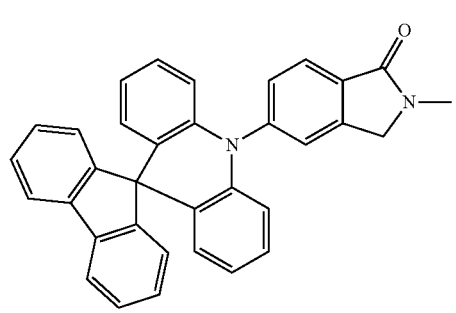
378 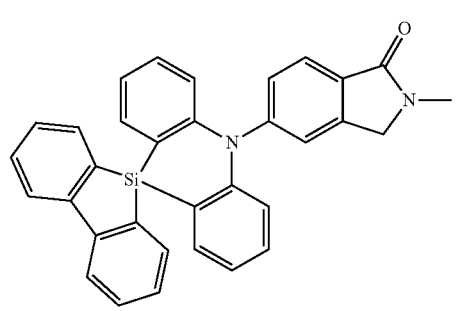
379 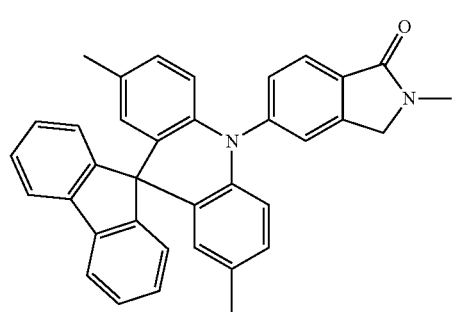
380 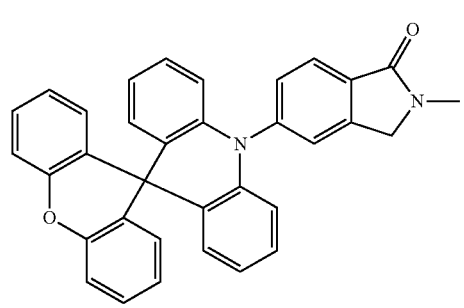
381 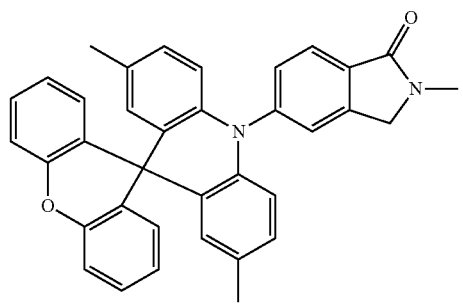
382 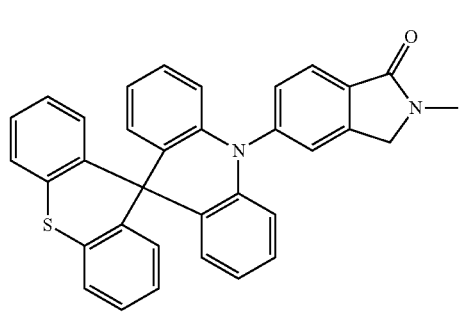
383 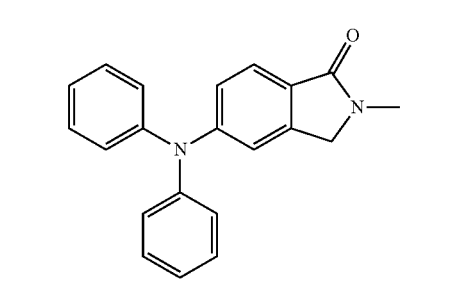
384 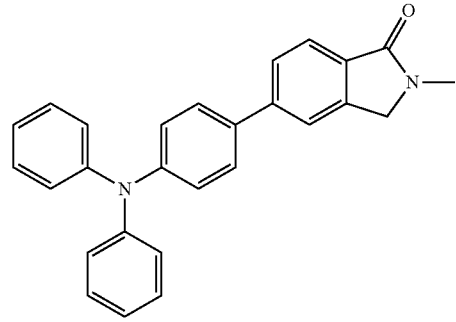
385 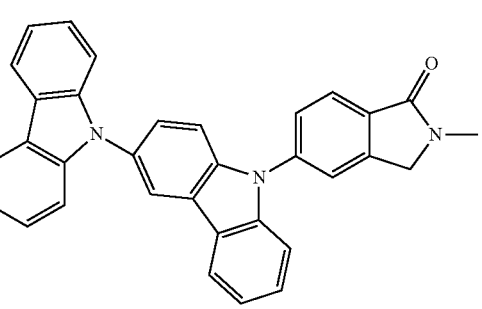

215
-continued
386
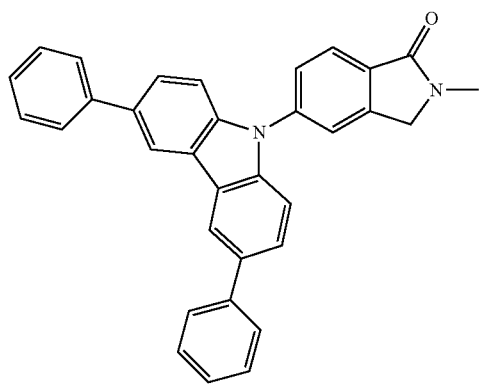
387
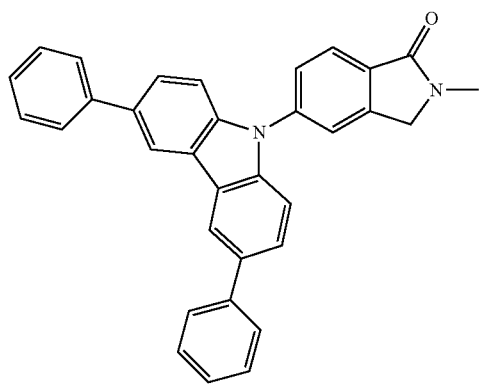
388
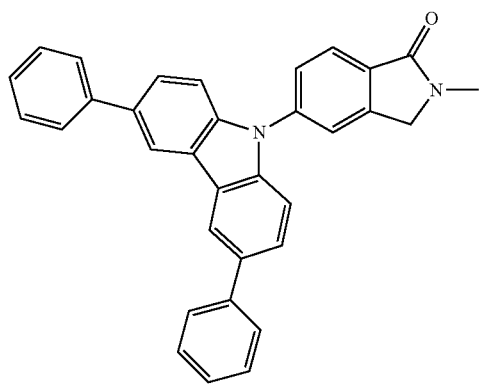
389
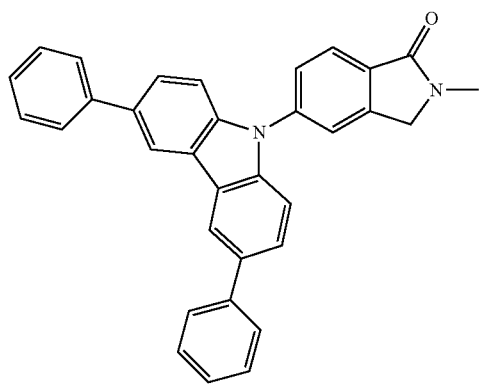
216
-continued
390
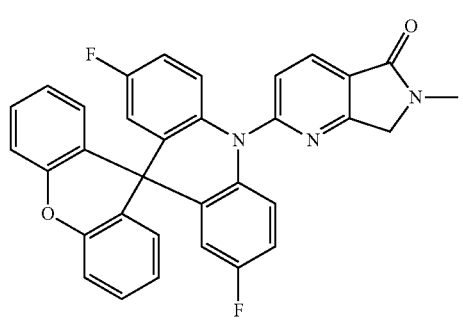
391
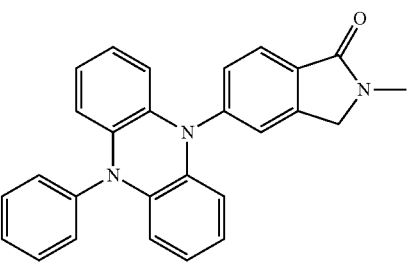
392
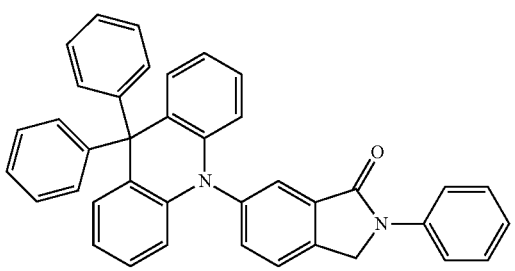
393
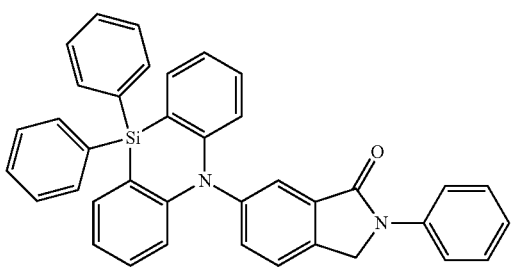
394
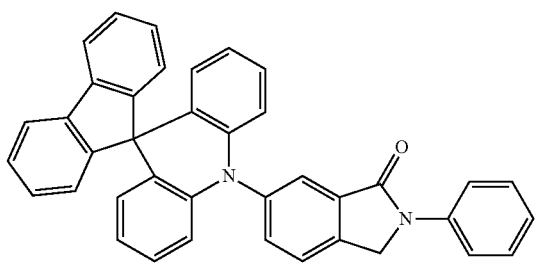

US 10,714,693 B2
217
-continued
395
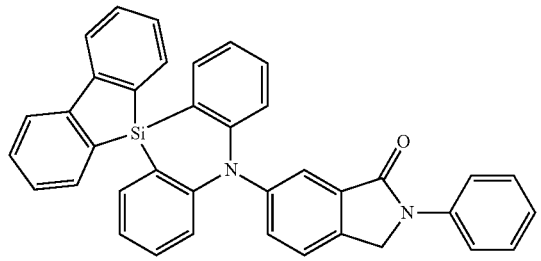
396
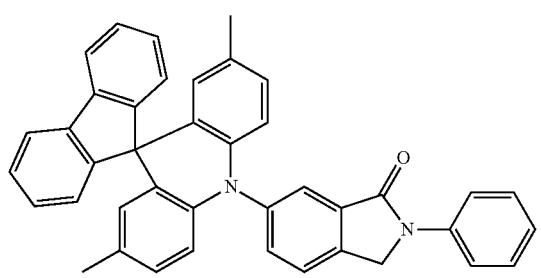
397
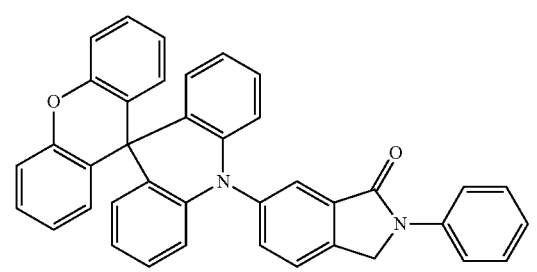
398
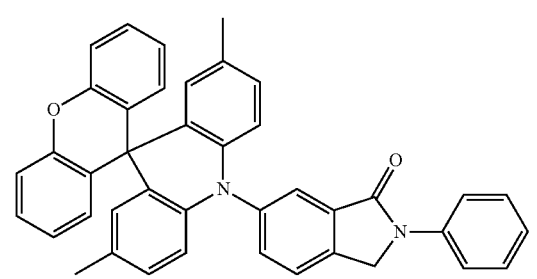
399
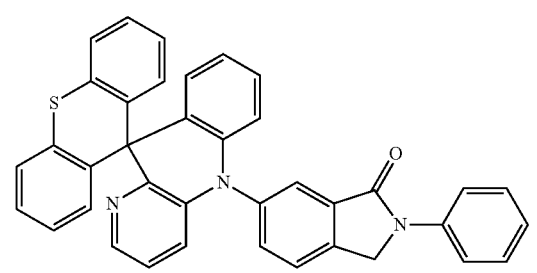
218
-continued
400
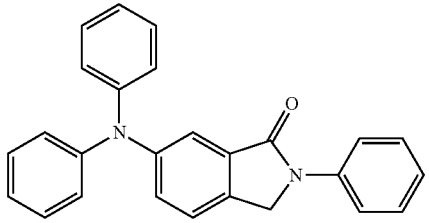
401
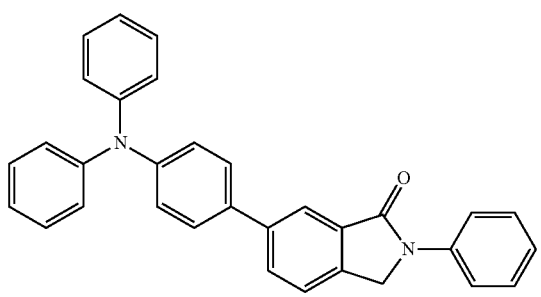
402
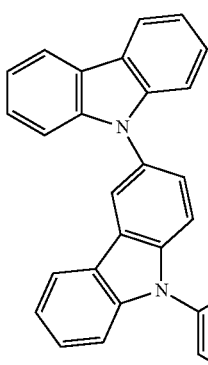
403
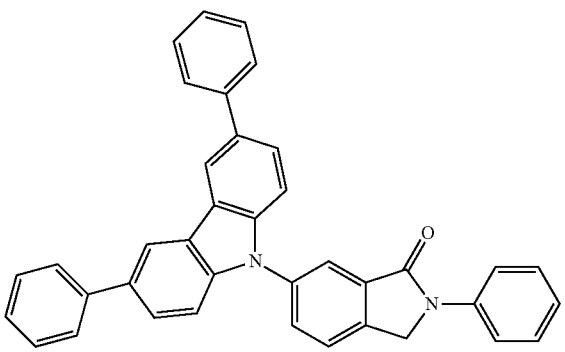

-continued
404
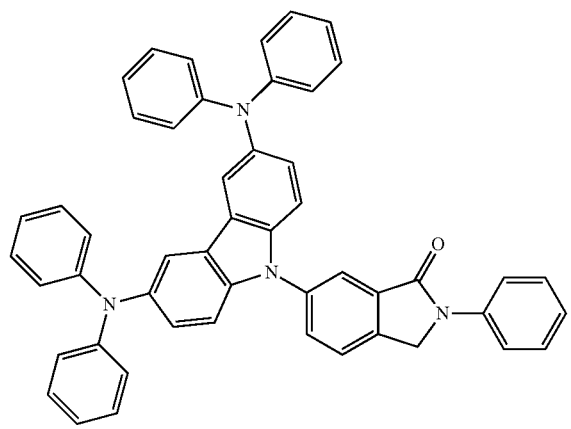
405
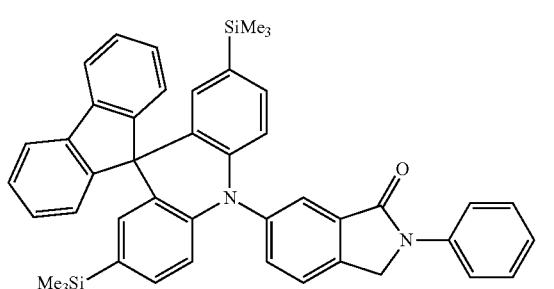
406
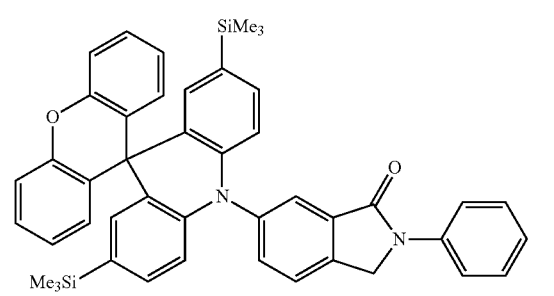
407
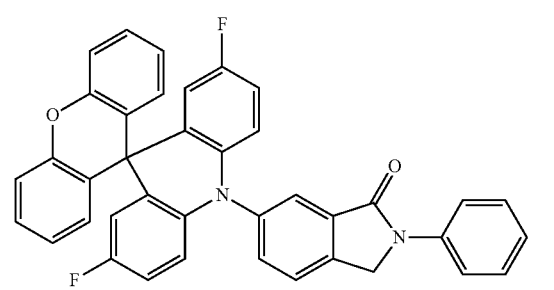
408
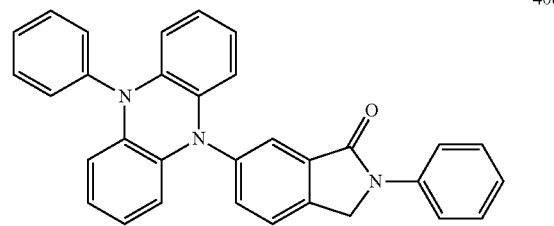
-continued
409
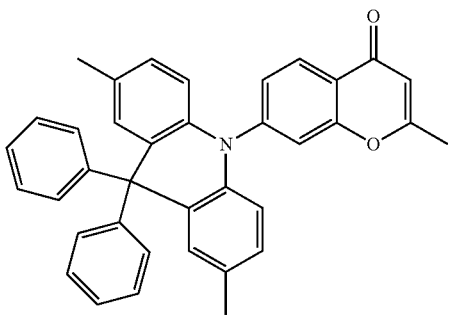
410
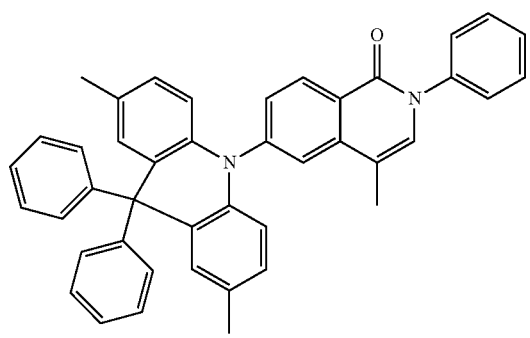
411
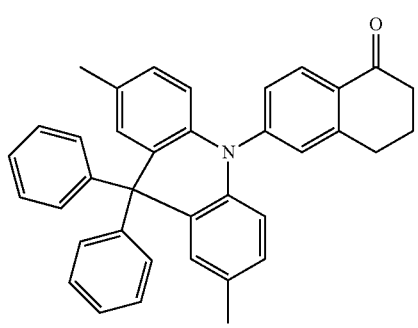
412
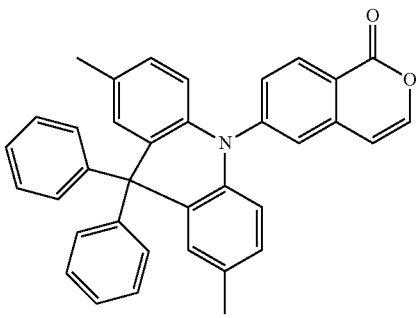
413
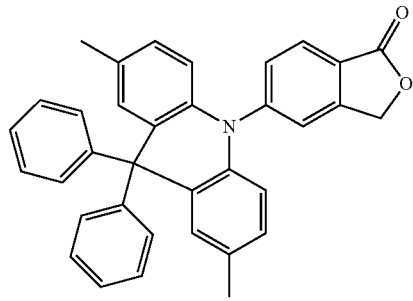

-continued

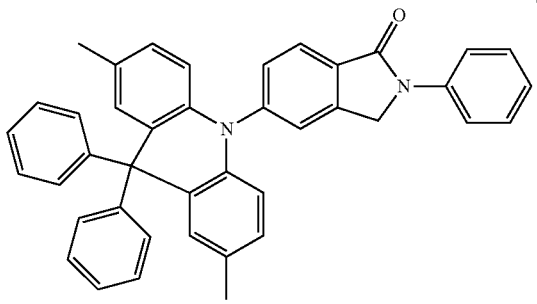
414

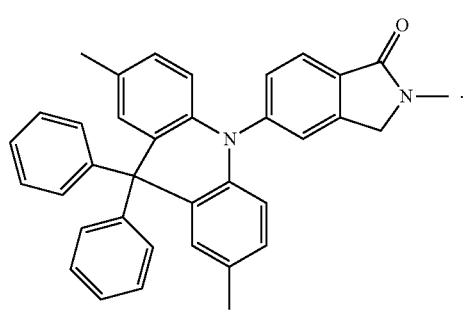
415

14. An organic electroluminescence device comprising:
a first electrode;
an emission layer; and
a second electrode, the emission layer being between the first electrode and the second electrode, the emission layer including a polycyclic compound represented by the following Formula 1:

[Formula 1]

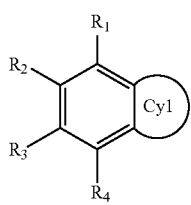

wherein in Formula 1,
Cy1 is a substituted or unsubstituted five- or six-membered cyclic hydrocarbon containing a single carbonyl-group, or a substituted or unsubstituted five- or six-membered heterocycle containing a single carbonyl-group, and
$R_1$ to $R_4$ are each independently a hydrogen atom or a group represented by the following Formula 2 or 3,

[Formula 2]

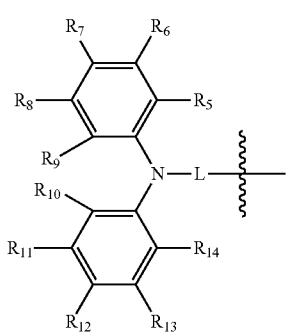

[Formula 3]

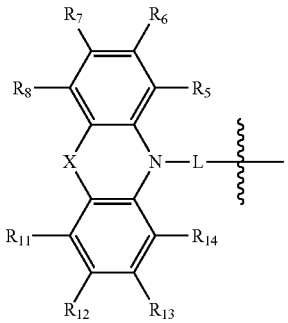

wherein in Formulae 2 and 3,
L is a direct linkage or substituted or unsubstituted arylene group having 6 to 30 carbon atoms forming a ring,
$R_5$ to $R_{14}$ are each independently a hydrogen atom, deuterium atom, halogen atom, substituted or unsubstituted silyl group, substituted or unsubstituted arylamine group, substituted or unsubstituted alkyl group having 1 to 15 carbon atoms, substituted or unsubstituted aryl group having 6 to 30 carbon atoms forming a ring, or substituted or unsubstituted heteroaryl group having 2 to 30 carbon atoms forming a ring,
X is a direct linkage, $CR_{15}R_{16}$, $SiR_{17}R_{18}$, $GeR_{19}R_{20}$, $NR_{21}$, O, or S, and
$R_{15}$ to $R_{21}$ are each independently a substituted or unsubstituted aryl group having 6 to 12 carbon atoms forming a ring, where the aryl group may combine with an adjacent group to form a ring,
wherein a substituent of the substituted five- or six-membered cyclic hydrocarbon containing a single carbonyl-group, and a substituent of substituted five- or six-membered heterocycle containing a single carbonyl-group are each independently a deuterium atom, halogen atom, cyano group, nitro group, amino group, silyl group, boron group, arylamine group, phosphine oxide group, phosphine sulfide group, alkyl group, alkenyl group, aryl group, or heteroaryl group.

15. The organic electroluminescence device as claimed in claim 14, wherein the polycyclic compound represented by Formula 1 has a value of absolute difference of about 0.2 eV or less between a singlet energy level and a triplet energy level.

16. The organic electroluminescence device as claimed in claim 14, wherein the polycyclic compound represented by Formula 1 exhibits thermally activated delayed fluorescence.

17. The organic electroluminescence device as claimed in claim 14, wherein the polycyclic compound represented by Formula 1 is represented by one of the following Formulae 1-3 to 1-8:

[Formula 1-3]

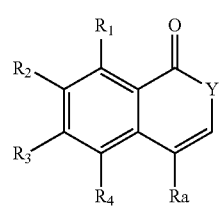

-continued

[Formula 1-4]
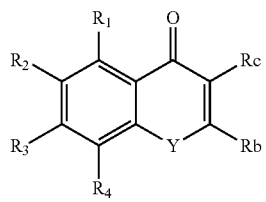

[Formula 1-5]
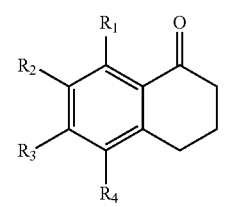

[Formula 1-6]
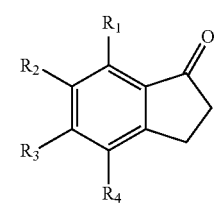

[Formula 1-7]
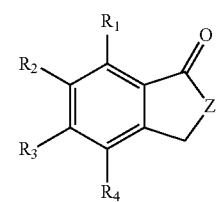

[Formula 1-8]
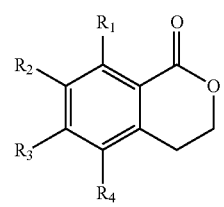

wherein in Formulae 1-3 and 1-4,
Y is O or $NR_{22}$,
$R_{22}$ is a hydrogen atom, substituted or unsubstituted alkyl group having 1 to 15 carbon atoms, or substituted or unsubstituted aryl group having 6 to 30 carbon atoms forming a ring,
Ra to Rc are each independently a hydrogen atom or substituted or unsubstituted alkyl group having 1 to 15 carbon atoms,
wherein in Formula 1-7,
Z is O or $NR_{23}$,
$R_{23}$ is a hydrogen atom, substituted or unsubstituted alkyl group having 1 to 15 carbon atoms, or substituted or unsubstituted aryl group having 6 to 30 carbon atoms forming a ring, and
wherein in Formulae 1-3 to 1-8,
$R_1$ to $R_4$ are the same as defined in claim 14.

18. The organic electroluminescence device as claimed in claim 14, wherein:
one of $R_2$ and $R_3$ is represented by Formula 2 or 3, and the remaining one of $R_2$ and $R_3$, $R_1$, and $R_4$ are a hydrogen atom.

19. The organic electroluminescence device as claimed in claim 14, wherein L is a direct linkage.

20. The organic electroluminescence device as claimed in claim 14, wherein the polycyclic compound represented by Formula 1 is one of compounds represented in the following Compound Group 1:

1
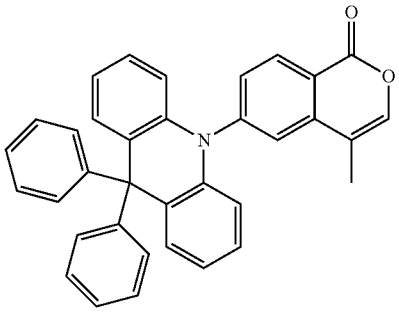

2
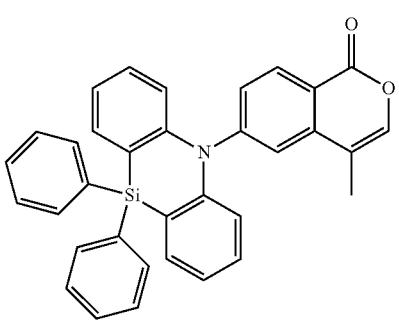

3
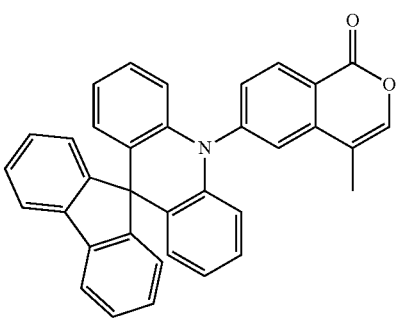

4
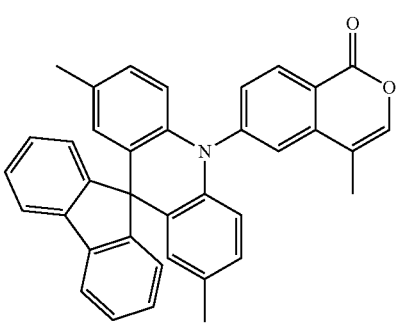

5
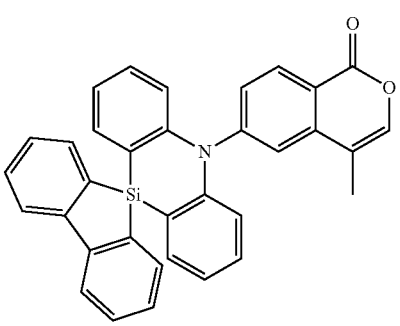

-continued
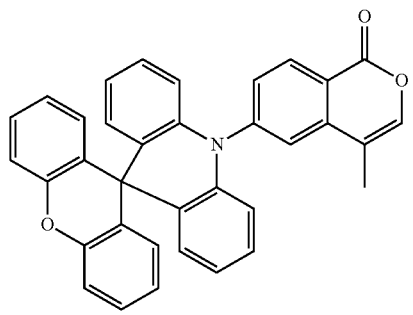
6
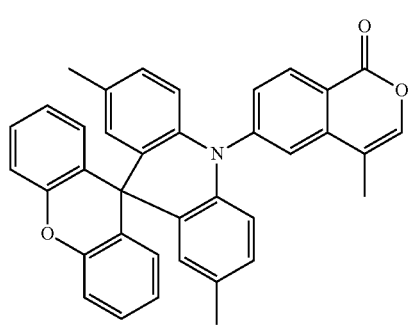
7
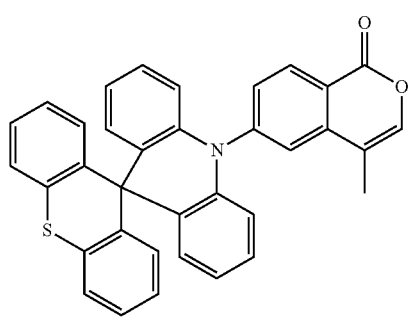
8
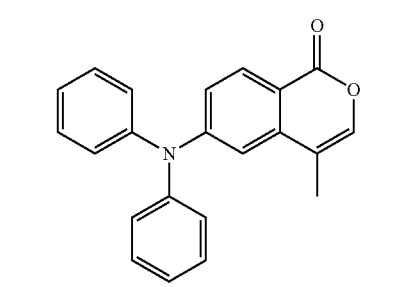
9
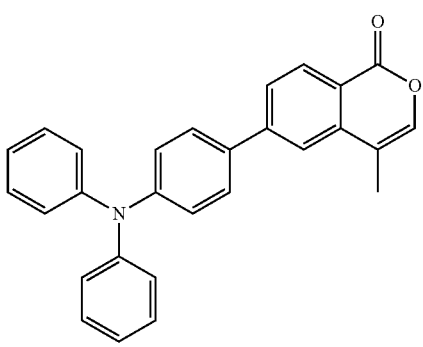
10
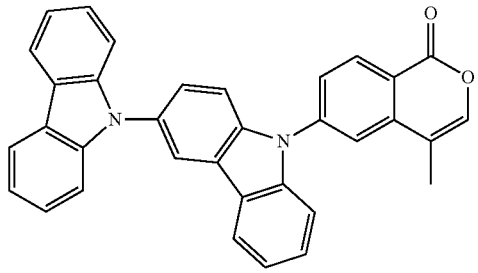
11
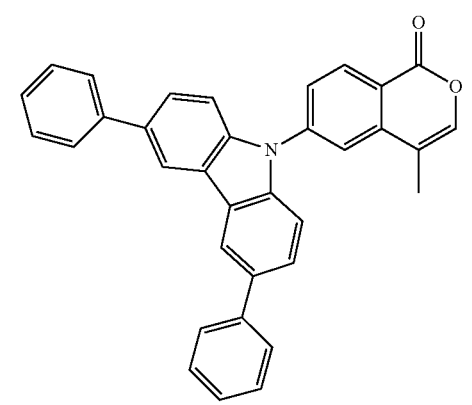
12
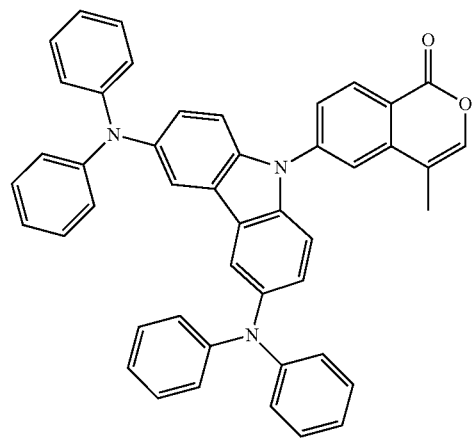
13
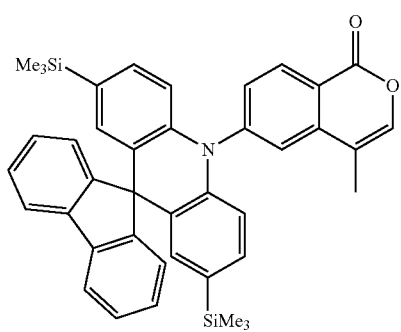
14

| 227 -continued | | 228 -continued | |
|---|---|---|---|
| 15 | 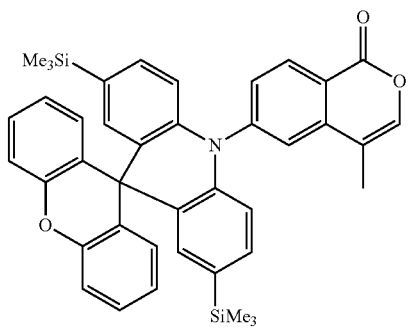 | 20 | 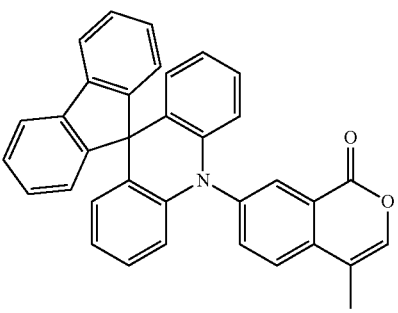 |
| 16 | 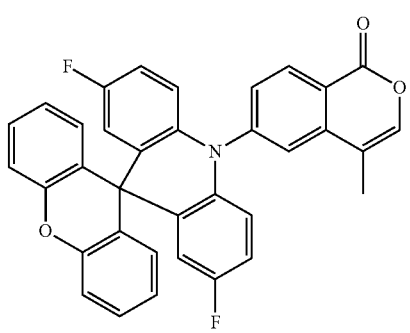 | 21 | 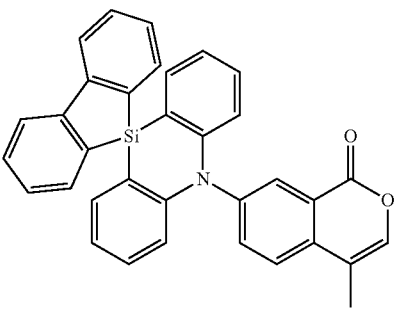 |
| 17 | 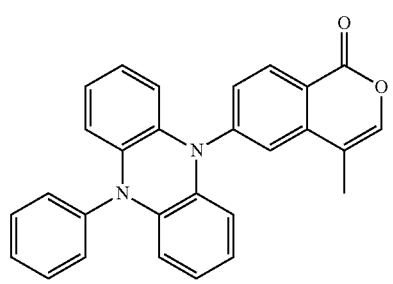 | 22 | 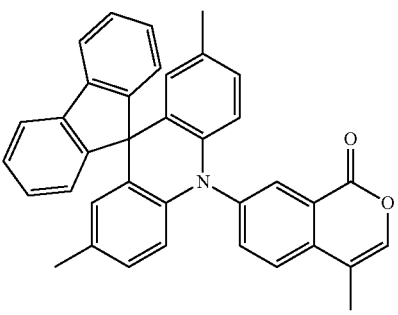 |
| 18 | 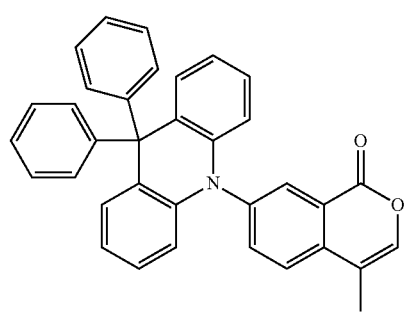 | 23 | 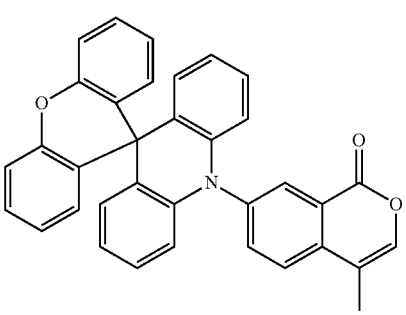 |
| 19 | 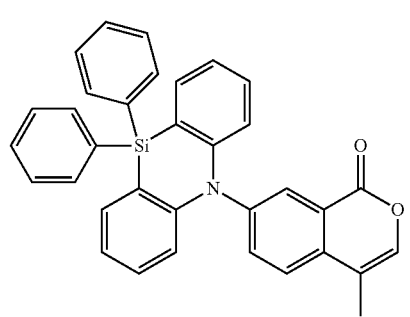 | 24 | 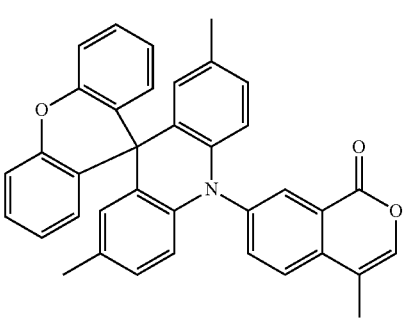 |

| 229 -continued | 230 -continued |
|---|---|
| 25 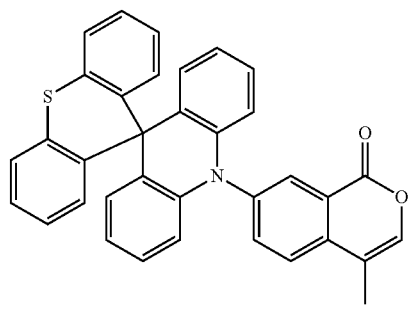 | 30 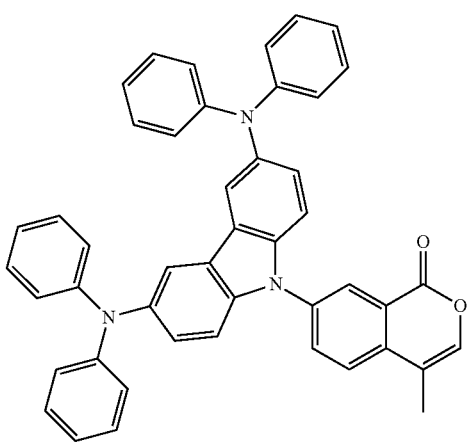 |
| 26 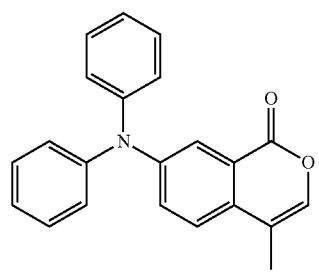 | |
| 27 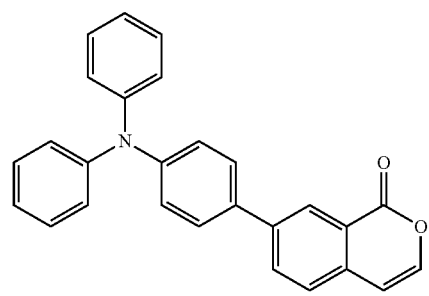 | 31 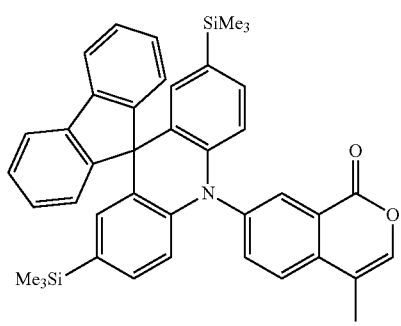 |
| 28 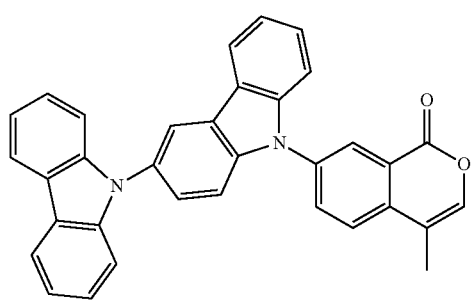 | 32 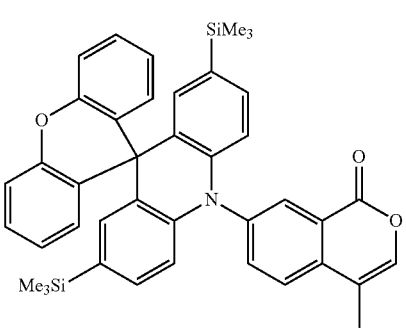 |
| 29 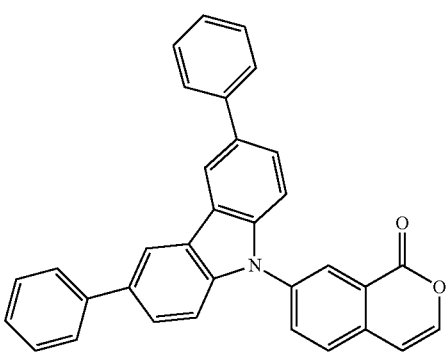 | 33 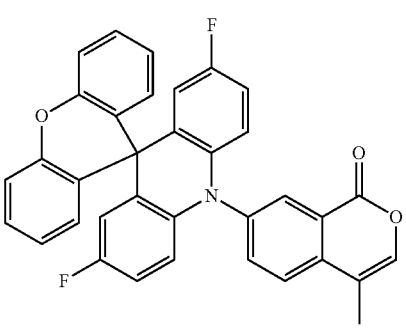 |

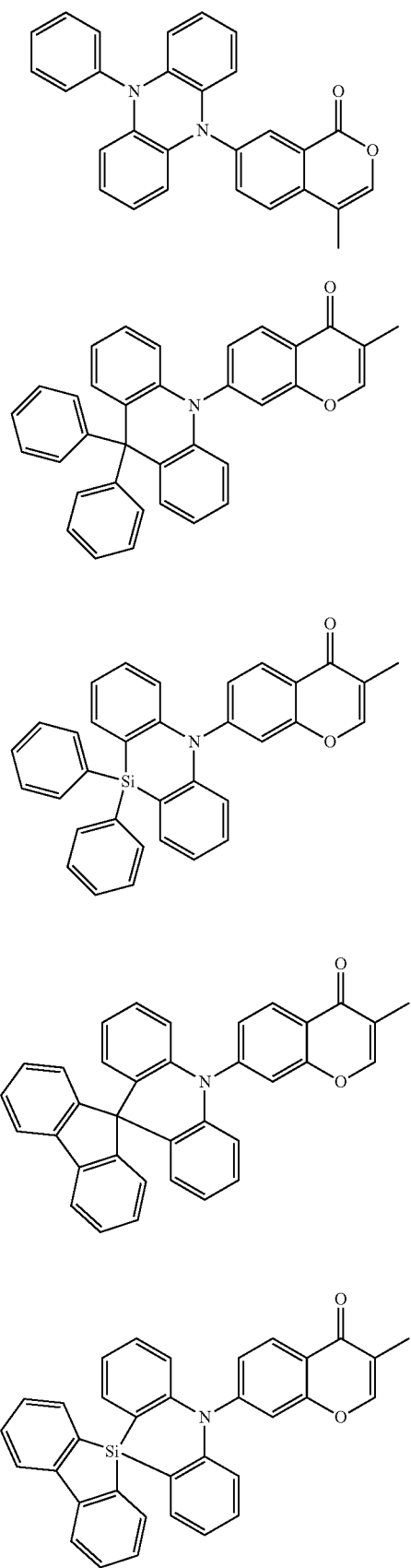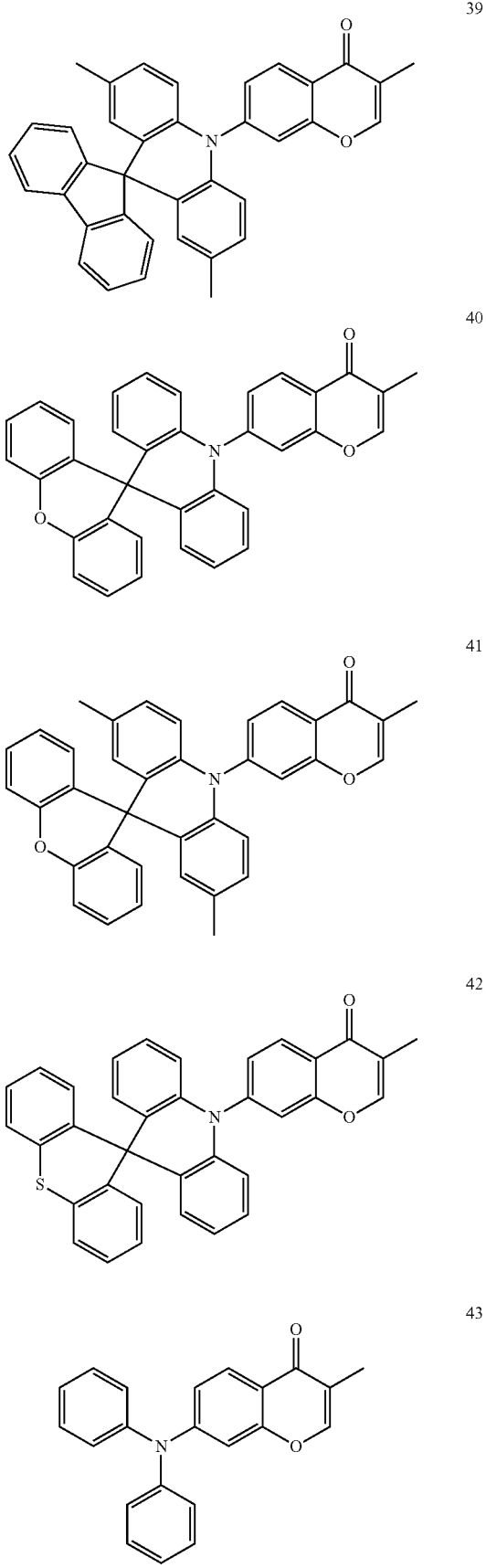

-continued
44
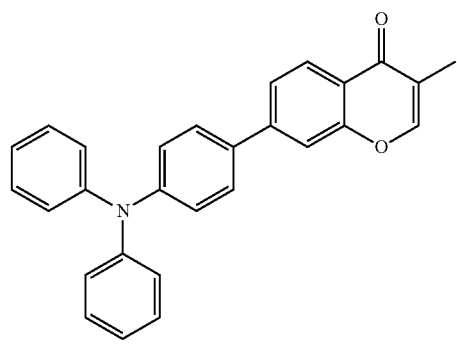
45
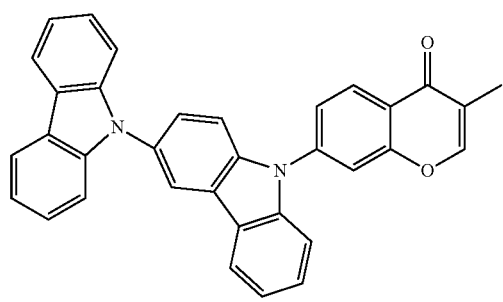
46
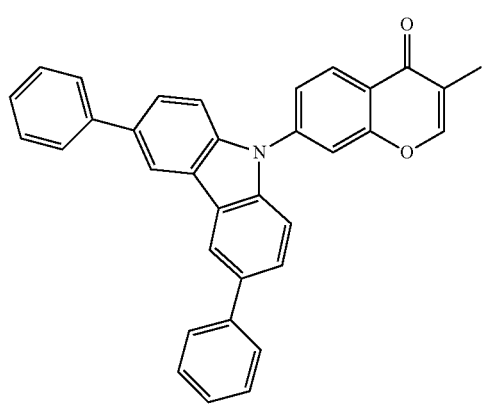
47
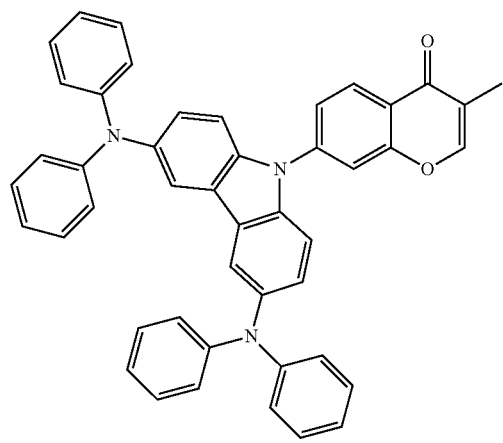
-continued
48
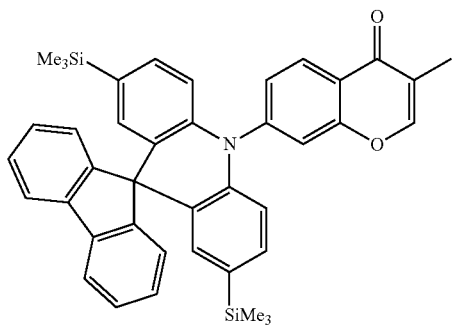
49
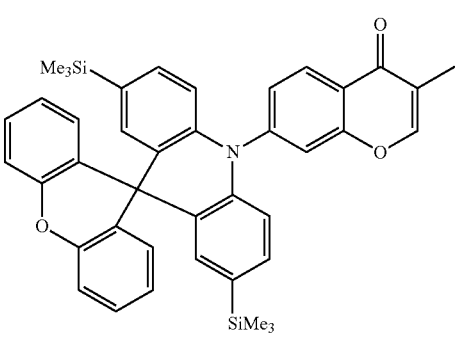
50
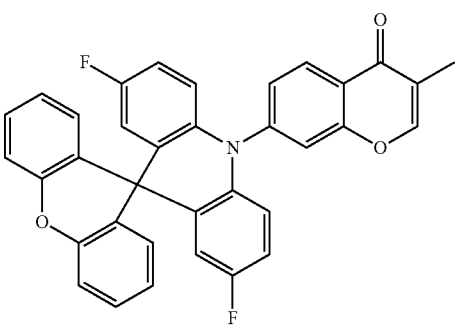
51
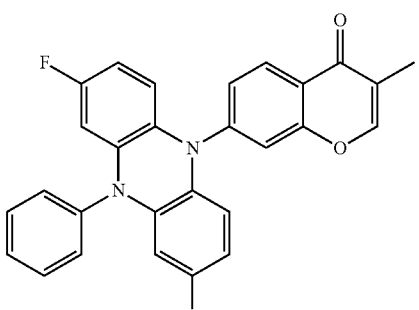
52
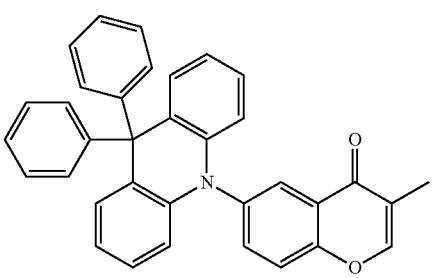

-continued
| | |
|---|---|
| 53 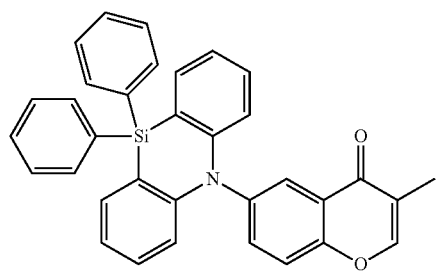 | 58 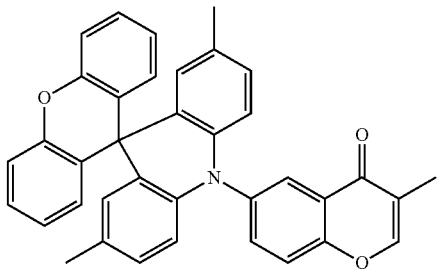 |
| 54 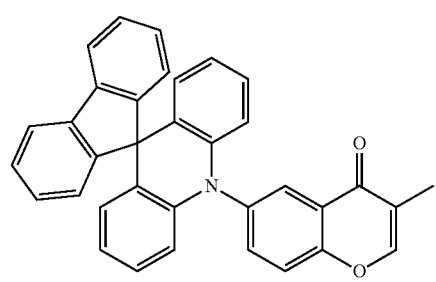 | 59 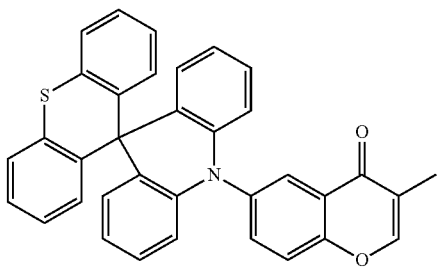 |
| 55 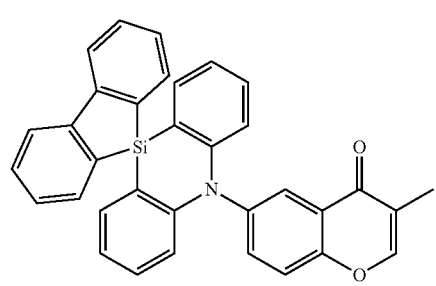 | 60 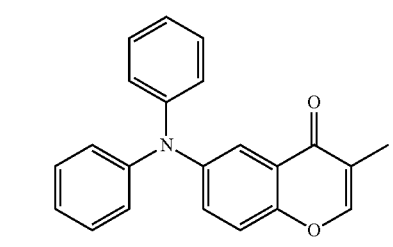 |
| 56 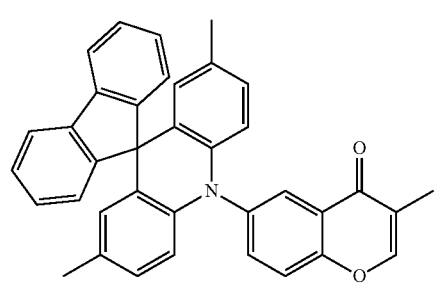 | 61 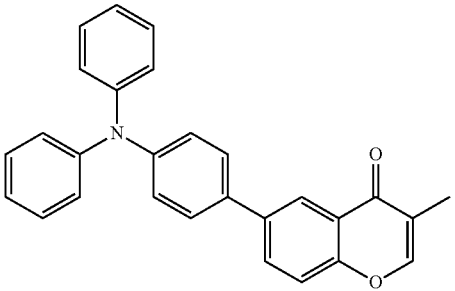 |
| 57 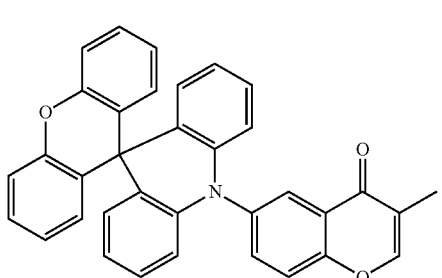 | 62 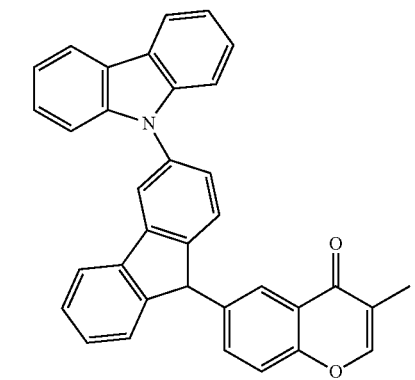 |

-continued
63
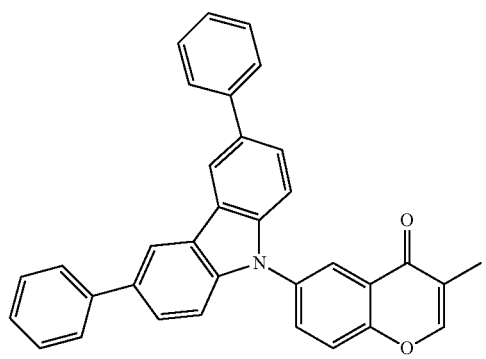
64
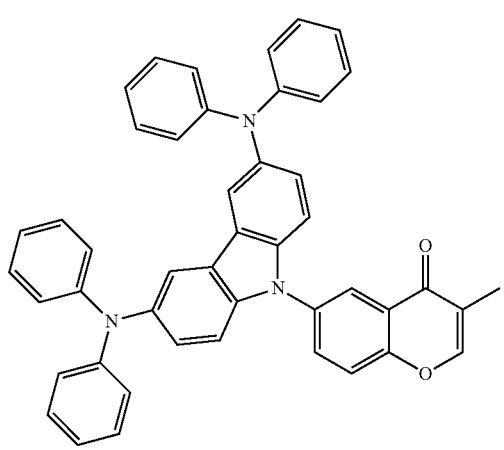
65
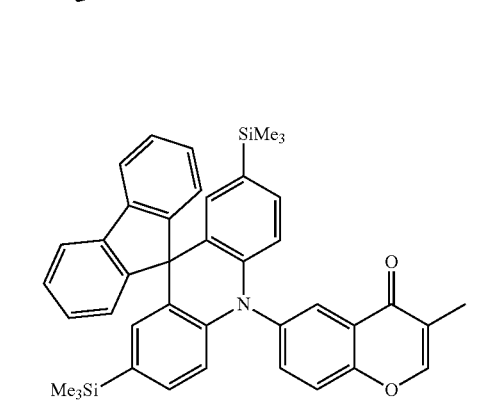
66
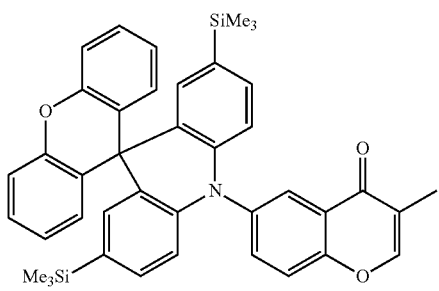
-continued
67
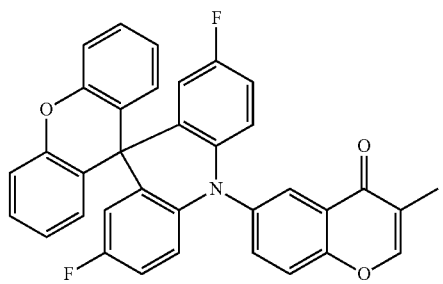
68
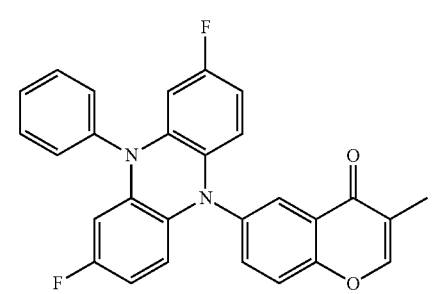
69
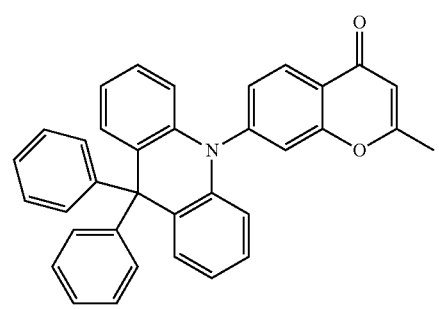
70
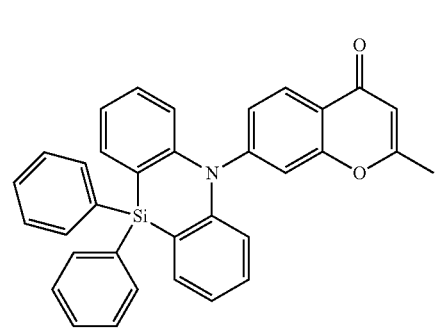
71
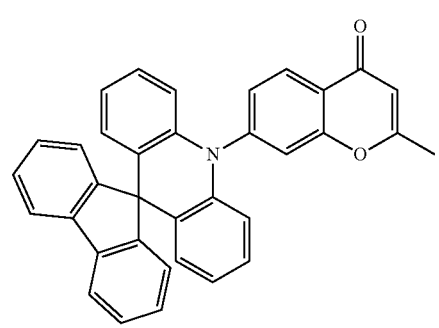

239
-continued
72
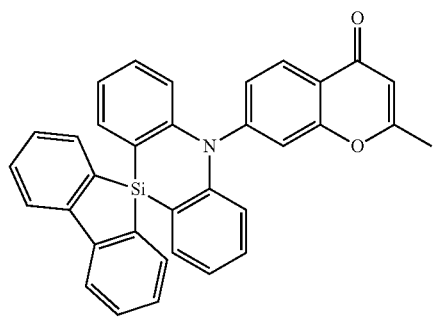
73
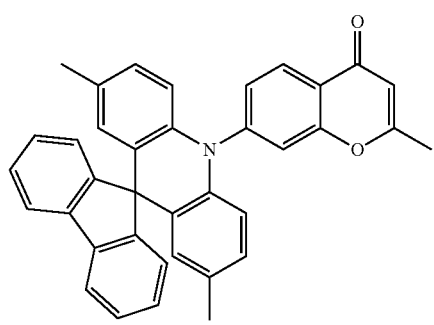
74
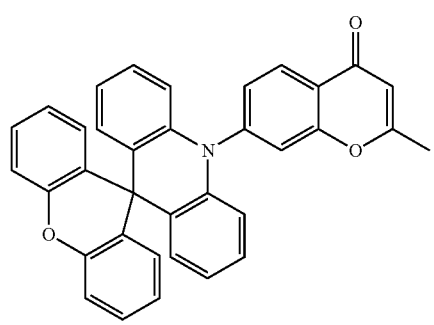
75
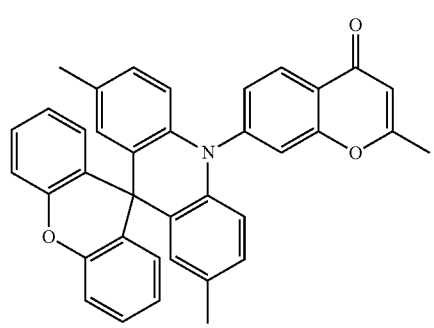
76
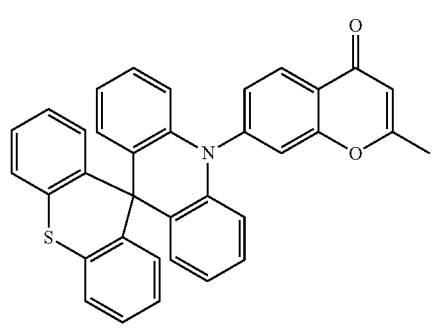
240
-continued
77
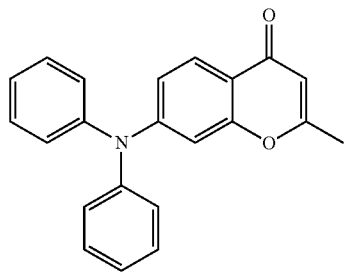
78
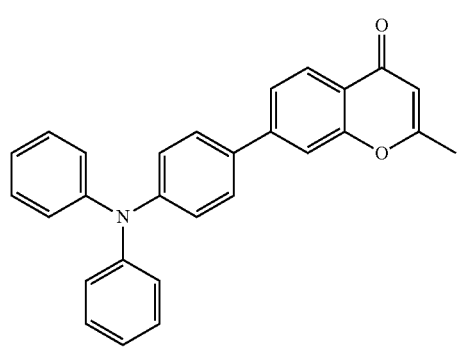
79
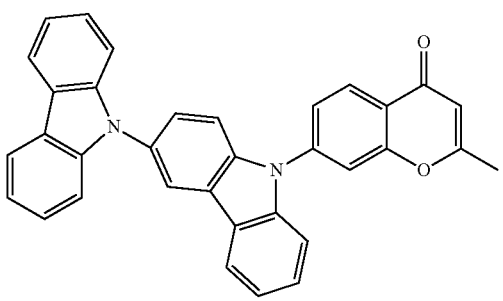
80
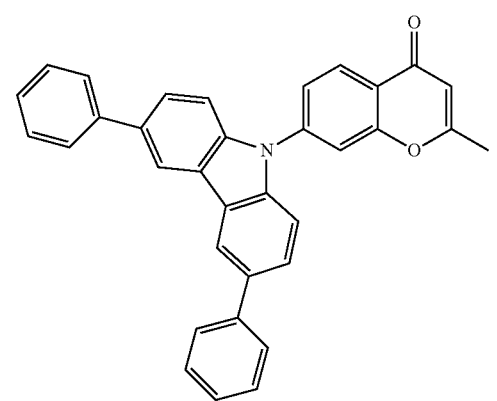

81
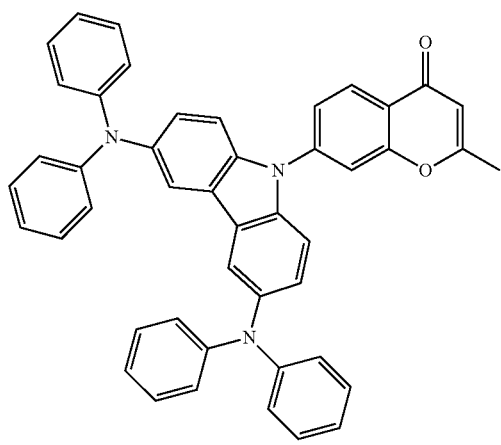
82
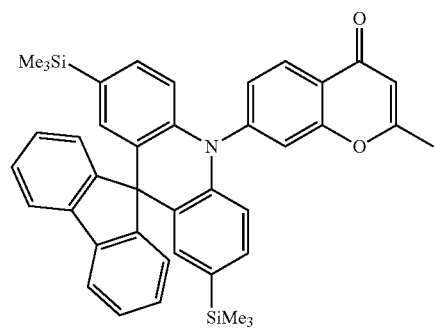
83
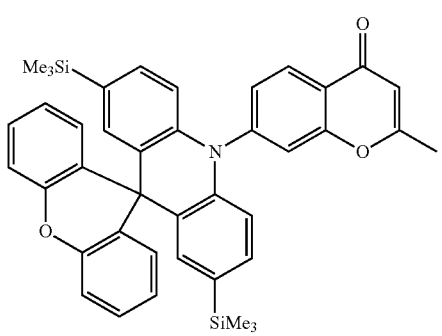
84
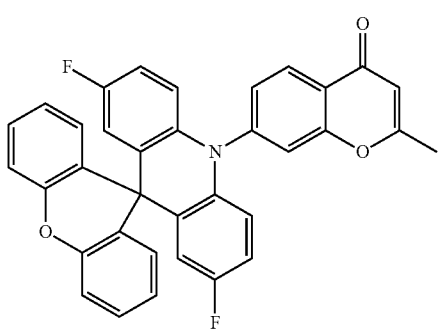
85
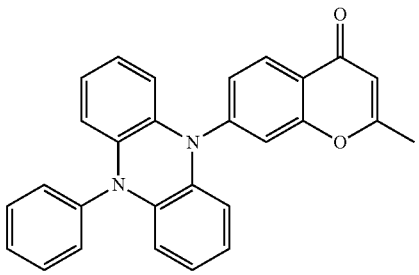
86
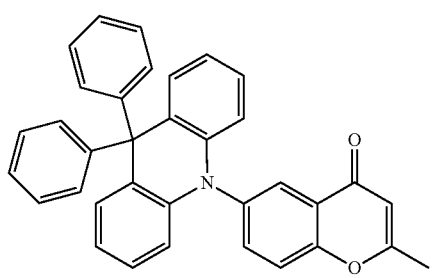
87
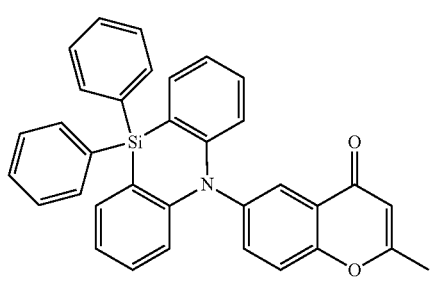
88
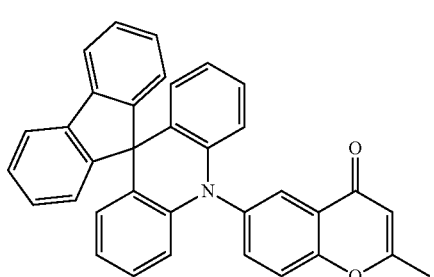
89
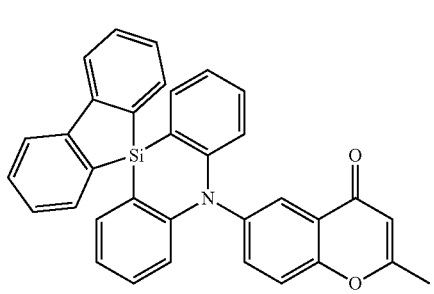

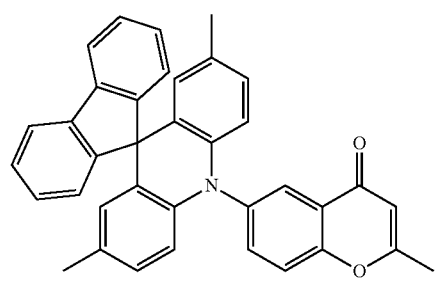
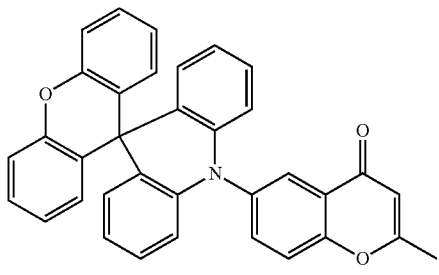
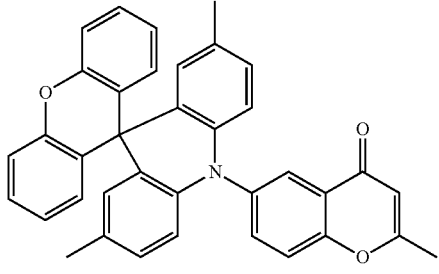
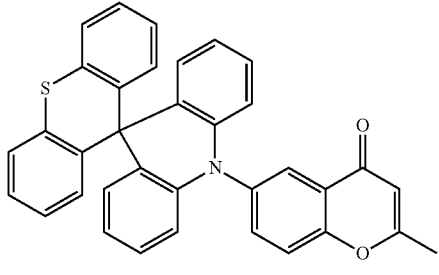
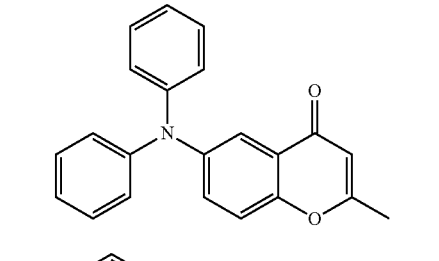
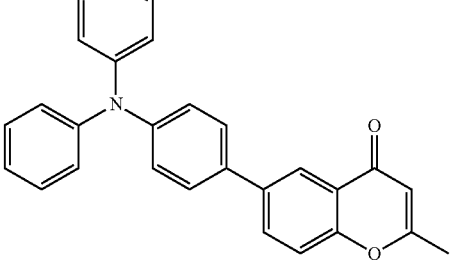
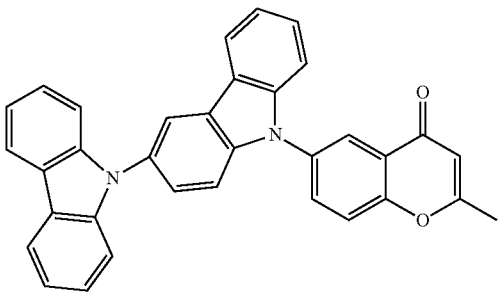
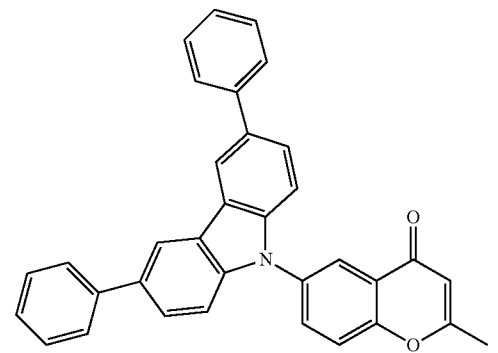
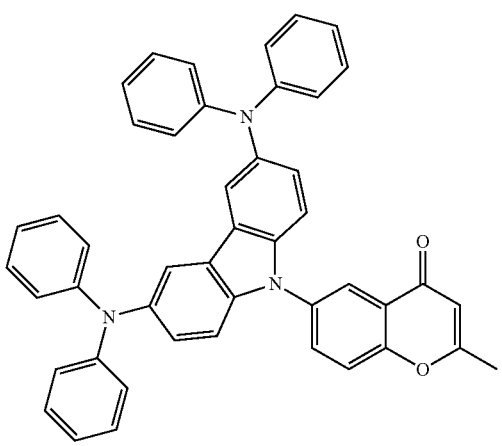
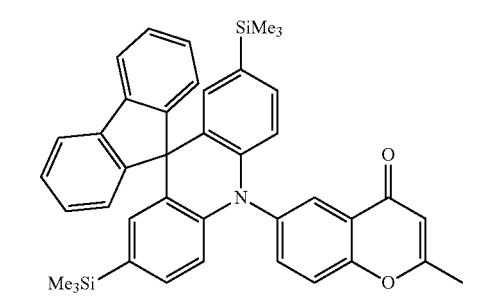

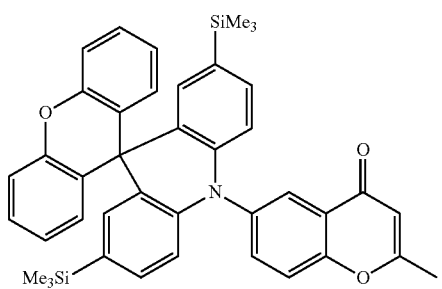
100
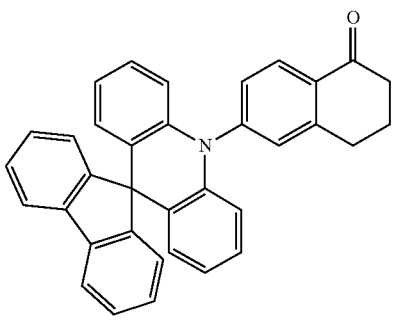
105
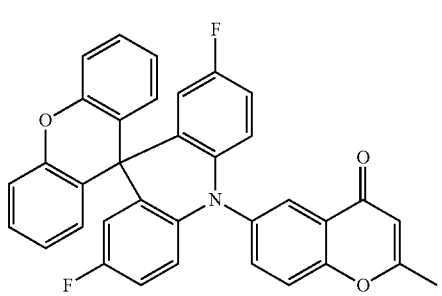
101
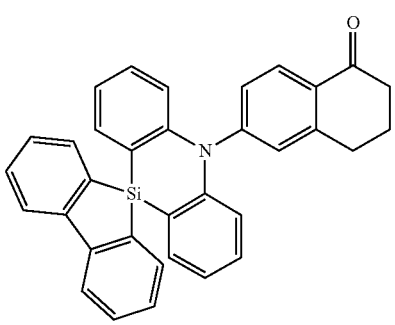
106
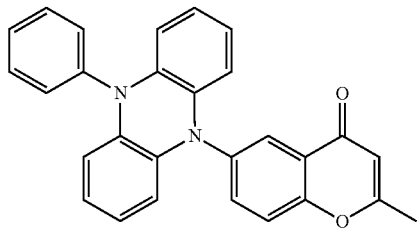
102
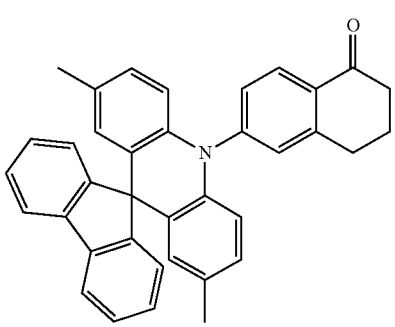
107
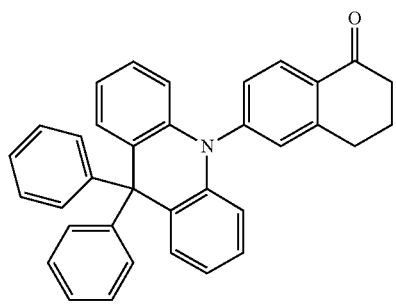
103
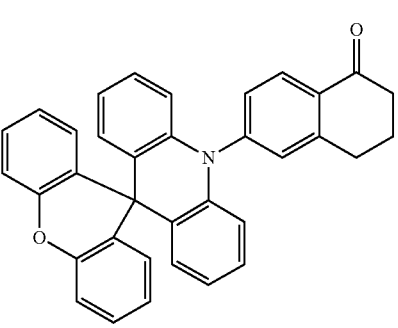
108
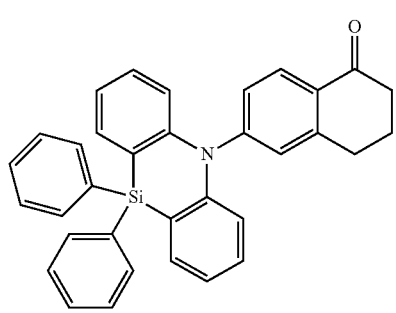
104
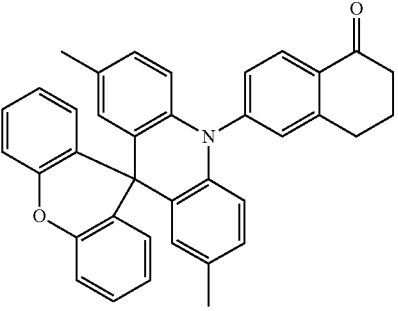
109

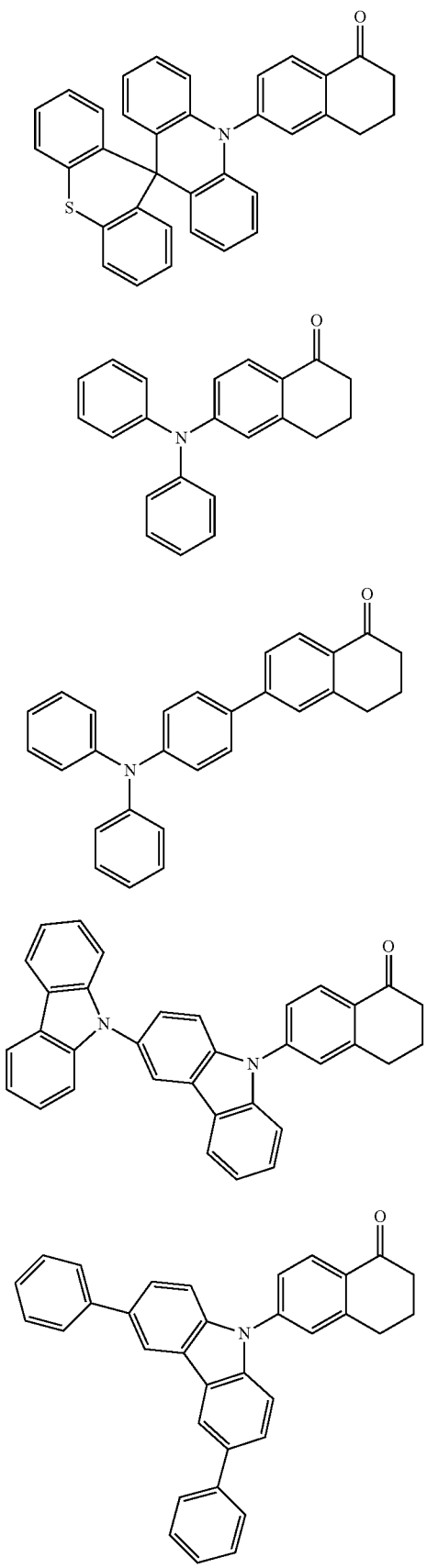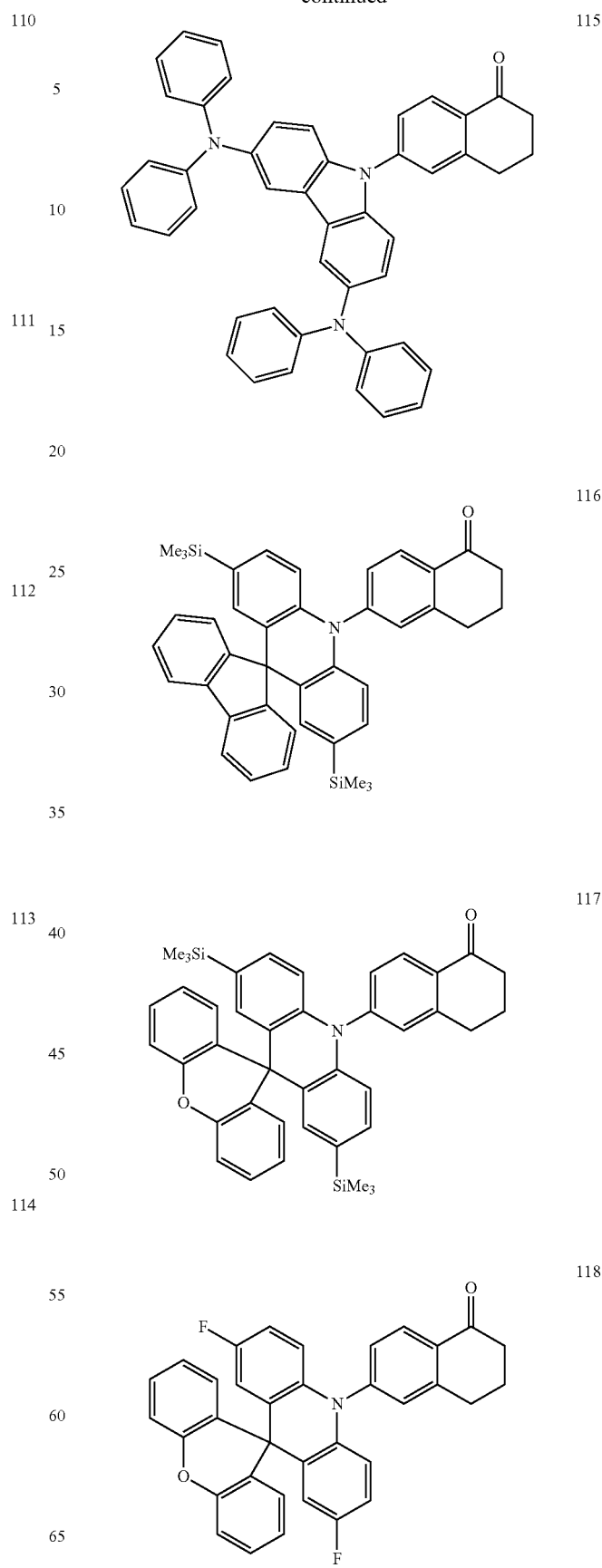

119 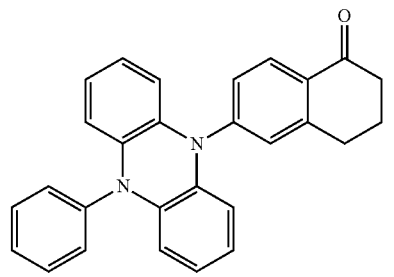
120 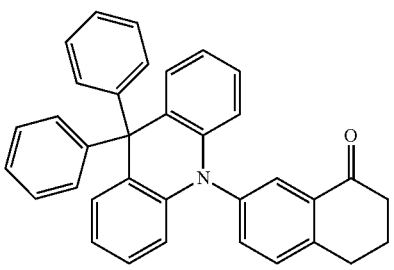
121 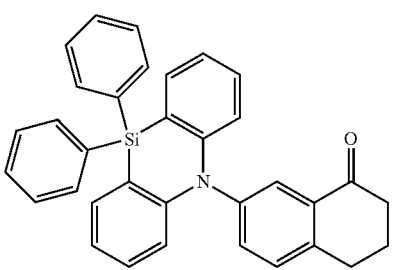
122 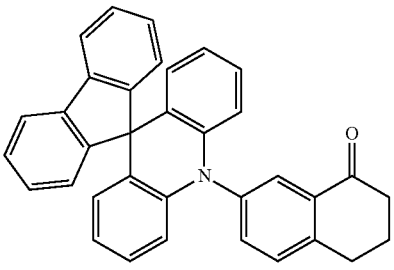
123 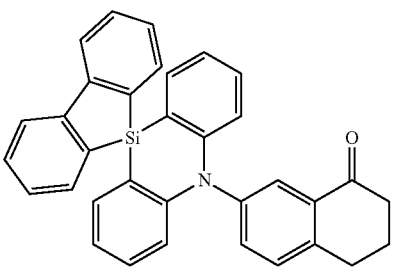
124 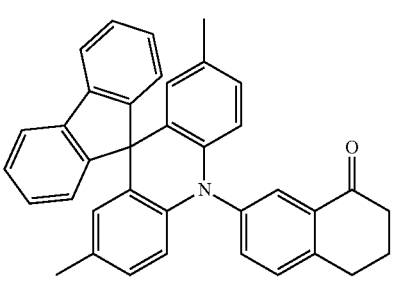
125 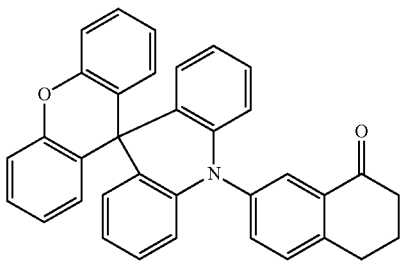
126 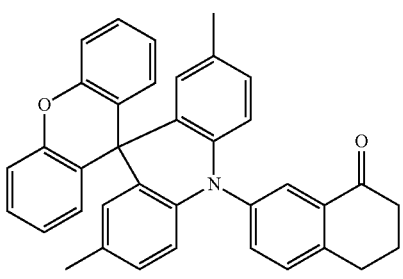
127 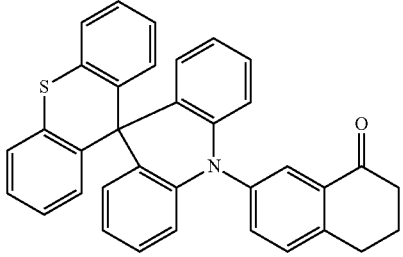
128 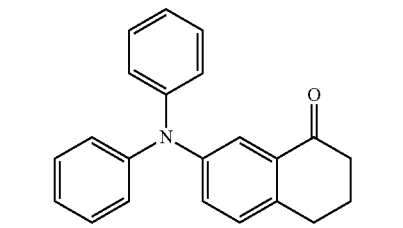
129 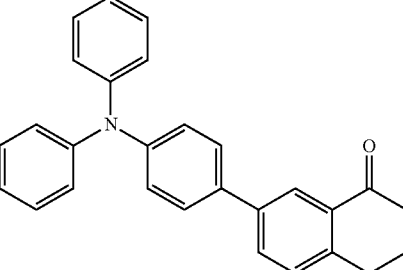

251  
-continued
130
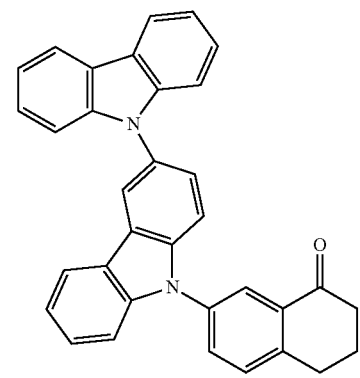
131
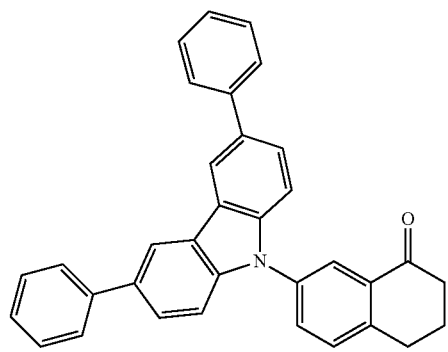
132
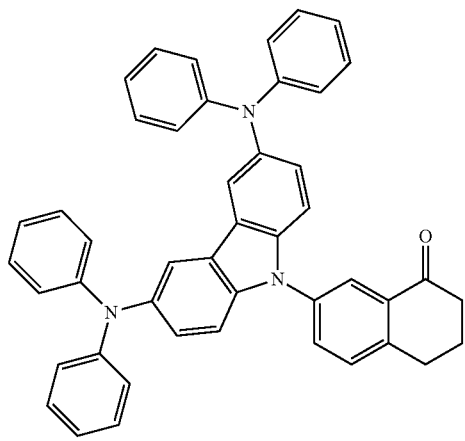
133
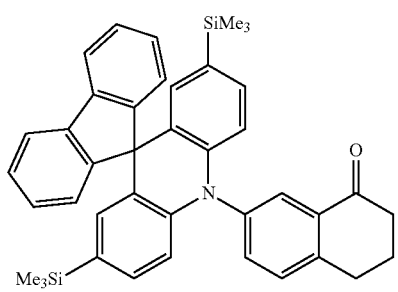
252  
-continued
134
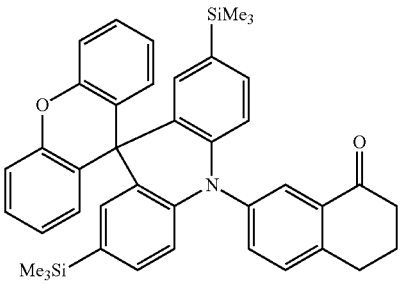
135
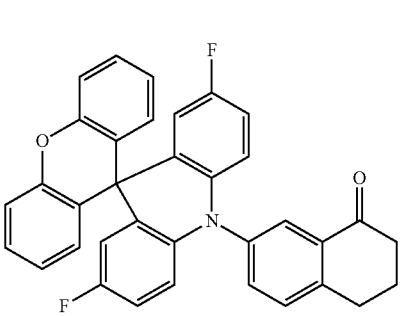
136
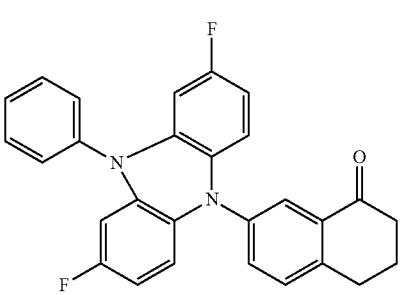
137
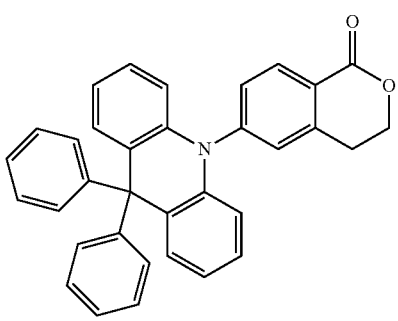
138
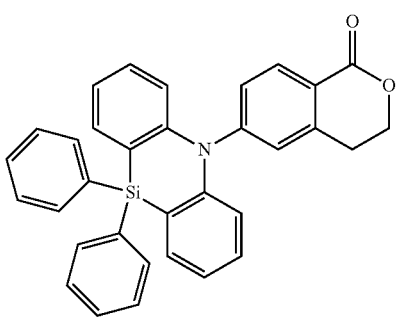

| | |
|---|---|
| 139 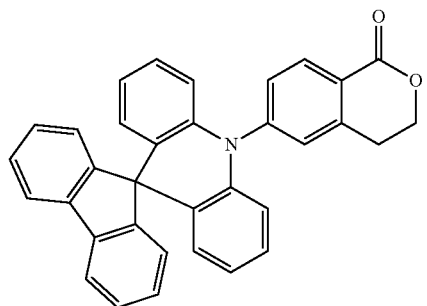 | 144 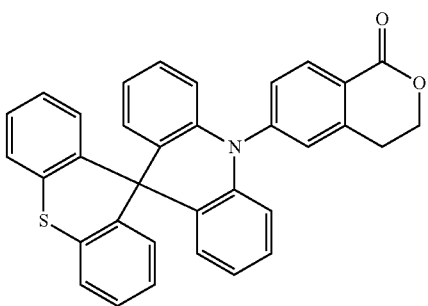 |
| 140 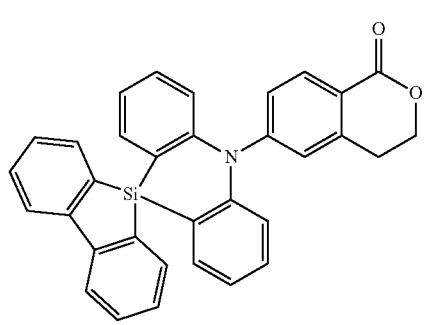 | 145 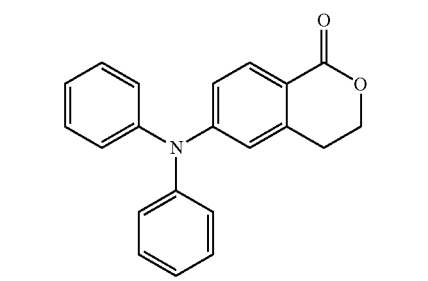 |
| 141 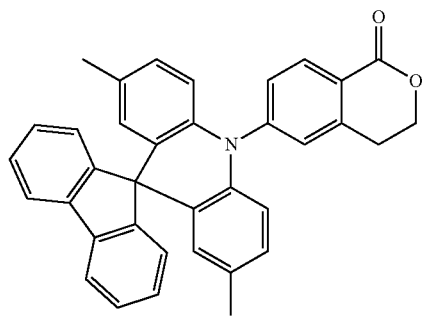 | 146 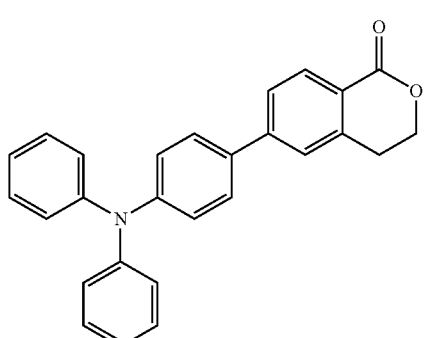 |
| 142 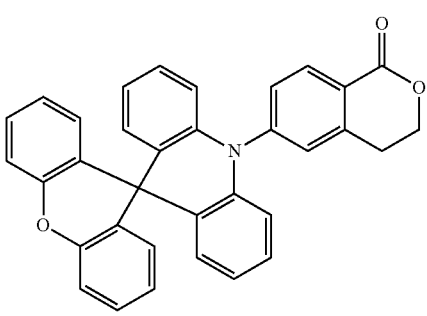 | 147 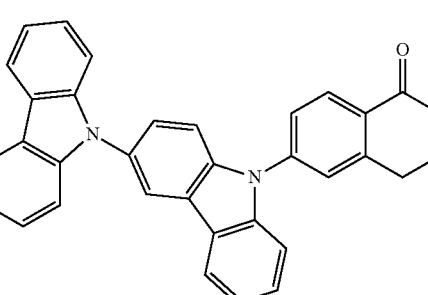 |
| 143 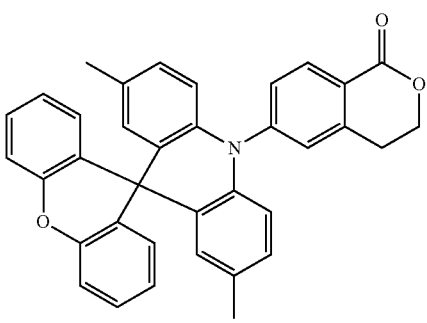 | 148 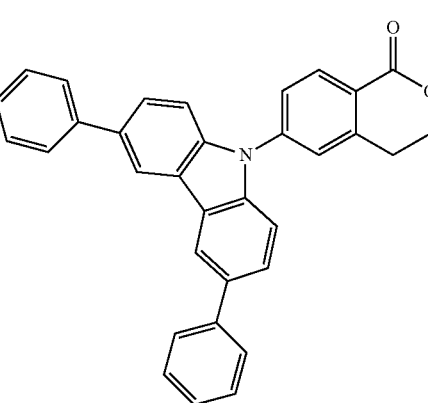 |

255
-continued
149
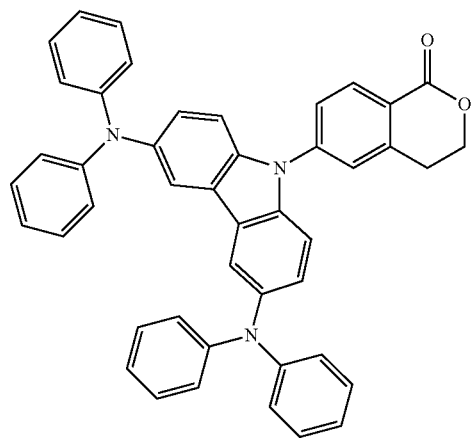
150
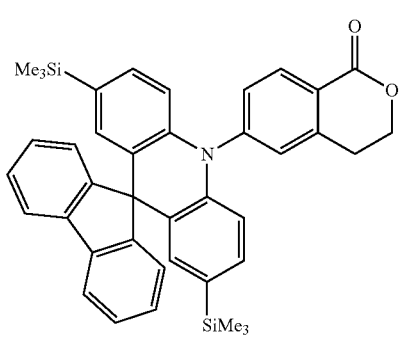
151
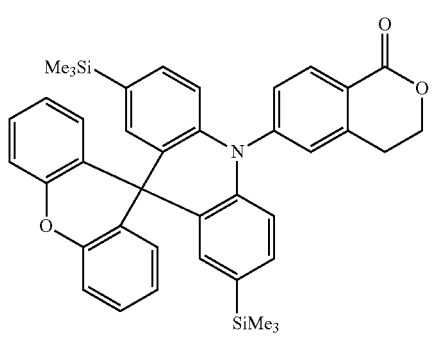
152
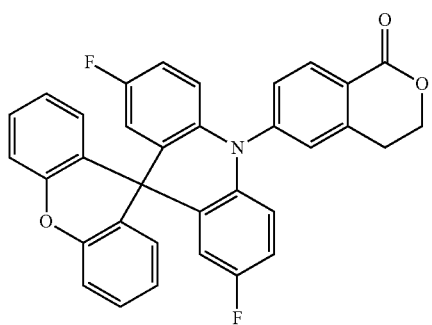
256
-continued
153
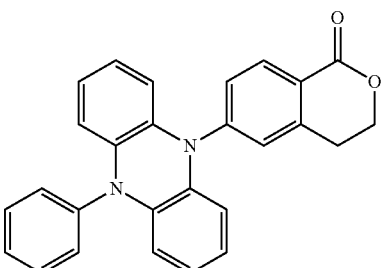
154
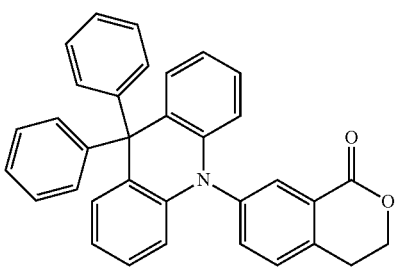
155
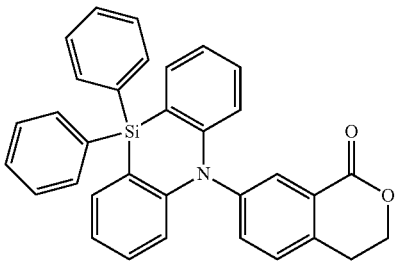
156
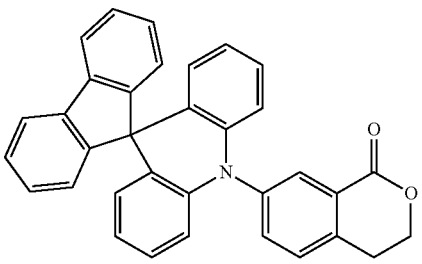
157
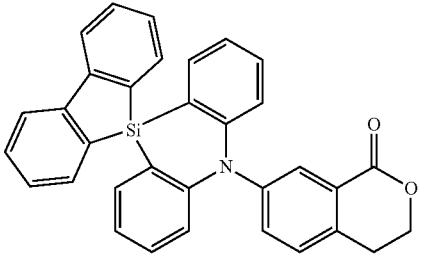
158
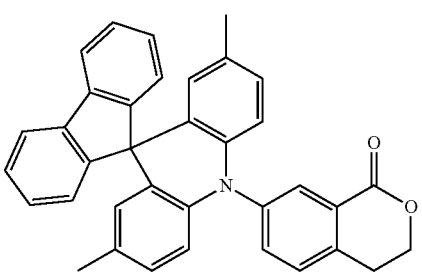

159
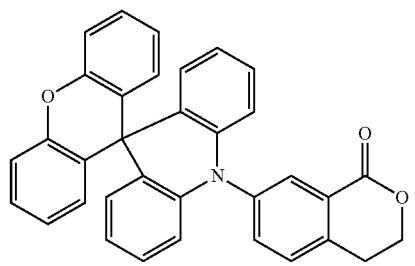
160
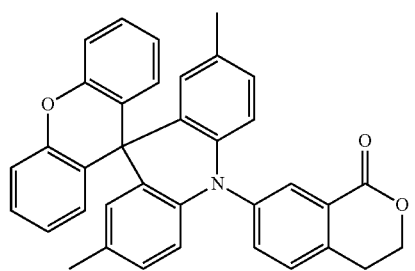
161
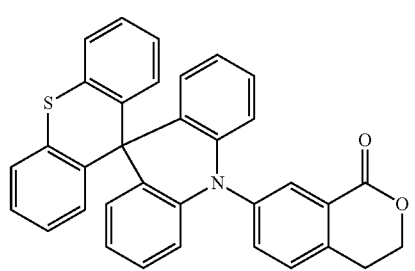
162
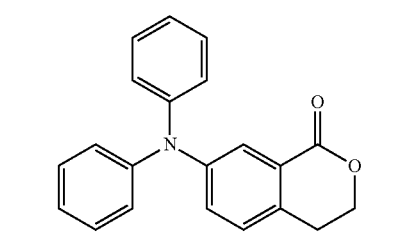
163
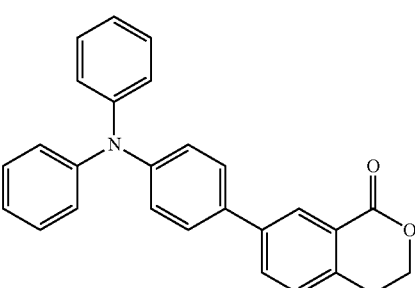
164
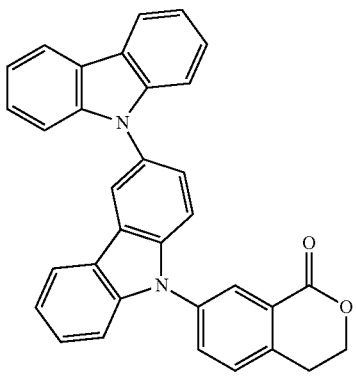
165
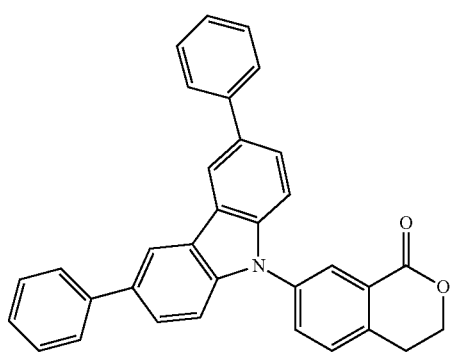
166
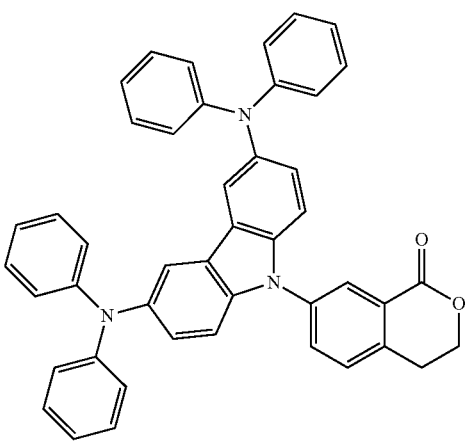
167
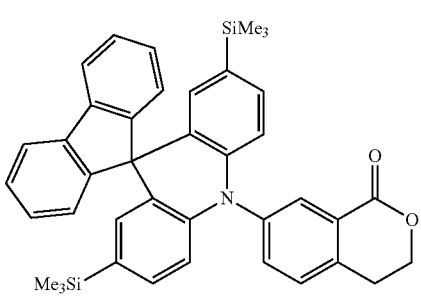

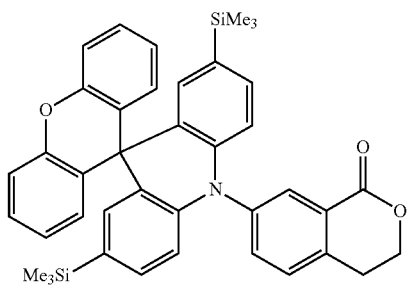 168
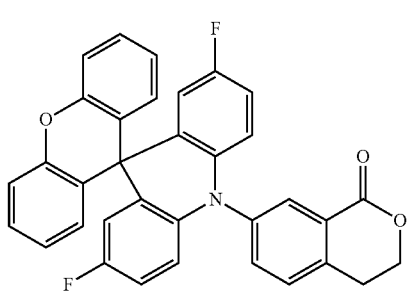 169
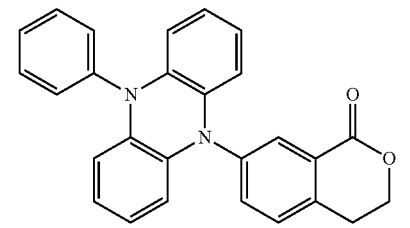 170
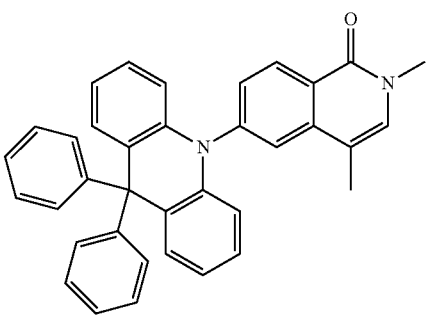 171
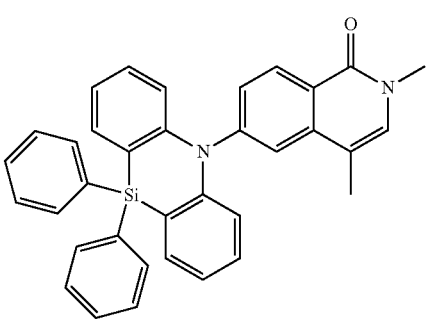 172
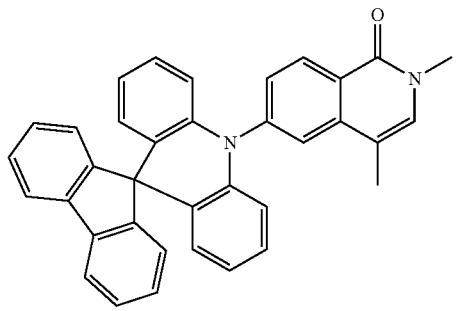 173
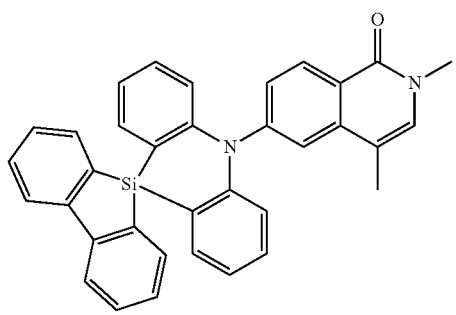 174
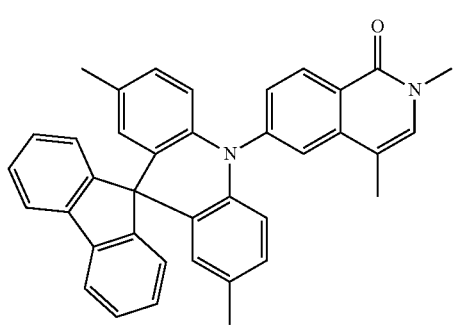 175
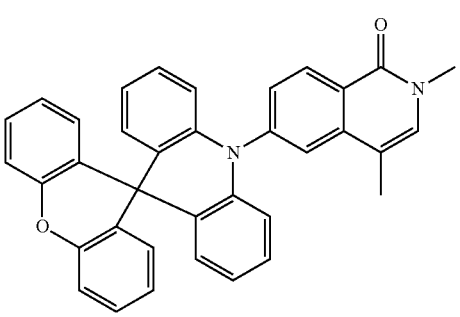 176
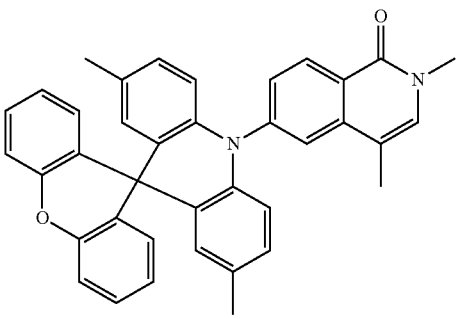 177

| 178 | 183 |
|---|---|
| 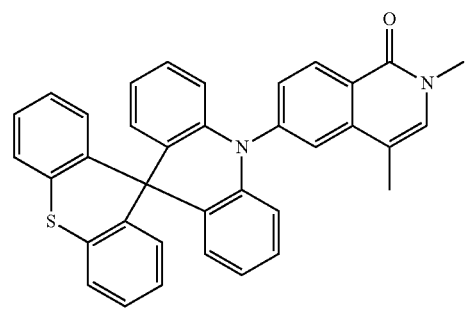 | 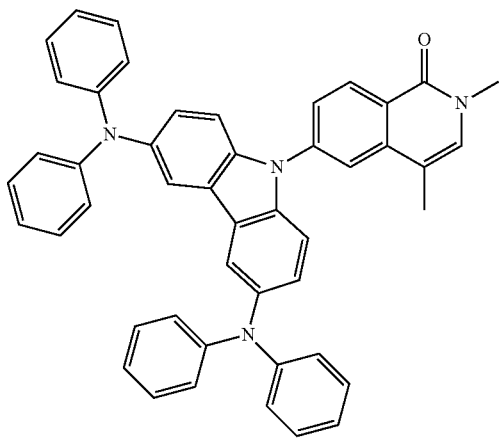 |
| 179 | |
| 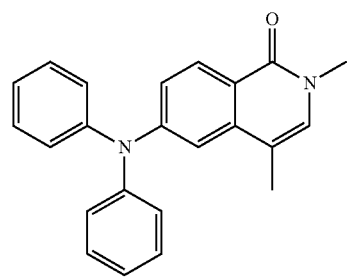 | |
| | 184 |
| 180 | 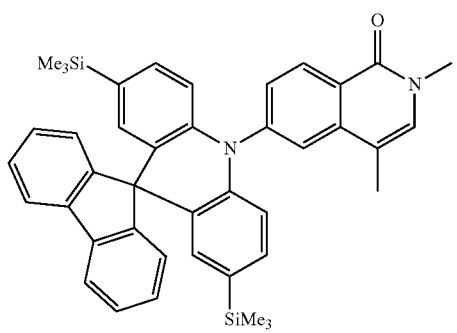 |
| 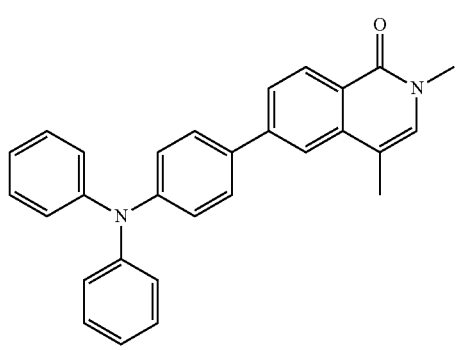 | |
| | 185 |
| 181 | 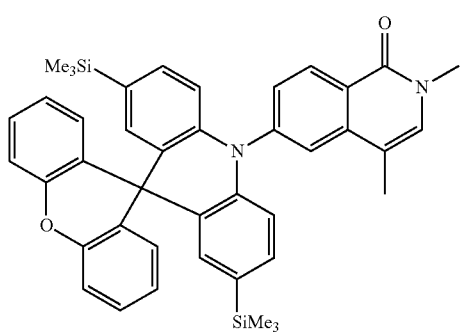 |
| 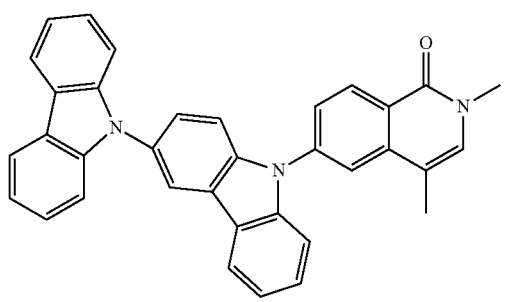 | |
| | 186 |
| 182 | 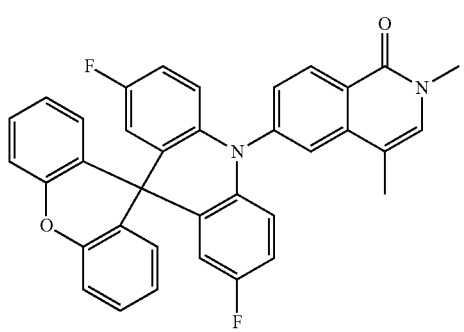 |
| 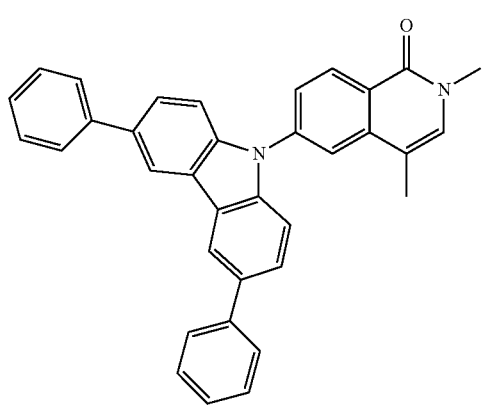 | |

-continued
187
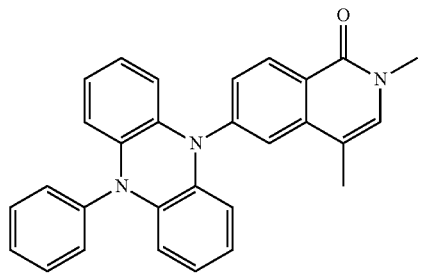
188
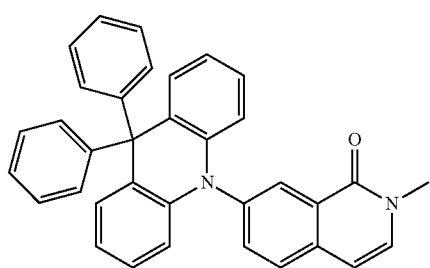
189
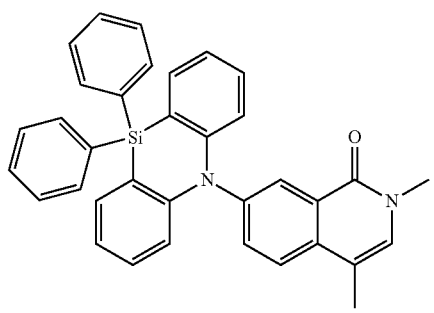
190
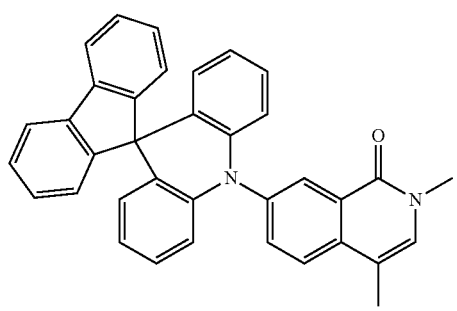
191
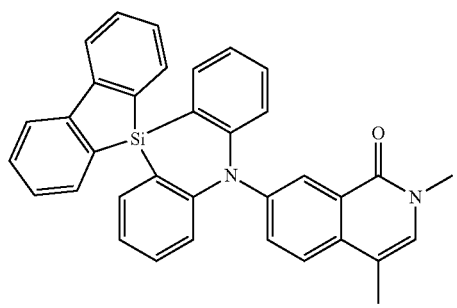
-continued
192
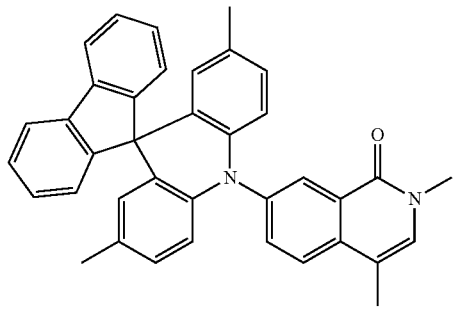
193
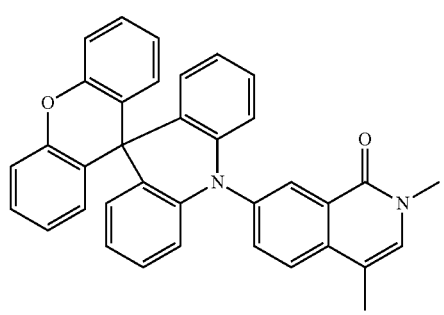
194
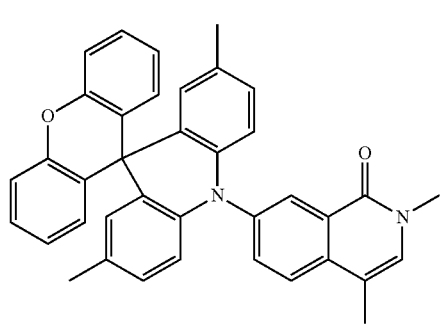
195
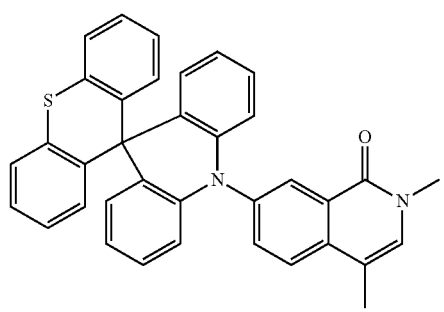
196
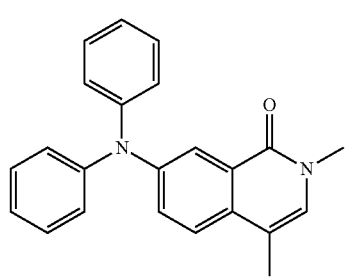

| | |
|---|---|
| 197 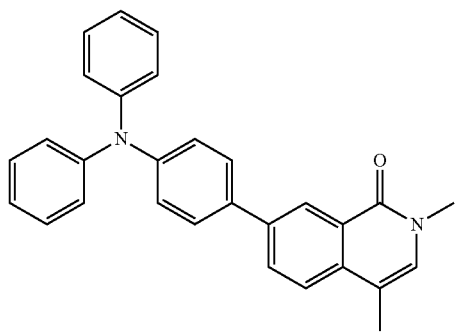 | 201 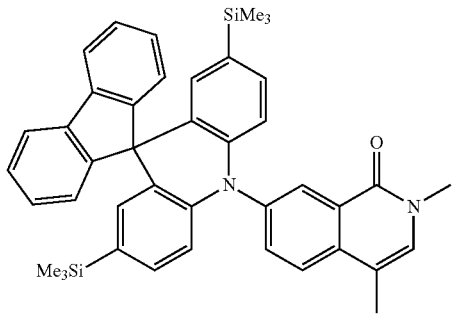 |
| 198 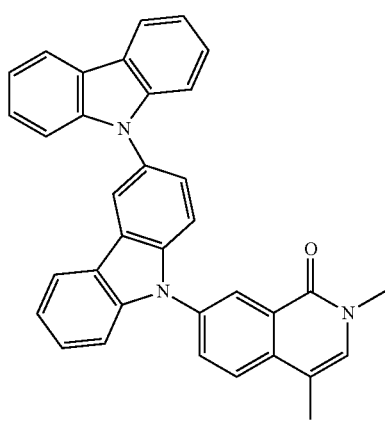 | 202 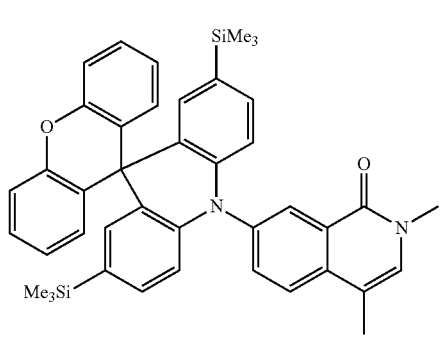 |
| 199 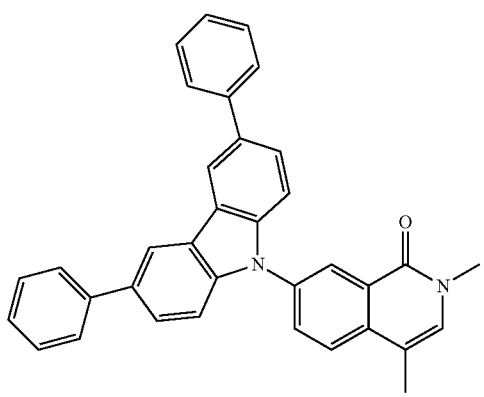 | 203 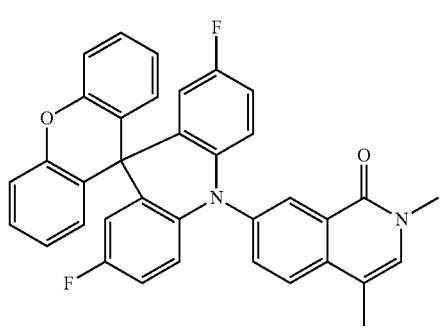 |
| | 204 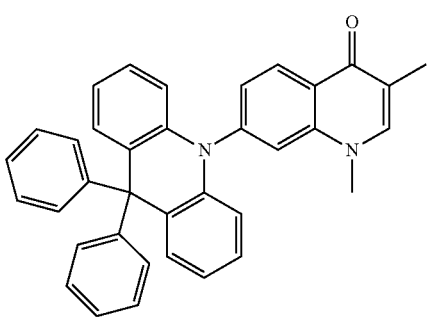 |
| 200 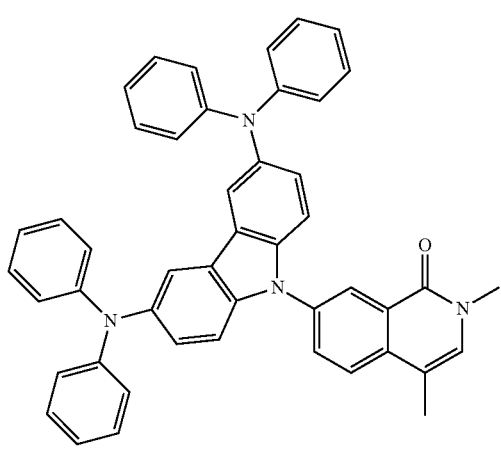 | 205 |

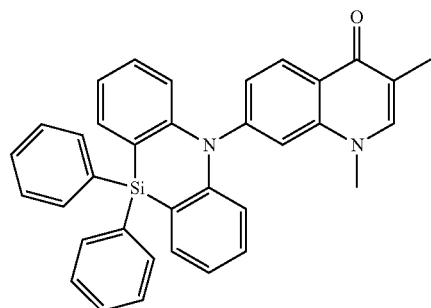
206
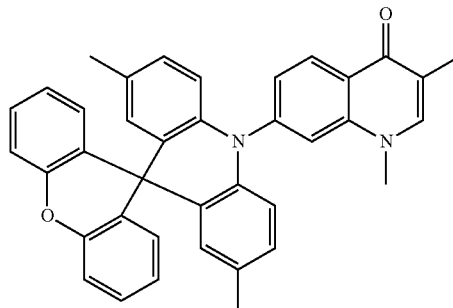
211
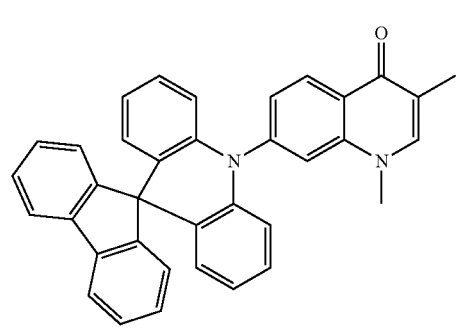
207
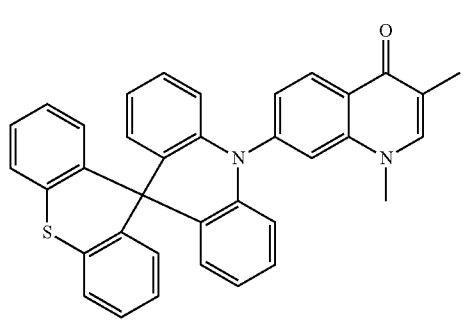
212
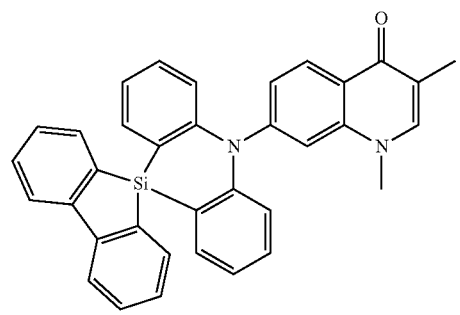
208
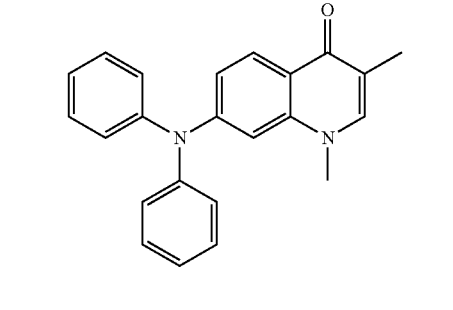
213
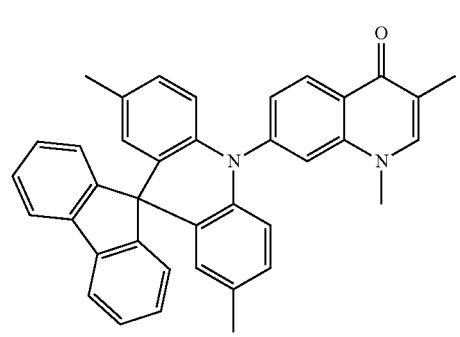
209
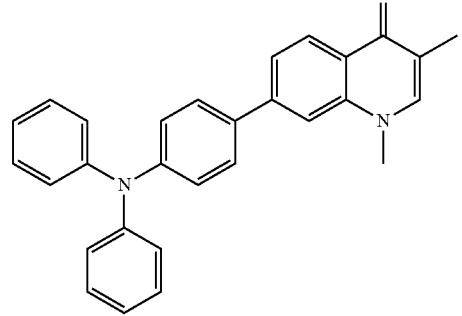
214
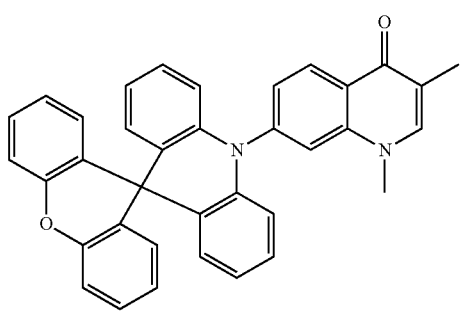
210
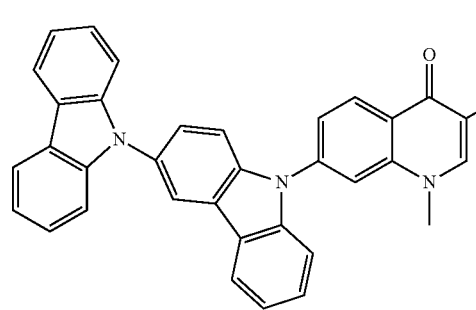
215

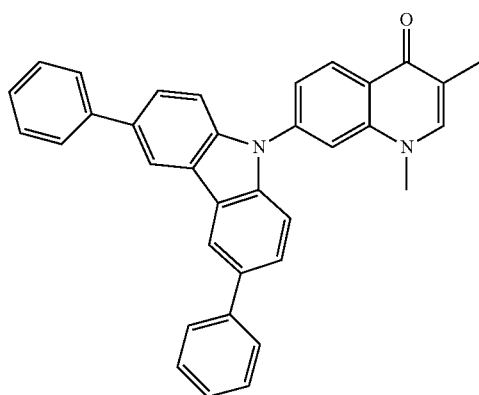
216
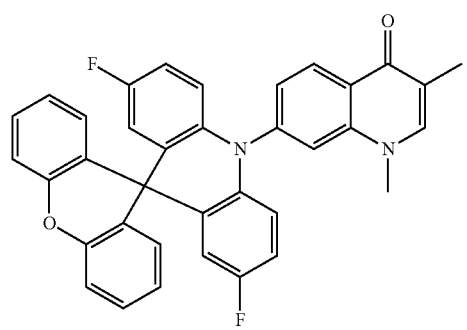
220
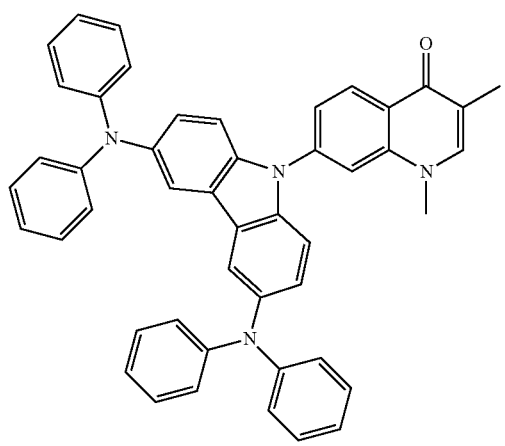
217
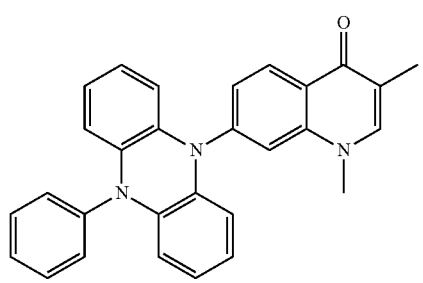
221
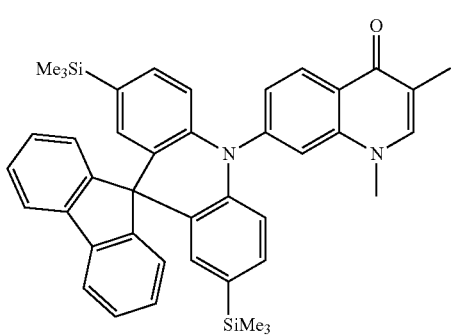
218
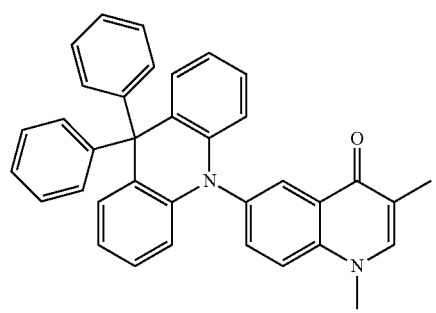
222
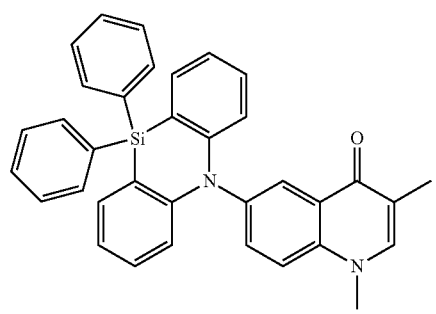
223
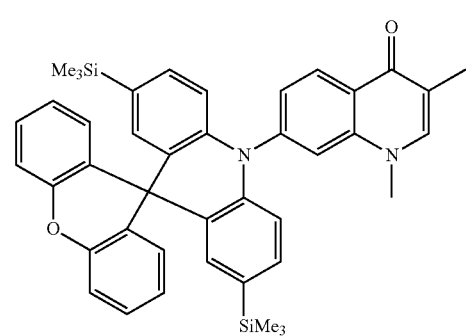
219
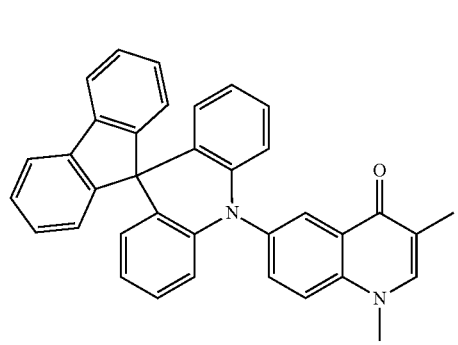
224

225
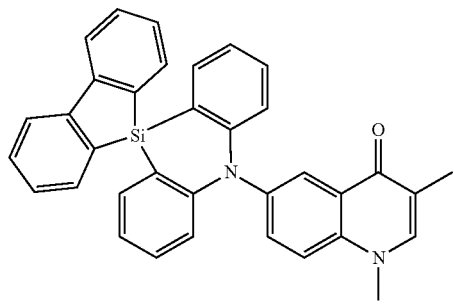
226
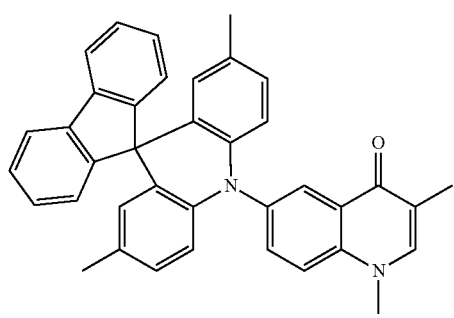
227
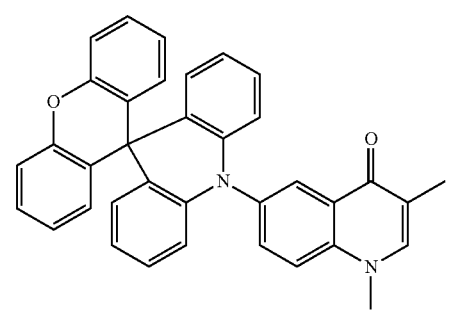
228
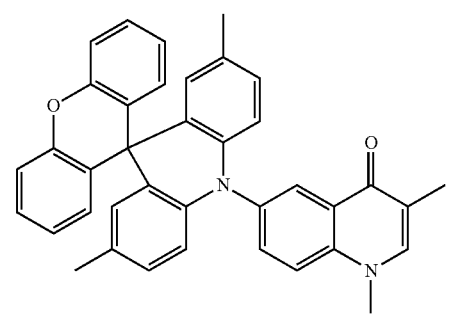
229
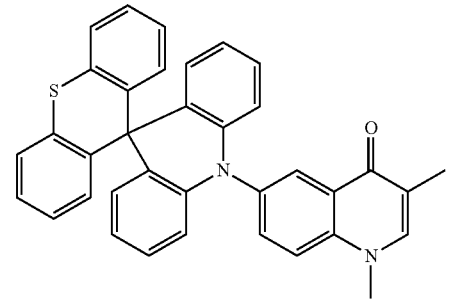
230
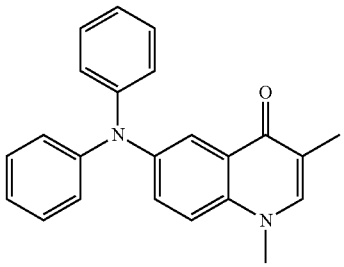
231
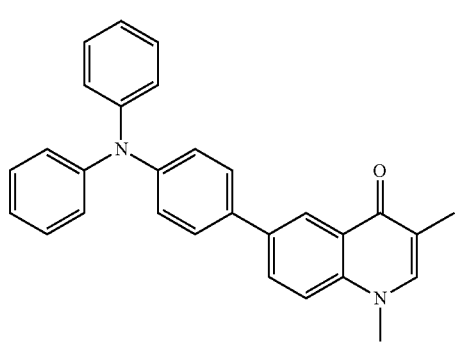
232
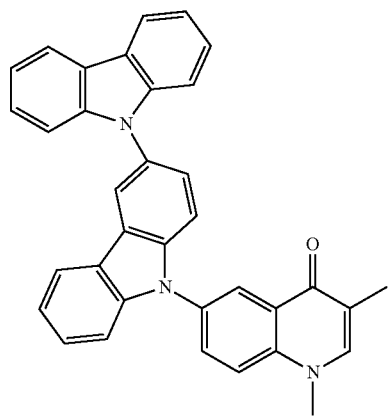
233
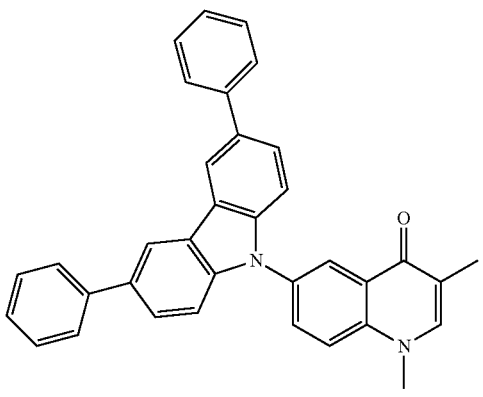

234
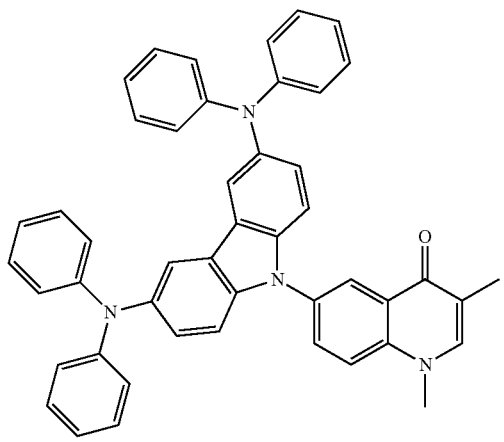
235
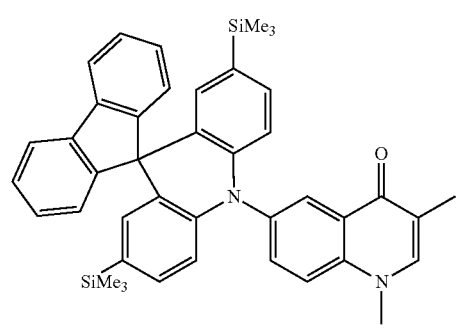
236
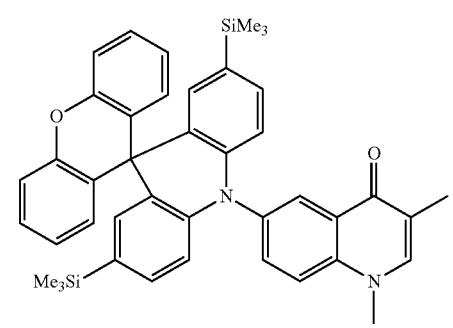
237
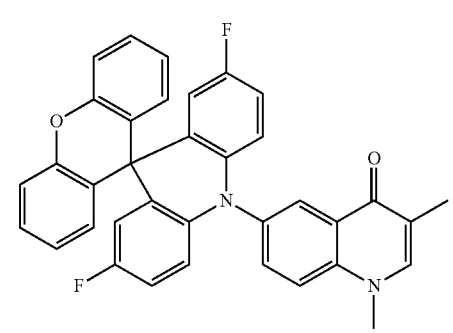
238
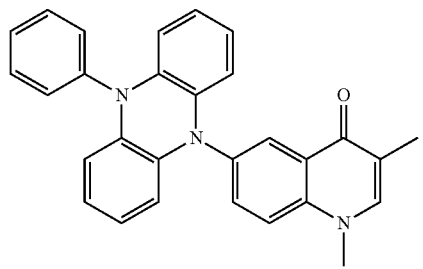
239
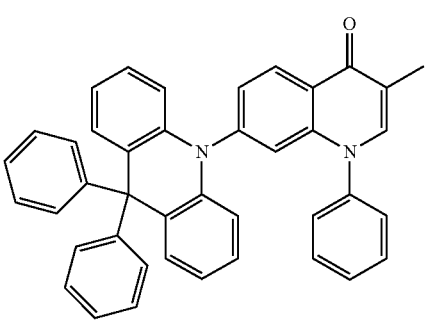
240
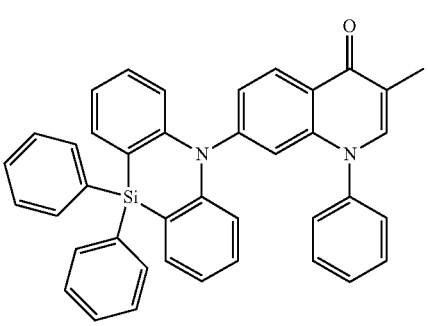
241
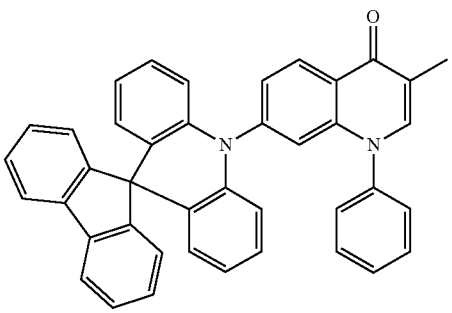
242
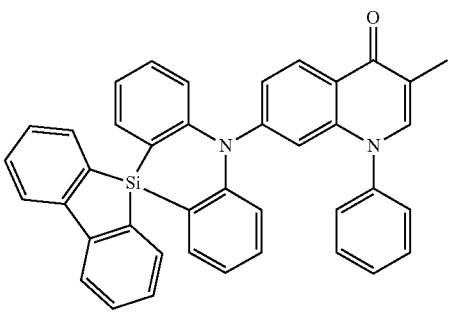

-continued
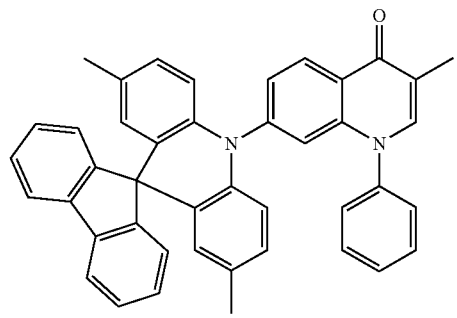
243
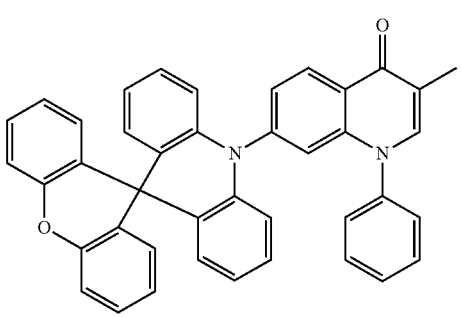
244
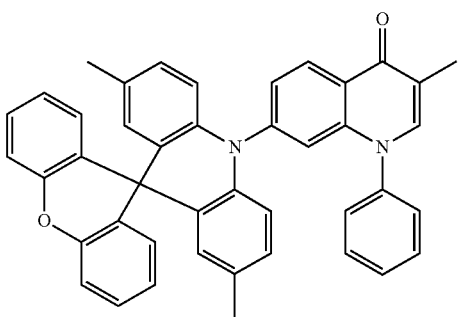
245
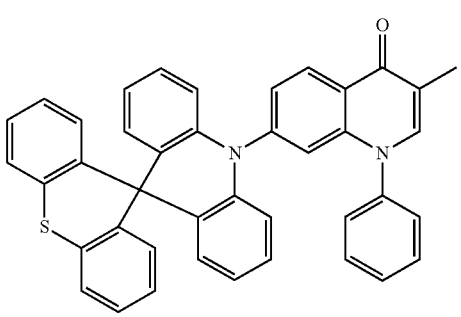
246
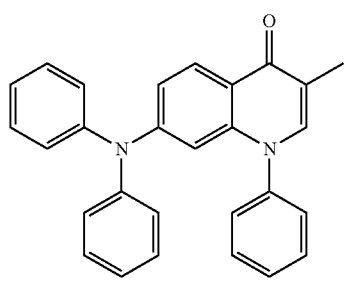
247
-continued
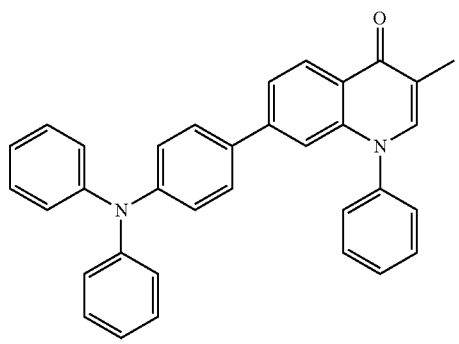
248
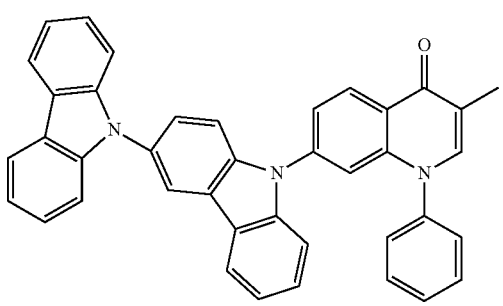
249
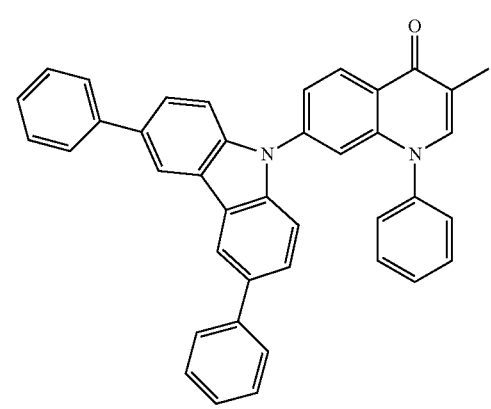
250
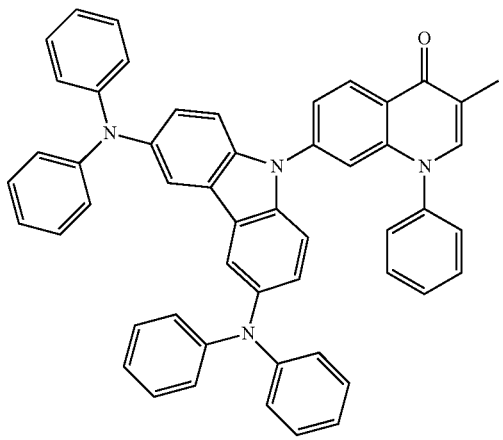
251

-continued
252
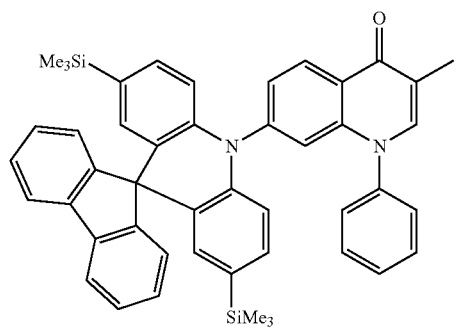
253
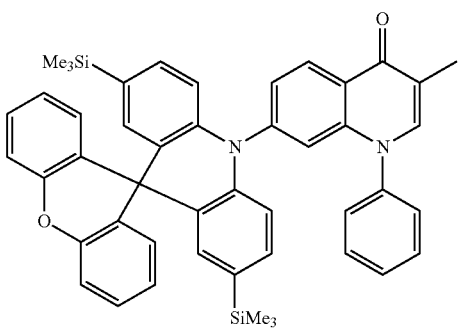
254
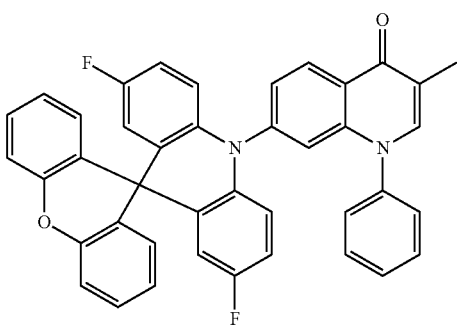
255
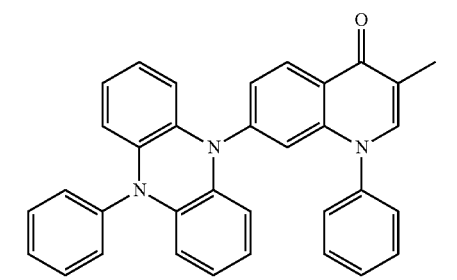
256
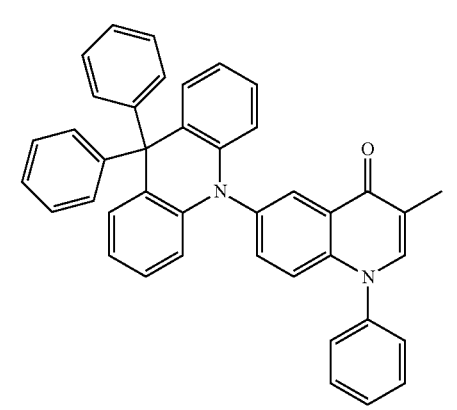
-continued
257
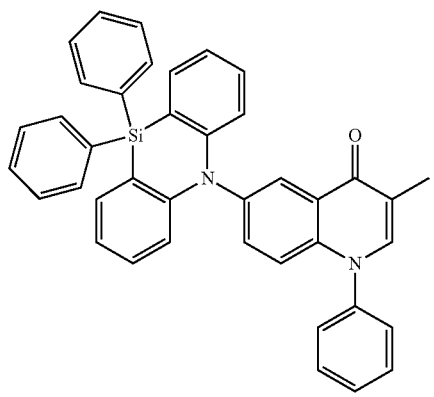
258
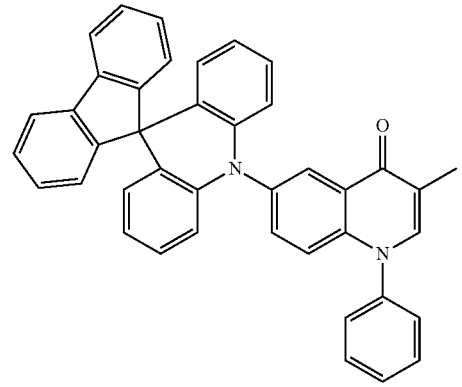
259
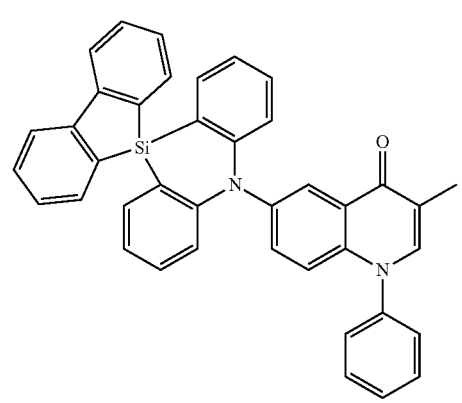
260
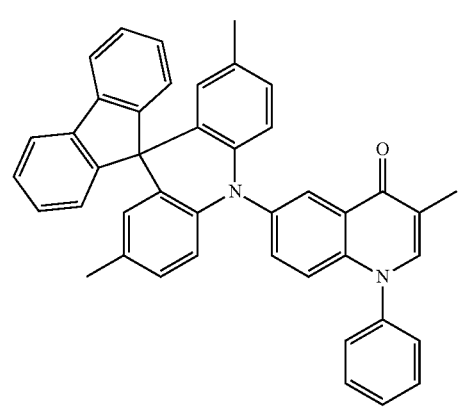

279
-continued
261
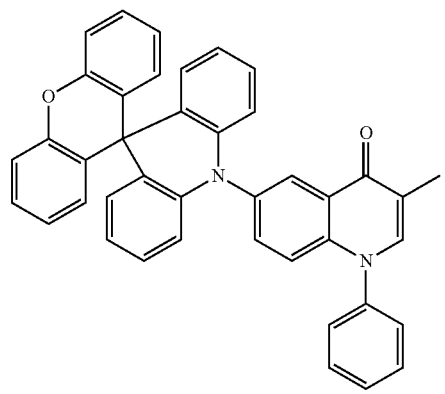
262
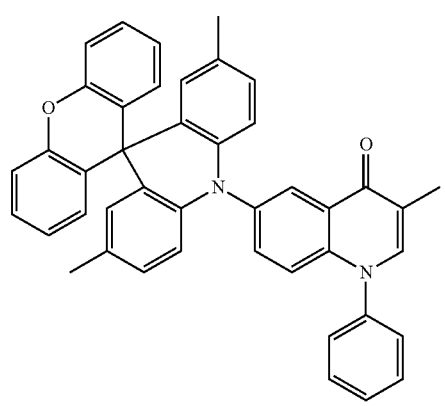
263
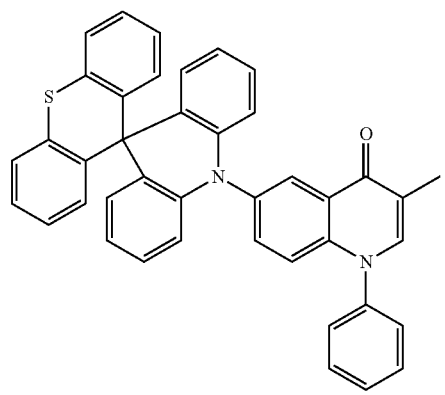
264
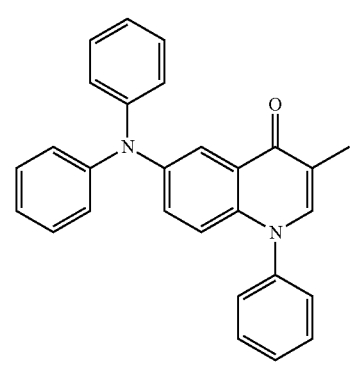
280
-continued
265
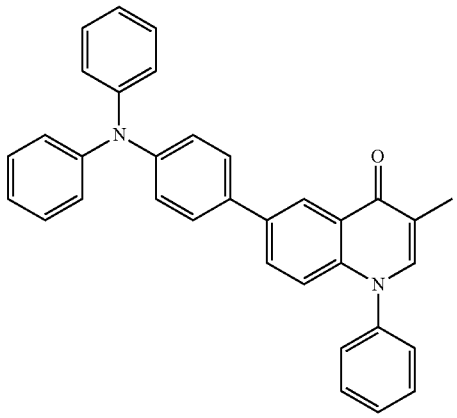
266
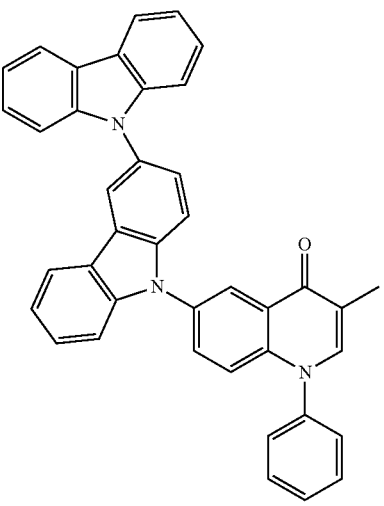
267
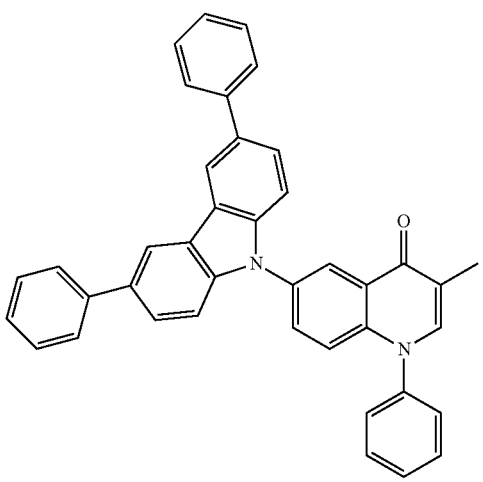

268
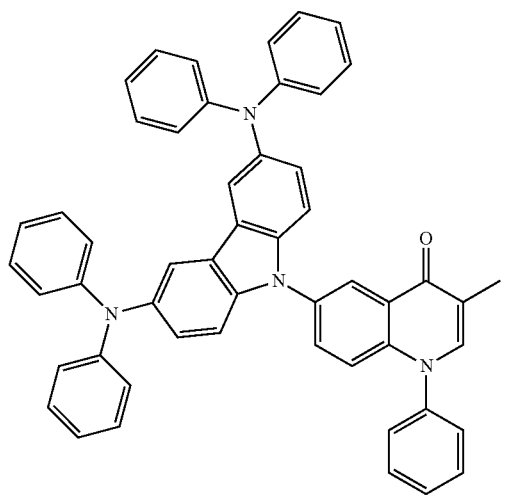
269
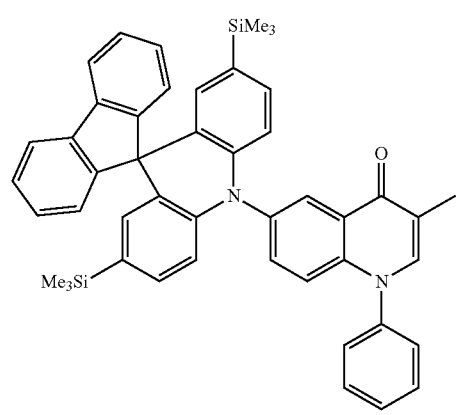
270
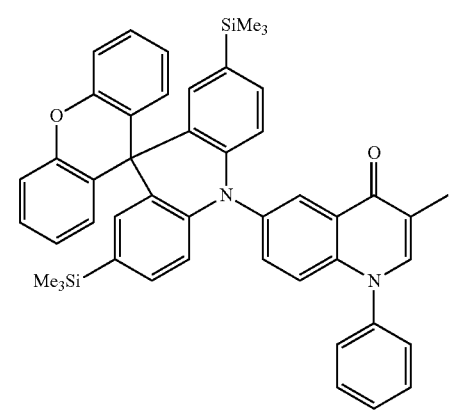
271
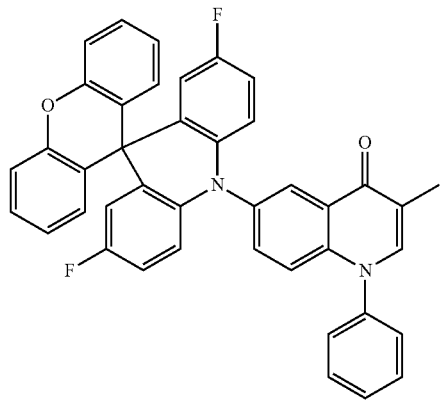
272
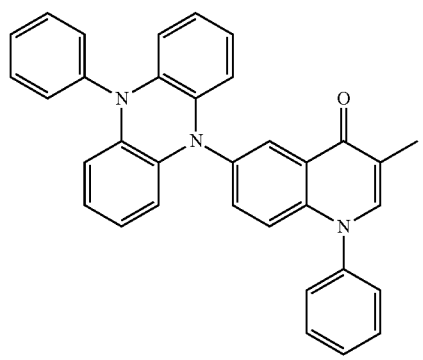
273
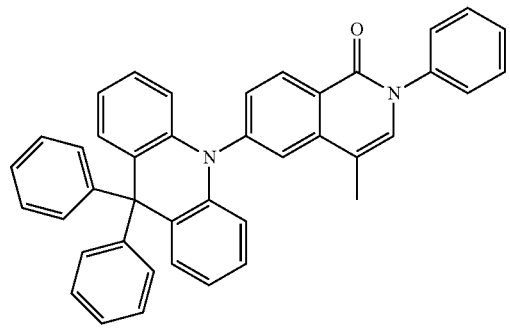
274
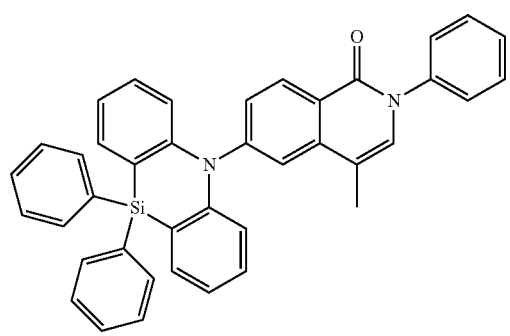

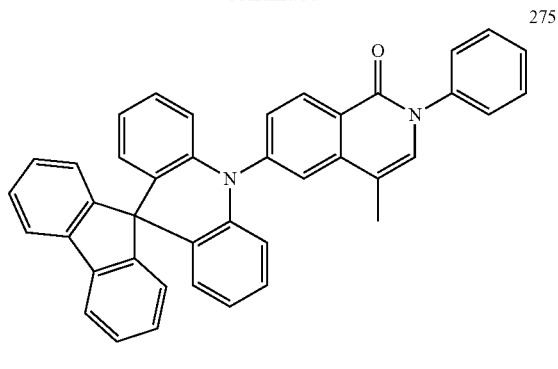
275
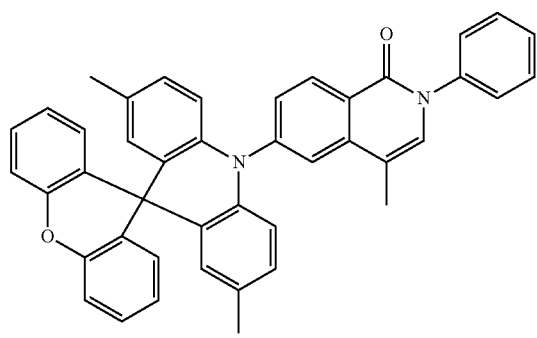
279
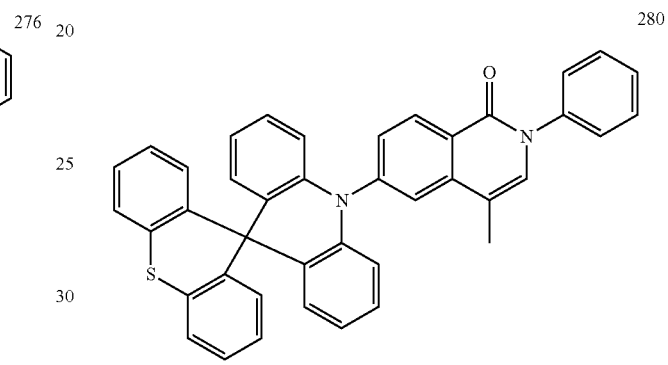
276
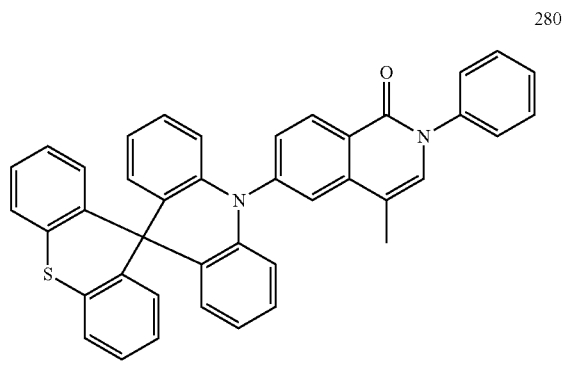
280
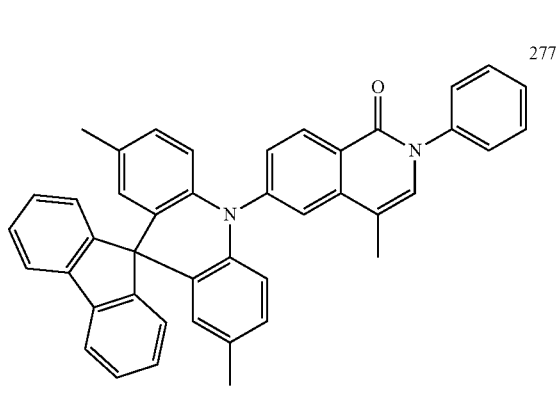
277
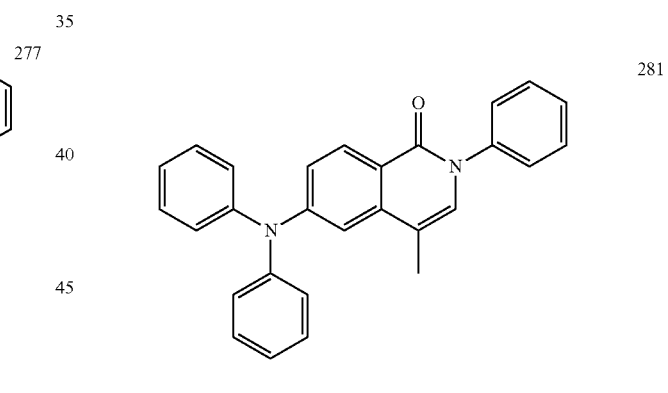
281
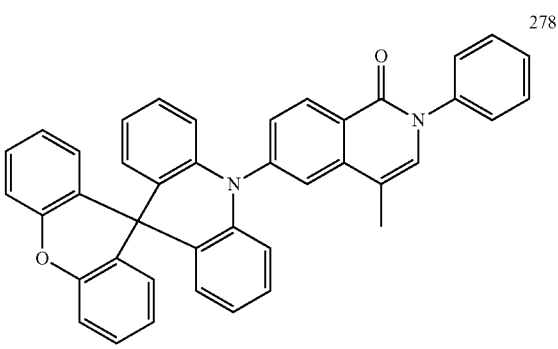
278
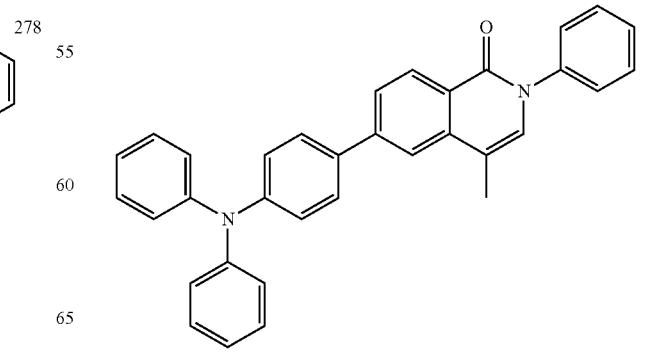
282

285
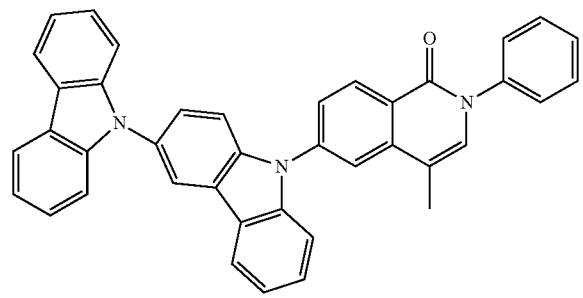
283
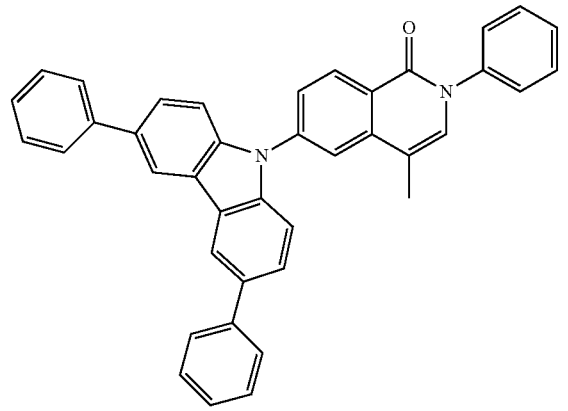
284
285
286
286
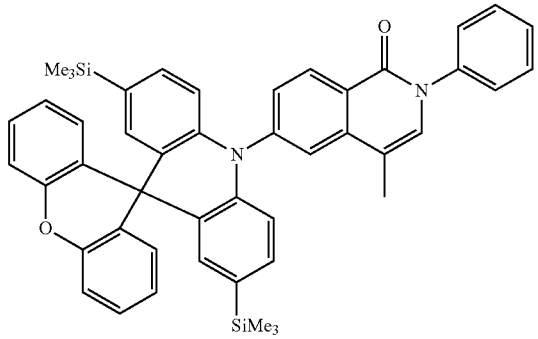
287
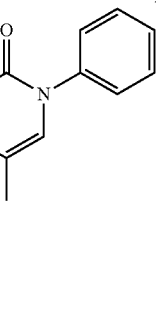
288
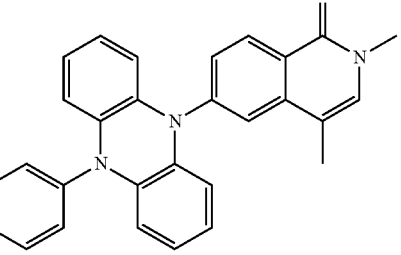
289
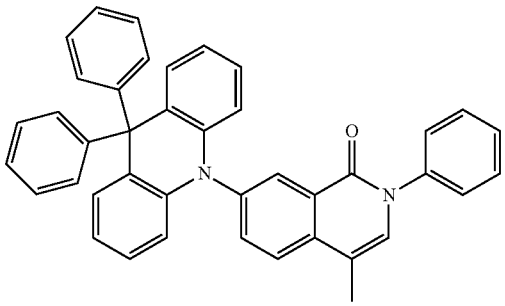
290
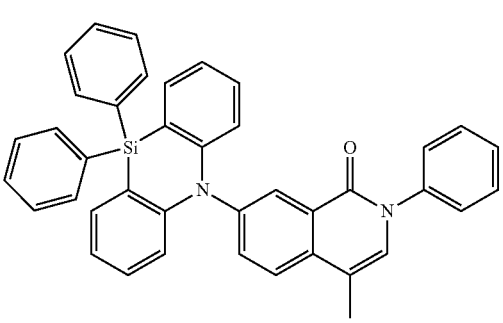
291

292
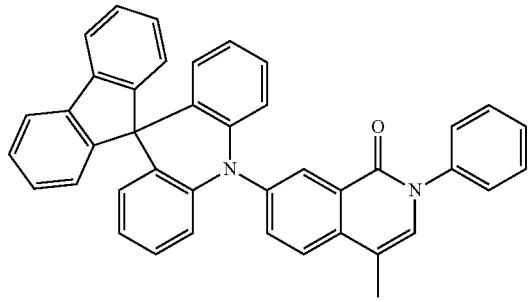
293
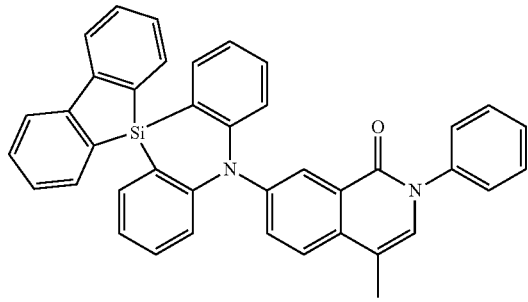
294
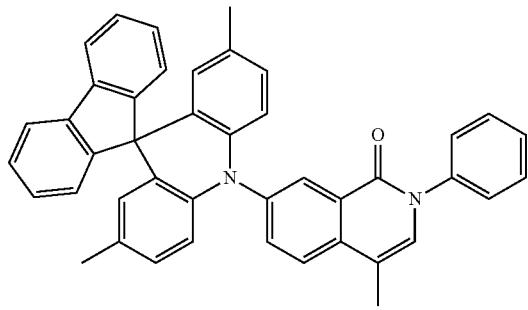
295
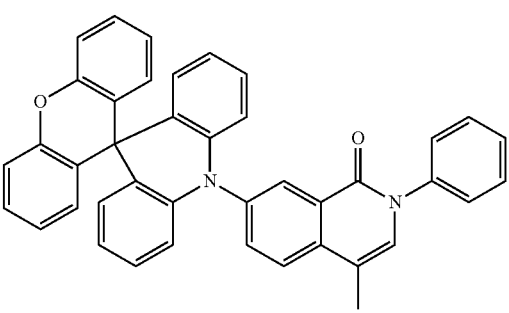
296
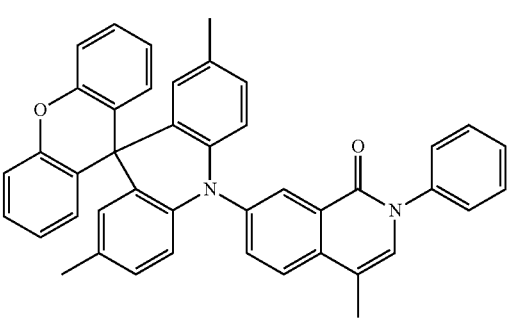
297
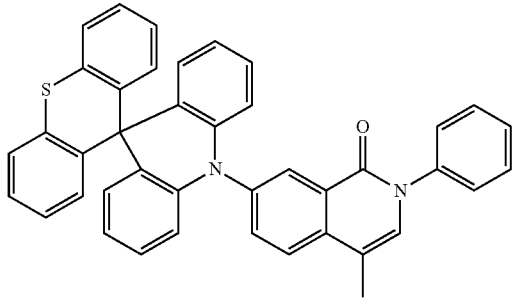
298
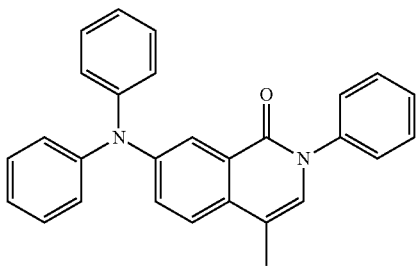
299
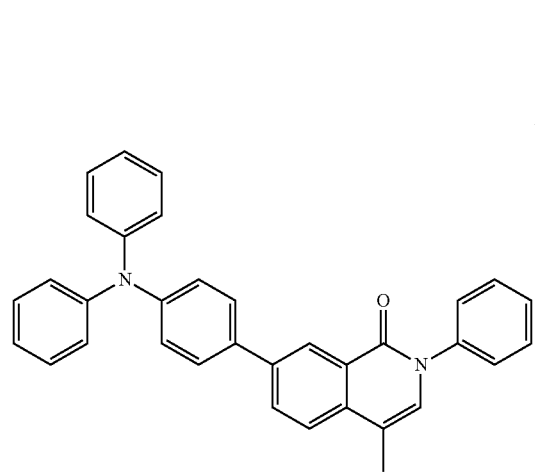
300
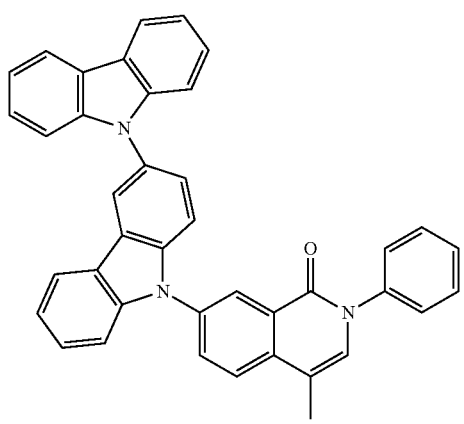

301
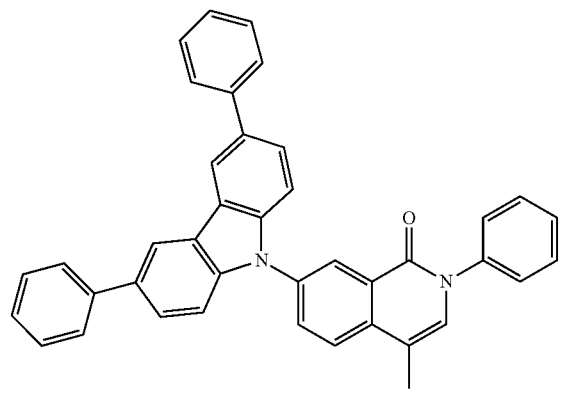
302
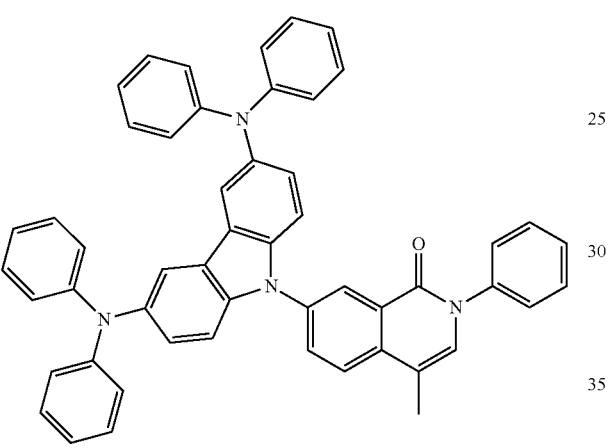
303
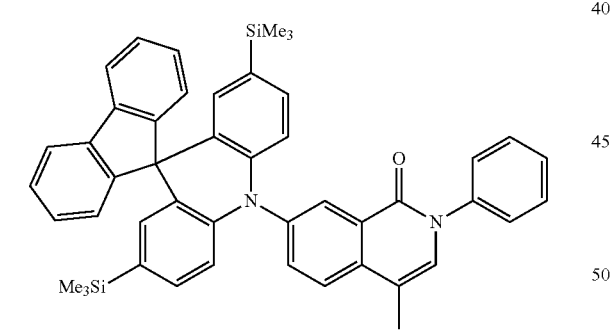
304
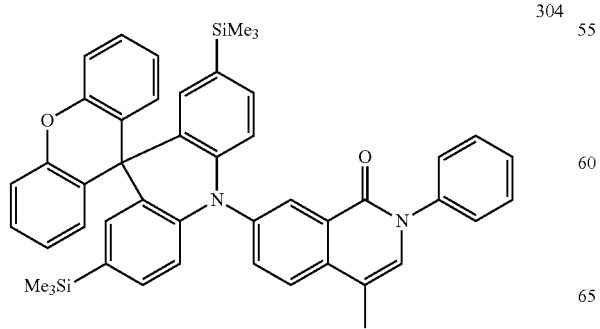
305
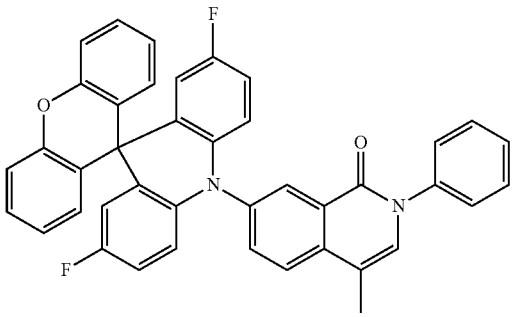
306
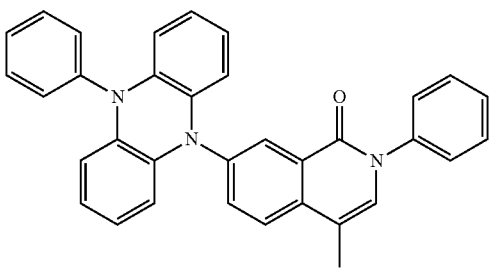
307
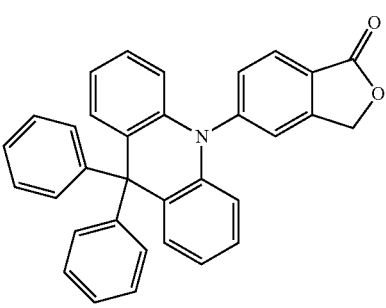
308
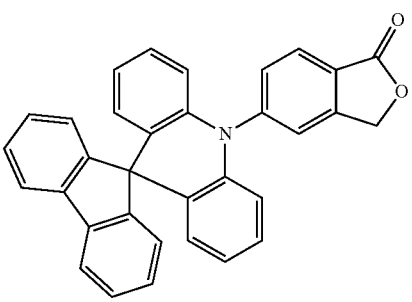
309

310
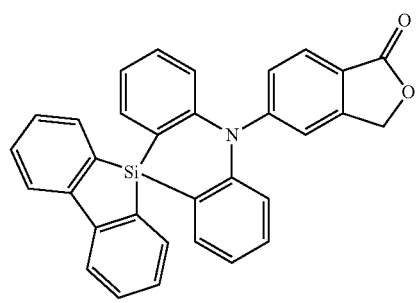
311
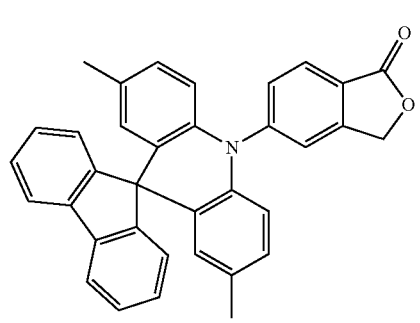
312
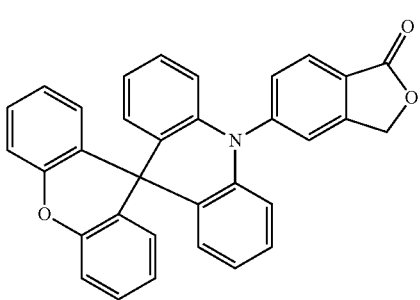
313
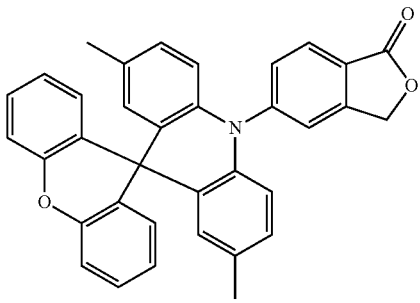
314
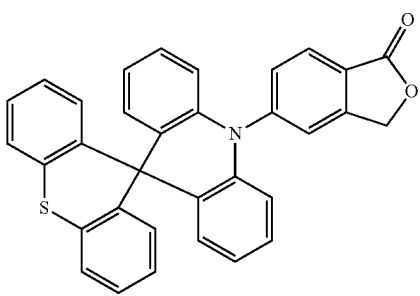
315
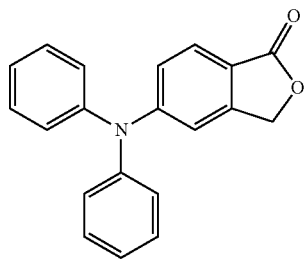
316
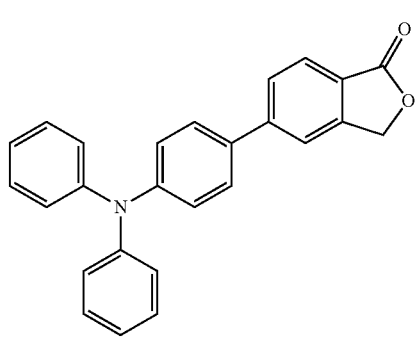
317
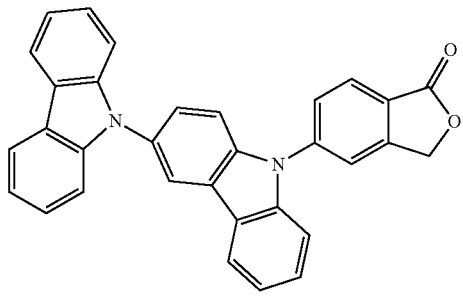
318
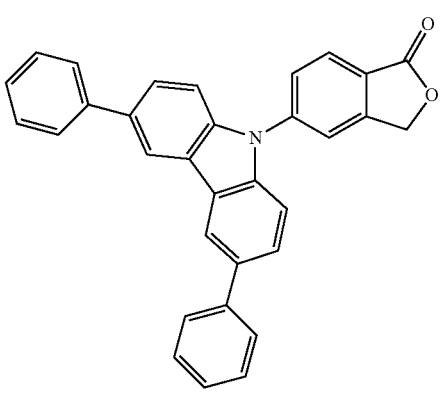

293
-continued
319
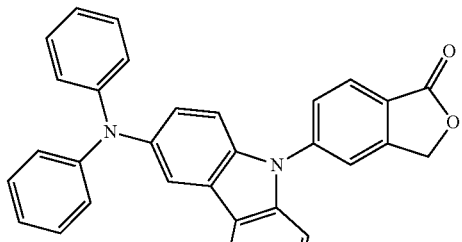
320
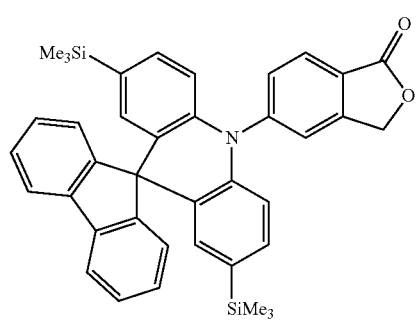
321
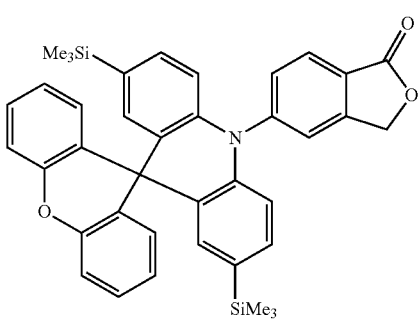
322
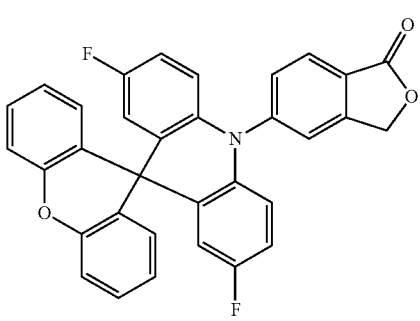
323
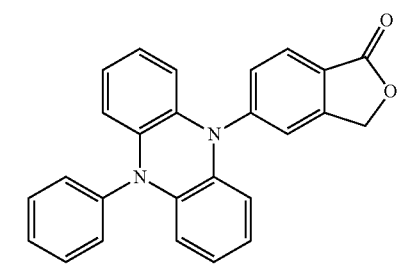
294
-continued
324
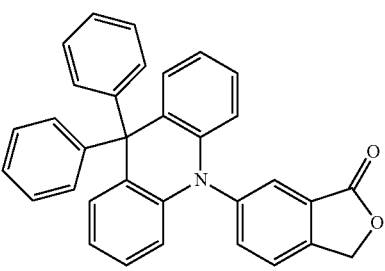
325
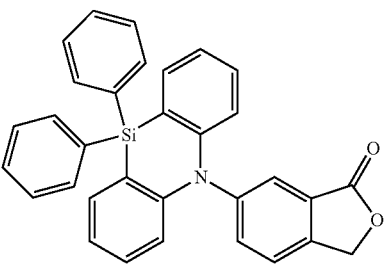
326
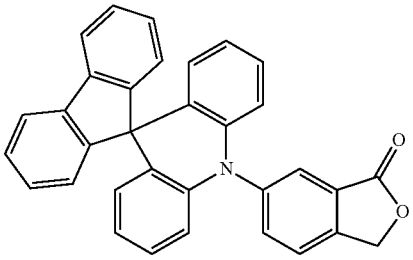
327
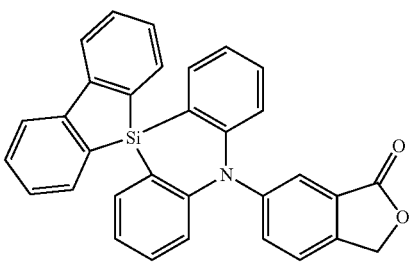
328
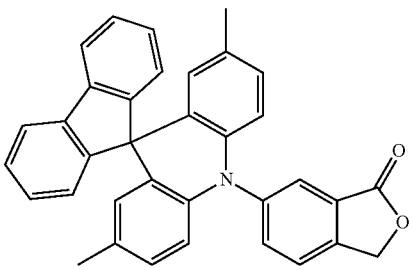
329
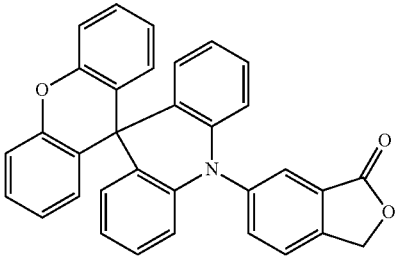

330 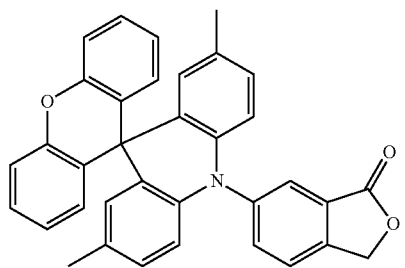
331 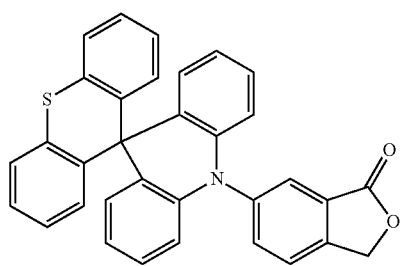
332 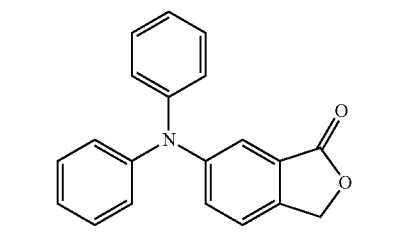
333 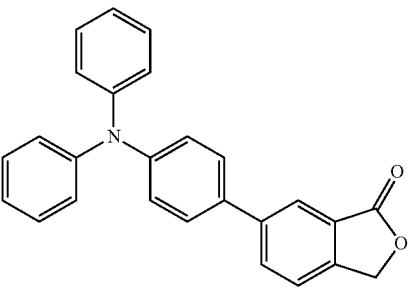
334 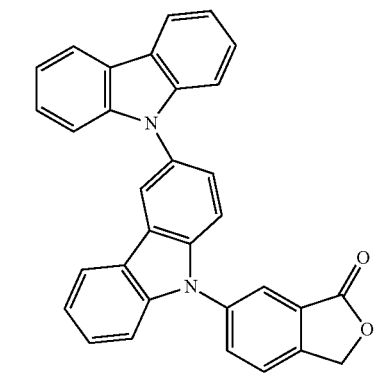
335 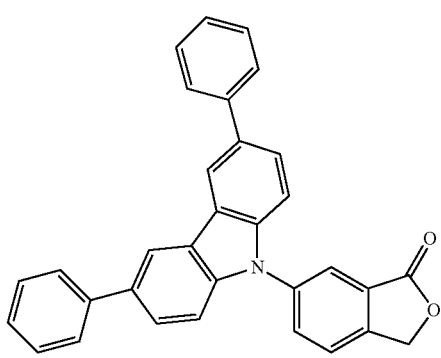
336 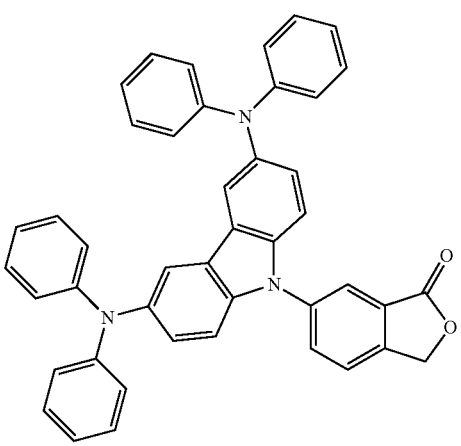
337 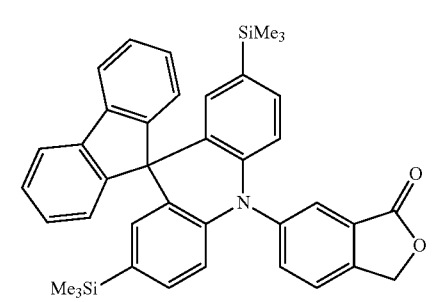
338 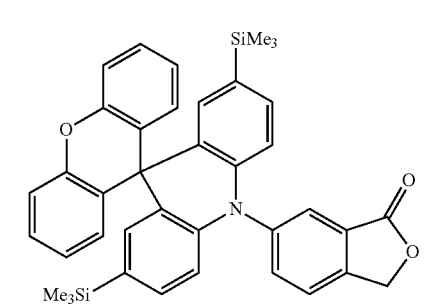

| | |
|---|---|
| 339 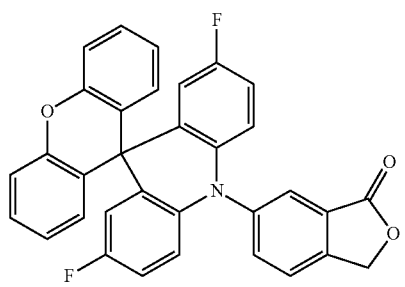 | 344 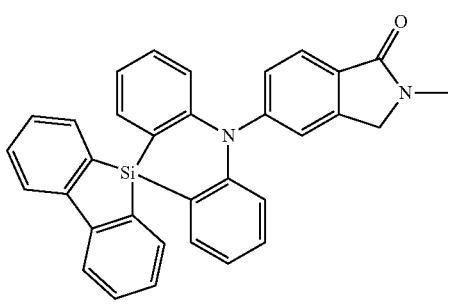 |
| 340 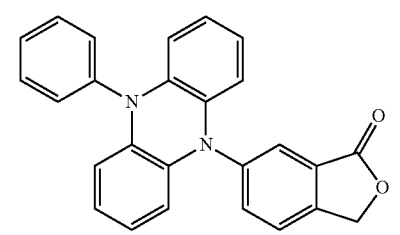 | 345 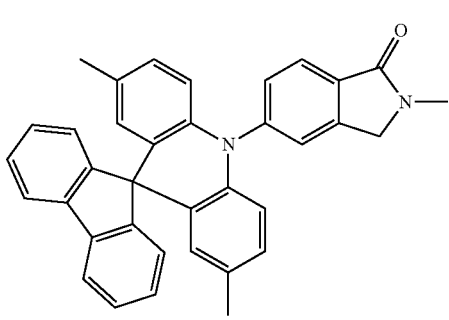 |
| 341 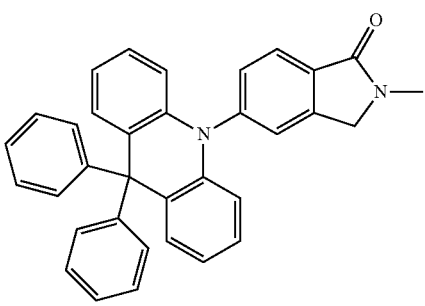 | 346 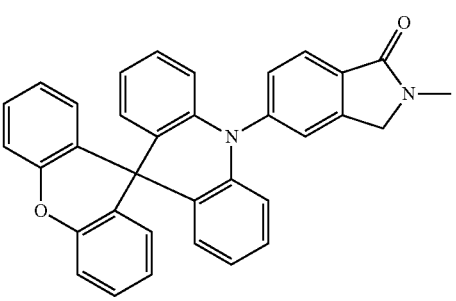 |
| 342 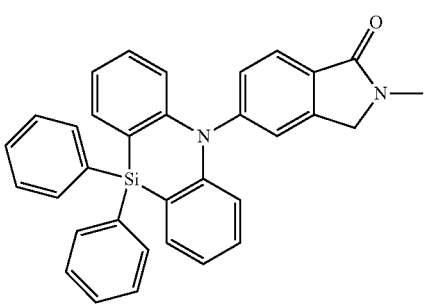 | 347 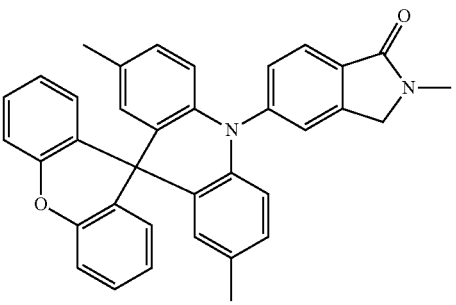 |
| 343 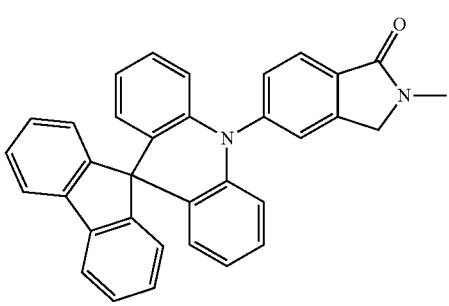 | 348 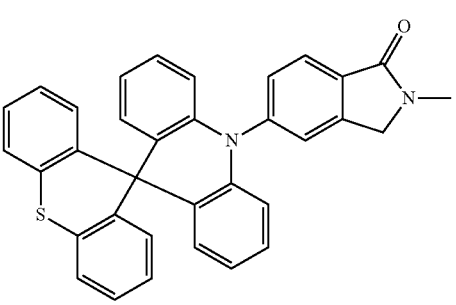 |

-continued
349
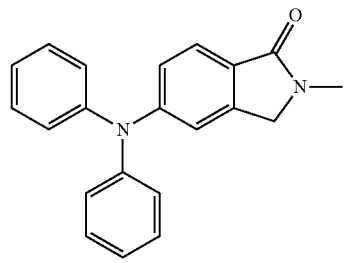
350
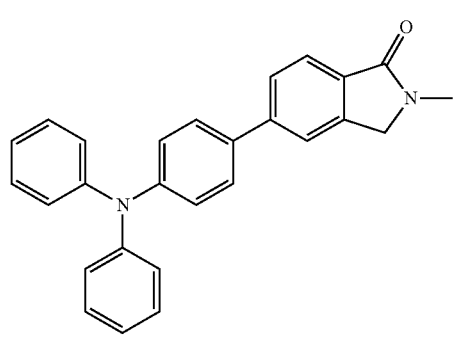
351
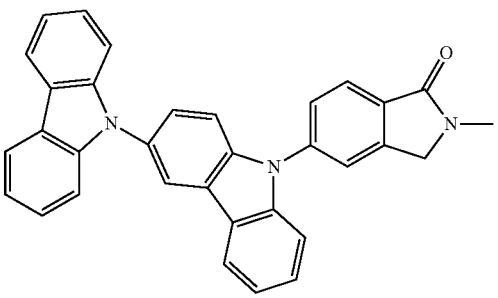
352
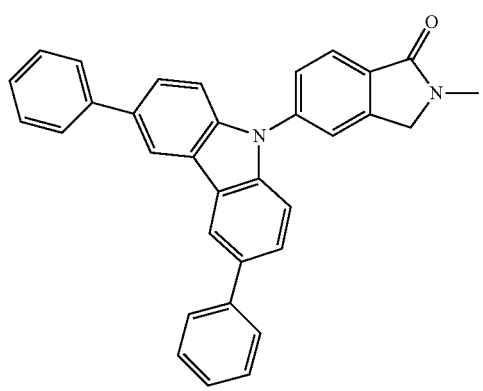
-continued
353
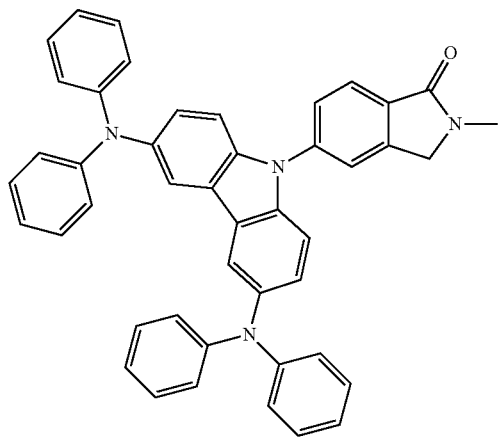
354
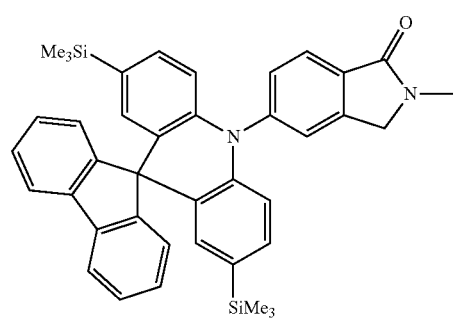
355
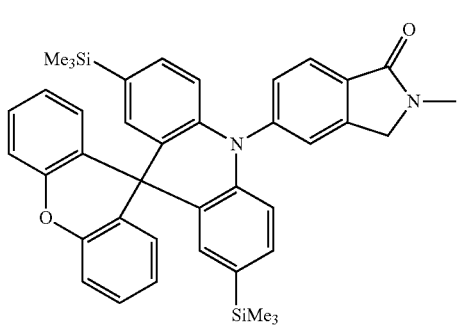
356
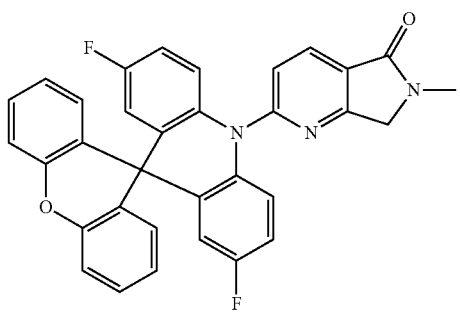

301
-continued
357
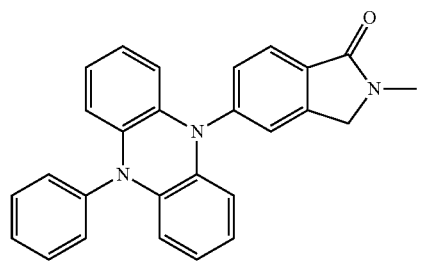
358
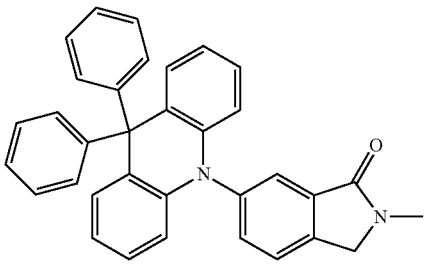
359
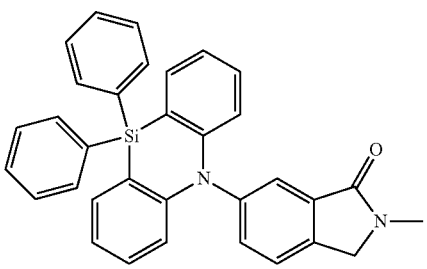
360
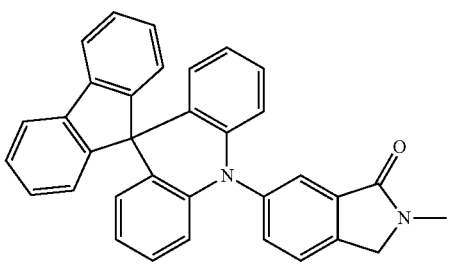
361
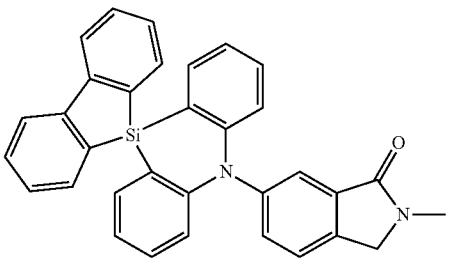
362
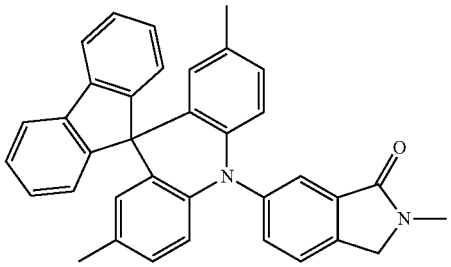
302
-continued
363
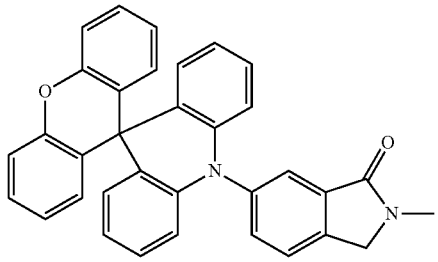
364
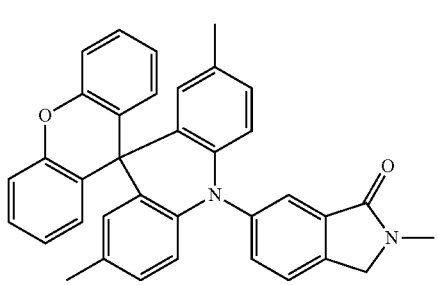
365
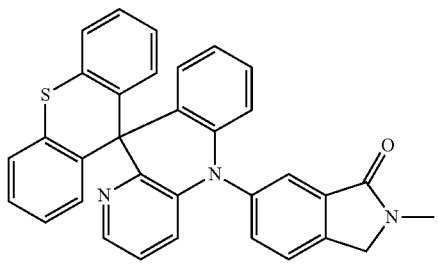
366
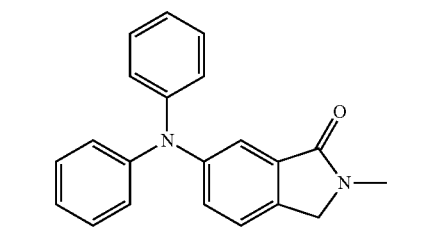
367
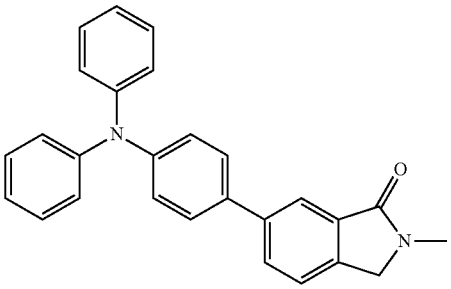

| 368 | 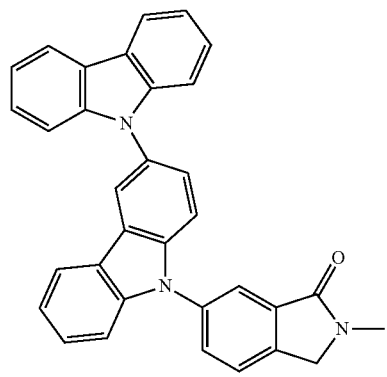 |
|---|---|
| 369 | 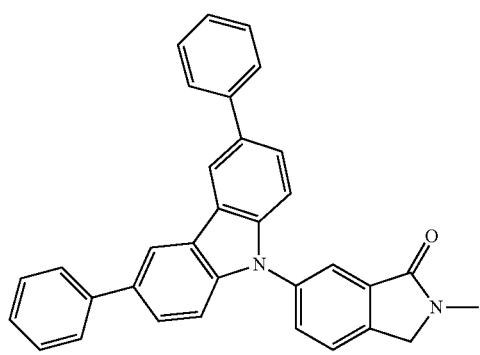 |
| 370 | 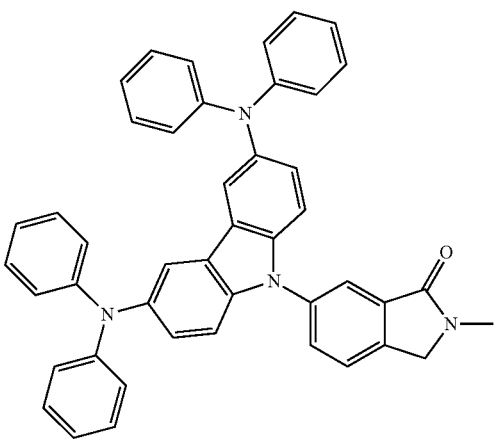 |
| 371 | 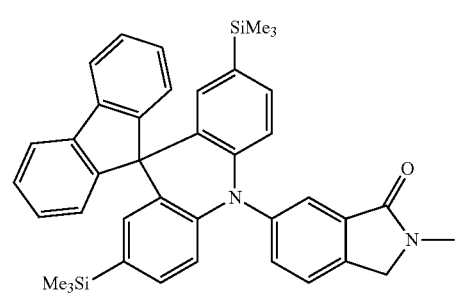 |
| 372 | 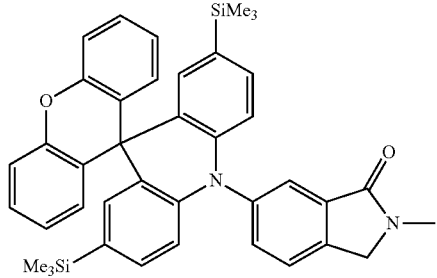 |
|---|---|
| 373 | 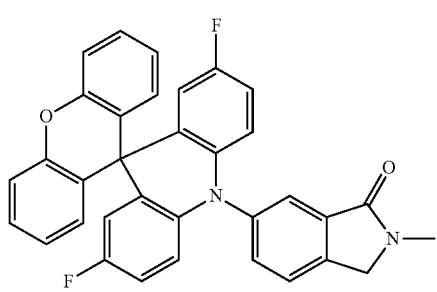 |
| 374 | 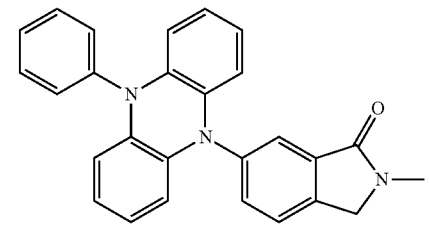 |
| 375 | 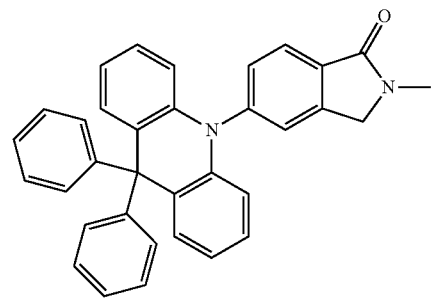 |
| 376 | 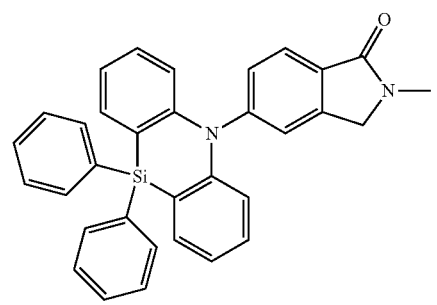 |

| | |
|---|---|
| 377 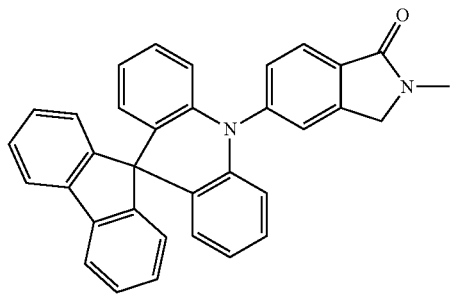 | 382 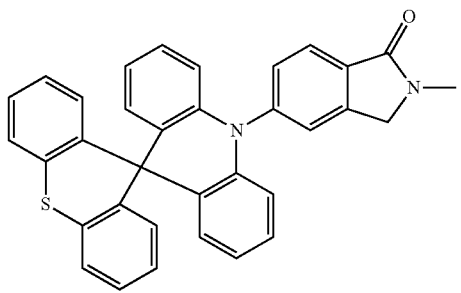 |
| 378 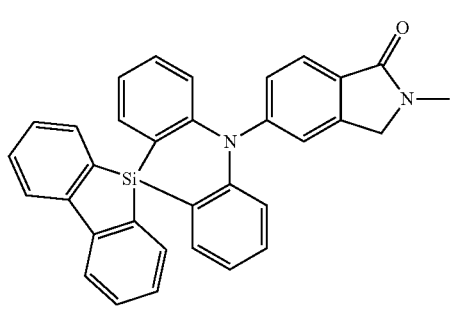 | 383 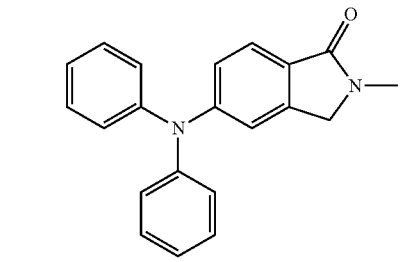 |
| 379 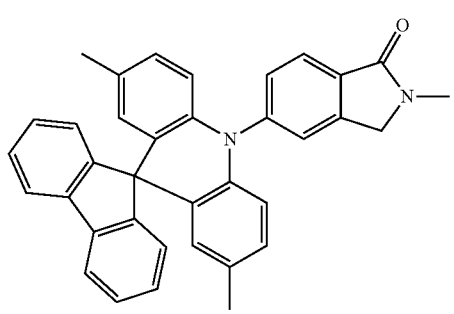 | 384 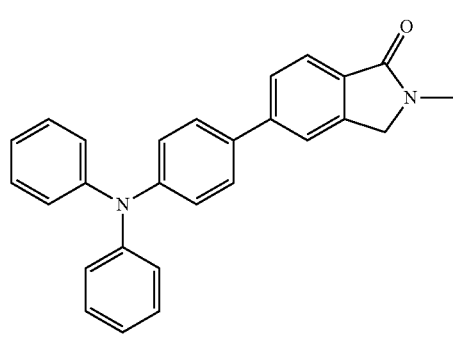 |
| 380 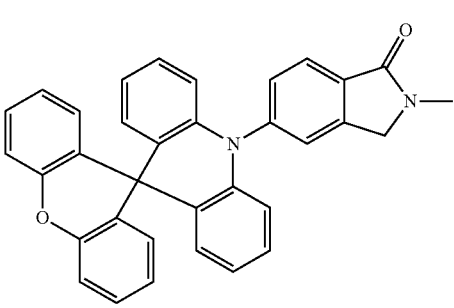 | 385 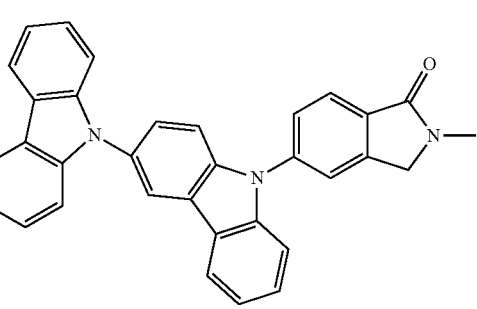 |
| 381 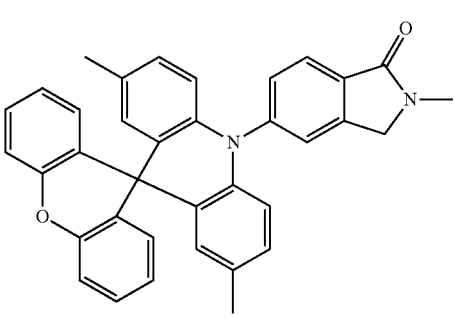 | 386 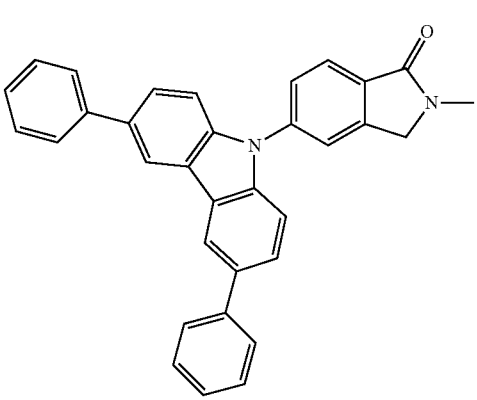 |

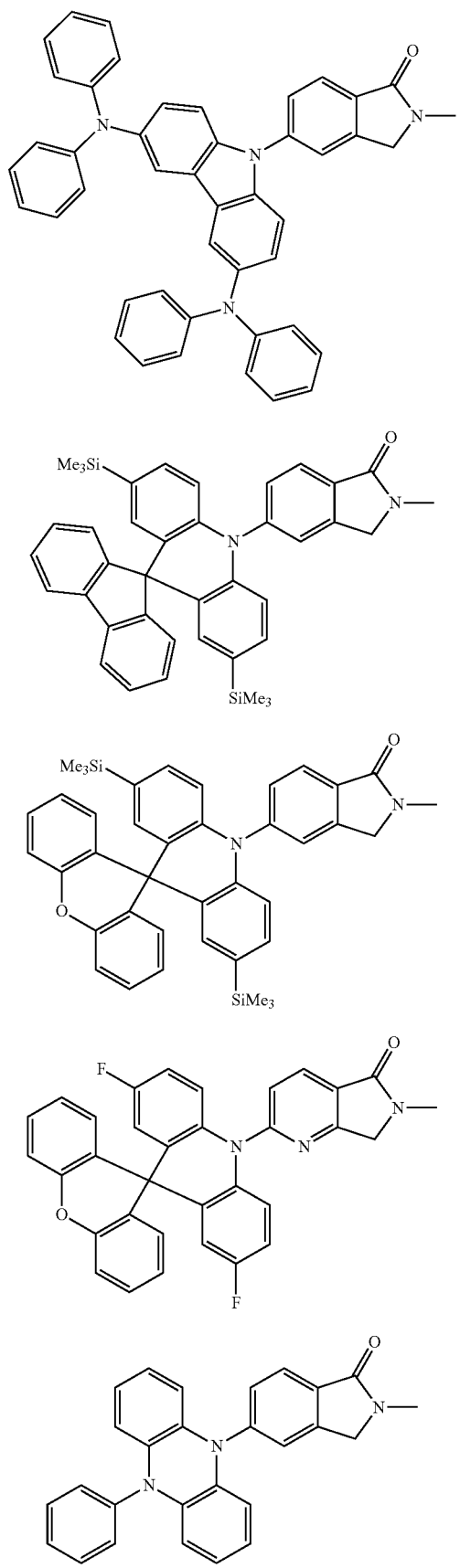
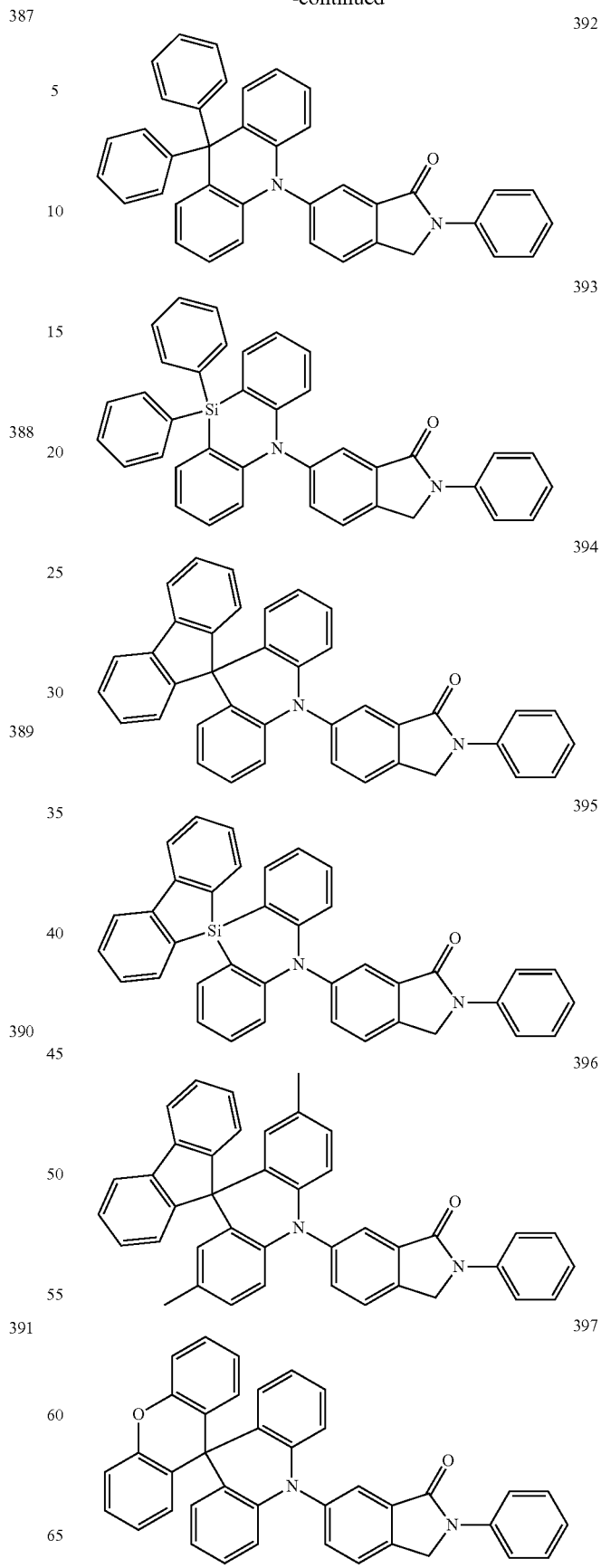

| 309 -continued | 310 -continued |
|---|---|
| 398 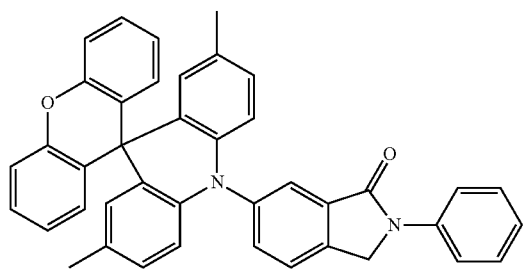 | 403 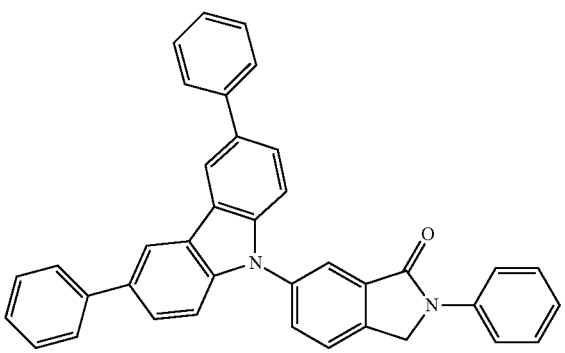 |
| 399 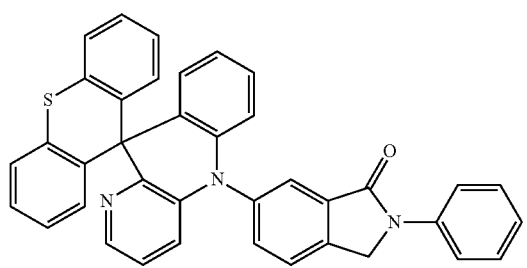 | 404 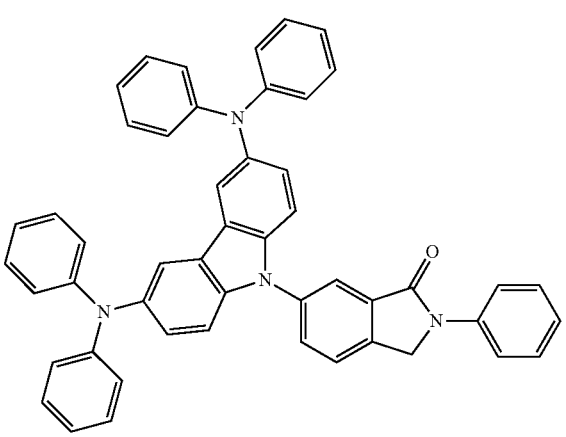 |
| 400 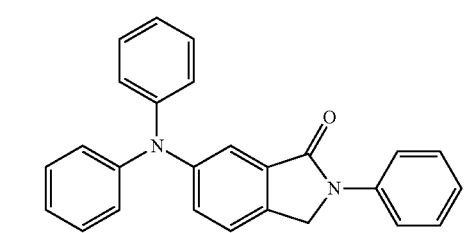 | |
| 401 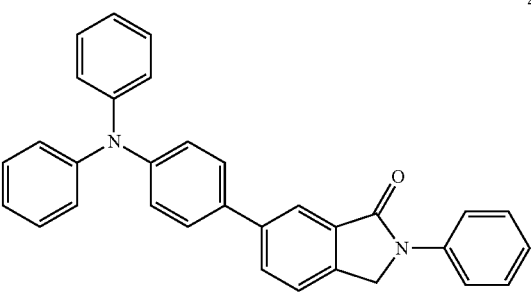 | 405 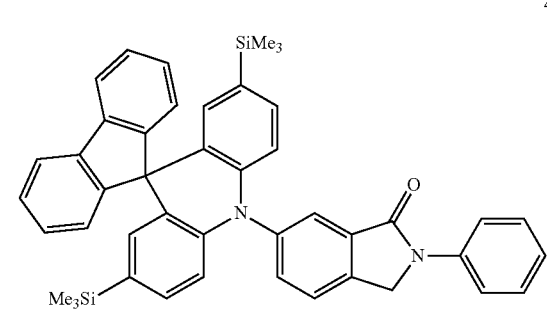 |
| 402 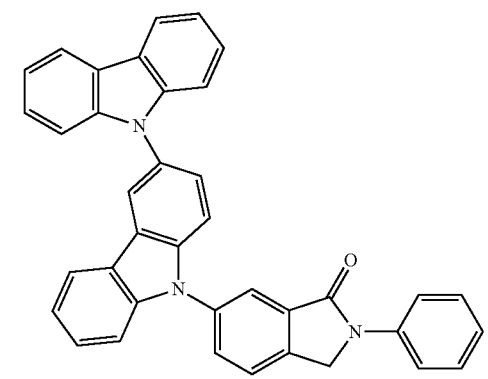 | 406 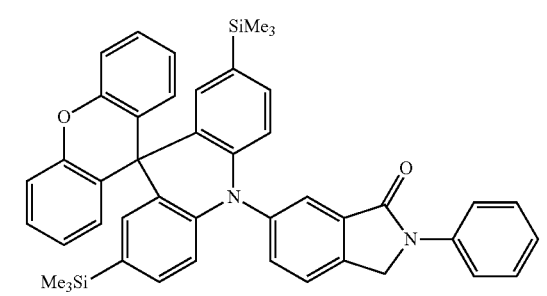 |

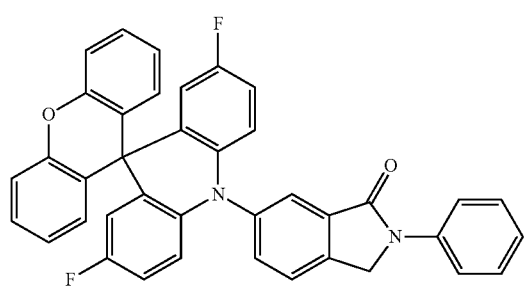
407
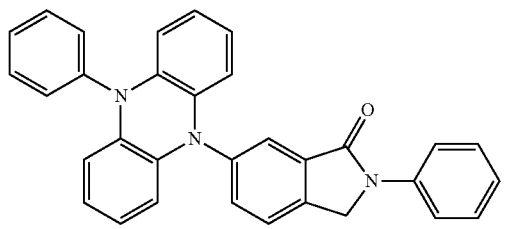
408
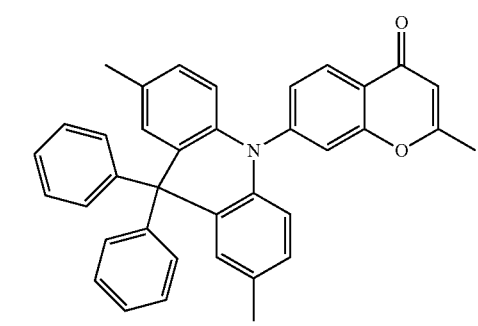
409
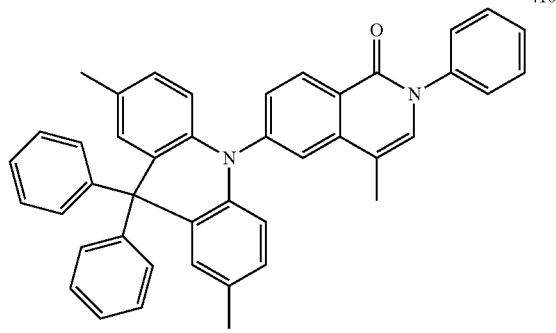
410
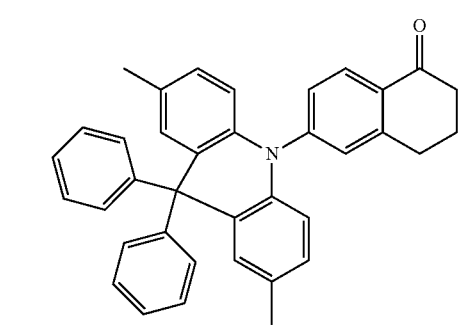
411
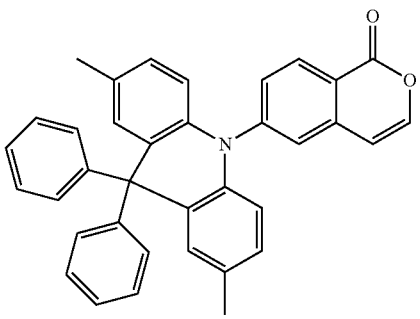
412
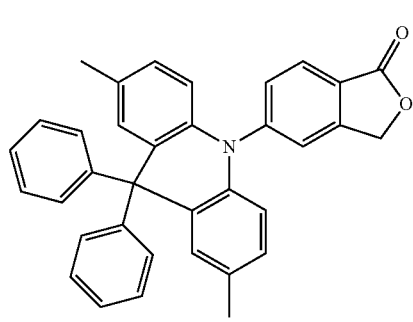
413
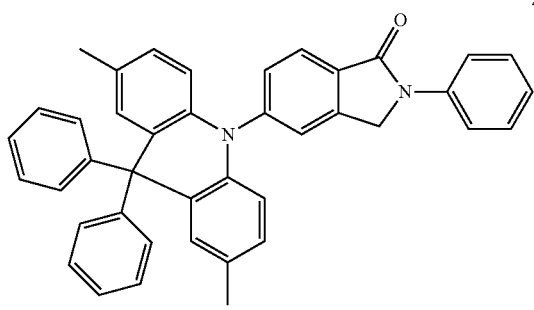
414
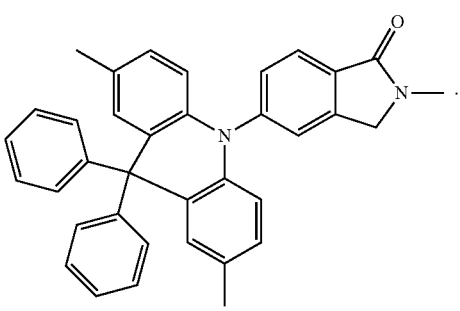
415
* * * * *